(12) United States Patent
Olson et al.

(10) Patent No.: US 10,156,559 B2
(45) Date of Patent: Dec. 18, 2018

(54) LIPOCALIN FUSION PARTNERS

(71) Applicant: Fred Hutchinson Cancer Research Center, Seattle, WA (US)

(72) Inventors: James Olson, Seattle, WA (US);
Christopher Mehlin, Seattle, WA (US);
Colin Correnti, Seattle, WA (US);
Roland Strong, Seattle, WA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 504 days.

(21) Appl. No.: 14/651,175

(22) PCT Filed: Dec. 10, 2013

(86) PCT No.: PCT/US2013/074215
§ 371 (c)(1),
(2) Date: Jun. 10, 2015

(87) PCT Pub. No.: WO2014/093403
PCT Pub. Date: Jun. 19, 2014

(65) Prior Publication Data
US 2015/0322123 A1    Nov. 12, 2015

Related U.S. Application Data

(60) Provisional application No. 61/735,516, filed on Dec. 10, 2012, provisional application No. 61/794,685, filed on Mar. 15, 2013.

(51) Int. Cl.
| | |
|---|---|
| *G01N 33/50* | (2006.01) |
| *G01N 33/53* | (2006.01) |
| *C07K 14/43* | (2006.01) |
| *A61K 49/00* | (2006.01) |
| *A61K 38/17* | (2006.01) |
| *A61K 45/06* | (2006.01) |
| *C07K 16/00* | (2006.01) |
| *C12N 9/00* | (2006.01) |
| *C07K 14/47* | (2006.01) |
| *C07K 14/435* | (2006.01) |
| *C12N 9/02* | (2006.01) |

(52) U.S. Cl.
CPC ..... *G01N 33/5008* (2013.01); *A61K 38/1767* (2013.01); *A61K 45/06* (2013.01); *A61K 49/00* (2013.01); *C07K 14/43522* (2013.01); *C07K 14/47* (2013.01); *C07K 16/00* (2013.01); *C12N 9/0083* (2013.01); *G01N 33/5308* (2013.01); *C07K 2319/00* (2013.01); *C12Y 114/99003* (2013.01); *G01N 2500/00* (2013.01); *G01N 2500/10* (2013.01); *G01N 2500/20* (2013.01)

(58) Field of Classification Search
None
See application file for complete search history.

(56) References Cited

U.S. PATENT DOCUMENTS

| | | |
|---|---|---|
| 4,444,744 A | 4/1984 | Goldenberg |
| 5,051,364 A | 9/1991 | Isacke et al. |
| 5,212,290 A | 5/1993 | Vogelstein et al. |
| 5,223,253 A | 6/1993 | Hall et al. |
| 5,236,844 A | 8/1993 | Basset et al. |
| 5,314,992 A | 5/1994 | Guyre et al. |
| 5,510,240 A | 4/1996 | Lam et al. |
| 5,591,829 A | 1/1997 | Matsushita |
| 5,626,862 A | 5/1997 | Brem et al. |
| 5,688,773 A | 11/1997 | Chiocca et al. |
| 5,750,376 A | 5/1998 | Weiss et al. |
| 5,756,340 A | 5/1998 | Hammock et al. |
| 5,866,570 A | 2/1999 | Liang et al. |
| 5,905,027 A | 5/1999 | Ullrich et al. |
| 5,935,795 A | 8/1999 | Lin et al. |
| 5,985,822 A | 11/1999 | Edelman et al. |
| 6,028,174 A | 2/2000 | Ullrich et al. |
| 6,130,101 A | 10/2000 | Mao et al. |
| 6,319,891 B1 | 11/2001 | Sontheimer et al. |
| 6,403,625 B1 | 6/2002 | Nagao et al. |
| 6,429,187 B1 | 8/2002 | Sontheimer et al. |
| 6,514,481 B1 | 2/2003 | Prasad et al. |
| 6,555,652 B1 | 4/2003 | Itoh et al. |
| 6,610,547 B1 | 8/2003 | Klaveness et al. |
| 6,667,156 B2 | 12/2003 | Lyons et al. |
| 6,767,635 B1 | 7/2004 | Bahr et al. |
| 6,849,714 B1 | 2/2005 | Bridon et al. |

(Continued)

FOREIGN PATENT DOCUMENTS

| | | |
|---|---|---|
| CN | 1924006 A | 3/2007 |
| CN | 101003788 A | 7/2007 |

(Continued)

OTHER PUBLICATIONS

Lakshmi et al., "Structure-Based Phylogenetic Analysis of the Lipocalin Superfamily", PLOS One, 10(8): e0135507. doi:10.1371/journal.pone.0135507.*
Park et al., "Retinol Binding Protein-Albumin Domain III Fusion Protein Deactivates Hepatic Stellate Cells", Mol. Cells, vol. 34, pp. 517-522, Published on-line Nov. 15, 2012, in-print Dec. 31, 2012. DOI/10.1007/s10059-012-0183-2.*
Smart Serum Albumin Domain Organization, Retrieved from < http://smart.embl.de/smart/do_annotation.pl?DOMAIN=SM00103 > on Nov. 2, 2017.*

(Continued)

*Primary Examiner* — Suzanne M Noakes
(74) *Attorney, Agent, or Firm* — Lee & Hayes PC; C. Rachal Winger

(57) ABSTRACT

Methods and systems for producing fusion proteins and peptides are disclosed. Fusion proteins and peptides created using the methods are also provided. Also provided are methods of using the fusion proteins and peptides produced according to the present disclosure.

22 Claims, 28 Drawing Sheets

Specification includes a Sequence Listing.

(56) References Cited

U.S. PATENT DOCUMENTS

| | | | |
|---|---|---|---|
| 6,870,029 B2 | 3/2005 | Sontheimer et al. | |
| 6,926,896 B2 | 8/2005 | Bosslet et al. | |
| 6,972,326 B2 | 12/2005 | Haugland et al. | |
| 7,094,868 B2 | 8/2006 | Samoylova et al. | |
| 7,252,998 B2 | 8/2007 | Skerra et al. | |
| 7,462,446 B2 | 12/2008 | Zhang et al. | |
| 7,678,759 B2 | 3/2010 | Sontheimer et al. | |
| 8,227,439 B2 | 7/2012 | O'Neill et al. | |
| 8,470,607 B2 | 6/2013 | Jacoby et al. | |
| 8,778,310 B2 | 7/2014 | Zhang et al. | |
| 2001/0007025 A1 | 7/2001 | Bennett et al. | |
| 2002/0065216 A1 | 5/2002 | Sontheimer et al. | |
| 2002/0146749 A1 | 10/2002 | Lyons et al. | |
| 2003/0021810 A1 | 1/2003 | Sontheimer et al. | |
| 2003/0105000 A1 | 6/2003 | Pero et al. | |
| 2003/0201208 A1 | 10/2003 | Koch et al. | |
| 2003/0216322 A1 | 11/2003 | Samoylova et al. | |
| 2003/0232013 A1 | 12/2003 | Sieckman et al. | |
| 2004/0101822 A1 | 5/2004 | Wiesner et al. | |
| 2004/0102381 A1 | 5/2004 | Ekwuribe et al. | |
| 2004/0105980 A1 | 6/2004 | Sudarshan et al. | |
| 2004/0141981 A1 | 7/2004 | Sontheimer et al. | |
| 2004/0180846 A1 | 9/2004 | Huang et al. | |
| 2005/0142062 A1 | 6/2005 | Sontheimer et al. | |
| 2005/0261191 A1 | 11/2005 | Barasch et al. | |
| 2006/0019256 A1 | 1/2006 | Clarke et al. | |
| 2006/0019347 A1 | 1/2006 | Cho et al. | |
| 2006/0088899 A1 | 4/2006 | Alvarez et al. | |
| 2006/0088908 A1* | 4/2006 | Skerra .................. | C07K 14/47 435/69.1 |
| 2006/0166892 A1 | 7/2006 | Alvarez et al. | |
| 2007/0071764 A1 | 3/2007 | Sullivan et al. | |
| 2007/0154965 A1 | 7/2007 | Zhang et al. | |
| 2007/0237714 A1 | 10/2007 | Alvarez | |
| 2007/0275902 A1 | 11/2007 | Gonda et al. | |
| 2008/0153745 A1 | 6/2008 | Alvarez et al. | |
| 2008/0153746 A1 | 6/2008 | Alvarez et al. | |
| 2008/0279780 A1 | 11/2008 | Zhang et al. | |
| 2009/0004105 A1 | 1/2009 | Cheng et al. | |
| 2009/0123946 A1 | 5/2009 | Birkenmeyer et al. | |
| 2009/0123970 A1 | 5/2009 | Tu et al. | |
| 2009/0124022 A1 | 5/2009 | Birkenmeyer et al. | |
| 2009/0176274 A1 | 7/2009 | Tu et al. | |
| 2009/0203598 A1 | 8/2009 | McCarty et al. | |
| 2009/0220430 A1 | 9/2009 | Rajopadhye et al. | |
| 2009/0263894 A1 | 10/2009 | Birkenmeyer et al. | |
| 2009/0269777 A1 | 10/2009 | Birkenmeyer et al. | |
| 2009/0304592 A1 | 12/2009 | O'Neill et al. | |
| 2009/0311224 A1 | 12/2009 | Lee et al. | |
| 2010/0098637 A1 | 4/2010 | Orringer et al. | |
| 2010/0105150 A1 | 4/2010 | Adamczyk et al. | |
| 2010/0210546 A1 | 8/2010 | Alvarez et al. | |
| 2010/0215575 A1 | 8/2010 | O'Neill et al. | |
| 2010/0215576 A1 | 8/2010 | Sontheimer et al. | |
| 2011/0027177 A1 | 2/2011 | Jacoby et al. | |
| 2011/0055751 A1 | 3/2011 | Morrison et al. | |
| 2011/0091380 A1 | 4/2011 | Jacoby et al. | |
| 2011/0311445 A1 | 12/2011 | Alvarez et al. | |
| 2012/0156131 A1 | 6/2012 | Alvarez | |
| 2012/0164741 A1 | 6/2012 | Chen et al. | |
| 2012/0183544 A1 | 7/2012 | Sontheimer et al. | |
| 2013/0028836 A1 | 1/2013 | Sentissi et al. | |
| 2013/0045163 A1 | 2/2013 | O'Neill et al. | |
| 2013/0195760 A1 | 8/2013 | Olson | |
| 2014/0179560 A1 | 6/2014 | Olson et al. | |
| 2014/0241993 A1 | 8/2014 | Zhang et al. | |
| 2014/0315762 A1 | 10/2014 | Keefe et al. | |

FOREIGN PATENT DOCUMENTS

| | | |
|---|---|---|
| CN | 101270158 A | 9/2008 |
| CN | 101381405 A | 3/2009 |
| CN | 101824084 A | 9/2010 |
| CN | 101921769 A | 12/2010 |
| EP | 0155396 A2 | 9/1985 |
| EP | 1430131 B1 | 11/2005 |
| EP | 2182004 A1 | 5/2010 |
| JP | H08505615 A | 6/1996 |
| JP | H08325291 A | 12/1996 |
| JP | H0971599 A | 3/1997 |
| JP | 2002542206 A | 12/2002 |
| JP | 2005537234 A | 12/2005 |
| JP | 2008-538506 | 10/2008 |
| JP | 2009280567 | 12/2009 |
| JP | 2009300110 | 12/2009 |
| JP | 2010085108 | 4/2010 |
| WO | WO198802117 A1 | 3/1988 |
| WO | WO199311222 A1 | 6/1993 |
| WO | WO199415615 A1 | 7/1994 |
| WO | WO 97/24619 A1 | 7/1997 |
| WO | WO199743301 A2 | 11/1997 |
| WO | WO199929715 A1 | 6/1999 |
| WO | WO200011208 A1 | 3/2000 |
| WO | WO 00/62807 A1 | 10/2000 |
| WO | WO200062810 A1 | 10/2000 |
| WO | WO 03/000203 A2 | 1/2003 |
| WO | WO2003008583 A2 | 1/2003 |
| WO | WO 03/101474 A1 | 12/2003 |
| WO | WO 03/101475 A1 | 12/2003 |
| WO | WO2004085618 A2 | 10/2004 |
| WO | WO 2005/002604 A1 | 1/2005 |
| WO | WO 2005/053611 A2 | 6/2005 |
| WO | WO 2005/099774 A2 | 10/2005 |
| WO | WO 2005/107793 A2 | 11/2005 |
| WO | WO 2006/040574 A2 | 4/2006 |
| WO | WO 2006/095164 A1 | 9/2006 |
| WO | WO2006110581 A2 | 10/2006 |
| WO | WO2006110582 A1 | 10/2006 |
| WO | WO 2006/115633 A2 | 11/2006 |
| WO | WO2006116156 A2 | 11/2006 |
| WO | WO 2007/044994 A2 | 4/2007 |
| WO | WO 2007/047458 A2 | 4/2007 |
| WO | WO 2007/117467 A2 | 10/2007 |
| WO | WO 2007/137163 A2 | 11/2007 |
| WO | WO 2008/088422 A2 | 7/2008 |
| WO | WO 2008/155134 A1 | 12/2008 |
| WO | WO 2009/021136 A1 | 2/2009 |
| WO | WO2009029760 A1 | 3/2009 |
| WO | WO 2009/049184 A2 | 4/2009 |
| WO | WO 2009/052390 A1 | 4/2009 |
| WO | WO 2009/052392 A1 | 4/2009 |
| WO | WO 2009/052400 A1 | 4/2009 |
| WO | WO 2009/062520 A1 | 5/2009 |
| WO | WO 2009/108762 A2 | 9/2009 |
| WO | WO 2009/117018 A1 | 9/2009 |
| WO | WO2009114776 A2 | 9/2009 |
| WO | WO 2009/140599 A1 | 11/2009 |
| WO | WO2009133362 A2 | 11/2009 |
| WO | WO 2009/156456 A1 | 12/2009 |
| WO | WO 2011/057295 A2 | 5/2011 |
| WO | WO 2011/094671 A2 | 8/2011 |
| WO | WO 2011/097533 A1 | 8/2011 |
| WO | WO 2011/142858 A2 | 11/2011 |
| WO | WO 2012/022742 A1 | 2/2012 |
| WO | WO2012064658 | 5/2012 |

OTHER PUBLICATIONS

Akcan, et al. Chemical re-engineering of chlorotoxin improves bioconjugation properties for tumor imaging and targeted therapy. J Med Chem. Feb. 10, 2011;54(3):782-7. doi: 10.1021/jm101018r. Epub Jan. 6, 2011.

Bandaranayake, et al. Daedalus: a robust, turnkey platform for rapid production of decigram quantities of active recombinant proteins in human cell lines using novel lentiviral vectors. Nucleic Acids Res. Nov. 2011;39(21):e143. doi: 10.1093/nar/gkr706. Epub Sep. 12, 2011.

Berlier, J.E., et al., Quantitative Comparison of Long-Wavelength Alexa Fluor Dyes to Cy Dyes: Fluorscence of the Dyes and Their Bioconjugates, The Journal of Histochemistry & Cytochemistry 51(12) :1699-1712, 2003.

(56) References Cited

OTHER PUBLICATIONS

Butterworth, et al. Preparation of Ultrafine Silica- and PEG-Coated Magnetite Particles. Colloids and Surfaces A: Physicochemical and Engineering Aspects 179:93-102, 2001.
Citrin, et al. In vivo tumor imaging in mice with near-infrared labeled endostatin. Mol Cancer Ther. Apr. 2004;3(4):481-8.
Colman. Effects of amino acid sequence changes on antibody-antigen interactions. Res Immunol. Jan. 1994;145(1):33-6.
CyDye™ mono-reactive NHS-Esters. Amersham Biosciences, 2002, pp. 1-20.
Database Geneseq [Online] Oct. 16, 2008 (Oct. 16, 2008), "Alpha-scorpion toxin family member CTX toxin peptide analog, SEQ: 473.", XP002714000, retrieved from EBI accession No. GSP:ATD17606 Database accession No. ATD17606 * sequence.
Deshane, et al. Chlorotoxin inhibits glioma cell invasion via matrix metalloproteinase-2. J Biol Chem. Feb. 7, 2003;278(6):4135-44. Epub Nov. 25, 2002.
Egleton, R.D. and Davis, T.P., Development of Neuropeptide Drugs that Cross the Blood-Brain Barrier, J. Am. Soc. Exp. NeuroTherapeutics 2:44-53 (2005).
European search report and search opinion dated Oct. 15, 2013 for EP Application No. 11780950.9.
Fischer, et al. Pyrrolopyrrole cyanine dyes: a new class of near-infrared dyes and fluorophores. Chemistry. 2009;15(19):4857-64. doi: 10.1002/chem.200801996.
Flower, et al. Structure and sequence relationships in the lipocalins and related proteins. Protein Sci. May 1993;2(5):753-61.
Goetz, et al. The neutrophil lipocalin NGAL is a bacteriostatic agent that interferes with siderophore-mediated iron acquisition. Mol Cell. Nov. 2002;10(5):1033-43.
Gunn, J. et al., Smart Superparamagnetic Imaging Probes for Brain Tumor Research, in D.B. Baer and C.T. Campbell (eds.), Joint Institute for Nanoscience Annual Report, 2004, Nov. 2005, pp. 3.65-3.66.
Hatton, et al. The Smo/Smo model: hedgehog-induced medulloblastoma with 90% incidence and leptomeningeal spread. Cancer Res. Mar. 15, 2008;68(6):1768-76. doi: 10.1158/0008-5472.CAN-07-5092.
Hockaday, D.C. et al., Imaging Glioma Extent with 131I-TM-601, J. Nuc. Med. 46(4): 580-586 (2005).
Huys, et al. Structure-function study of a chlorotoxin-chimer and its activity on Kv1.3 channels. J Chromatogr B Analyt Technol Biomed Life Sci. Apr. 15, 2004;803(1):67-73.
Ibragimova, et al. Stability of the beta-sheet of the WW domain: A molecular dynamics simulation study. Biophys J. Oct. 1999 77(4):2191-8.
International search report and written opinion dated Apr. 8, 2014 for PCT/US2013/074215.
International search report and written opinion dated Apr. 22, 2014 for PCT/US2013/074218.
International search report and written opinion dated Oct. 6, 2010 for PCT/US2006/010170.
International search report and written opinion dated Nov. 18, 2011 for PCT/US2011/023797.
Invitation Pursuant to Article 94(3) and Rule 71(1) EPC, dated Mar. 1, 2010, in corresponding European Application No. 06 739 100.3, filed Mar. 20, 2006, 3 pages.
Jiang, T. et al., Tumor Imaging by Means of Proteolytic Activation of Cell-Penetrating Peptides, Proceedings of the National Academy of Sciences USA (PNAS) 101(51):17867-17872, Dec. 2004.
Kohler, et al. A bifunctional poly(ethylene glycol) silane immobilized on metallic oxide-based nanoparticles for conjugation with cell targeting agents. J Am Chem Soc. Jun. 16, 2004;126(23):7206-11.
Lee, M. J., et al., Rapid Pharmacokinetic and Biodistribution Studies Using Cholorotoxin-conjugated Iron oxide Nanoparticles: A Novel Non-Radioactive Method, PLoS One 5(3):e9536 1-8 (2010).
Milross, et al. Relationship of mitotic arrest and apoptosis to antitumor effect of paclitaxel. J Natl Cancer Inst. Sep. 18, 1996;88(18):1308-14.
Notice of allowance dated Mar. 11, 2014 for U.S. Appl. No. 11/897,721.
Notice of allowance dated Nov. 15, 2013 for U.S. Appl. No. 11/897,721.
Office action dated Mar. 12, 2015 for U.S. Appl. No. 13/673,779.
Office action dated Mar. 24, 2010 for U.S. Appl. No. 11/897,721.
Office action dated Jun. 23, 2014 for U.S. Appl. No. 14/102,396.
Office action dated Sep. 3, 2015 for U.S. Appl. No. 13/673,779.
Office action dated Sep. 15, 2009 for U.S. Appl. No. 11/897,721.
Rudikoff, et al. Single amino acid substitution altering antigen-binding specificity. Proc Natl Acad Sci U S A. Mar. 1982;79(6):1979-83.
Shiue. Identification of candidate genes for drug discovery by differential display. Drug Development Research. New York. 1997; 41:142-159.
Soroceanu, et al. Use of chlorotoxin for targeting of primary brain tumors. Cancer Res. Nov. 1, 1998;58(21):4871-9.
Sun, et al. Size-controlled synthesis of magnetite nanoparticles. J Am Chem Soc. Jul. 17, 2002;124(28):8204-5.
Tatikolov, A.S. and Costa, S.M.B., Complexation of polymethine dyes with human serum albumin: a spectroscopic study, Biophys. Chem. 107:33-49 (2004).
Thermo Scientific Pierce Fluorescent Products Guide—fluorescent labeling and Detection. ThermoScientific Jan. 2012.
Tytgat, et al. Purification and partial characterization of a 'short' insectotoxin-like peptide from the venom of the scorpion *Parabuthus schlechteri*. FEBS Lett. Dec. 28, 1998;441(3):387-91.
Veiseh, et al. Specific targeting of brain tumors with an optical/magnetic resonance imaging nanoprobe across the blood-brain barrier. Cancer Res. Aug. 1, 2009;69(15):6200-7. doi: 10.1158/0008-5472.CAN-09-1157. Epub Jul. 28, 2009.
Veiseh, et al. Tumor paint: a chlorotoxin:Cy5.5 bioconjugate for intraoperative visualization of cancer foci. Cancer Res. Jul. 15, 2007;67(14):6882-8.
Veiseh, O., et al., Optical and MRI Multifunctional nanoprobe for Targeting Gliomas, Nano Letters 5(6):1003-1008, 2005.
Velde, et al. The use of fluorescent dyes and probes in surgical oncology. Eur J Surg Oncol. Jan. 2010;36(1):6-15. doi: 10.1016/j.ejso.2009.10.014. Epub Nov. 18, 2009.
VivoTag® 680 XL In Vivo Fluorochrome Label. Perkin Elmer, 2010, Product No. NEV11119.
Weissleder, et al. Shedding light onto live molecular targets. Nat Med. Jan. 2003;9(1):123-8.
Wishart, et al. 1H, 13C and 15N chemical shift referencing in biomolecular NMR. J Biomol NMR. Sep. 1995;6(2):135-40.
Zhang et al ., Surface Modification of Superparamagnetic magnetite Nanoparticles and Their Intracellular Uptake, Biomaterial 23:1553 15-61, 2002.
Giacomotto, et al., "High-throughput screening and small animal models, where are we?" Br. J. Pharmacol., vol. 160, No. 2, 2010, pp. 204-216.
Goetz, et al., "The neutrophil lipocalin NGAL is a bacteriostatic agent that interferes with siderophore-mediated iron acquisition," Mol Cell., vol. 10, No. 5, 2002, pp. 1033-1043.
Gorecki, "Prospects and problems of gene therapy: an update," Expert Opin. Emerg. Drugs, vol. 6, No. 2, 2001, pp. 187-198.
Grissimer, et al., "Calcium-activated potassium channels in resting and activated human T lymphocytes. Expression levels, calcium dependence, ion selectivity, and pharmacology," J. Gen. Physiol., vol. 102, No. 4, 1993, pp. 601-630.
Gunn, et al., "Smart Superparamagnetic Imaging Probes for Brain Tumor Research," in D.B. Baer and C.T. Campbell (eds.), Joint Institute for Nanoscience Annual Report, 2004, pp. 2.61-2.67.
Gura, "Systems for identifying new drugs are often faulty," Science, vol. 278, No. 5340, 1997, pp. 1041-1042.
Hajjar, et al., "Annexin II: a mediator of the plasmin/plasminogen activator system," Trends Cardiovasc Med., vol. 9, No. 5, 1999, pp. 128-138.
Hartwell, et al., "Integrating genetic approaches into the discovery of anticancer drugs," Science, vol. 278, No. 5340, 1997, pp. 1064-1068.

(56) References Cited

OTHER PUBLICATIONS

Hatton, et al., "The Smo/Smo model: hedgehog-induced medulloblastoma with 90% incidence and leptomeningeal spread," Cancer Res., vol. 68, No. 6, 2008, pp. 1768-1776.
He, et al., "A simple and effective "capping" approach to readily tune the fluorescence of nearinfrared cyanines," Chem. Sci., vol. 6, No. 8, 2015, pp. 4530-4536.
Hockaday, et al., "Imaging Glioma Extent with 131I-TM-601," J. Nuc. Med., vol. 46, No. 4, 2005, pp. 580-586.
Holmes, et al., "Protein labeling with fluorescent probes," Methods Cell Biol., vol. 63, 2001, pp. 185-204.
Holsi, et al., "Evidence for GABAb-receptors on cultured astrocytes of rat CNS; autoradiographic binding studies," Exp. Brain Res, vol. 80, 1990, pp. 621-625.
Huang, et al., "Potassium channel induction by the Ras/Raf signal transduction cascade," J. Biol. Chem., vol. 269, No. 49, 1994, pp. 31183-31189.
Huys, et al., "Structure-function study of a chlorotoxin-chimer and its activity on Kv1.3 channels," J. Chromatogr. B. Analyt. Technol. Biomed Life Sci., vol. 801, No. 1, 2004, pp. 67-73.
Ibragimova, et al., "Stability of the beta-sheet of the WW domain: A molecular dynamics simulation study," Biophys. J., vol. 77, No. 4, 1999, pp. 2191-2198.
International Preliminary Report on Patentability dated Jun. 16, 2015 in International Application No. PCT/US13/74215, 5 pages.
International Preliminary Report on Patentability dated Oct. 11, 2006 in International Application No. PCT/US2005/011523, 7 pages.
International Preliminary Report on Patentability dated Oct. 23, 2007 in International Application No. PCT/US2006/010170, 9 pages.
International Preliminary Report on Patentability dated Nov. 17, 2010 in International Application No. PCT/US2009/044149, 7 pages.
International Preliminary Report on Patentability dated Apr. 13, 2010 in International Application No. PCT/US2008/079547, 4 pages.
International Preliminary Report on Patentability dated May 29, 2001 in International Application No. PCT/US2000/010453, 4 pages.
International Preliminary Report on Patentability dated May 29, 2006 in International Application No. PCT/US2004/039325, 4 pages.
International Preliminary Report on Patentability dated Sep. 21, 2010 in International Application No. PCT/US2008/076740, 6 pages.
International Preliminary Report on Patentability dated Sep. 30, 2008 for International Application No. PCT/2007/008309, 9 pages.
International Preliminary Report on Patentability dated Sep. 30, 2010 for International Application No. PCT/US2008/07640, 6 pages.
Jacoby, et al., "Potent pleiotropic anti-angiogenic effects of TM601, a synthetic chlorotoxin peptide," Anticancer Res., vol. 30, No. 1, 2010, pp. 39-46.
Jiang, et al., "Evaluation of a 64Cu-Labeled Cystine-Knot Peptide Based on Agouti-Related Proteinfor PET of Tumors Expressing avb3 Integrin," J. Nucl. Med., vol. 51, No. 2, 2010, pp. 251-258.
Jiang, et al., "Tumor Imaging by Means of Proteolytic Activation of Cell-Penetrating Peptides," PNAS, vol. 101, No. 51, 2004, pp. 17867-17872.
Jianping, Chinese and Foreign Sciences Yearbook, The Second Military Medical University (SMMU) Press, 2004, p. 126.
Office Action dated Nov. 1, 2017 in Japanese Application No. 2015-545938, 15 pages.
Kaiser, "First Pass at Cancer Genome Reveals Complex Landscape," Science, vol. 313, No. 5792, 2006, 2 pages.
Kastin, et al., "Orexin A but not orexin B rapidly enters brain from blood by simple diffusion," J. Pharmacol. Exp. Ther., vol. 289, No. 1, 1999, pp. 219-223.
Kato-Takagaki et al., "Structural and Interaction Analysis of Glycoprotein VI-Binding Peptide Selected From a Phage Display Library," J. Biol. Chem., vol. 284, No. 16, 2009, pp. 10720-10727.
Kaye, et al., "A single amino acid substitution results in a retinoblastoma protein defective in phosphorylation and oncoprotein binding," PNAS, vol. 87, No. 17, 1990, pp. 6922-6926.
Kellenberger, et al., "Serine Protease Inhibition by Insect Peptides Containing a Cysteine Knot and a Triple-Stranded beta-Sheet," J. Biol. Chem., vol. 270, No. 43, 1995, pp. 25514-25519.
Kesavan, et al., "Annexin A2 is a molecular target for TM601, a peptide with tumor-targeting and anti-angiogenic affects," J. Biol. Chem., vol. 285, No. 7, 2010, pp. 4366-4374.
Kessler, et al., "Identification of the putative brain tumor antigen BF7/GE2 as the (de)toxifying enzyme microsomal apoxide hydrolase," Cancer Res., vol. 60, No. 5, 2000, pp. 1403-1409.
Kimura, et al., "A dual-labeled knottin peptide for PET and near-infrared fluorescence imaging of integrin expression in living subjects," Bioconjug. Chem., vol. 21, No. 3, 2010, pp. 436-444.
Klein, et al., "Surface IgM-kappa specificity on a Burkitt lymphoma cell in vivo and in derived culture lines," Cancer Res., vol. 28, No. 7, 1968, pp. 1300-1310.
Kraft, et al., "Interactions of indocyanine green and lipid in enhancing near-infrared fluorescence properties: the basis for near-infrared imaging in vivo," Biochemistry, vol. 53, No. 8, 2014, pp. 1275-1283.
Kuan, et al., "EGFRvIII as a promising target for antibody-based brain tumor therapy," Brain Tumor Pathol., vol. 17, No. 2, 2000, pp. 71-78.
Laumonnier, et al., "Identification of the annexin A2 heterotetramer as a receptor for the plasmin-induced signaling in human peripheral monocytes," Blood, vol. 107, 2006, pp. 3342-3349.
Lazar, et al., "Transforming growth factor alpha: mutation of aspartic acid 47 and leucine 48 results in different biological activities," Mol. Cell. Biol., vol. 8, No. 3, 1988, pp. 1247-1252.
Lee, et al., "Increased vaccine-specific T cell frequency after peptide-based vaccination correlates with increased susceptibility to in vitro stimulation but does not lead to tumor regression," J. Immunol., vol. 163, No. 1, 1999, pp. 6292-6300.
Lee, et al., "Rapid Pharmacokinetic and Biodistribution Studies Using Cholorotoxin-conjugated Iron oxide Nanoparticles: A Novel Non-Radioactive Method," PLoS One, vol. 5, No. 3, 2010, e9536.
Lippens, et al., "NMR sequential assignments and solution structure of chlorotoxin, a small scorpion toxin that blocks chloride channels," Biochemistry, vol. 34, No. 1, 1995, pp. 13-21.
Lynch, "Chemoprevention with special reference to inherited colorectal cancer," Fam. Cancer., vol. 7, No. 1, 2008, pp. 59-64.
Lyons, et al., "Chlorotoxin, a scorpion-derived peptide, specifically binds to gliomas and tumors of neuroectodermal origin," Glia, vol. 39, No. 2, 2002, pp. 162-173.
Malinowski, et al., "Recombinant chlorotoxin: An inhibitor of gastric Cl-channels," Abstract, Biophysical Journal, vol. 36, No. 2:A, 1994, p. 100.
Adelstein, et al., "Radiotoxicity of iodine-125 and other auger-electron-emitting radionuclides: background to therapy," Cancer Biother. Radiopharm., vol. 18, No. 3, 2003, pp. 301-316.
Akabani, et al., "Dosimetry and radiographic analysis of 131I-labeled anti-tenascin 81 C6 murine monoclonal antibody in newly diagnosed patients with malignant gliomas: a phase II study," J. Nucl. Med., vol. 46, No. 6, 2005, pp. 1042-1051.
Akabani, et al., "Dosimetry of 131I-labeled 81 C6 monoclonal antibody administered into surgically created resection cavities in patients with malignant brain tumors," J. Nucl. Med., vol. 40, No. 4, 1999, pp. 631-638.
Alander, et al., "A review of indocyanine green fluorescent imaging in surgery," Int. J. Biomed. Imaging, vol. 2012, 2012, 26 pages.
Appelbaum, et al., "Treatment of malignant lymphoma in 100 patients with chemotherapy, total body irradiation, and marrow transplantation," J. Clin. Oncol., vol. 5, No. 9, 1987, pp. 1340-1347.
Office Action dated Jun. 23, 2017 in Australian Application No. 2013359426, 4 pages.
Banks, "Characteristics of compounds that cross the blood-brain barrier," BMC Neurol., vol. 9, Suppl 1, 2009, 5 pages.
Becker and Terlau, "Toxins from cone snails: properties, applications, and biotechnological production," Appl. Microbiol. Biotechnol., vol. 79, 2008, 9 pages.

(56) References Cited

OTHER PUBLICATIONS

Berezin, et al., "Rational approach to select small peptide molecular probes labeled with fluorescent cyanine dyes for in vivo optical imaging," Biochemistry, vol. 50, No. 13, 2011, pp. 2691-2700.
Bernal, "Tumor Paint Brings Light to Toddler's Brain Tumor," On the Pulse (Sep. 22, 2016). Seattle Children's Hospital. Web article. URL: <http://pulse.seattlechildrens.org/tumor-paint-brings-light-to-toddlers-brain-tumor/>, 3 pages.
Bertolini, et al., "Inhibition of angiogenesis and induction of endothelial and tumor cell apoptosis by green tea in animal models of human high-grade non-Hodgkin's lymphoma," Leukemia, vol. 14, No. 8, 2000, pp. 1477-1482.
Bigner, et al., "Iodine-131-labeled antitenascin monoclonal antibody 81C6 treatment of patients with recurrent malignant gliomas: phase I trial results," J. Clin. Oncol., vol. 16, No. 6, 1998, pp. 2202-2212.
Bowie, et al., "Deciphering the message in protein sequences: tolerance to amino acid substitutions," Science, vol. 247, No. 4948, 1990, pp. 1306-1310.
Bradley, et al., "Limits of cooperativity in a structurally modular protein: response of the Notch ankyrin domain to analogous alanine substitutions in each repeat," J. Mal. Biol., vol. 324, No. 2, 2002, pp. 373-386.
Brem, et al., "Placebo-controlled trial of safety and efficacy of intraoperative controlled delivery by biodegradable polymers of chemotherapy for recurrent gliomas," The Polymer-brain Tumor Treatment Group, Lancet, vol. 345, No. 8956, 1995, pp. 1008-1012.
Britton, et al., "Prostate cancer: the contribution of nuclear medicine," BJU International, vol. 86, No. s1, 2000, pp. 135-142.
Burgess, et al., "Possible dissociation of the heparin-binding and mitogenic activities of heparin-binding (acidic fibroblast) growth factor-1 from its receptor-binding activities by sitedirected mutagenesis of a single lysine residue," J. Cell. Biol., vol. 111, 5 Pt 1, 1990, pp. 2129-2138.
Butte, et al., "Near-infrared imaging of brain tumors using the Tumor Paint BLZ-100 to achieve near-complete resection of brain tumors," Neurosurg. Focus., vol. 36, No. 2, 2014, 8 pages.
Office Action dated Jan. 8, 2010 in Canadian Patent Application No. 2487425, 5 pages.
Castro, et al. "Gene therapy for Parkinson's disease: recent achievements and remaining challenges," Histol. Histopathol., vol. 16, No. 4, 2001, pp. 1225-1238.
Chien, et al. "The two-hybrid system: a method to identify and clone genes for proteins that interact with a protein of interest," PNAS, vol. 88, No. 21, 1991, pp. 9578-9582.
Chui, et al., "The role of potassium channels in Schwann cell proliferation in Wallerian degeneration of explant rabbit sciatic nerves," J. Physiol., vol. 408, 1989 pp. 199-222.
Chuthapisith, et al., "Annexins in human breast cancer: Possible predictors of pathological response to neoadjuvant chemotherapy," Eur. J. Cancer, vol. 45, No. 7, 2009, pp. 1274-1281.
Daly, et al., "Pumiliotoxin alkaloids: a new class of sodium channel agents," Biochem. Pharmacol., vol. 40, No. 2, 1990, Abstract.
Deane, et al., "An alternative pathway of B cell activation: stilbene disulfonates interact with a CI-binding motif on AEn-related proteins to stimulate mitogenesis," Eur. J. Immunol., vol. 22, No. 5, 1992, pp. 1165-11671.
DeBin, et al., "Chloride channel inhibition by the venom of the scorpion *Leiurus quinquestriatus*," Toxicon., vol. 29, No. 11, 1991, pp. 1403-1408.
DeBin, et al., "Purification and characterization of chlorotoxin, a chloride channel ligand from the venom of the scorpion," Am. J. Physiol., vol. 264, 2 Pt. 1, 1993, pp. C361-C369.
Dermer, "Another Anniversary for the War on Cancer," Nature Biotechnology, vol. 12, No. 320, 1994, 2 pages.
Dictionary.com, Definition of the word "moiety", 4 pages, http://www.dictionary.com/browse/moiety (last accessed: Feb. 23, 2018).
Entrez Genome, ANXA2 annexin A2 [*Homo sapiens*]. Gene ID: 302, updated on Aug. 26, 2010, Retrieved on Sep. 7, 2010. URL:< http://www.ncbi.nlm.nih.gov/gene/302>.

EP Office Action dated Nov. 8, 2017 in European Application No. 13814341.7, 5 pages.
EP Office Action dated May 25, 2018 for European Patent Application No. 13814341.7, 3 pages.
EP Partial Search Report dated Apr. 8, 2010 in European Application No. EP09150772.3, 5 pages.
EP Extended European Search Report dated Nov. 23, 2010 in European Application No. EP08837002.8, 4 pages.
EP Extended European Search Report dated Jul. 30, 2010 in European Application No. 09150772.3, 11 pages.
EP Extended European Search Report dated Apr. 6, 2010 in European Application No. EP09176234.4, 4 pages.
EP Supplemental Partial European Search Report dated Mar. 11, 2003 in European Application No. EP00926105, 2 pages.
EP Supplementary Partial Search Report dated Aug. 28, 2007 in European Application No. EP03731504, 9 pages.
EP Supplementary European Search Report dated Sep. 24, 2007 in European Application No. EP057638892, 2 pages.
Fauchere, "Elements for the rational design of peptide drugs," Advances in Drug Research, vol. 15, Academic Press, 1986, pp. 29-69.
Fields, et al., "A novel genetic system to detect protein-protein interactions," Letters to Nature, Nature, vol. 340, 1989, pp. 245-246.
Fiveash, et al., "Safety and tolerance of multiple weekly intracavitary injectio s of 1311-chlorotoxin (TM-601): Preliminary results of a prospective clinical trial in patients with recurrent glioblastoma multiforme," Poster, J. Clin. Oncol., 2006 ASCO Annual Meeting Proceedings, Abstact No. 1555.
Fiveash, et al., Tumor Specific Targeting of Intravenous 1311-chlorotoxin (TM-601) in Patients With Recurrent Glioma. International Journal of Radiation Oncology, ASTRO. Nov. 1, 2007, vol. 69, No. 3, Supplement, pp. S257-S258.
Flower, et al., "Structure and sequence relationships in the lipocalins and related proteins," Protein Sci., vol. 2, No. 5, 1993, pp. 753-761.
Final Office Action dated Mar. 22, 2017 in U.S. Appl. No. 14/273,374, 16 pages.
Final Office Action dated Mar. 24, 2010 in U.S. Appl. No. 11/897,721, 7 pages.
Office Action dated Sep. 3, 2015 in U.S. Appl. No. 13/673,779, 21 pages.
Final Office Action dated Sep. 8, 2016 for U.S. Appl. No. 13/673,779, 17 pages.
Friedman, et al., "Temozolomide and treatment of malignant glioma," Clin. Cancer Res., vol. 6, No. 7, 2000, pp. 2585-2597.
Geysen, et al. "Isotope or mass encoding of combinatorial libraries," Chem Biol., vol. 3, No. 8, 1996, pp. 679-688.
Mamelak et al., "Phase I Single-Dose Study of Intracavitary-Administered Iodine-131-TM-601 in Adults With Recurrent High-Grade Glioma," Expert Opin. Drug Deliv., vol. 4, No. 2, 2007, pp. 175-186.
Marshall, et al., "Near-Infrared Fluorescence Imaging in Humans with Indocyanine Green: A Review and Update," Open Surg. Oncol. J., vol. 2, No. 2, 2010, pp. 12-25.
McBride, et al., "Indentification of Chymotrypsin Inhibitors From a Second-Generation Template Assisted Combinatorial Peptide Library, " J. Pept. Sci., vol. 6, 2000, pp. 446-452.
McFerrin, et al., "A role for ion channels in glioma cell invasion," Neuron Glia Biol., vol. 2, No. 1, 2006, pp. 39-49.
McKie, "Cancer research set back a decade: Mislabelling of samples so common that new treatments have been wrecked, warn scientists," The Observer, 2001, 3 pages.
Mellman, "Where Next for Cancer Immunotherapy?" The Scientist, vol. 20, No. 1, 2006, pp. 47-56.
Milross, et al., "Relationship of mitotic arrest and apoptosis to antitumor effect of paclitaxel," J. Natl. Cancer Inst., vol. 38, No. 18, 1996, pp. 1308-1314.
Minowada, et al., "Rosette-Forming Human Lymphoid Cell Lines. I. Establishment and Evidence for Origin of Thymus-Derived Lymphocytes," J. Natl. Cancer Inst., vol. 49, No. 3, 1972, pp. 891-895.

(56) References Cited

OTHER PUBLICATIONS

Muro, et al., "Convection-enhanced and local delivery of targeted cytotoxins in the treatment of malignant gliomas," Technology in Cancer Research and Treatment, vol. 5, No. 3, 2006, pp. 201-213.
Nakashima, et al., "Application of 13C stable isotope labeling liquid chromatography-multiple reaction monitoring-tandem mass spectrometry method for determining intact absorption of bioactive dipeptides in rats," Analytical Biochemistry, vol. 414, No. 1, 2011, pp. 109-116.
Newlands, et al., "Temozolomide: a review of its discovery, chemical properties, pre-clinical development and clinical trials," Cancer Treat. Rev., vol. 23, No. 1, 1997, pp. 35-61.
Ngo, et al., "Computational Complexity, Protein Structure Prediction, and the Levinthal Paradox. The Protein Folding Problem and Ternary Structure Prediction," 1994, pp. 433-506.
Nolting, et al., "Molecular imaging probe development: a chemistry perspective," Am. J. Nucl. Med. Mol. Imaging, vol. 2, No. 3, 2012, pp. 273-306.
Nolting, et al., "Near-Infrared Dyes: Probe Development and Applications in Optical Molecular Imaging," Curr. Org. Synth., vol. 8, No. 4, 2011, pp. 521-534.
Office Action dated Jan. 6, 2016 in U.S. Appl. No. 13/673,779, 18 pages.
Office Action dated Nov. 13, 2017 in U.S. Appl. No. 14/273,374, 15 pages.
Office Action dated Mar. 12, 2015 for U.S. Appl. No. 13/673,779, 14 pages.
Office Action dated Jun. 23, 2014 in U.S. Appl. No. 14/102,396, 10 pages.
Office Action dated Jul. 1, 2016 in U.S. Appl. No. 14/273,374, 11 pages.
Office Action dated Jul. 3, 2017 in U.S. Appl. No. 13/673,770, 23 pages.
Office Action dated Jul. 31, 2017 in U.S. Appl. No. 14/651,172, 16 pages.
Office Action dated Sep. 15, 2009 in U.S. Appl. No. 11/897,721, 13 pages.
Ogawa, et al., "In vivo molecular imaging of cancer with a quenching near-infrared fluorescent probe using conjugates of monoclonal antibodies and indocyanine green," Cancer Res., vol. 69, No. 4, 2009, pp. 1268-1272.
Ohnishi, et al., "Organic alternatives to quantum dots for intraoperative near-infrared fluorescent sentinel lymph node mapping," Mol. Imaging., vol. 4, No. 3, 2005, pp. 172-181.
Pappone, et al., "Blockers of voltage-gated K channels inhibit proliferation of cultured brown fat cells," Am. J. Physiol., vol. 264, pp. C1014-C1019.
Parungo, et al., "Intraoperative identification of esophageal sentinel lymph nodes with near-infrared fluorescence imaging," J. Thorac. Cardiovasc. Surg., vol. 129, No. 4, 2005, pp. 844-850.
Puro, et al., "Retinal glial cell proliferation and ion channels: a possible link," Invest Ophthalmol. Vis. Sci., vol. 30, No. 3, 1989, pp. 521-529.
Ramakrishnan, et al., "Targeting tumor vasculature using VEGF-toxin conjugates," Methods Mol. Biol., vol. 166, 2001, pp. 219-234.
Rawstron, et al., "Quantitation of minimal disease levels in chronic lymphocytic leukemia using a sensitive flow cytometric assay improves the prediction of outcome and can be used to optimize therapy," Blood, vol. 98, No. 1, 2001, pp. 29-35.
Reardon, et al., "A pilot study: 131I-Antitenascin monoclonal antibody 81 c6 to deliver a 44-Gyresection cavity boost," Neuro Oneal., vol. 10, No. 2, 2008, 8 pages.
Reardon, et al., "Phase II trial of murine (131)1-labeled antitenascin monoclonal antibody 81 C6 administered into surgically created resection cavities of patients with newly diagnosed malignant gliomas," J. Clin. Oncol., vol. 20, No. 5, 2002, pp. 1389-1397.
Rescher, et al., "Annexins-unique membrane binding proteins with diverse functions," J. Cell Sci., vol. 117, Pt. 13, 2004, pp. 2631-2639.

Ricotti, et al., "C-Kit Is Expressed in Soft Tissue Sarcoma of Neuroectodermic Origin and Its Ligand Prevents Apoptosis of Neoplastic Cells," Blood, vol. 91, No. 7, 1998, pp. 2397-2405.
Rousselle, et al., "New advances in the transport of doxorubicin through the blood-brain barrier by a peptide vector-mediated strategy," Mol. Pharmacol., vol. 57, No. 4, 2000, pp. 679-686.
Rudikoff, et al., "Single amino acid substitution altering antigen-binding specificity," PNAS, vol. 79, No. 6, 1982, pp. 1979-1983.
Sakamoto, et al., "Identification of a new outwardly rectifying CI-channel that belongs to a subfamily of the CIC CI-channels," J. Biol. Chem., vol. 271, No. 17, 1996, pp. 10210-10216.
Schaafsma, et al., "The clinical use of indocyanine green as a near-infrared fluorescent contrast agent for image-guided oncologic surgery," J. Surg. Oncol., vol. 104, No. 3, 2011, pp. 323-332.
Sgouros, "Bone marrow dosimetry for radioimmunotherapy: theoretical considerations," J. Nucl. Med., vol. 34, No. 4, 1993, pp. 689-694.
Sharma, et al., "The role of annexin II in angiogenesis and tumor progression: a potential therapeutic target," Curr. Pharm. Des., vol. 13, No. 35, 2007, pp. 3568-3575, Abstract.
Shen, et al. "Dosimetry of Phase I/II study of intracavitary administered 1-131-TM-601 peptide in patients with recurrent high-grade glioma," vol. 60, No. 1, Supplement, 2004, p. S259.
Shen, et al., "Patient-specific dosimetry of pretargeted radioimmunotherapy using CC49 fusion protein in patients with gastrointestinal malignancies," J. Nucl. Med., vol. 46, No. 4, 2005, pp. 642-651.
Shen, et al., "Practical determination of patient-specific marrow dose using radioactivity concentration in blood and body," J. Nucl. Med., vol. 40, No. 12, 1999, pp. 2102-2106.
Shen, et al., "Radiation dosimetry of 131I-chlorotoxin for targeted radiotherapy in glioma-bearing mice," J. Neurooncol., vol. 71, No. 2, 2005, pp. 113-119.
Shimizu, et al., "Development of novel nanocarrier-based near-infrared optical probes for in vivo tumor imaging," J. Fluoresc., vol. 22, No. 2, 2012, pp. 719-727.
Sigma Genosys, Custom Peptide Synthesis: Designing Custom Peptides, 2004, Sigma Genosys. Accessed Dec. 16, 2004, 2 pages. URL:< http://www.sigmagenosys.com/peptide_design_asp>.
Silva, et al., "Agents That Bind Annexin A2 Suppress Ocular Neovascularization," J. Cell. Physiol., vol. 225, No. 3, 2010, pp. 855-864.
Silverman, et al., "Cystine-knot peptides engineered with specificities for allbb3 or allbb3 and avb3 integrins are potent inhibitors of platelet aggregation," J. Mol. Recognit., vol. 24, 2011, pp. 127-135.
Silverman, et al., "Engineered cystine-knot peptides that bind alpha(v)beta(3) integrin with antibody-like affinities," J. of Molecular Biology, vol. 385, No. 4, 2009, pp. 1064-1075.
Skerra, "Alternative binding proteins: Anticalins—harnessing the structural plasticity of the lipocalin ligand pocket to engineer novel binding activities, " FEBS Journal, vol. 275, 2008, 2677-2683.
Skolnick, et al., "From genes to protein structure and function: novel applications of computational approaches in the genomic era," Trends Biotechnol., vol. 18, No. 1, 2000, pp. 34-39.
Somogyi, et al., "Subcellular localization of benzodiazepine/ GABBA receptors in the cerebellum of rat, cat, and monkey using monoclonal antibodies," J. Neurosci., vol. 9, No. 6, 1989, pp. 2197-2209.
Soroceanu, et al., "Modulation of glioma cell migration and invasion using CI(−) and K(+) ion channel blockers," J. Neurosci., vol. 19, No. 14, 1999, pp. 5942-5954.
Soroceanu, et al., "Use of chlorotoxin for targeting of primary brain tumors," Cancer Res., vol. 58, No. 21, 1998, pp. 4871-4879.
Search Report dated Nov. 13, 2003 in International Application No. PCT/US2003/017410, 2 pages.
Search Report dated Nov. 18, 2011 in International Application No. PCT/US11/23797, 6 pages.
Search Report dated Jun. 19, 2014 in International Application No. PCT/US2013/074218, 5 pages.
Stabin, "MIRDOSE: personal computer software for internal dose assessment in nuclear medicine," J. Nucl. Med., vol. 37, No. 3, 1996, pp. 538-546.

(56) References Cited

OTHER PUBLICATIONS

Steinmeyer, et al., "Cloning and functional expression of rat CLC-5, a chloride channel related to kidney disease," J. Biol. Chem., vol. 270, No. 52, 1995, pp. 31172-31177.

Stewart, "Chemotherapy in adult high-grade glioma: a systematic review and metaanalysis of individual patient data from 12 randomised trials," Lancet, vol. 359, No. 9311, 2002, pp. 1011-1018.

Stroud, et al, "In Vivo Bio-imaging Using Chlorotoxin-based Conjugates," Curr. Pharm. Des, Vo.17, No. 38, 2011, pp. 4362-4371.

Stupp, et al., "Current and future developments in the use of temozolomide for the treatment of brain tumours," Lancet Oneal, vol. 2, No. 9, 2001, pp. 552-560.

Sun, et al., "In vivo MRI detection of gliomas by chlorotoxin-conjugated superparamagnetic nanoprobes," Small., vol. 4, No. 3, 2008, pp. 372-379.

Sun, et al., "Tumor-targeted drug delivery and MRI contrast enhancement by chlorotoxinconjugated iron oxide nanoparticles," Nanomedicine (Land), vol. 3, No. 4, 2008, pp. 495-505.

Swart, et al., "Homing of negatively charged albumins to the lymphatic system: general implications for drug targeting to peripheral tissues and viral reservoirs," Biochem. Pharmacol., vol. 58, No. 9, 1999, pp. 1425-1435.

Syed, et al., "Angiostatin receptor annexin 11 in vascular tumors including angiosarcoma," Hum. Pathol., vol. 38, No. 3, 2007, pp. 508-513.

Tan, et al., "Deduction of Functional Peptide Motifs in Scorpion Toxins," J. Pept. Sci., vol. 12, No. 6, 2006, pp. 420-427.

Tanaka, et al., "Image-guided oncologic surgery using invisible light: completed preclinical development for sentinel lymph node mapping," Ann. Surg. Oncol., vol. 13, No. 12, 2006, pp. 1671-1681.

Tanaka, et al., "Redox regulation of annexin 2 and its implications for oxidative stress-induced renal carcinogenesis and metastasis," Oncogene, vol. 23, No. 22, 2004, pp. 3980-3989.

Tatikolov and Costa, "Complexation of polymethine dyes with human serum albumin: a spectroscopic study," Biophys. Chem., vol. 107, 2004, pp. 33-49.

Te Velde, et al., "The use of fluorescent dyes and probes in surgical oncology," Eur. J. Surg. Oneal., vol. 36, No. 1, 2010, 10 pages.

The Free Dictionary, American Heritage Medical Dictionary defines the word "systemic", 2018, 1 page.

Torchilin, et al., "Peptide and protein drug delivery to and into tumors: challenges and solutions," Drug Discov. Today, vol. 8, No. 6, 2003, pp. 259-266.

Transmolecular, A Phase I Imaging and Safety Study of Intravenous 131-1-TM-601 Labeled Chlorotoxin in Patients With Recurrent or Refractory Somatic and/or Cerebral Metastatic Solid Tumors. Clinical Trials NCT00379132. 3 pages (Aug. 2006).

Troyan, et al., "The FLARE intraoperative near-infrared fluorescence imaging system: a first-in-human clinical trial in breast cancer sentinel lymph node mapping," Ann. Surg. Oncol., vol. 16, No. 10, 2009, pp. 2943-2952.

Tytgat, et al., "Purification and partial characterization of a 'short' insectotoxin-like peptide from the venom of the scorpion *Parabuthus schlechteri*," FEES Lett., vol. 441, No. 3, 1998, pp. 387-391.

Uchida, et al., "Localization and functional characterization of rat kidney-specific chloride channel, CIC-K1," J. Clin. Invest., vol. 95, No. 1, 1995, pp. 104-113.

Ullrich, et al., "Biophysical and pharmacological characterization of chloride currents in human astrocytoma cells," Am. J. Physiol., vol. 270, 5 Pt. 1, 1996, pp. C1511-C1521.

Ullrich, et al., "Cell cycle-dependent expression of a glioma-specific chloride current: proposed link to cytoskeletal changes," Am. J. Physiol., vol. 273, 4 Pt. 1, 1997, pp. C1290-C1297.

Ullrich, et al., "Expression of voltage-activated chloride currents in acute slices of human gliomas," Neuroscience, vol. 33, No. 4, 1998, pp. 1161-1173.

Ullrich, et al., "Human astrocytoma cells express a unique chloride current," Neuroreport., vol. 7, No. 5, 1996, pp. 1020-1024.

UniProt Database, Accession No. P45639 (accessed 2018), 3 pages.

Veber and Freidinger, "The design of metabolically-stable peptide analogs," Trends in Neurosciences, vol. 8, 1985, pp. 392-396.

Veiseh, et al., "A ligand-mediated nanovector for targeted gene delivery and transfection in cancer cells," Biomaterials, vol. 30, No. 4, 2009, pp. 649-657.

Veiseh, et al., "Optical and MRI Multifunctional nanoprobe for Targeting Gliomas," Nano Letters, vol. 5, No. 6, 2005, pp. 1003-1008.

Veiseh, et al., "Specific targeting of brain tumors with an optical/magnetic resonance imaging nanoprobe across the blood-brain barrier," Cancer Res., vol. 69, No. 15, 2009, 17 pages.

Veiseh, et al., "Tumor paint: a chlorotoxin:Cy5.5 bioconjugate for intraoperative visualization of cancer foci," Cancer Res., vol. 67, No. 14, 2007, pp. 6882-6888.

Velde, et al., "The use of fluorescent dyes and probes in surgical oncology," Eur. J. Surg. Oncol., vol. 36, No. 1, 2010, pp. 6-15.

Voet, et al., Biochemistry, Second Edition, John Wiley & Sons, Inc., 1995, pp. 235-241.

Weissleder, et al., "Shedding light onto live molecular targets," Nat Med., vol. 9, No. 1, 2003, pp. 123-128.

Wen, et al., "PTEN controls tumor-induced angiogenesis," PNAS, vol. 98, No. 8, 2001, pp. 4622-4627.

Wilson, et al., "Mitogenic factors regulate ion channels in Schwann cells cultured from newborn rat sciatic nerve," J. Physiol., vol. 470, 1993, pp. 501-520.

Woodfork, et al., "Inhibition of ATP-sensitive potassium channels causes reversible cell-cycle arrest of human breast cancer cells in tissue culture," J. Cell Physiol., vol. 162, No. 2, 1995, pp. 163-171.

Yasuda, et al., "Identification of a tumour associated antigen in lung cancer patients with asbestos exposure," Anticancer Res., vol. 30, No. 7, 2010, pp. 2631-2639.

Ye, et al., "Integrin targeting for tumor optical imaging," Theranostics, vol. 1, 2011, pp. 102-126.

Zellner, et al., "Disparity in expression of protein kinase C alpha in human glioma versus glioma-derived primary cell lines: therapeutic implications," Clin. Cancer Res., vol. 4, No. 7, 1998, pp. 1797-1802.

Zhang, et al., "Surface Modification of Superparamagnetic magnetite Nanoparticles and Their Intracellular Uptake", Biomaterial, vol. 23, 2002, pp. 1552-1561.

Zips, et al., "New anticancer agents: in vitro and in vivo evaluation," In Vivo, vol. 19, No. 1, 2005, pp. 1-7.

\* cited by examiner

```
GSEISCEPGRTFRDRCNQCFCGFDGRRAACTIRACPNQ(SEQ ID NO: 128)
GSEIHCQPGRTFRDRCNTCYCGWYGRSAACTLRACPNQ(SEQ ID NO: 129)
GSEISCEPGGTFEDRCNVCRCGADGRSAGCTLRACPNQ(SEQ ID NO: 130)
GSRIDCRPGRTFRDRCNTCMCGWTGHSAACTLRACPNQ(SEQ ID NO: 131)
GSEISCEPGRTFRDRCNTCHCWADGRGAACTERACPNQ(SEQ ID NO: 132)
GSESSCEPGATWRDRCNTCRCRADGRSAACTVRQCPNQ(SEQ ID NO: 133)
GSEIFCIPGRTFRDRCNTCRCGRRGISAACTLRACPNQ(SEQ ID NO: 134)
GSEISCEPGRTFRDRCNTCRCGADGRSAACTLFDCSLQ(SEQ ID NO: 135)
GSEISCEPGRTSRDRCNTCRCGADGRSAACTLIDCPGQ(SEQ ID NO: 136)
GSEISCEPGRTFRDRCNTCRCGADGRDAACTLGHCFFY(SEQ ID NO: 137)
GSEISCEPGFTEQDRCNTCRCGAIGRSAACTLRACPNQ(SEQ ID NO: 138)
GSEISCEPYSTFRDRCNTCSCGADGRGAACTMRACPNQ(SEQ ID NO: 139)
GSEISCEPGRTFRDRCNTCRCGADGRSAACTLVACLIT(SEQ ID NO: 140)
GSEIFCIPGVTFRFRCNTCRCGMDGRSAACTLRACPNQ(SEQ ID NO: 141)
GSENDCHPGTTFRDRCNTCRCGGEGRSAACTLRACPNQ(SEQ ID NO: 142)
GSQRSCEPGRTFRDRCNTCRCGADGRSAACTLFICPFQ(SEQ ID NO: 143)
GSEISCEPGRTFRDRCNTCRCGADGRSAACTLFLCGFI(SEQ ID NO: 144)
GSEISCEPDSTTRDRCNSCRCGNDGRSAACTLRACPNQ(SEQ ID NO: 145)
GSEISCEPGRTFRDRCNTCRCGADGRSEACTLHNCREQ(SEQ ID NO: 146)
GSDISCEPGSTHRDRCNTCRCSADGRSRACTLRACPNQ(SEQ ID NO: 147)
GSEDSCEPGWTQRMRCNTCRCTADGRSAACTLRACPNQ(SEQ ID NO: 148)
GSEISCEPGRTFRDRCNTCRCGADGRSAACTLHHCIYW(SEQ ID NO: 149)
GSEVSCEPGRTFRSRCNDCVCGADGRHAACTIRACPNQ(SEQ ID NO: 150)
GSEISCEPGRTFRDRCNTCRCGADGRSAACTLVFCHED(SEQ ID NO: 151)
GSEISCEPWRTFRDRCNTCRCGADGRGAACTLVICGMQ(SEQ ID NO: 152)
GSEISCEPGRTFRDRCNMCGCGADGRWARCTRRACPNQ(SEQ ID NO: 153)
GSEISCEPGRTFRDRCNTCRCGADGRSAACTLFTCTYF(SEQ ID NO: 154)
GSEISCEPGRTWRDRCNTCRCGADGRSAACTLNGCLLQ(SEQ ID NO: 155)
GSEISCEPGRTFRDRCNTCRCGADGRSAACTLANCFFA(SEQ ID NO: 156)
```

kDa

170

72

55

26

1  2  3

Gel 1
1: Ladder
2: Scn-Imperatoxin fusion
3: Scn-Imperatoxin cleaved

Imperatoxin

FIG. 21

US 10,156,559 B2

```
                              SEQUENCE LISTING

<160> NUMBER OF SEQ ID NOS: 176

<210> SEQ ID NO 1
<211> LENGTH: 721
<212> TYPE: DNA
<213> ORGANISM: artificial
<220> FEATURE:
<223> OTHER INFORMATION: IgK-SF-H6-GGS-lcn2C-GGS-ENLYFQ-GG-PARENTAL

<400> SEQUENCE: 1
gactgagtcg cccgctcgag accatggaga cagacacact cctgctatgg gtactgctgc      60
tctgggttcc aggttccact ggtgactaca aggacgagca tcaccatcat caccatggtg     120
gaagccagga ctccacctca gacctgatcc cagccccacc tctgagcaag gtccctctgc     180
agcagaactt ccaggacaac caattccagg ggaagtggta tgtggtaggc ctggcaggga     240
atgcaattct cagagaagac aaagacccgc aaaagatgta tgccaccatc tatgagctga     300 agaagacaa gagctacaat gtcacctccg tcctgtttag gaaaaagaag tgtgactact      360
ggatcaggac ttttgttcca ggttgccagc ccggcgagtt cacgctgggc aacattaaga     420
gttaccctgg attaacgagt tacctcgtcc gagtggtgag caccaactac aaccagcatg     480
ctatggtgtt cttcaagaaa gtttctcaaa acagggagta cttcaagatc accctctacg     540
ggagaaccaa ggagctgact tcggaactaa aggagaactt catccgcttc tccaaatctc     600
tgggcctccc tgaaaaccac atcgtcttcc ctgtcccaat cgaccagtgt atcgacggcg     660
gaggtagcga aaacctgtat tttcagggag gcggccgcta aggatcccgg accgcctctc     720
c                                                                     721

<210> SEQ ID NO 2
<211> LENGTH: 903
<212> TYPE: DNA
<213> ORGANISM: artificial
<220> FEATURE:
<223> OTHER INFORMATION: IgK-SF-H6-GGS-lcn2C-GGS-ENLYFQ-GG-BubbleProtein

<400> SEQUENCE: 2
gactgagtcg cccgctcgag accatggaga cagacacact cctgctatgg gtactgctgc      60
tctgggttcc aggttccact ggtgactaca aggacgagca tcaccatcat caccatggtg     120
gaagccagga ctccacctca gacctgatcc cagccccacc tctgagcaag gtccctctgc     180
agcagaactt ccaggacaac caattccagg ggaagtggta tgtggtaggc ctggcaggga     240
```

| | | |
|---|---|---|
| atgcaattct cagagaagac aaagacccgc aaaagatgta tgccaccatc tatgagctga | 300 |
| aagaagacaa gagctacaat gtcacctccg tcctgtttag gaaaaagaag tgtgactact | 360 |
| ggatcaggac ttttgttcca ggttgccagc ccggcgagtt cacgctgggc aacattaaga | 420 |
| gttaccctgg attaacgagt tacctcgtcc gagtggtgag caccaactac aaccagcatg | 480 |
| ctatggtgtt cttcaagaaa gtttctcaaa acagggagta cttcaagatc accctctacg | 540 |
| ggagaaccaa ggagctgact tcggaactaa aggagaactt catccgcttc tccaaatctc | 600 |
| tgggcctccc tgaaaaccac atcgtcttcc ctgtcccaat cgaccagtgt atcgacggcg | 660 |
| gaggtagcga aaacctgtat tttcagggag gcgatacctg cggcagcggc tataatgtgg | 720 |
| atcagcgtcg taccaatagc ggctgcaaag cgggcaatgg cgatcgtcat ttttgcggct | 780 |
| gcgatcgtac cggcgtggtg aatgcaaag cggcaaatg accgaagtg caggattgcg | 840 |
| gcagcagcag ctgcaaaggc accagcaatg gcggcgcgac ctgctaatgc taaggatccc | 900 |
| gga | 903 |

<210> SEQ ID NO 3
<211> LENGTH: 861
<212> TYPE: DNA
<213> ORGANISM: artificial
<220> FEATURE:
<223> OTHER INFORMATION: IgK-SF-H6-GGS-lcn2C-GGS-ENLYFQ-GG-BubbleProtein
    coding sequence

<400> SEQUENCE: 3

| | | |
|---|---|---|
| atggagacag acacactcct gctatgggta ctgctgctct gggttccagg ttccactggt | 60 |
| gactacaagg acgagcatca ccatcatcac catggtggaa gccaggactc cacctcagac | 120 |
| ctgatcccag ccccacctct gagcaaggtc cctctgcagc agaacttcca ggacaaccaa | 180 |
| ttccagggga agtggtatgt ggtaggcctg gcagggaatg caattctcag agaagacaaa | 240 |
| gacccgcaaa agatgtatgc caccatctat gagctgaaag aagacaagag ctacaatgtc | 300 |
| acctccgtcc tgtttaggaa aaagaagtgt gactactgga tcaggacttt tgttccaggt | 360 |
| tgccagcccg gcgagttcac gctgggcaac attaagagtt accctggatt aacgagttac | 420 |
| ctcgtccgag tggtgagcac caactacaac cagcatgcta tggtgttctt caagaaagtt | 480 |
| tctcaaaaca gggagtactt caagatcacc ctctacggga accaagga gctgacttcg | 540 |
| gaactaaagg agaacttcat ccgcttctcc aaatctctgg gcctccctga aaaccacatc | 600 |
| gtcttccctg tcccaatcga ccagtgtatc gacggcggag gtagcgaaaa cctgtatttt | 660 |
| cagggaggcg atacctgcgg cagcggctat aatgtggatc agcgtcgtac caatagcggc | 720 |
| tgcaaagcgg gcaatggcga tcgtcatttt tgcggctgcg atcgtaccgg cgtggtggaa | 780 |
| tgcaaaggcg gcaaatggac cgaagtgcag gattgcggca gcagcagctg caaaggcacc | 840 |
| agcaatggcg gcgcgacctg c | 861 |

<210> SEQ ID NO 4
<211> LENGTH: 885
<212> TYPE: DNA
<213> ORGANISM: artificial
<220> FEATURE:
<223> OTHER INFORMATION: IgK-SF-H6-GGS-lcn2C-GGS-ENLYFQ-GG-Attractin

<400> SEQUENCE: 4

| | | |
|---|---|---|
| gactgagtcg cccgctcgag accatggaga cagacacact cctgctatgg gtactgctgc | 60 |
| tctgggttcc aggttccact ggtgactaca aggacgagca tcaccatcat caccatggtg | 120 |

| | |
|---|---|
| gaagccagga ctccacctca gacctgatcc cagccccacc tctgagcaag gtccctctgc | 180 |
| agcagaactt ccaggacaac caattccagg ggaagtggta tgtggtaggc ctggcaggga | 240 |
| atgcaattct cagagaagac aaagacccgc aaaagatgta tgccaccatc tatgagctga | 300 |
| aagaagacaa gagctacaat gtcacctccg tcctgtttag gaaaaagaag tgtgactact | 360 |
| ggatcaggac ttttgttcca ggttgccagc ccggcgagtt cacgctgggc aacattaaga | 420 |
| gttaccctgg attaacgagt tacctcgtcc gagtggtgag caccaactac aaccagcatg | 480 |
| ctatggtgtt cttcaagaaa gtttctcaaa acagggagta cttcaagatc accctctacg | 540 |
| ggagaaccaa ggagctgact tcggaactaa aggagaactt catccgcttc tccaaatctc | 600 |
| tgggcctccc tgaaaaccac atcgtcttcc ctgtcccaat cgaccagtgt atcgacggcg | 660 |
| gaggtagcga aaacctgtat tttcagggag gcgatcagaa ttgcgatatt ggcaatatta | 720 |
| ccagccagtg ccagatgcag cataaaaatt gcgaagatgc gaatggctgc gataccatta | 780 |
| ttgaagaatg caaaaccagc atggtggaac gttgccagaa tcaggaattt gaaagcgcgg | 840 |
| cgggcagcac caccctgggc cgcagtaat gctaaggatc ccgga | 885 |

```
<210> SEQ ID NO 5
<211> LENGTH: 843
<212> TYPE: DNA
<213> ORGANISM: artificial
<220> FEATURE:
<223> OTHER INFORMATION: IgK-SF-H6-GGS-lcn2C-GGS-ENLYFQ-GG-Attractin
      coding sequence

<400> SEQUENCE: 5
```

| | |
|---|---|
| atggagacag acacactcct gctatgggta ctgctgctct gggttccagg ttccactggt | 60 |
| gactacaagg acgagcatca ccatcatcac catggtggaa gccaggactc cacctcagac | 120 |
| ctgatcccag ccccacctct gagcaaggtc cctctgcagc agaacttcca ggacaaccaa | 180 |
| ttccagggga gtggtatgt ggtaggcctg cagggaatg caattctcag agaagacaaa | 240 |
| gacccgcaaa agatgtatgc caccatctat gagctgaaag aagacaagag ctacaatgtc | 300 |
| acctccgtcc tgtttaggaa aaagaagtgt gactactgga tcaggacttt tgttccaggt | 360 |
| tgccagcccg gcgagttcac gctgggcaac attaagagtt accctggatt aacgagttac | 420 |
| ctcgtccgag tggtgagcac caactacaac cagcatgcta tggtgttctt caagaaagtt | 480 |
| tctcaaaaca gggagtactt caagatcacc ctctacggga gaaccaagga gctgacttcg | 540 |
| gaactaaagg agaacttcat ccgcttctcc aaatctctgg gcctccctga aaaccacatc | 600 |
| gtcttccctg tcccaatcga ccagtgtatc gacggcggag gtagcgaaaa cctgtatttt | 660 |
| cagggaggcg atcagaattg cgatattggc aatattacca gccagtgcca gatgcagcat | 720 |
| aaaaattgcg aagatgcgaa tggctgcgat accattattg aagaatgcaa aaccagcatg | 780 |
| gtggaacgtt gccagaatca ggaatttgaa agcgcggcgg gcagcaccac cctgggcccg | 840 |
| cag | 843 |

```
<210> SEQ ID NO 6
<211> LENGTH: 782
<212> TYPE: DNA
<213> ORGANISM: artificial
<220> FEATURE:
<223> OTHER INFORMATION: IgK-SF-H6-GGS-lcn2C-GGS-ENLYFQ-GG-Hefutoxin

<400> SEQUENCE: 6
```

| | |
|---|---|
| gactgagtcg cccgctcgag accatggaga cagacacact cctgctatgg gtactgctgc | 60 |

```
tctgggttcc aggttccact ggtgactaca aggacgagca tcaccatcat caccatggtg      120
gaagccagga ctccacctca gacctgatcc cagccccacc tctgagcaag gtccctctgc      180
agcagaactt ccaggacaac caattccagg ggaagtggta tgtggtaggc ctggcaggga      240
atgcaattct cagagaagac aaagacccgc aaaagatgta tgccaccatc tatgagctga      300
aagaagacaa gagctacaat gtcacctccg tcctgtttag gaaaaagaag tgtgactact      360
ggatcaggac ttttgttcca ggttgccagc ccggcgagtt cacgctgggc aacattaaga      420
gttaccctgg attaacgagt tacctcgtcc gagtggtgag caccaactac aaccagcatg      480
ctatggtgtt cttcaagaaa gtttctcaaa cagggagta cttcaagatc accctctacg      540
ggagaaccaa ggagctgact tcggaactaa aggagaactt catccgcttc tccaaatctc      600
tgggcctccc tgaaaaccac atcgtcttcc ctgtcccaat cgaccagtgt atcgacggcg      660
gaggtagcga aaacctgtat ttcagggag gcggccatgc gtgctatcgt aattgctggc      720
gtgaaggcaa tgatgaagaa acctgcaaag aacgttgcta atgctaagga tcccggaccg      780
cc                                                                    782

<210> SEQ ID NO 7
<211> LENGTH: 735
<212> TYPE: DNA
<213> ORGANISM: artificial
<220> FEATURE:
<223> OTHER INFORMATION: IgK-SF-H6-GGS-lcn2C-GGS-ENLYFQ-GG-Hefutoxin
      coding sequence

<400> SEQUENCE: 7
atggagacag acacactcct gctatgggta ctgctgctct gggttccagg ttccactggt      60
gactacaagg acgagcatca ccatcatcac catggtggaa gccaggactc cacctcagac      120
ctgatcccag ccccacctct gagcaaggtc cctctgcagc agaacttcca ggacaaccaa      180
ttccagggga gtggtatgt ggtaggcctg gcagggaatg caattctcag agaagacaaa      240
gacccgcaaa agatgtatgc caccatctat gagctgaaag aagacaagag ctacaatgtc      300
acctccgtcc tgtttaggaa aaagaagtgt gactactgga tcaggacttt tgttccaggt      360
tgccagcccg gcgagttcac gctgggcaac attaagagtt accctggatt aacgagttac      420
ctcgtccgag tggtgagcac caactacaac cagcatgcta tggtgttctt caagaaagtt      480
tctcaaaaca gggagtactt caagatcacc ctctacggga gaaccaagga gctgacttcg      540
gaactaaagg agaacttcat ccgcttctcc aaatctctgg gcctccctga aaaccacatc      600
gtcttccctg tcccaatcga ccagtgtatc gacggcggag gtagcgaaaa cctgtatttt      660
cagggaggcg gccatgcgtg ctatcgtaat tgctggcgtg aaggcaatga tgaagaaacc      720
tgcaaagaac gttgc                                                      735

<210> SEQ ID NO 8
<211> LENGTH: 816
<212> TYPE: DNA
<213> ORGANISM: artificial
<220> FEATURE:
<223> OTHER INFORMATION: IgK-SF-H6-GGS-lcn2C-GGS-ENLYFQ-GG-Hanatoxin

<400> SEQUENCE: 8
gactgagtcg cccgctcgag accatggaga cagacacact cctgctatgg gtactgctgc      60
tctgggttcc aggttccact ggtgactaca aggacgagca tcaccatcat caccatggtg      120
gaagccagga ctccacctca gacctgatcc cagccccacc tctgagcaag gtccctctgc      180
```

```
agcagaactt ccaggacaac caattccagg ggaagtggta tgtggtaggc ctggcaggga    240
atgcaattct cagagaagac aaagacccgc aaaagatgta tgccaccatc tatgagctga    300
aagaagacaa gagctacaat gtcacctccg tcctgtttag gaaaaagaag tgtgactact    360
ggatcaggac ttttgttcca ggttgccagc ccggcgagtt cacgctgggc aacattaaga    420
gttaccctgg attaacgagt tacctcgtcc gagtggtgag caccaactac aaccagcatg    480
ctatggtgtt cttcaagaaa gtttctcaaa cagggagta cttcaagatc ccctctacg    540 ggagaaccaa ggagctgact tcggaactaa aggagaactt catccgcttc tccaaatctc    600
tgggcctccc tgaaaaccac atcgtcttcc ctgtcccaat cgaccagtgt atcgacggcg    660
gaggtagcga aaacctgtat tttcagggag gcgaatgccg ttatctgttt ggcggctgca    720
aaaccaccag cgattgctgc aaacatctgg gctgcaaatt tcgtgataaa tattgcgcgt    780
gggattttac ctttagctaa tgctaaggat cccgga                             816

<210> SEQ ID NO 9
<211> LENGTH: 774
<212> TYPE: DNA
<213> ORGANISM: artificial
<220> FEATURE:
<223> OTHER INFORMATION: IgK-SF-H6-GGS-lcn2C-GGS-ENLYFQ-GG-Hanatoxin
      coding sequence

<400> SEQUENCE: 9
atggagacag acacactcct gctatgggta ctgctgctct gggttccagg ttccactggt     60
gactacaagg acgagcatca ccatcatcac catggtggaa gccaggactc cacctcagac    120
ctgatcccag ccccacctct gagcaaggtc cctctgcagc agaacttcca ggacaaccaa    180
ttccagggga gtggtatgt ggtaggcctg cagggaatg caattctcag agaagacaaa    240
gacccgcaaa agatgtatgc caccatctat gagctgaaag aagacaagag ctacaatgtc    300
acctccgtcc tgtttaggaa aaagaagtgt gactactgga tcaggacttt tgttccaggt    360
tgccagcccg gcgagttcac gctgggcaac attaagagtt accctggatt aacgagttac    420
ctcgtccgag tggtgagcac caactacaac cagcatgcta tggtgttctt caagaaagtt    480
tctcaaaaca gggagtactt caagatcacc ctctacggga accaaggagc tgacttcg    540 gaactaaagg agaacttcat ccgcttctcc aaatctctgg gcctccctga aaaccacatc    600
gtcttccctg tcccaatcga ccagtgtatc gacggcggag gtagcgaaaa cctgtatttt    660
cagggaggcg aatgccgtta tctgtttggc ggctgcaaaa ccaccagcga ttgctgcaaa    720
catctgggct gcaaatttcg tgataaatat tgcgcgtggg attttacctt tagc         774

<210> SEQ ID NO 10
<211> LENGTH: 819
<212> TYPE: DNA
<213> ORGANISM: artificial
<220> FEATURE:
<223> OTHER INFORMATION: IgK-SF-H6-GGS-lcn2C-GGS-ENLYFQ-GG-Chymotrypsin
      Inhibitor

<400> SEQUENCE: 10
gactgagtcg cccgctcgag accatggaga cagacacact cctgctatgg gtactgctgc     60
tctgggttcc aggttccact ggtgactaca aggacgagca tcaccatcat caccatggtg    120
gaagccagga ctccacctca gacctgatcc cagccccacc tctgagcaag gtccctctgc    180
agcagaactt ccaggacaac caattccagg ggaagtggta tgtggtaggc ctggcaggga    240
```

```
atgcaattct cagagaagac aaagacccgc aaaagatgta tgccaccatc tatgagctga      300
aagaagacaa gagctacaat gtcacctccg tcctgtttag gaaaaagaag tgtgactact      360
ggatcaggac ttttgttcca ggttgccagc ccggcgagtt cacgctgggc aacattaaga      420
gttaccctgg attaacgagt tacctcgtcc gagtggtgag caccaactac aaccagcatg      480
ctatggtgtt cttcaagaaa gtttctcaaa cagggagta cttcaagatc accctctacg       540
ggagaaccaa ggagctgact cggaactaa aggagaactt catccgcttc tccaaatctc       600
tgggcctccc tgaaaaccac atcgtcttcc ctgtcccaat cgaccagtgt atcgacggcg      660
gaggtagcga aaacctgtat tttcagggag gcgaaattag ctgcgaaccg ggcaaaacct      720
ttaaagataa atgcaatacc tgccgttgcg gcgcggatgg caaaagcgcg gcgtgcaccc      780
tgaaagcgtg cccgaatcag taatgctaag gatcccgga                            819
```

<210> SEQ ID NO 11
<211> LENGTH: 777
<212> TYPE: DNA
<213> ORGANISM: artificial
<220> FEATURE:
<223> OTHER INFORMATION: IgK-SF-H6-GGS-lcn2C-GGS-ENLYFQ-GG-Chymotrypsin
      Inhibitor coding sequence

<400> SEQUENCE: 11

```
atggagacag acacactcct gctatgggta ctgctgctct ggttccagg ttccactggt       60 gactacaagg acgagcatca ccatcatcac catggtggaa gccaggactc cacctcagac     120
ctgatcccag ccccacctct gagcaaggtc cctctgcagc agaacttcca ggacaaccaa     180
ttccagggga agtggtatgt ggtaggcctg cagggaatg caattctcag agaagacaaa     240
gacccgcaaa agatgtatgc caccatctat gagctgaaag aagacaagag ctacaatgtc     300
acctccgtcc tgtttaggaa aaagaagtgt gactactgga tcaggacttt tgttccaggt     360
tgccagcccg gcgagttcac gctgggcaac attaagagtt accctggatt aacgagttac     420
ctcgtccgag tggtgagcac caactacaac cagcatgcta tggtgttctt caagaaagtt     480
tctcaaaaca gggagtactt caagatcacc ctctacggga gaaccaagga gctgacttcg     540
gaactaaagg agaacttcat ccgcttctcc aaatctctgg gcctccctga aaaccacatc     600
gtcttccctg tcccaatcga ccagtgtatc gacggcggag gtagcgaaaa cctgtatttt     660
cagggaggca aaattagctg cgaaccgggc aaaaccttta agataaatg caatacctgc     720 cgttgcggcg cggatggcaa agcgcggcg tgcaccctga agcgtgccc gaatcag        777
```

<210> SEQ ID NO 12
<211> LENGTH: 822
<212> TYPE: DNA
<213> ORGANISM: artificial
<220> FEATURE:
<223> OTHER INFORMATION: IgK-SF-H6-GGS-lcn2C-GGS-ENLYFQ-GG-ToxinK

<400> SEQUENCE: 12

```
gactgagtcg cccgctcgag accatggaga cagacacact cctgctatgg gtactgctgc      60
tctgggttcc aggttccact ggtgactaca aggacgagca tcaccatcat caccatggtg     120 aagccagga ctccacctca gacctgatcc cagccccacc tctgagcaag gtccctctgc      180
agcagaactt ccaggacaac caattccagg ggaagtggta tgtggtaggc ctggcaggga     240
atgcaattct cagagaagac aaagacccgc aaaagatgta tgccaccatc tatgagctga     300
aagaagacaa gagctacaat gtcacctccg tcctgtttag gaaaaagaag tgtgactact     360
```

| ggatcaggac ttttgttcca ggttgccagc ccggcgagtt cacgctgggc aacattaaga | 420 |
| gttaccctgg attaacgagt tacctcgtcc gagtggtgag caccaactac aaccagcatg | 480 |
| ctatggtgtt cttcaagaaa gtttctcaaa acagggagta cttcaagatc accctctacg | 540 |
| ggagaaccaa ggagctgact tcggaactaa aggagaactt catccgcttc tccaaatctc | 600 |
| tgggcctccc tgaaaaccac atcgtcttcc ctgtcccaat cgaccagtgt atcgacggcg | 660 |
| gaggtagcga aaacctgtat ttcaggggag gcgtgtgccg tgattggttt aaagaaaccg | 720 |
| cgtgccgtca tgcgaaaagc ctgggcaatt gccgtaccag ccagaaatat cgtgcgaatt | 780 |
| gcgcgaaaac ctgcgaactg tgctaatgct aaggatcccg ga | 822 |

<210> SEQ ID NO 13
<211> LENGTH: 780
<212> TYPE: DNA
<213> ORGANISM: artificial
<220> FEATURE:
<223> OTHER INFORMATION: IgK-SF-H6-GGS-lcn2C-GGS-ENLYFQ-GG-ToxinK coding sequence

<400> SEQUENCE: 13

| atggagacag acacactcct gctatgggta ctgctgctct ggttccaggt tccactggt | 60 |
| gactacaagg acgagcatca ccatcatcac catggtggaa gccaggactc cacctcagac | 120 |
| ctgatcccag ccccacctct gagcaaggtc cctctgcagc agaacttcca ggacaaccaa | 180 |
| ttccagggga agtggtatgt ggtaggcctg gcagggaatg caattctcag agaagacaaa | 240 |
| gacccgcaaa agatgtatgc caccatctat gagctgaaag aagacaagag ctacaatgtc | 300 |
| acctccgtcc tgtttaggaa aaagaagtgt gactactgga tcaggacttt tgttccaggt | 360 |
| tgccagcccg cgagttcac gctgggcaac attaagagtt accctggatt aacgagttac | 420 |
| ctcgtccgag tggtgagcac caactacaac cagcatgcta tggtgttctt caagaaagtt | 480 |
| tctcaaaaca gggagtactt caagatcacc ctctacggga gaaccaagga gctgacttcg | 540 |
| gaactaaagg agaacttcat ccgcttctcc aaatctctgg gcctccctga aaaccacatc | 600 |
| gtcttccctg tcccaatcga ccagtgtatc gacggcggag gtagcgaaaa cctgtatttt | 660 |
| cagggaggcg tgtgccgtga ttggtttaaa gaaaccgcgt gccgtcatgc gaaaagcctg | 720 |
| ggcaattgcc gtaccagcca gaaatatcgt gcgaattgcg cgaaaacctg cgaactgtgc | 780 |

<210> SEQ ID NO 14
<211> LENGTH: 849
<212> TYPE: DNA
<213> ORGANISM: artificial
<220> FEATURE:
<223> OTHER INFORMATION: IgK-SF-H6-GGS-lcn2C-GGS-ENLYFQ-GG-EGFepiregulinCore

<400> SEQUENCE: 14

| gactgagtcg cccgctcgag accatggaga cagacacact cctgctatgg gtactgctgc | 60 |
| tctgggttcc aggttccact ggtgactaca aggacgagca tcaccatcat caccatggtg | 120 |
| gaagccagga ctccacctca gacctgatcc cagccccacc tctgagcaag gtccctctgc | 180 |
| agcagaactt ccaggacaac caattccagg ggaagtggta tgtggtaggc ctggcaggga | 240 |
| atgcaattct cagagaagac aaagacccgc aaaagatgta tgccaccatc tatgagctga | 300 |
| aagaagacaa gagctacaat gtcacctccg tcctgtttag gaaaaagaag tgtgactact | 360 |
| ggatcaggac ttttgttcca ggttgccagc ccggcgagtt cacgctgggc aacattaaga | 420 |
| gttaccctgg attaacgagt tacctcgtcc gagtggtgag caccaactac aaccagcatg | 480 |

```
ctatggtgtt cttcaagaaa gtttctcaaa acagggagta cttcaagatc accctctacg    540
ggagaaccaa ggagctgact tcggaactaa aggagaactt catccgcttc tccaaatctc    600
tgggcctccc tgaaaaccac atcgtcttcc ctgtcccaat cgaccagtgt atcgacggcg    660
gaggtagcga aaacctgtat tttcagggag gcgtgagcat taccaaatgc agcagcgata    720
tgaatggcta ttgcctgcat ggccagtgca tttatctggt ggatatgagc cagaattatt    780
gccgttgcga agtgggctat accggcgtgc gttgcgaaca tttttttctg taatgctaag    840
gatcccgga                                                           849
```

<210> SEQ ID NO 15
<211> LENGTH: 807
<212> TYPE: DNA
<213> ORGANISM: artificial
<220> FEATURE:
<223> OTHER INFORMATION: IgK-SF-H6-GGS-lcn2C-GGS-
      ENLYFQ-GG-EGFepiregulinCore coding sequence

<400> SEQUENCE: 15

```
atggagacag acacactcct gctatgggta ctgctgctct ggttccagg ttccactggt      60
gactacaagg acgagcatca ccatcatcac catggtggaa gccaggactc cacctcagac    120
ctgatcccag ccccacctct gagcaaggtc cctctgcagc agaacttcca ggacaaccaa    180
ttccagggga agtggtatgt ggtaggcctg cagggaatgc aattctcag agaagacaaa    240
gacccgcaaa agatgtatgc caccatctat gagctgaaag aagacaagag ctacaatgtc    300
acctccgtcc tgtttaggaa aaagaagtgt gactactgga tcaggacttt tgttccaggt    360
tgccagcccg gcgagttcac gctgggcaac attaagagtt accctggatt aacgagttac    420
ctcgtccgag tggtgagcac caactacaac agcatgcta tggtgttctt caagaaagtt    480
tctcaaaaca gggagtactt caagatcacc ctctacggga gaaccaagga gctgacttcg    540
gaactaaagg agaacttcat ccgcttctcc aaatctctgg gcctcctga aaaccacatc    600
gtcttccctg tcccaatcga ccagtgtatc gacggcggag gtagcgaaaa cctgtatttt    660
cagggaggcg tgagcattac caaatgcagc agcgatatga atggctattg cctgcatggc    720
cagtgcattt atctggtgga tatgagccag aattattgcc gttgcgaagt gggctatacc    780
ggcgtgcgtt gcgaacattt ttttctg                                        807
```

<210> SEQ ID NO 16
<211> LENGTH: 801
<212> TYPE: DNA
<213> ORGANISM: artificial
<220> FEATURE:
<223> OTHER INFORMATION: IgK-SF-H6-GGS-lcn2C-GGS-ENLYFQ-GG-Circulin

<400> SEQUENCE: 16

```
gactgagtcg cccgctcgag accatggaga cagacacact cctgctatgg gtactgctgc    60
tctgggttcc aggttccact ggtgactaca aggacgagca tcaccatcat caccatggtg    120
aagccagga ctccacctca gacctgatcc cagccccacc tctgagcaag gtccctctgc    180
agcagaactt ccaggacaac caattccagg ggaagtggta tgtggtaggc ctggcaggga    240
atgcaattct cagagaagac aaagacccgc aaaagatgta tgccaccatc tatgagctga    300
aagaagacaa gagctacaat gtcacctccg tcctgtttag gaaaaagaag tgtgactact    360
ggatcaggac ttttgttcca ggttgccagc ccggcgagtt cacgctgggc aacattaaga    420
gttaccctgg attaacgagt tacctcgtcc gagtggtgag caccaactac aaccagcatg    480
```

```
ctatggtgtt cttcaagaaa gtttctcaaa acagggagta cttcaagatc accctctacg    540
ggagaaccaa ggagctgact tcggaactaa aggagaactt catccgcttc tccaaatctc    600
tgggcctccc tgaaaccac atcgtcttcc ctgtcccaat cgaccagtgt atcgacggcg     660
gaggtagcga aaacctgtat tttcagggag cggcattcc gtgcggcgaa agctgcgtgt    720
ggattccgtg cattagcgcg gcgctgggct gcagctgcaa aaataaagtg tgctatcgta    780
attaatgcta aggatcccgg a                                              801

<210> SEQ ID NO 17
<211> LENGTH: 759
<212> TYPE: DNA
<213> ORGANISM: artificial
<220> FEATURE:
<223> OTHER INFORMATION: IgK-SF-H6-GGS-lcn2C-GGS-ENLYFQ-GG-Circulin
      coding sequence

<400> SEQUENCE: 17
atggagacag acacactcct gctatgggta ctgctgctct gggttccagg ttccactggt     60
gactacaagg acgagcatca ccatcatcac catggtggaa gccaggactc cacctcagac    120
ctgatcccag ccccacctct gagcaaggtc cctctgcagc agaacttcca ggacaaccaa    180
ttccagggga gtggtatgt ggtaggcctg cagggaatg caattctcag agaagacaaa     240
gacccgcaaa agatgtatgc caccatctat gagctgaaag aagacaagag ctacaatgtc    300
acctccgtcc tgtttaggaa aaagaagtgt gactactgga tcaggacttt tgttccaggt    360
tgccagcccg gcgagttcac gctgggcaac attaagagtt accctggatt aacgagttac    420
ctcgtccgag tggtgagcac caactacaac cagcatgcta tggtgttctt caagaaagtt    480
tctcaaaaca gggagtactt caagatcacc ctctacggga gaaccaagga gctgacttcg    540
gaactaaagg agaacttcat ccgcttctcc aaatctctgg gcctcctga aaaccacatc     600 gtcttccctg tcccaatcga ccagtgtatc gacggcggag tagcgaaaa cctgtatttt     660 cagggaggcg gcattccgtg cggcgaaagc tgcgtgtgga ttccgtgcat tagcgcggcg    720
ctgggctgca gctgcaaaaa taaagtgtgc tatcgtaat                            759

<210> SEQ ID NO 18
<211> LENGTH: 873
<212> TYPE: DNA
<213> ORGANISM: artificial
<220> FEATURE:
<223> OTHER INFORMATION: IgK-SF-H6-GGS-lcn2C-GGS-ENLYFQ-GG-Brazzein

<400> SEQUENCE: 18
gactgagtcg cccgctcgag accatggaga cagacacact cctgctatgg gtactgctgc     60
tctgggttcc aggttccact ggtgactaca aggacgagca tcaccatcat caccatggtg    120 aagccagga ctccacctca gacctgatcc cagccccacc tctgagcaag gtccctctgc     180
agcagaactt ccaggacaac caattccagg ggaagtggta tgtggtaggc ctggcaggga    240
atgcaattct cagagaagac aaagacccgc aaaagatgta tgccaccatc tatgagctga    300 agaagacaa gagctacaat gtcacctccg tcctgtttag gaaaaagaag tgtgactact    360
ggatcaggac ttttgttcca ggttgccagc ccggcgagtt cacgctgggc aacattaaga    420
gttaccctgg attaacgagt tacctcgtcc gagtggtgag caccaactac aaccagcatg    480
ctatggtgtt cttcaagaaa gtttctcaaa acagggagta cttcaagatc accctctacg    540
ggagaaccaa ggagctgact tcggaactaa aggagaactt catccgcttc tccaaatctc    600
```

```
tgggcctccc tgaaaaccac atcgtcttcc ctgtcccaat cgaccagtgt atcgacggcg    660
gaggtagcga aaacctgtat tttcagggag gccaggataa atgcaaaaaa gtgtatgaaa    720
attatccggt gagcaaatgc cagctggcga atcagtgcaa ttatgattgc aaactggata    780
aacatgcgcg tagcggcgaa tgcttttatg atgaaaaacg taatctgcag tgcatttgcg    840
attattgcga atattaatgc taaggatccc gga                                 873
```

```
<210> SEQ ID NO 19
<211> LENGTH: 831
<212> TYPE: DNA
<213> ORGANISM: artificial
<220> FEATURE:
<223> OTHER INFORMATION: IgK-SF-H6-GGS-lcn2C-GGS-ENLYFQ-GG-Brazzein
      coding sequence

<400> SEQUENCE: 19
```

```
atggagacag acacactcct gctatgggta ctgctgctct gggttccagg ttccactggt     60
gactacaagg acgagcatca ccatcatcac catggtggaa gccaggactc cacctcagac    120
ctgatcccag ccccacctct gagcaaggtc cctctgcagc agaacttcca ggacaaccaa    180
ttccagggga agtggtatgt ggtaggcctg cagggaatgc aattctcag agaagacaaa     240 gacccgcaaa agatgtatgc caccatctat gagctgaaag aagacaagag ctacaatgtc    300
acctccgtcc tgtttaggaa aaagaagtgt gactactgga tcaggacttt tgttccaggt    360
tgccagcccg gcgagttcac gctgggcaac attaagagtt accctggatt aacgagttac    420
ctcgtccgag tggtgagcac caactacaac cagcatgcta tggtgttctt caagaaagtt    480
tctcaaaaca gggagtactt caagatcacc ctctacggga gaaccaagga gctgacttcg    540
gaactaaagg agaacttcat ccgcttctcc aaatctctgg gcctccctga aaaccacatc    600
gtcttccctg tcccaatcga ccagtgtatc gacggcggag gtagcgaaaa cctgtatttt    660
cagggaggcc aggataaatg caaaaaagtg tatgaaatt atccggtgag caaatgccag    720
ctggcgaatc agtgcaatta tgattgcaaa ctggataaac atgcgcgtag cggcgaatgc    780
ttttatgatg aaaaacgtaa tctgcagtgc atttgcgatt attgcgaata t             831
```

```
<210> SEQ ID NO 20
<211> LENGTH: 777
<212> TYPE: DNA
<213> ORGANISM: artificial
<220> FEATURE:
<223> OTHER INFORMATION: IgK-SF-H6-GGS-lcn2C-GGS-ENLYFQ-GG-chlorotoxin
      coding sequence

<400> SEQUENCE: 20
```

```
atggagacag acacactcct gctatgggta ctgctgctct gggttccagg ttccactggt     60
gactacaagg acgagcatca ccatcatcac catggtggaa gccaggactc cacctcagac    120
ctgatcccag ccccacctct gagcaaggtc cctctgcagc agaacttcca ggacaaccaa    180
ttccagggga agtggtatgt ggtaggcctg cagggaatgc aattctcag agaagacaaa     240 gacccgcaaa agatgtatgc caccatctat gagctgaaag aagacaagag ctacaatgtc    300
acctccgtcc tgtttaggaa aaagaagtgt gactactgga tcaggacttt tgttccaggt    360
tgccagcccg gcgagttcac gctgggcaac attaagagtt accctggatt aacgagttac    420
ctcgtccgag tggtgagcac caactacaac cagcatgcta tggtgttctt caagaaagtt    480
tctcaaaaca gggagtactt caagatcacc ctctacggga gaaccaagga gctgacttcg    540
```

```
gaactaaagg agaacttcat ccgcttctcc aaatctctgg gcctccctga aaaccacatc    600
gtcttccctg tcccaatcga ccagtgtatc gacggcggag gtagcgaaaa cctgtattt     660 cagggaggca tgtgcatgcc gtgctttacc accgatcatc agatggcgcg taaatgcgat    720
gattgctgcg gcggcaaagg ccgtggcaaa tgctatggcc cgcagtgcct gtgccgt       777
```

<210> SEQ ID NO 21
<211> LENGTH: 734
<212> TYPE: DNA
<213> ORGANISM: artificial
<220> FEATURE:
<223> OTHER INFORMATION: IgK-SF-H6-GGS-lcn2C-GGS-ENLYFQ-GS-PARENTAL

<400> SEQUENCE: 21

```
gactgagtcg cccgctcgag accatggaga cagacacact cctgctatgg gtactgctgc    60
tctgggttcc aggttccact ggtgactaca aggacgagca tcaccatcat caccatggtg   120
gaagccagga ctccacctca gacctgatcc cagccccacc tctgagcaag gtccctctgc   180
agcagaactt ccaggacaac caattccagg ggaagtggta tgtggtaggc ctggcaggga   240
atgcaattct cagagaagac aaagacccgc aaaagatgta tgccaccatc tatgagctga   300
aagaagacaa gagctacaat gtcacctccg tcctgtttag gaaaaagaag tgtgactact   360
ggatcaggac ttttgttcca ggttgccagc ccggcgagtt cacgctgggc aacattaaga   420
gttaccctgg attaacgagt tacctcgtcc gagtggtgag caccaactac aaccagcatg   480
ctatggtgtt cttcaagaaa gtttctcaaa acagggagta cttcaagatc accctctacg   540
ggagaaccaa ggagctgact tcggaactaa aggagaactt catccgcttc tccaaatctc   600
tgggcctccc tgaaaaccac atcgtcttcc ctgtcccaat cgaccagtgt atcgacggcg   660
gaggtagcga aaacctgtat tttcagggat cctaatgttg gccatgatgt taggcggccg   720
ctaaggatcc cgga                                                     734
```

<210> SEQ ID NO 22
<211> LENGTH: 734
<212> TYPE: DNA
<213> ORGANISM: artificial
<220> FEATURE:
<223> OTHER INFORMATION: IgK-SF-H6-GGS-lcn2C-GGS-furin-GS-PARENTAL

<400> SEQUENCE: 22

```
gactgagtcg cccgctcgag accatggaga cagacacact cctgctatgg gtactgctgc    60
tctgggttcc aggttccact ggtgactaca aggacgagca tcaccatcat caccatggtg   120
gaagccagga ctccacctca gacctgatcc cagccccacc tctgagcaag gtccctctgc   180
agcagaactt ccaggacaac caattccagg ggaagtggta tgtggtaggc ctggcaggga   240
atgcaattct cagagaagac aaagacccgc aaaagatgta tgccaccatc tatgagctga   300
aagaagacaa gagctacaat gtcacctccg tcctgtttag gaaaaagaag tgtgactact   360
ggatcaggac ttttgttcca ggttgccagc ccggcgagtt cacgctgggc aacattaaga   420
gttaccctgg attaacgagt tacctcgtcc gagtggtgag caccaactac aaccagcatg   480
ctatggtgtt cttcaagaaa gtttctcaaa acagggagta cttcaagatc accctctacg   540
ggagaaccaa ggagctgact tcggaactaa aggagaactt catccgcttc tccaaatctc   600
tgggcctccc tgaaaaccac atcgtcttcc ctgtcccaat cgaccagtgt atcgacggcg   660
gaggtagccg cgcgcgctat aaacgcggat cctaatgttg gccatgatgt taggcggccg   720
ctaaggatcc cgga                                                     734
```

```
<210> SEQ ID NO 23
<211> LENGTH: 848
<212> TYPE: DNA
<213> ORGANISM: artificial
<220> FEATURE:
<223> OTHER INFORMATION: IgK-SF-H6-GGS-lcn2C-GGS-ENLYFQ-GS-MIDKINE

<400> SEQUENCE: 23
gactgagtcg cccgctcgag accatggaga cagacacact cctgctatgg gtactgctgc      60
tctgggttcc aggttccact ggtgactaca aggacgagca tcaccatcat caccatggtg     120
gaagccagga ctccacctca gacctgatcc agccccacc tctgagcaag gtccctctgc      180
agcagaactt ccaggacaac caattccagg ggaagtggta tgtggtaggc ctggcaggga     240
atgcaattct cagagaagac aaagacccgc aaaagatgta tgccaccatc tatgagctga     300
aagaagacaa gagctacaat gtcacctccg tcctgtttag gaaaaagaag tgtgactact     360
ggatcaggac ttttgttcca ggttgccagc ccggcgagtt cacgctgggc aacattaaga     420
gttaccctgg attaacgagt tacctcgtcc gagtggtgag caccaactac aaccagcatg     480
ctatggtgtt cttcaagaaa gtttctcaaa cagggagta cttcaagatc accctctacg     540
ggagaaccaa ggagctgact tcggaactaa aggagaactt catccgcttc tccaaatctc     600
tgggcctccc tgaaaaccac atcgtcttcc ctgtcccaat cgaccagtgt atcgacggcg     660
gaggtagcga aaacctgtat tttcagagcg attgcaaata taaatttgaa actggggcg     720 cgtgcgatgg cggcaccggc accaaagtgc gccagggcac cctgaaaaaa gcgcgctata     780
acgcgcagtg ccaggaaacc attcgcgtga ccaaaccgtg ctaatgctgg atcccggacc     840
gcctctcc                                                              848

<210> SEQ ID NO 24
<211> LENGTH: 798
<212> TYPE: DNA
<213> ORGANISM: artificial
<220> FEATURE:
<223> OTHER INFORMATION: IgK-SF-H6-GGS-lcn2C-GGS-ENLYFQ-GS-MIDKINE
      coding sequence

<400> SEQUENCE: 24
atggagacag acacactcct gctatgggta ctgctgctct gggttccagg ttccactggt      60
gactacaagg acgagcatca ccatcatcac catggtggaa gccaggactc cacctcagac     120
ctgatcccag ccccacctct gagcaaggtc cctctgcagc agaacttcca ggacaaccaa     180
ttccagggga agtggtatgt ggtaggcctg gcagggaatg caattctcag agaagacaaa     240
gacccgcaaa agatgtatgc caccatctat gagctgaaag aagacaagag ctacaatgtc     300
acctccgtcc tgtttaggaa aaagaagtgt gactactgga tcaggacttt tgttccaggt     360
tgccagcccg gcgagttcac gctgggcaac attaagagtt accctggatt aacgagttac     420
ctcgtccgag tggtgagcac caactacaac cagcatgcta tggtgttctt caagaaagtt     480
tctcaaaaca gggagtactt caagatcacc ctctacggga gaaccaagga gctgacttcg     540
gaactaaagg agaacttcat ccgcttctcc aaatctctgg gcctccctga aaaccacatc     600
gtcttccctg tcccaatcga ccagtgtatc gacggcggag gtagcgaaaa cctgtatttt     660
cagagcgatt gcaaatataa atttgaaaac tggggcgcgt gcgatggcgg caccggcacc     720
aaagtgcgcc agggcaccct gaaaaaagcg cgctataacg cgcagtgcca ggaaaccatt     780
cgcgtgacca aaccgtgc                                                   798
```

<210> SEQ ID NO 25
<211> LENGTH: 796
<212> TYPE: DNA
<213> ORGANISM: artificial
<220> FEATURE:
<223> OTHER INFORMATION: IgK-SF-H6-GGS-lcn2C-GGS-ENLYFQ-GG-Violacin A

<400> SEQUENCE: 25

```
gactgagtcg cccgctcgag accatggaga cagacacact cctgctatgg gtactgctgc    60
tctgggttcc aggttccact ggtgactaca aggacgagca tcaccatcat caccatggtg   120
gaagccagga ctccacctca gacctgatcc cagccccacc tctgagcaag gtccctctgc   180
agcagaactt ccaggacaac caattccagg ggaagtggta tgtggtaggc ctggcaggga   240
atgcaattct cagagaagac aaagacccgc aaaagatgta tgccaccatc tatgagctga   300
aagaagacaa gagctacaat gtcacctccg tcctgtttag gaaaaagaag tgtgactact   360
ggatcaggac ttttgttcca ggttgccagc ccggcgagtt cacgctgggc aacattaaga   420
gttaccctgg attaacgagt tacctcgtcc gagtggtgag caccaactac aaccagcatg   480
ctatggtgtt cttcaagaaa gtttctcaaa acagggagta cttcaagatc accctctacg   540
ggagaaccaa ggagctgact tcggaactaa ggagaacttc atccgcttc tccaaatctc    600
tgggcctccc tgaaaaccac atcgtcttcc ctgtcccaat cgaccagtgt atcgacggcg   660
gaggtagcga aaacctgtat tttcagggag gcagcgccat cagctgcggc gagacctgct   720
tcaagttcaa gtgctacacc cccagatgca gctgcagcta ccccgtgtgc aagtaagcta   780
aggatcccgg accgcc                                                   796
```

<210> SEQ ID NO 26
<211> LENGTH: 750
<212> TYPE: DNA
<213> ORGANISM: artificial
<220> FEATURE:
<223> OTHER INFORMATION: IgK-SF-H6-GGS-lcn2C-GGS-ENLYFQ-GG-Violacin A
      coding sequence

<400> SEQUENCE: 26

```
atggagacag acacactcct gctatgggta ctgctgctct gggttccagg ttccactggt    60
gactacaagg acgagcatca ccatcatcac catggtggaa gccaggactc cacctcagac   120
ctgatcccag ccccacctct gagcaaggtc cctctgcagc agaacttcca ggacaaccaa   180
ttccagggga gtggtatgt ggtaggcctg gcagggaatg caattctcag agaagacaaa   240
gacccgcaaa agatgtatgc caccatctat gagctgaaag aagacaagag ctacaatgtc   300
acctccgtcc tgtttaggaa aaagaagtgt gactactgga tcaggacttt tgttccaggt   360
tgccagcccg gcgagttcac gctgggcaac attaagagtt accctggatt aacgagttac   420
ctcgtccgag tggtgagcac caactacaac cagcatgcta tggtgttctt caagaaagtt   480
tctcaaaaca gggagtactt caagatcacc ctctacggga gaaccaagga gctgacttcg   540
gaactaaagg agaacttcat ccgcttctcc aaatctctgg gcctccctga aaaccacatc   600
gtcttccctg tcccaatcga ccagtgtatc gacggcggag gtagcgaaaa cctgtatttt   660
cagggaggca gcgccatcag ctgcggcgag acctgcttca agttcaagtg ctacaccccc   720
agatgcagct gcagctaccc cgtgtgcaag                                    750
```

<210> SEQ ID NO 27
<211> LENGTH: 745

```
<212> TYPE: DNA
<213> ORGANISM: artificial
<220> FEATURE:
<223> OTHER INFORMATION: IgK-SF-H6-GGS-lcn2C-GGS-ENLYFQ-GG-Lambda Toxin

<400> SEQUENCE: 27
gactgagtcg cccgctcgag accatggaga cagacacact cctgctatgg gtactgctgc      60
tctgggttcc aggttccact ggtgactaca aggacgagca tcaccatcat caccatggtg     120
gaagccagga ctccacctca gacctgatcc cagccccacc tctgagcaag gtccctctgc     180
agcagaactt ccaggacaac caattccagg ggaagtggta tgtggtaggc ctggcaggga     240
atgcaattct cagagaagac aaagacccgc aaaagatgta tgccaccatc tatgagctga     300
agaagacaa gagctacaat gtcacctccg tcctgtttag gaaaaagaag tgtgactact     360
ggatcaggac ttttgttcca ggttgccagc ccggcgagtt cacgctgggc aacattaaga     420
gttaccctgg attaacgagt tacctcgtcc gagtggtgag caccaactac aaccagcatg     480
ctatggtgtt cttcaagaaa gtttctcaaa acagggagta cttcaagatc accctctacg     540
ggagaaccaa ggagctgact tcggaactaa aggagaactt catccgcttc tccaaatctc     600
tgggcctccc tgaaaaccac atcgtcttcc ctgtcccaat cgaccagtgt atcgacggcg     660
gaggtagcga aaacctgtat tttcagggag gcgtgtgctg cggctacaag ctgtgccacc     720
cctgctaagc taaggatccc ggacc                                           745

<210> SEQ ID NO 28
<211> LENGTH: 702
<212> TYPE: DNA
<213> ORGANISM: artificial
<220> FEATURE:
<223> OTHER INFORMATION: IgK-SF-H6-GGS-lcn2C-GGS-ENLYFQ-GG-Lambda Toxin
      coding sequence

<400> SEQUENCE: 28
atggagacag acacactcct gctatgggta ctgctgctct gggttccagg ttccactggt      60
gactacaagg acgagcatca ccatcatcac catggtggaa gccaggactc cacctcagac     120
ctgatcccag ccccacctct gagcaaggtc cctctgcagc agaacttcca ggacaaccaa     180
ttccagggga agtggtatgt ggtaggcctg cagggaatg caattctcag agaagacaaa     240
gacccgcaaa agatgtatgc caccatctat gagctgaaag aagacaagag ctacaatgtc     300
acctccgtcc tgtttaggaa aaagaagtgt gactactgga tcaggacttt tgttccaggt     360
tgccagcccg gcgagttcac gctgggcaac attaagagtt accctggatt aacgagttac     420
ctcgtccgag tggtgagcac caactacaac agcatgcta tggtgttctt caagaaagtt     480
tctcaaaaca gggagtactt caagatcacc ctctacggga gaaccaagga gctgacttcg     540
gaactaaagg agaacttcat ccgcttctcc aaatctctgg gcctcctga aaaccacatc     600
gtcttccctg tcccaatcga ccagtgtatc gacggcggag gtagcgaaaa cctgtatttt     660
cagggaggcg tgtgctgcgg ctacaagctg tgccacccct gc                        702

<210> SEQ ID NO 29
<211> LENGTH: 751
<212> TYPE: DNA
<213> ORGANISM: artificial
<220> FEATURE:
<223> OTHER INFORMATION: IgK-SF-H6-GGS-lcn2C-GGS-ENLYFQ-GG-Lambda Toxin
      NG

<400> SEQUENCE: 29
```

```
gactgagtcg cccgctcgag accatggaga cagacacact cctgctatgg gtactgctgc    60
tctgggttcc aggttccact ggtgactaca aggacgagca tcaccatcat caccatggtg   120
gaagccagga ctccacctca gacctgatcc cagccccacc tctgagcaag gtccctctgc   180
agcagaactt ccaggacaac caattccagg ggaagtggta tgtggtaggc ctggcaggga   240
atgcaattct cagagaagac aaagacccgc aaaagatgta tgccaccatc tatgagctga   300
aagaagacaa gagctacaat gtcacctccg tcctgtttag gaaaaagaag tgtgactact   360
ggatcaggac ttttgttcca ggttgccagc ccggcgagtt cacgctgggc aacattaaga   420
gttaccctgg attaacgagt tacctcgtcc agtggtgag caccaactac aaccagcatg    480
ctatggtgtt cttcaagaaa gtttctcaaa acagggagta cttcaagatc accctctacg   540
ggagaaccaa ggagctgact tcggaactaa aggagaactt catccgcttc tccaaatctc   600
tgggcctccc tgaaaaccac atcgtcttcc ctgtcccaat cgaccagtgt atcgacggcg   660
gaggtagcga aaacctgtat tttcagggag gcaacggcgt gtgctgcggc tacaagctgt   720 gccaccctg ctaagctaag gatcccggac c                                   751
```

<210> SEQ ID NO 30
<211> LENGTH: 708
<212> TYPE: DNA
<213> ORGANISM: artificial
<220> FEATURE:
<223> OTHER INFORMATION: IgK-SF-H6-GGS-lcn2C-GGS-ENLYFQ-GG-Lambda Toxin
  NG coding sequence

<400> SEQUENCE: 30

```
atggagacag acacactcct gctatgggta ctgctgctct gggttccagg ttccactggt    60
gactacaagg acgagcatca ccatcatcac catggtggaa gccaggactc cacctcagac   120
ctgatcccag ccccacctct gagcaaggtc cctctgcagc agaacttcca ggacaaccaa   180
ttccagggga gtggtatgt ggtaggcctg gcagggaatg caattctcag agaagacaaa    240
gacccgcaaa agatgtatgc caccatctat gagctgaaag aagacaagag ctacaatgtc   300
acctccgtcc tgtttaggaa aaagaagtgt gactactgga tcaggacttt tgttccaggt   360
tgccagcccg gcgagttcac gctgggcaac attaagagtt accctggatt aacgagttac   420
ctcgtccgag tggtgagcac caactacaac cagcatgcta tggtgttctt caagaaagtt   480
tctcaaaaca gggagtactt caagatcacc ctctacggga gaaccaagga gctgacttcg   540
gaactaaagg agaacttcat ccgcttctcc aaatctctgg gcctccctga aaaccacatc   600
gtcttccctg tcccaatcga ccagtgtatc gacggcggag gtagcgaaaa cctgtatttt   660
cagggaggca acggcgtgtg ctgcggctac aagctgtgcc accctgc                 708
```

<210> SEQ ID NO 31
<211> LENGTH: 831
<212> TYPE: DNA
<213> ORGANISM: artificial
<220> FEATURE:
<223> OTHER INFORMATION: IgK-SF-H6-GGS-lcn2C-GGS-ENLYFQ-GG-Potato
  Carboxypeptidase Inhibitor

<400> SEQUENCE: 31

```
gactgagtcg cccgctcgag accatggaga cagacacact cctgctatgg gtactgctgc    60
tctgggttcc aggttccact ggtgactaca aggacgagca tcaccatcat caccatggtg   120
gaagccagga ctccacctca gacctgatcc cagccccacc tctgagcaag gtccctctgc   180
agcagaactt ccaggacaac caattccagg ggaagtggta tgtggtaggc ctggcaggga   240
```

```
atgcaattct cagagaagac aaagacccgc aaaagatgta tgccaccatc tatgagctga      300
aagaagacaa gagctacaat gtcacctccg tcctgtttag gaaaaagaag tgtgactact      360
ggatcaggac ttttgttcca ggttgccagc ccggcgagtt cacgctgggc aacattaaga      420
gttaccctgg attaacgagt tacctcgtcc gagtggtgag caccaactac aaccagcatg      480
ctatggtgtt cttcaagaaa gtttctcaaa cagggagta cttcaagatc accctctacg      540
ggagaaccaa ggagctgact tcggaactaa aggagaactt catccgcttc tccaaatctc      600
tgggcctccc tgaaaaccac atcgtcttcc ctgtcccaat cgaccagtgt atcgacggcg      660
gaggtagcga aaacctgtat tttcagggag ccagcagca tgcggatccg atttgcaaca      720
aaccgtgcaa aacccatgat gattgcagcg gcgcgtggtt tgccaggcg tgctggaaca      780 gcgcgcgcac ctgcggcccg tatgtgggct aatgctaagg atcccggacc g             831
```

<210> SEQ ID NO 32
<211> LENGTH: 789
<212> TYPE: DNA
<213> ORGANISM: artificial
<220> FEATURE:
<223> OTHER INFORMATION: IgK-SF-H6-GGS-lcn2C-GGS-ENLYFQ-GG-Potato
     Carboxypeptidase Inhibitor coding sequence

<400> SEQUENCE: 32

```
atggagacag acacactcct gctatgggta ctgctgctct ggttccagg ttccactggt       60 gactacaagg acgagcatca ccatcatcac catggtggaa gccaggactc cacctcagac     120
ctgatcccag ccccacctct gagcaaggtc cctctgcagc agaacttcca ggacaaccaa     180
ttccagggga agtggtatgt ggtaggcctg cagggaatg caattctcag agaagacaaa     240
gacccgcaaa agatgtatgc caccatctat gagctgaaag aagacaagag ctacaatgtc     300
acctccgtcc tgtttaggaa aaagaagtgt gactactgga tcaggacttt tgttccaggt     360
tgccagcccg gcgagttcac gctgggcaac attaagagtt accctggatt aacgagttac     420
ctcgtccgag tggtgagcac caactacaac cagcatgcta tggtgttctt caagaaagtt     480
tctcaaaaca gggagtactt caagatcacc ctctacggga gaaccaagga gctgacttcg     540
gaactaaagg agaacttcat ccgcttctcc aaatctctgg gcctccctga aaaccacatc     600
gtcttccctg tcccaatcga ccagtgtatc gacggcggag gtagcgaaaa cctgtatttt     660
cagggaggcc agcagcatgc ggatccgatt tgcaacaaac cgtgcaaaac ccatgatgat     720
tgcagcggcg cgtggttttg ccaggcgtgc tggaacagcg cgcgcacctg cggcccgtat     780
gtgggctaa                                                            789
```

<210> SEQ ID NO 33
<211> LENGTH: 269
<212> TYPE: PRT
<213> ORGANISM: artificial
<220> FEATURE:
<223> OTHER INFORMATION: The anti-CD3 is an OKT3 variant from the C-
     terminus of patent 7635462

<400> SEQUENCE: 33

Gly Ser Asp Ile Lys Leu Gln Gln Ser Gly Ala Glu Leu Ala Arg Pro
1               5                   10                  15

Gly Ala Ser Val Lys Met Ser Cys Lys Thr Ser Gly Tyr Thr Phe Thr
            20                  25                  30

Arg Tyr Thr Met His Trp Val Lys Gln Arg Pro Gly Gln Gly Leu Glu
        35                  40                  45

```
Trp Ile Gly Tyr Ile Asn Pro Ser Arg Gly Tyr Thr Asn Tyr Asn Gln
         50                  55                  60

Lys Phe Lys Asp Lys Ala Thr Leu Thr Thr Asp Lys Ser Ser Ser Thr
 65                  70                  75                  80

Ala Tyr Met Gln Leu Ser Ser Leu Thr Ser Glu Asp Ser Ala Val Tyr
                 85                  90                  95

Tyr Cys Ala Arg Tyr Tyr Asp Asp His Tyr Cys Leu Asp Tyr Trp Gly
                100                 105                 110

Gln Gly Thr Thr Leu Thr Val Ser Ser Val Glu Gly Gly Ser Gly Gly
            115                 120                 125

Ser Gly Gly Ser Gly Gly Ser Gly Gly Val Asp Asp Ile Gln Leu Thr
130                 135                 140

Gln Ser Pro Ala Ile Met Ser Ala Ser Pro Gly Glu Lys Val Thr Met
145                 150                 155                 160

Thr Cys Arg Ala Ser Ser Ser Val Ser Tyr Met Asn Trp Tyr Gln Gln
                165                 170                 175

Lys Ser Gly Thr Ser Pro Lys Arg Trp Ile Tyr Asp Thr Ser Lys Val
            180                 185                 190

Ala Ser Gly Val Pro Tyr Arg Phe Ser Gly Ser Gly Ser Gly Thr Ser
        195                 200                 205

Tyr Ser Leu Thr Ile Ser Ser Met Glu Ala Glu Asp Ala Ala Thr Tyr
    210                 215                 220

Tyr Cys Gln Gln Trp Ser Ser Asn Pro Leu Thr Phe Gly Ala Gly Thr
225                 230                 235                 240

Lys Leu Glu Leu Lys Gly Gly Gly Gly Ser Asn Ser Ser Asn Tyr Cys
                245                 250                 255

Cys Glu Leu Cys Cys Asn Pro Ala Cys Thr Gly Cys Tyr
                260                 265
```

<210> SEQ ID NO 34
<211> LENGTH: 848
<212> TYPE: DNA
<213> ORGANISM: artificial
<220> FEATURE:
<223> OTHER INFORMATION: anti-CD3 is an OKT3 variant from the C-terminus of patent 7635462 dropped into the Bam/Not cut library vector as a TEV-cleavable siderocalin fusion

<400> SEQUENCE: 34

```
acctgtattt tcagggatcc gatattaaac tgcagcagag cggcgcggaa ctggcgcgcc      60
cgggcgcgag cgtgaaaatg agctgcaaaa ccagcggcta tacctttacc cgctatacca     120
tgcattgggt gaaacagcgc ccgggccagg cctggaatg gattggctat attaacccga     180
gccgcggcta taccaactat aaccagaaat ttaaagataa agcgaccctg accaccgata     240
aaagcagcag caccgcgtat atgcagctga gcagcctgac cagcgaagat agcgcggtgt     300
attattgcgc gcgctattat gatgatcatt attgcctgga ttattgggc cagggcacca     360 ccctgaccgt gagcagcgtg aaggcggca gcggcggcag cggcggcagc ggcggcagcg     420
gcggcgtgga tgatattcag ctgacccaga gcccggcgat tatgagcgcg agcccgggcg     480
aaaaagtgac catgacctgc cgcgcgagca gcagcgtgag ctatatgaac tggtatcagc     540
agaaaagcgg caccagcccg aaacgctgga tttatgatac cagcaaagtg gcgagcggcg     600
tgccgtatcg ctttagcggc agcggcagcg gcaccagcta tagcctgacc attagcagca     660
tggaagcgga agatgcggcg acctattatt gccagcagtg gagcagcaac ccgctgacct     720
```

```
ttggcgcggg caccaaactg gaactgaaag gcggcggcgg cagcaacagc agcaactatt    780
gctgcgaact gtgctgcaac ccggcgtgca ccggctgcta ttaatgcggc cgctcatcac    840
cattaatc                                                            848

<210> SEQ ID NO 35
<211> LENGTH: 684
<212> TYPE: DNA
<213> ORGANISM: artificial
<220> FEATURE:
<223> OTHER INFORMATION: Parental cloning construct 1:
      IgK-sFLAG-H6-GGS-humanScn-GGS-ENLYFQ-GG-NotI

<400> SEQUENCE: 35
ctcgagacca tggagacaga cacactcctg ctatgggtac tgctgctctg ggttccaggt     60
tccactggtg actacaagga cgagcatcac catcatcacc atggtggaag ccaggactcc    120
acctcagacc tgatcccagc cccacctctg agcaaggtcc ctctgcagca gaacttccag    180
gacaaccaat tccaggggaa gtggtatgtg gtaggcctgg cagggaatgc aattctcaga    240
gaagacaaag acccgcaaaa gatgtatgcc accatctatg agctgaaaga agacaagagc    300
tacaatgtca cctccgtcct gtttaggaaa aagaagtgtg actactggat caggactttt    360
gttccaggtt gccagcccgg cgagttcacg ctgggcaaca ttaagagtta ccctggatta    420
acgagttacc tcgtccgagt ggtgagcacc aactacaacc agcatgctat ggtgttcttc    480
aagaaagttt ctcaaaacag ggagtacttc aagatcaccc tctacgggag aaccaaggag    540
ctgacttcgg aactaaagga gaacttcatc cgcttctcca atctctgggg cctccctgaa    600
aaccacatcg tcttccctgt cccaatcgac cagtgtatcg acggcggagg tagcgaaaac    660
ctgtattttc agggaggcgg ccgc                                          684

<210> SEQ ID NO 36
<211> LENGTH: 1402
<212> TYPE: DNA
<213> ORGANISM: artificial
<220> FEATURE:
<223> OTHER INFORMATION: Parental cloning construct 2:
      IgK-sFLAG-H6-GGS-humanScnC87S-GGS-ENLYFQ-GS-STUFFER

<400> SEQUENCE: 36
ctcgagacca tggagacaga cacactcctg ctatgggtac tgctgctctg ggttccaggt     60
tccactggtg actacaagga cgagcatcac catcatcacc atggtggaag ccaggactcc    120
acctcagacc tgatcccagc cccacctctg agcaaggtcc ctctgcagca gaacttccag    180
gacaaccaat tccaggggaa gtggtatgtg gtaggcctgg cagggaatgc aattctcaga    240
gaagacaaag acccgcaaaa gatgtatgcc accatctatg agctgaaaga agacaagagc    300
tacaatgtca cctccgtcct gtttaggaaa aagaagtgtg actactggat caggactttt    360
gttccaggtt cccagcccgg cgagttcacg ctgggcaaca ttaagagtta ccctggatta    420
acgagttacc tcgtccgagt ggtgagcacc aactacaacc agcatgctat ggtgttcttc    480
aagaaagttt ctcaaaacag ggagtacttc aagatcaccc tctacgggag aaccaaggag    540
ctgacttcgg aactaaagga gaacttcatc cgcttctcca atctctgggg cctccctgaa    600
aaccacatcg tcttccctgt cccaatcgac cagtgtatcg acggcggagg tagcgaaaac    660
ctgtattttc agggatccat gtacggtctt aagggacccg acatttacaa aggagtttac    720
caatttaagt cagtggagtt tgatatgtca catctgaacc tgaccatgcc caacgcatgt    780
tcagccaaca actcccacca ttacatcagt atggggactt ctggactaga attgaccttc    840
```

```
accaatgatt ccatcatcag tcacaacttt tgcaatctga cctctgcctt caacaaaaag    900
acctttgacc acacactcat gagtatagtt tcgagcctac acctcagtat cagagggaac    960
tccaactata aggcagtatc ctgcgacttc aacaatggca taaccatcca atacaacttg   1020
acattctcag atcgacaaag tgctcagagc cagtgtagaa ccttcagagg tagagtccta   1080
gatatgttta gaactgcctt cgggggggaaa tacatgagga gtggctgggg ctggacaggc   1140
tcagatggca agaccacctg tgtagccag acgagttacc aatacctgat tatacaaaat    1200
agaacctggg aaaaccactg cacatatgca ggtccttttg ggatgtccag gattctcctt   1260
tcccaagaga agactaagtt cttcactagg agactggtgc ccaggggcag cggcctgaac    1320
gacatcttcg aggcccagaa gatcgagtgg cacgagtaat gcggccgctc atcaccatta    1380
atcatcacca ttaatcggac cg                                             1402

<210> SEQ ID NO 37
<211> LENGTH: 1299
<212> TYPE: DNA
<213> ORGANISM: artificial
<220> FEATURE:
<223> OTHER INFORMATION: Parental cloning construct 3: LightChain-
      GRGGSGGS-humanScnC87S

<400> SEQUENCE: 37
ctcgagacca tggatttcca ggtgcagatt tttagctttc tgctgatttc cgcttccgtg     60
attatgagcc gaggcgacat tgtgatgacc caggcagctc ctagcgtgcc agtcacccca    120
ggagagtcag tgagcatctc ctgcagaagt actaagtcac tgctgcacag caacggcaat    180
acctacctgt attggttcct gcagagacct gggcagtccc cacagaggct gatctactat    240
atgagtaacc tggcatcagg agtgcctgac aggttcagcg gacgaggcag cggcactgat    300
tttaccctgc ggatttctag agtggaggca gaagacgccg gcgtctacta ttgcatgcag    360
agtctggagt acccttatac tttcggcggg ggaaccaaac tggaaatcaa gagggccgat    420
gccgctccaa ccgtgtccat ttttcccccct agctccgagc agctgacatc tggcggggct    480
agtgtggtct gtttcctgaa caatttttac ccaaaggaca tcaacgtgaa atggaagatt    540
gatggaagtg aaaggcagaa cggcgtcctg aattcatgga cagaccagga tagcaaagac    600
tccacttatt ctatgtctag taccctgaca ctgactaagg atgagtacga acgccacaat    660
tcttatacat gcgaggcaac tcataaaacc tctacaagtc ccatcgtgaa gagctttaac    720
cgaaatgaat gcggccgcgg aggctccgga ggctcccagg actcaacaag cgatctgatt    780
ccagccccac ccctgagcaa agtgcccctg cagcagaact tccaggacaa tcagttttcag   840 ggcaagtggt acgtggtcgg gctggctgga acgcaatcc tgcgggagga caaagatccc    900
cagaagatgt acgccactat ctacgagctg aaagaagaca agtcatacaa tgtgaccagc    960
gtcctgttcc gcaagaaaaa gtgtgattat tggatcagaa cattcgtgcc cggctcccag   1020
cctggggagt ttactctggg gaatattaag tcctaccctg gactgacctc ttatctggtg   1080
cgagtggtct ctacaaacta caatcagcat gctatggtgt ctttttaaaaa ggtcagccag   1140 aaccgggagt actttaaaat caccctgtat ggcagaacca agaactgac aagcgagctg    1200 aaggaaaatt tcattcgctt ttccaagtct ctggggctgc cagagaatca tattgtgttc    1260
ccagtcccca ttgaccagtg tattgacggg tgaggatcc                          1299

<210> SEQ ID NO 38
<211> LENGTH: 606
```

```
<212> TYPE: DNA
<213> ORGANISM: artificial
<220> FEATURE:
<223> OTHER INFORMATION: Super stable ScnC87S (humanScn-I8C-N39C-C87S)

<400> SEQUENCE: 38
ctcgagatgc ccctgggcct gctgtggctg ggcctggccc tgctgggcgc cctgcacgcc      60
caggcccagg actccacctc agacctgtgt ccagcccac ctctgagcaa ggtccctctg     120
cagcagaact tccaggacaa ccaattccag gggaagtggt atgtggtagg cctggcaggg     180
tgtgcaattc tcagagaaga caaagacccg caaagatgt atgccaccat ctatgagctg     240
aaagaagaca gagctacaa tgtcacctcc gtcctgttta ggaaaaagaa gtgtgactac     300
tggatcagga cttttgttcc aggttcccag ccgggcgagt tcacgctggg caacattaag     360
agttaccctg gattaacgag ttacctcgtc gagtggtga gcaccaacta caaccagcat     420
gctatggtgt tcttcaagaa agtttctcaa acagggagt acttcaagat cacctctac     480
gggagaacca aggagctgac ttcggaacta aaggagaact tcatccgctt ctccaaatct     540
ctgggcctcc ctgaaaacca catcgtcttc cctgtcccaa tcgaccagtg tatcgacggc     600
ggatcc                                                              606

<210> SEQ ID NO 39
<211> LENGTH: 178
<212> TYPE: PRT
<213> ORGANISM: Homo sapiens

<400> SEQUENCE: 39

Gln Asp Ser Thr Ser Asp Leu Ile Pro Ala Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
        50                  55                  60

Asn Val Thr Ser Val Leu Phe Arg Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 40
<211> LENGTH: 178
<212> TYPE: PRT
<213> ORGANISM: Pan troglodytes

<400> SEQUENCE: 40
```

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
        50                  55                  60

Asn Val Thr Ser Val Leu Phe Arg Lys Lys Cys Asp Tyr Trp Ile
65                  70                  75                  80

Arg Thr Phe Val Pro Gly Arg Gln Pro Gly Glu Phe Thr Leu Gly Asn
                85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
        130                 135                 140

Thr Ser Glu Leu Gln Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 41
<211> LENGTH: 178
<212> TYPE: PRT
<213> ORGANISM: Canis familiaris

<400> SEQUENCE: 41

Gln Asp Ser Thr Pro Ser Leu Ile Pro Ala Pro Pro Leu Lys Val
1               5                   10                  15

Pro Leu Gln Pro Asp Phe Gln His Asp Gln Phe Gln Gly Lys Trp Tyr
            20                  25                  30

Val Ile Gly Ile Ala Gly Asn Ile Leu Lys Lys Glu Gly His Gly Gln
            35                  40                  45

Leu Lys Met Tyr Thr Thr Thr Tyr Glu Leu Lys Asp Asp Gln Ser Tyr
        50                  55                  60

Asn Val Thr Ser Thr Leu Leu Arg Asn Glu Arg Cys Asp Tyr Trp Asn
65                  70                  75                  80

Arg Asp Phe Val Pro Ser Phe Gln Pro Gly Gln Phe Ser Leu Gly Asp
                85                  90                  95

Ile Gln Leu Tyr Pro Gly Val Gln Ser Tyr Leu Val Gln Val Val Ala
                100                 105                 110

Thr Asn Tyr Asn Gln Tyr Ala Leu Val Tyr Phe Arg Lys Val Tyr Lys
            115                 120                 125

Ser Gln Glu Tyr Phe Lys Ile Thr Leu Tyr Gly Arg Thr Lys Glu Leu
        130                 135                 140

Pro Leu Glu Leu Lys Lys Glu Phe Ile Arg Phe Ala Lys Ser Ile Gly
145                 150                 155                 160

Leu Thr Glu Asp His Ile Ile Phe Pro Val Pro Ile Asp Gln Cys Ile
                165                 170                 175

Asp Glu
```

-continued

<210> SEQ ID NO 42
<211> LENGTH: 179
<212> TYPE: PRT
<213> ORGANISM: Bos taurus

<400> SEQUENCE: 42

Arg Ser Ser Ser Ser Arg Leu Leu Arg Ala Pro Pro Leu Ser Arg Ile
1               5                   10                  15

Pro Leu Gln Pro Asn Phe Gln Ala Asp Gln Phe Gln Gly Lys Trp Tyr
            20                  25                  30

Thr Val Gly Val Ala Gly Asn Ala Ile Lys Lys Glu Glu Gln Asp Pro
        35                  40                  45

Leu Lys Met Tyr Ser Ser Asn Tyr Glu Leu Lys Glu Asp Gly Ser Tyr
    50                  55                  60

Asn Val Thr Ser Ile Leu Leu Lys Asp Asp Leu Cys Asp Tyr Trp Ile
65                  70                  75                  80

Arg Thr Phe Val Pro Ser Ser Gln Pro Gly Gln Phe Thr Leu Gly Asn
                85                  90                  95

Ile Lys Ser Tyr Arg Gly Ile Arg Ser Tyr Thr Val Arg Val Val Asn
            100                 105                 110

Thr Asp Tyr Asn Gln Phe Ala Ile Val Tyr Phe Lys Lys Val Gln Arg
        115                 120                 125

Lys Lys Thr Tyr Phe Lys Ile Thr Leu Tyr Gly Arg Thr Lys Glu Leu
    130                 135                 140

Thr Pro Glu Val Arg Glu Asn Phe Ile Asn Phe Ala Lys Ser Leu Gly
145                 150                 155                 160

Leu Thr Asp Asp His Ile Val Phe Thr Val Pro Ile Asp Arg Cys Ile
                165                 170                 175

Asp Asp Gln

<210> SEQ ID NO 43
<211> LENGTH: 180
<212> TYPE: PRT
<213> ORGANISM: Mus musculus

<400> SEQUENCE: 43

Gln Asp Ser Thr Gln Asn Leu Ile Pro Ala Pro Ser Leu Leu Thr Val
1               5                   10                  15

Pro Leu Gln Pro Asp Phe Arg Ser Asp Gln Phe Arg Gly Arg Trp Tyr
            20                  25                  30

Val Val Gly Leu Ala Gly Asn Ala Val Gln Lys Lys Thr Glu Gly Ser
        35                  40                  45

Phe Thr Met Tyr Ser Thr Ile Tyr Glu Leu Gln Glu Asn Asn Ser Tyr
    50                  55                  60

Asn Val Thr Ser Ile Leu Val Arg Asp Gln Asp Gln Gly Cys Arg Tyr
65                  70                  75                  80

Trp Ile Arg Thr Phe Val Pro Ser Ser Arg Ala Gly Gln Phe Thr Leu
                85                  90                  95

Gly Asn Met His Arg Tyr Pro Gln Val Gln Ser Tyr Asn Val Gln Val
            100                 105                 110

Ala Thr Thr Asp Tyr Asn Gln Phe Ala Met Val Phe Phe Arg Lys Thr
        115                 120                 125

Ser Glu Asn Lys Gln Tyr Phe Lys Ile Thr Leu Tyr Gly Arg Thr Lys
    130                 135                 140

Glu Leu Ser Pro Glu Leu Lys Glu Arg Phe Thr Arg Phe Ala Lys Ser

```
145                 150                 155                 160
Leu Gly Leu Lys Asp Asp Asn Ile Ile Phe Ser Val Pro Thr Asp Gln
                165                 170                 175
Cys Ile Asp Asn
            180

<210> SEQ ID NO 44
<211> LENGTH: 178
<212> TYPE: PRT
<213> ORGANISM: Rattus norvegicus

<400> SEQUENCE: 44

Gln Asp Ser Thr Gln Asn Leu Ile Pro Ala Pro Leu Ile Ser Val
1               5                   10                  15

Pro Leu Gln Pro Gly Phe Trp Thr Glu Arg Phe Gln Gly Arg Trp Phe
                20                  25                  30

Val Val Gly Leu Ala Ala Asn Ala Val Gln Lys Glu Arg Gln Ser Arg
                35                  40                  45

Phe Thr Met Tyr Ser Thr Ile Tyr Glu Leu Gln Glu Asp Asn Ser Tyr
            50                  55                  60

Asn Val Thr Ser Ile Leu Val Arg Gly Gln Gly Cys Arg Tyr Trp Ile
65                  70                  75                  80

Arg Thr Phe Val Pro Ser Ser Arg Pro Gly Gln Phe Thr Leu Gly Asn
                85                  90                  95

Ile His Ser Tyr Pro Gln Ile Gln Ser Tyr Asp Val Gln Val Ala Asp
                100                 105                 110

Thr Asp Tyr Asp Gln Phe Ala Met Val Phe Phe Gln Lys Thr Ser Glu
            115                 120                 125

Asn Lys Gln Tyr Phe Lys Val Thr Leu Tyr Gly Arg Thr Lys Gly Leu
        130                 135                 140

Ser Asp Glu Leu Lys Glu Arg Phe Val Ser Phe Ala Lys Ser Leu Gly
145                 150                 155                 160

Leu Lys Asp Asn Asn Ile Val Phe Ser Val Pro Thr Asp Gln Cys Ile
                165                 170                 175

Asp Asn

<210> SEQ ID NO 45
<211> LENGTH: 178
<212> TYPE: PRT
<213> ORGANISM: Macaca mulatta

<400> SEQUENCE: 45

Gln Asp Ser Ser Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ser Gly Asn Ala Val Gly Arg Lys Asp Glu Ala Pro
                35                  40                  45

Leu Lys Met Tyr Ala Thr Ile Tyr Glu Leu Lys Glu Asp Lys Ser Tyr
            50                  55                  60

Asn Val Thr Ser Ile Leu Phe Arg Lys Glu Lys Cys Asp Tyr Trp Ile
65                  70                  75                  80

Arg Thr Phe Val Pro Gly Ser Gln Pro Gly Glu Phe Thr Leu Gly Asn
                85                  90                  95

Ile Gln Asn His Pro Gly Leu Thr Ser Tyr Val Val Arg Val Val Ser
                100                 105                 110
```

```
Thr Asn Tyr Lys Gln Tyr Ala Met Val Phe Lys Lys Val Ser Gln
        115                 120                 125

Asn Lys Glu Tyr Phe Lys Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Ser Val Pro Ile Asp Gln Cys Ile
                165                 170                 175

Asn Gly

<210> SEQ ID NO 46
<211> LENGTH: 181
<212> TYPE: PRT
<213> ORGANISM: Tursiops truncatus

<400> SEQUENCE: 46

Gln Asp Ser Thr Pro Asn Leu Ile Pro Ala Pro Pro Leu Phe Arg Val
1               5                   10                  15

Pro Leu Gln Pro Asn Phe Gln Pro Asp Gln Phe Gln Gly Lys Trp Tyr
                20                  25                  30

Ile Val Gly Leu Ala Gly Asn Ala Phe Lys Lys Glu Lys Gln Gly Gln
            35                  40                  45

Phe Lys Met Tyr Ala Thr Thr Tyr Glu Leu Lys Glu Asp Arg Ser Tyr
    50                  55                  60

Asn Val Thr Ser Ala Leu Leu Arg Gly Lys Thr Gln Arg Cys Asp His
65                  70                  75                  80

Trp Ile Arg Thr Phe Val Pro Ser Ser Arg Pro Gly Gln Phe Thr Leu
                85                  90                  95

Gly Asn Ile Lys Gly Phe Pro Gly Val Gln Ser Tyr Thr Val Arg Val
            100                 105                 110

Ala Thr Thr Asn Tyr Asn Gln Phe Ala Ile Val Tyr Phe Lys Lys Val
        115                 120                 125

Tyr Lys Asn Gln Glu Tyr Phe Lys Thr Thr Leu Tyr Gly Arg Thr Lys
    130                 135                 140

Glu Leu Thr Pro Gln Leu Lys Glu Asn Phe Ile His Phe Ala Lys Ser
145                 150                 155                 160

Leu Gly Leu Thr Asp Glu Tyr Ile Leu Phe Pro Val Pro Ile Asp Lys
                165                 170                 175

Cys Ile Asp Asp Gln
            180

<210> SEQ ID NO 47
<211> LENGTH: 180
<212> TYPE: PRT
<213> ORGANISM: Gorilla gorilla

<400> SEQUENCE: 47

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
    50                  55                  60
```

-continued

```
Asn Val Thr Ser Val Leu Phe Arg Glu Lys Ala Gln Lys Cys Asp Tyr
 65                  70                  75                  80

Trp Ile Arg Thr Phe Val Pro Gly Ser Gln Pro Gly Glu Phe Thr Leu
                 85                  90                  95

Gly Asn Ile Lys Ser Tyr Pro Gly Leu Thr Ser Tyr Leu Val Arg Val
                100                 105                 110

Val Ser Thr Asn Tyr Asn Gln His Ala Met Val Phe Lys Lys Val
                115                 120                 125

Ser Gln Asn Arg Glu Tyr Phe Lys Ile Thr Leu Tyr Gly Arg Thr Lys
            130                 135                 140

Glu Leu Thr Ser Glu Leu Lys Glu Asn Phe Ile Arg Phe Ser Lys Ser
145                 150                 155                 160

Leu Gly Leu Pro Glu Asn His Ile Val Phe Pro Val Pro Ile Asp Gln
                165                 170                 175

Cys Ile Asp Gly
            180
```

<210> SEQ ID NO 48
<211> LENGTH: 179
<212> TYPE: PRT
<213> ORGANISM: Procavia capensis

<400> SEQUENCE: 48

```
Gln Glu Pro Thr Pro Thr Leu Ile Pro Ala Pro Leu Ser Ser Ile
  1               5                  10                  15

Pro Leu Lys Pro Asn Phe His Asn Asp Lys Phe Gln Gly Lys Trp Tyr
                 20                  25                  30

Val Val Gly Val Ala Gly Asn Ala Ile Thr Lys Glu Lys Asp Pro Ser
                 35                  40                  45

Leu Met Tyr Thr Thr Thr Tyr Glu Leu Arg Asp Asp Gly Ser Tyr Asn
     50                  55                  60

Val Thr Ser Thr Gln Phe Arg Glu Lys Ile Asn Cys Thr His Trp Thr
 65                  70                  75                  80

Arg Thr Phe Val Pro Thr Ser Gln Pro Gly Gln Phe Ser Leu Gly Asn
                 85                  90                  95

Ile Asp Lys Tyr Pro His Leu Ser Ser Tyr Thr Val Arg Val Thr Ala
                100                 105                 110

Thr Asn Tyr Asn Tyr Phe Ala Ile Val Tyr Phe Lys Lys Val Ser Lys
            115                 120                 125

Asn Gln Glu Tyr Phe Lys Thr Thr Leu Tyr Lys Arg Ile Lys Lys Leu
            130                 135                 140

Thr His Gly Leu Lys Lys His Phe Ile Gln Phe Ala Lys Ser Leu Gly
145                 150                 155                 160

Leu Pro Asp Asn His Ile Thr Phe Leu Val Pro Thr Asp Arg Cys Ile
                165                 170                 175

Asp Asp Ala
```

<210> SEQ ID NO 49
<211> LENGTH: 179
<212> TYPE: PRT
<213> ORGANISM: Callithrix jacchus

<400> SEQUENCE: 49

```
Gln Asp Ser Pro Ser Pro Leu Ile Pro Ala Pro Pro Leu Ser Lys Val
  1               5                  10                  15

Pro Leu Gln Gln Asn Phe Gln Asp Asn Gln Phe Gln Gly Lys Trp Tyr
```

```
            20                  25                  30
Val Val Gly Leu Ala Gly Asn Ala Ile Arg Arg Glu Asp Gln Asp Ser
            35                  40                  45

Leu Lys Met Tyr Ala Thr Ile Tyr Glu Leu Lys Glu Asp Lys Ser Tyr
 50                  55                  60

Asn Val Thr Ser Val Leu Phe Arg Lys Ala Gln Lys Cys Asp Tyr Trp
 65                  70                  75                  80

Ile Arg Thr Phe Val Pro Ser Ser Arg Pro Gly Glu Phe Lys Leu Gly
                     85                  90                  95

Asn Ile Glu Ser His Pro Gly Leu Thr Ser Tyr Ile Val Arg Val Val
            100                 105                 110

Asn Thr Asp Tyr Lys Gln His Ala Met Val Phe Phe Met Lys Ala Ser
            115                 120                 125

His Asn Arg Lys Tyr Phe Lys Val Thr Leu Tyr Gly Arg Thr Lys Glu
            130                 135                 140

Leu Thr Ser Asp Leu Lys Glu Asn Phe Thr Ser Phe Ser Lys Ser Leu
145                 150                 155                 160

Gly Leu Thr Glu Asn His Ile Ile Phe Pro Val Pro Ile Asp Gln Cys
                165                 170                 175

Ile Asp Gly

<210> SEQ ID NO 50
<211> LENGTH: 178
<212> TYPE: PRT
<213> ORGANISM: Microcebus murinus

<400> SEQUENCE: 50

Gln Asp Ser Lys Glu Lys Leu Ile Pro Ala Pro Pro Leu Leu Arg Val
 1               5                  10                  15

Pro Leu Gln Pro Asp Phe Gln Asp Asp Gln Phe Arg Glu Thr Ser Trp
                20                  25                  30

Pro Arg Gly Ser Lys Met Lys Glu Thr Pro Ala Gly Ser Arg Asp Ala
            35                  40                  45

Gly Thr Gly Trp Ala Thr Thr Tyr Glu Leu Lys Asp His Ser Tyr Asn
 50                  55                  60

Val Thr Ser Thr Leu Leu Arg Gln Asn Gly Lys Cys Asp Tyr Trp Ile
 65                  70                  75                  80

Arg Thr Phe Val Leu Thr Ser Gln Pro Gly Gln Phe Ala Leu Gly Asn
                     85                  90                  95

Ile Asn Arg Tyr Pro Gly Ile Gln Ser Tyr Thr Val Arg Val Val Thr
            100                 105                 110

Thr Asn Tyr Asn Gln Phe Ala Ile Val Phe Phe Lys Lys Val Ser Glu
            115                 120                 125

Asn Lys Glu Tyr Phe Lys Thr Thr Leu Tyr Gly Arg Thr Lys Glu Leu
            130                 135                 140

Pro Pro Glu Leu Lys Glu Asn Phe Ile Arg Phe Ala Lys Ser Leu Gly
145                 150                 155                 160

Leu Thr Glu Asp His Ile Ile Tyr Pro Val Pro Ile Asp Gln Cys Ile
                165                 170                 175

Asp Asp

<210> SEQ ID NO 51
<211> LENGTH: 178
<212> TYPE: PRT
<213> ORGANISM: Pongo abelii
```

<400> SEQUENCE: 51

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Arg Arg Glu Asp Lys Asp Ser
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Cys Asp Tyr Trp Ile
65                  70                  75                  80

Arg Thr Phe Val Pro Gly Ser Gln Pro Gly Glu Phe Thr Leu Gly Asn
                85                  90                  95

Thr Lys Gly Tyr Pro Gly Leu Thr Ser Tyr Leu Val Arg Val Val Ser
            100                 105                 110

Thr Asn Tyr Asn Gln Tyr Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Ala Pro Ile Asp Gln Cys Ile
                165                 170                 175

Asp Gly

<210> SEQ ID NO 52
<211> LENGTH: 181
<212> TYPE: PRT
<213> ORGANISM: Ochotona princeps

<400> SEQUENCE: 52

Gln Glu Leu Thr Thr Asp Leu Ile Pro Val Pro Ser Leu Arg Lys Ile
1               5                   10                  15

His Val Gln Lys Asn Phe Gln Ser Asp Gln Phe Gln Gly Lys Trp Tyr
            20                  25                  30

Val Val Gly Leu Ala Gly Asn Asn Ile His Asn Ser Asp Gln Glu His
        35                  40                  45

Gln Gln Met Tyr Ser Thr Thr Tyr Glu Leu Lys Glu Asp Gly Ser Tyr
    50                  55                  60

Asn Val Thr Ser Thr Leu Leu Arg Gln Arg Asn Gln Gln Cys Asp His
65                  70                  75                  80

Trp Ile Arg Thr Phe Val Pro Gly Ser Lys Leu Gly His Phe Asn Leu
                85                  90                  95

Gly Asn Ile Lys Ser Tyr Pro Thr Leu Lys Ser Tyr Leu Ile Arg Val
            100                 105                 110

Val Thr Thr Asp Tyr Asn Gln Phe Ala Ile Val Phe Phe Arg Lys Val
        115                 120                 125

Tyr Lys Asn Asn Lys Lys Phe Phe Lys Ile Val Leu Tyr Gly Arg Thr
    130                 135                 140

Lys Glu Leu Ser Pro Glu Leu Arg Gly Arg Phe Thr Ser Phe Ala Lys
145                 150                 155                 160

Thr Leu Gly Leu Thr Asp Asn His Ile Val Phe Pro Ala Pro Ile Gly
                165                 170                 175

```
Gln Cys Ile Asp Asp
            180

<210> SEQ ID NO 53
<211> LENGTH: 178
<212> TYPE: PRT
<213> ORGANISM: Loxodonta africana

<400> SEQUENCE: 53

Gln Thr His Ser Pro Thr Leu Ile Pro Ala Pro Pro Leu Leu Arg Val
1               5                   10                  15

Pro Leu Gln Pro Asp Phe Gln Asp Lys Phe Gln Gly Lys Trp Tyr
            20                  25                  30

Val Ile Gly Leu Ala Gly Asn Ala Val Glu Lys Lys Glu Gln Gly Gln
        35                  40                  45

Phe Lys Met Tyr Thr Thr Thr Tyr Glu Leu Lys Glu Asp Gly Ser Tyr
    50                  55                  60

Asn Val Thr Ser Thr Leu Leu Gln Glu Asp Gly Lys Cys Ser Tyr Trp
65                  70                  75                  80

Ile Arg Thr Phe Val Pro Ser Phe Gln Pro Gly Gln Phe Asn Leu Gly
                85                  90                  95

Asn Ile Lys Asn Phe Pro Gly Leu Gln Ser Tyr Thr Val Arg Val Thr
            100                 105                 110

Ala Thr Asn Tyr Asn Gln Phe Ala Ile Val Phe Phe Lys Lys Val Ser
        115                 120                 125

Lys Asn Gly Glu Tyr Phe Lys Thr Thr Leu Tyr Gly Arg Thr Lys Glu
    130                 135                 140

Leu Thr Pro Glu Leu Lys Glu Arg Phe Ile Arg Phe Ala Lys Ser Leu
145                 150                 155                 160

Gly Leu Ser Asp His Ile Ile Phe Pro Val Pro Ile Asp Arg Cys Ile
                165                 170                 175

Asp Asp

<210> SEQ ID NO 54
<211> LENGTH: 178
<212> TYPE: PRT
<213> ORGANISM: Oryctolagus cuniculus

<400> SEQUENCE: 54

Gln Asp Pro Thr Pro Lys Leu Ile Pro Ala Pro Ser Leu Arg Arg Val
1               5                   10                  15

Pro Leu Gln Arg Asn Phe Gln Asp Glu Gln Phe Gln Gly Lys Trp Tyr
            20                  25                  30

Val Val Gly Leu Ala Gly Asn Ala Val Gln Lys Arg Glu Glu Gly Gln
        35                  40                  45

Glu Pro Met Tyr Ser Thr Thr Tyr Glu Leu Asn Glu Asp Arg Ser Phe
    50                  55                  60

Asn Val Thr Ser Thr Leu Leu Arg Asp Gln Arg Cys Asp His Trp Ile
65                  70                  75                  80

Arg Thr Phe Val Pro Thr Ser Arg Pro Gly Gln Tyr Asn Leu Gly Asn
                85                  90                  95

Ile Lys Ser Tyr Pro Gly Val Lys Asn Tyr Ile Val Arg Val Val Ala
            100                 105                 110

Thr Asp Tyr Ser Gln Tyr Ala Met Met Phe Phe Arg Lys Gly Ser Arg
        115                 120                 125

Asn Lys Gln Phe Phe Lys Thr Thr Leu Tyr Gly Arg Thr Lys Glu Leu
```

Ser Pro Glu Leu Arg Glu Arg Phe Thr Arg Phe Ala Lys Ser Leu Gly
145                 150                 155                 160

Leu Pro Asp Asp Arg Ile Val Phe Pro Thr Pro Ile Asp Gln Cys Ile
                165                 170                 175

Asp Asp

<210> SEQ ID NO 55
<211> LENGTH: 997
<212> TYPE: DNA
<213> ORGANISM: artificial
<220> FEATURE:
<223> OTHER INFORMATION: Murine Scn construct for downstream viral
      fusions: IgK-H6-murineScn-StrepII-GGGGS-E7.16

<400> SEQUENCE: 55

```
ctcgagacca tggagaccga cacgctcttg ttgtgggttc tcttgttgtg ggtgcctggg    60
tctacaggcg accaccacca tcatcaccac ctcgttccta gaggcagcca ggatagtacc   120
cagaatctta tcccagcacc atctttgctc acagtaccat gcaacccga ctttcggtct    180
gatcaatttc ggggacgctg gtacgtggtt ggactggccg gcaatgctgt acagaaaaaa   240
acagagggca gtttcaccat gtactcaaca atctatgagc tccaagagaa taatagttac   300
aacgttacct ccatcttggt gagggaccag gatcagggat gtcgctactg gattcggaca   360
ttcgtaccaa gttctcgggc cggtcagttt actctgggca acatgcacag gtatccccaa   420
gttcaatctt acaacgtgca ggtggcgact accgactaca accaattcgc tatggtgttc   480
ttccgcaaaa caagcgagaa caagcagtat tttaaaatca ctctgtacgg tagaactaag   540
gagctgagcc tgaacttaa ggagcggttc accagattcg ctaagtccct gggactgaag    600
gatgataata taatctttc cgtccccacc gatcagtgta tcgataattc agcttggtca    660
catccccagt tcgagaaagg aggcggtgga tccatgcatg cgacactcc gaccctgcac    720
gaatacatgc tggacctgca gcccgaaacc actgacctgt attgttacga gcaactcaac   780
gattctagcg aggaggagga cgagatcgat ggaccggcag ccaggccga ccagaccgc    840
gcacattata acattgttac cttctgttgc aaatgtgatt caactcttag actttgtgtc   900
cagagtacac acgtggacat ccgcaccctg gaagatctgc tgatgggaac tctgggtatc   960
gtgtgtccta tatgtagcca gaaaccctga cggaccg                           997
```

<210> SEQ ID NO 56
<211> LENGTH: 326
<212> TYPE: PRT
<213> ORGANISM: artificial
<220> FEATURE:
<223> OTHER INFORMATION: IgK-H6-murineScn-StrepII-GGGGS-E7.16

<400> SEQUENCE: 56

Met Glu Thr Asp Thr Leu Leu Leu Trp Val Leu Leu Leu Trp Val Pro
1               5                   10                  15

Gly Ser Thr Gly Asp His His His His His His Leu Val Pro Arg Gly
            20                  25                  30

Ser Gln Asp Ser Thr Gln Asn Leu Ile Pro Ala Pro Ser Leu Leu Thr
        35                  40                  45

Val Pro Leu Gln Pro Asp Phe Arg Ser Asp Gln Phe Arg Gly Arg Trp
    50                  55                  60

Tyr Val Val Gly Leu Ala Gly Asn Ala Val Gln Lys Lys Thr Glu Gly
65                  70                  75                  80

Ser Phe Thr Met Tyr Ser Thr Ile Tyr Glu Leu Gln Glu Asn Asn Ser
            85                  90                  95

Tyr Asn Val Thr Ser Ile Leu Val Arg Asp Gln Asp Gln Gly Cys Arg
            100                 105                 110

Tyr Trp Ile Arg Thr Phe Val Pro Ser Arg Ala Gly Gln Phe Thr
            115                 120                 125

Leu Gly Asn Met His Arg Tyr Pro Gln Val Gln Ser Tyr Asn Val Gln
            130                 135                 140

Val Ala Thr Thr Asp Tyr Asn Gln Phe Ala Met Val Phe Arg Lys
145                 150                 155                 160

Thr Ser Glu Asn Lys Gln Tyr Phe Lys Ile Thr Leu Tyr Gly Arg Thr
            165                 170                 175

Lys Glu Leu Ser Pro Glu Leu Lys Glu Arg Phe Thr Arg Phe Ala Lys
            180                 185                 190

Ser Leu Gly Leu Lys Asp Asp Asn Ile Ile Phe Ser Val Pro Thr Asp
            195                 200                 205

Gln Cys Ile Asp Asn Ser Ala Trp Ser His Pro Gln Phe Glu Lys Gly
            210                 215                 220

Gly Gly Gly Ser Met His Gly Asp Thr Pro Thr Leu His Glu Tyr Met
225                 230                 235                 240

Leu Asp Leu Gln Pro Glu Thr Thr Asp Leu Tyr Cys Tyr Glu Gln Leu
            245                 250                 255

Asn Asp Ser Ser Glu Glu Glu Asp Glu Ile Asp Gly Pro Ala Gly Gln
            260                 265                 270

Ala Glu Pro Asp Arg Ala His Tyr Asn Ile Val Thr Phe Cys Cys Lys
            275                 280                 285

Cys Asp Ser Thr Leu Arg Leu Cys Val Gln Ser Thr His Val Asp Ile
            290                 295                 300

Arg Thr Leu Glu Asp Leu Leu Met Gly Thr Leu Gly Ile Val Cys Pro
305                 310                 315                 320

Ile Cys Ser Gln Lys Pro
            325

<210> SEQ ID NO 57
<211> LENGTH: 1189
<212> TYPE: DNA
<213> ORGANISM: artificial
<220> FEATURE:
<223> OTHER INFORMATION: IgK-H6-murineScn-StrepII-GGGGS-E6.16

<400> SEQUENCE: 57
ctcgagacca tggagaccga cacgctcttg ttgtgggttc tcttgttgtg ggtgcctggg    60
tctacaggcg accaccacca tcatcaccac ctcgttccta gaggcagcca ggatagtacc   120
cagaatctta tcccagcacc atctttgctc acagtaccat gcaacccga ctttcggtct    180
gatcaatttc gggacgctg gtacgtggtt ggactggccg gcaatgctgt acagaaaaaa    240
acagagggca gtttcaccat gtactcaaca atctatgagc tccaagagaa taatagttac    300
aacgttacct ccatcttggt gagggaccag gatcagggat gtcgctactg gattcggaca    360
ttcgtaccaa gttctcgggc cggtcagttt actctgggca acatgcacag gtatccccaa    420
gttcaatctt acaacgtgca ggtggcgact accgactaca accaattcgc tatggtgttc    480
ttccgcaaaa caagcgagaa caagcagtat tttaaaatca ctctgtacgg tagaactaag    540
gagctgagcc ctgaacttaa ggagcggttc accagattcg ctaagtccct gggactgaag    600

-continued

| | |
|---|---|
| gatgataata taatctttc cgtccccacc gatcagtgta tcgataattc agcttggtca | 660 |
| catccccagt tcgagaaagg aggcggtgga tccatgcacc agaagagaac cgccatgttc | 720 |
| caggacccac aagagcggcc ccggaaactg ccccaactgt gcactgaatt gcagaccacc | 780 |
| atccacgaca tcattttgga atgtgtctac tgtaagcagc agctcctcag gcgagaggtg | 840 |
| tatgacttcg ccttccggga tttgtgtatt gtctacaggg atggtaatcc ctatgccgtt | 900 |
| tgtgataagt gcctgaaatt ttatagcaag atcagcgagt accgacatta ctgttacagc | 960 |
| gtttatggaa caacattgga gcagcagtac aacaaacctc tttgcgacct cctgattcgc | 1020 |
| tgcatcaact gccagaagcc cctgtgcccc aagagaaac aaaggcattt ggataagaag | 1080 |
| cagaggttcc acaacatccg cggtcgctgg acggggcgct gcatgagttg ctgcaggagt | 1140 |
| tcccgcactc ggcgcgagac ccaactctga cggaccgcct ctccctccc | 1189 |

<210> SEQ ID NO 58
<211> LENGTH: 1189
<212> TYPE: DNA
<213> ORGANISM: artificial
<220> FEATURE:
<223> OTHER INFORMATION: IgK-H6-murineScn-StrepII-GGGGS-E6.18

<400> SEQUENCE: 58

| | |
|---|---|
| ctcgagacca tggagaccga cacgctcttg ttgtgggttc tcttgttgtg ggtgcctggg | 60 |
| tctacaggcg accaccacca tcatcaccac ctcgttccta gaggcagcca ggatagtacc | 120 |
| cagaatctta tcccagcacc atctttgctc acagtaccat tgcaacccga ctttcggtct | 180 |
| gatcaatttc ggggacgctg gtacgtggtt ggactggccg gcaatgctgt acagaaaaaa | 240 |
| acagagggca gtttcaccat gtactcaaca atctatgagc tccaagagaa taatagttac | 300 |
| aacgttacct ccatcttggt gagggaccag gatcagggat gtcgctactg gattcggaca | 360 |
| ttcgtaccaa gttctcgggc cggtcagttt actctgggca acatgcacag gtatccccaa | 420 |
| gttcaatctt acaacgtgca ggtggcgact accgactaca accaattcgc tatggtgttc | 480 |
| ttccgcaaaa caagcgagaa caagcagtat tttaaaatca ctctgtacgg tagaactaag | 540 |
| gagctgagcc ctgaacttaa ggagcggttc accagattcg ctaagtccct gggactgaag | 600 |
| gatgataata taatctttc cgtccccacc gatcagtgta tcgataattc agcttggtca | 660 |
| catccccagt tcgagaaagg aggcggtgga tccatggcca gatttgaaga ccccacaagg | 720 |
| cgcccctata aactgccgga tctttgcacc gaactgaata ctagcctgca agatattgag | 780 |
| attacctgcg tgtactgtaa aacggtgctc gaattgaccg aggttttga gttcgcattc | 840 |
| aaggacctgt tgttgtata tcgcgattcc atcccgcacg cagcttgcca taaatgcatt | 900 |
| gacttttact cccggatacg cgagctgcga cactatagtg atagcgtgta cggcgataca | 960 |
| cttgagaagc ttaccaacac cggtctgtac aatcttctga ttcggtgttt gaggtgccag | 1020 |
| aagccgctca acccagctga gaaactgcgg catctgaacg aaaaaagaag attccacaac | 1080 |
| attgctggcc actacagggg ccagtgccat tcttgttgta atagagcaag gcaggagcgg | 1140 |
| ctgcaacggc ggcgcgagac ccaggtatga cggaccgcct ctccctccc | 1189 |

<210> SEQ ID NO 59
<211> LENGTH: 1030
<212> TYPE: DNA
<213> ORGANISM: artificial
<220> FEATURE:
<223> OTHER INFORMATION: IgK-H6-murineScn-StrepII-GGGGS-E7.18

<400> SEQUENCE: 59

-continued

```
ctcgagacca tggagaccga cacgctcttg ttgtgggttc tcttgttgtg ggtgcctggg      60
tctacaggcg accaccacca tcatcaccac ctcgttccta gaggcagcca ggatagtacc     120
cagaatctta tcccagcacc atctttgctc acagtaccat tgcaacccga ctttcggtct     180
gatcaatttc ggggacgctg gtacgtggtt ggactggccg gcaatgctgt acagaaaaaa     240
acagagggca gtttcaccat gtactcaaca atctatgagc tccaagagaa taatagttac     300
aacgttacct ccatcttggt gagggaccag gatcagggat gtcgctactg gattcggaca     360
ttcgtaccaa gttctcgggc cggtcagttt actctgggca acatgcacag gtatccccaa     420
gttcaatctt acaacgtgca ggtggcgact accgactaca accaattcgc tatggtgttc     480
ttccgcaaaa caagcgagaa caagcagtat tttaaaatca ctctgtacgg tagaactaag     540
gagctgagcc ctgaacttaa ggagcggttc accagattcg ctaagtccct gggactgaag     600
gatgataata taatcttttc cgtccccacc gatcagtgta tcgataattc agcttggtca     660
catccccagt tcgagaaagg aggcggtgga tccatgcacg gacctaaagc aacactccag     720
gacatcgtcc tgcatttgga accacaaaac gaaatacccg tggaccttttt gtgtcacgaa     780
cagcttttcag attctgagga agagaatgat gaaatcgacg gtgtcaacca ccagcatctc     840
cccgctaggc gggcagaacc ccagcgccac acaatgctgt gcatgtgttg caaatgcgaa     900
gctcgaattg aactcgtggt tgagtcctcc gcggacgact tgagggcatt ccagcaactg     960
ttcctcaaca cactgagctt tgtctgtcct tggtgcgcta gtcagcagtg acggaccgcc    1020
tctccctccc                                                           1030
```

<210> SEQ ID NO 60
<211> LENGTH: 1162
<212> TYPE: DNA
<213> ORGANISM: artificial
<220> FEATURE:
<223> OTHER INFORMATION: IgK-H6-murineScn-StrepII-GGGGS-E6.33

<400> SEQUENCE: 60

```
ctcgagacca tggagaccga cacgctcttg ttgtgggttc tcttgttgtg ggtgcctggg      60
tctacaggcg accaccacca tcatcaccac ctcgttccta gaggcagcca ggatagtacc     120
cagaatctta tcccagcacc atctttgctc acagtaccat tgcaacccga ctttcggtct     180
gatcaatttc ggggacgctg gtacgtggtt ggactggccg gcaatgctgt acagaaaaaa     240
acagagggca gtttcaccat gtactcaaca atctatgagc tccaagagaa taatagttac     300
aacgttacct ccatcttggt gagggaccag gatcagggat gtcgctactg gattcggaca     360
ttcgtaccaa gttctcgggc cggtcagttt actctgggca acatgcacag gtatccccaa     420
gttcaatctt acaacgtgca ggtggcgact accgactaca accaattcgc tatggtgttc     480
ttccgcaaaa caagcgagaa caagcagtat tttaaaatca ctctgtacgg tagaactaag     540
gagctgagcc ctgaacttaa ggagcggttc accagattcg ctaagtccct gggactgaag     600
gatgataata taatcttttc cgtccccacc gatcagtgta tcgataattc agcttggtca     660
catccccagt tcgagaaagg aggcggtgga tccatgttcc aagacactga ggagaagcca     720
cgcacgctgc acgatctgtg ccaggccctt gagactacca tccataacat cgagctccag     780
tgtgtcgaat gcaggaatcc tcttcagcgg agcgaggtgt acgattttgc cttcgcggac     840
ctgacggtgg tctaccggga aggtaaccca ttcgggattt gcaagctgtg tctcagattt    900
cttagtaaga taagtgaata ccggcactac aactattcag tttacggtca cactctggaa    960
```

```
cagaccgtga acaaacccct gaacgagatc ctcattcgat gtatcatctg tcagagacct    1020
ctctgtccgc gcgaaaagaa gaggcacgtc gacctgaata agcgatttca taatatctct    1080
ggacggtggg cggggcgctg tgcagcctgt tggagatccc ggagacggga aacagctctt    1140
tgacggaccg cctctccctc cc                                             1162

<210> SEQ ID NO 61
<211> LENGTH: 1007
<212> TYPE: DNA
<213> ORGANISM: artificial
<220> FEATURE:
<223> OTHER INFORMATION: IgK-H6-murineScn-StrepII-GGGGS-E7.33

<400> SEQUENCE: 61
ctcgagacca tggagaccga cacgctcttg ttgtgggttc tcttgttgtg ggtgcctggg      60
tctacaggcg accaccacca tcatcaccac ctcgttccta gaggcagcca ggatagtacc     120
cagaatctta tcccagcacc atctttgctc acagtaccat gcaacccga ctttcggtct     180 gatcaatttc ggggacgctg gtacgtggtt ggactggccg gcaatgctgt acagaaaaaa    240
acagagggca gtttcaccat gtactcaaca atctatgagc tccaagagaa taatagttac    300
aacgttacct ccatcttggt gagggaccag gatcagggat gtcgctactg gattcggaca    360
ttcgtaccaa gttctcgggc cggtcagttt actctgggca acatgcacag gtatccccaa    420
gttcaatctt acaacgtgca ggtggcgact accgactaca accaattcgc tatggtgttc    480
ttccgcaaaa caagcgagaa caagcagtat tttaaaatca ctctgtacgg tagaactaag    540
gagctgagcc ctgaacttaa ggagcggttc accagattcg ctaagtccct gggactgaag    600
gatgataata taatctttc cgtccccacc gatcagtgta tcgataattc agcttggtca    660
catccccagt tcgagaaagg aggcggtgga tccatgcggg acatgaacc tactctgaag    720 gagtacgtcc tggacctta cccggagccg acagatcttt actgttacga gcaattgtct    780
gactccagcg acgaggatga gggccttgac agacctgatg gccaggctca gccagctact    840
gccgattatt atatcgttac gtgttgtcac acctgcaaca caaccgtaag gttgtgtgtg    900
aactccaccg ccagtgactt gagaacgata caacaactcc tcatgggcac tgtcaatatc    960
gtctgtccta catgtgctca gctgctgacg gaccgcctct ccctccc              1007

<210> SEQ ID NO 62
<211> LENGTH: 1189
<212> TYPE: DNA
<213> ORGANISM: artificial
<220> FEATURE:
<223> OTHER INFORMATION: IgK-H6-murineScn-StrepII-GGGGS-E6.45

<400> SEQUENCE: 62
ctcgagacca tggagaccga cacgctcttg ttgtgggttc tcttgttgtg ggtgcctggg      60
tctacaggcg accaccacca tcatcaccac ctcgttccta gaggcagcca ggatagtacc     120
cagaatctta tcccagcacc atctttgctc acagtaccat gcaacccga ctttcggtct     180 gatcaatttc ggggacgctg gtacgtggtt ggactggccg gcaatgctgt acagaaaaaa    240
acagagggca gtttcaccat gtactcaaca atctatgagc tccaagagaa taatagttac    300
aacgttacct ccatcttggt gagggaccag gatcagggat gtcgctactg gattcggaca    360
ttcgtaccaa gttctcgggc cggtcagttt actctgggca acatgcacag gtatccccaa    420
gttcaatctt acaacgtgca ggtggcgact accgactaca accaattcgc tatggtgttc    480
ttccgcaaaa caagcgagaa caagcagtat tttaaaatca ctctgtacgg tagaactaag    540
```

```
gagctgagcc ctgaacttaa ggagcggttc accagattcg ctaagtccct gggactgaag    600
gatgataata taatctttc cgtccccacc gatcagtgta tcgataattc agcttggtca    660
catccccagt tcgagaaagg aggcggtgga tccatggcca ggttcgatga tcccacccag    720
cgaccctata agttgcccga tctctgcaca gaacttaaca ctagcttgca ggacgtaagc    780
attgcatgtg tttactgtaa agctacgctg gagcgaaccg aggtgtacca attcgccttc    840
aaagacttgt tcatcgtgta tagagactgt atcgcttatg ccgcctgcca caaatgcata    900 gactttaca gcaggatcag ggaattgagg tactattcca actcagtcta tggagaaacg    960
ctggagaaga taactaacac tgagctttat aacctcctga ttcgctgcct ccggtgtcag    1020
aagccactga atcctgccga aaagagacgc catctgaagg acaagcggcg ctttcatagc    1080
attgcaggac agtacagagg ccaatgtaat acttgctgtg accaagcacg ccaagaaagg    1140
ctcaggagaa ggagagagac acaggtgtga cggaccgcct ctccctccc                1189

<210> SEQ ID NO 63
<211> LENGTH: 1033
<212> TYPE: DNA
<213> ORGANISM: artificial
<220> FEATURE:
<223> OTHER INFORMATION: IgK-H6-murineScn-StrepII-GGGGS-E7.45

<400> SEQUENCE: 63
ctcgagacca tggagaccga cacgctcttg ttgtgggttc tcttgttgtg ggtgcctggg     60
tctacaggcg accaccacca tcatcaccac ctcgttccta gaggcagcca ggatagtacc    120
cagaatctta tcccagcacc atctttgctc acagtaccat gcaacccga ctttcggtct    180 gatcaatttc ggggacgctg gtacgtggtt ggactggccg gcaatgctgt acagaaaaaa    240
acagagggca gtttcaccat gtactcaaca atctatgagc tccaagagaa taatagttac    300 aacgttaccct ccatcttggt gagggaccag gatcagggat gtcgctactg gattcggaca    360
ttcgtaccaa gttctcgggc cggtcagttt actctgggca catgcacag gtatccccaa    420 gttcaatctt acaacgtgca ggtggcgact accgactaca accaattcgc tatggtgttc    480
ttccgcaaaa caagcgagaa caagcagtat tttaaaatca ctctgtacgg tagaactaag    540
gagctgagcc ctgaacttaa ggagcggttc accagattcg ctaagtccct gggactgaag    600
gatgataata taatctttc cgtccccacc gatcagtgta tcgataattc agcttggtca    660
catccccagt tcgagaaagg aggcggtgga tccatgcacg gcccacaggc aaccctgcaa    720
gagatcgtgc tgcatctcga accacagaat gaattggacc ctgtggatct gctgtgttac    780
gagcagctct ctgaaagcga agaggagaat gacgaggccg acggcgtgtc tcatgcacag    840
ctgcctgctc gccgggccga acctcagcga cacaaaattc tgtgcgtgtg ctgcaaatgc    900
gacggccgca tagagctgac ggtagaatca tcagccgacg atctgcgaac tcttcaacaa    960
ctcttcctga gcacgctcag cttcgtgtgt ccttggtgtg ctacaaatca gtgacggacc    1020
gcctctccct ccc                                                        1033

<210> SEQ ID NO 64
<211> LENGTH: 1162
<212> TYPE: PRT
<213> ORGANISM: artificial
<220> FEATURE:
<223> OTHER INFORMATION: IgK-H6-murineScn-StrepII-GGGGS-E6.31

<400> SEQUENCE: 64
```

-continued

```
Cys Thr Cys Gly Ala Gly Ala Cys Cys Ala Thr Gly Gly Ala Gly Ala
1               5                   10                  15
Cys Cys Gly Ala Cys Ala Cys Gly Cys Thr Cys Thr Thr Gly Thr Thr
            20                  25                  30
Gly Thr Gly Gly Thr Thr Cys Thr Cys Thr Thr Gly Thr Thr Thr Gly
        35                  40                  45
Thr Gly Gly Gly Thr Gly Cys Cys Thr Gly Gly Thr Cys Thr Ala
    50                  55                  60
Cys Ala Gly Gly Cys Gly Ala Cys Cys Ala Cys Ala Cys Cys Ala
65                  70                  75                  80
Thr Cys Ala Thr Cys Ala Cys Cys Ala Cys Thr Cys Gly Thr Thr
            85                  90                  95
Cys Cys Thr Ala Gly Ala Gly Gly Cys Ala Gly Cys Cys Ala Gly Gly
            100                 105                 110
Ala Thr Ala Gly Thr Ala Cys Cys Ala Gly Ala Ala Thr Cys Thr
        115                 120                 125
Thr Ala Thr Cys Cys Ala Gly Cys Ala Cys Cys Ala Thr Cys Thr
    130                 135                 140
Thr Thr Gly Cys Thr Cys Ala Cys Ala Gly Thr Ala Cys Cys Ala Thr
145                 150                 155                 160
Thr Gly Cys Ala Ala Cys Cys Gly Ala Cys Thr Thr Cys Gly
        165                 170                 175
Gly Thr Cys Thr Gly Ala Thr Cys Ala Ala Thr Thr Cys Gly Gly
            180                 185                 190
Gly Gly Ala Cys Gly Cys Thr Gly Gly Thr Ala Cys Gly Thr Gly Gly
            195                 200                 205
Thr Thr Gly Gly Ala Cys Thr Gly Gly Cys Cys Gly Gly Cys Ala Ala
    210                 215                 220
Thr Gly Cys Thr Gly Thr Ala Cys Ala Gly Ala Ala Ala Ala Ala
225             230                 235                 240
Ala Cys Ala Gly Ala Gly Gly Cys Ala Gly Thr Thr Thr Cys Ala
            245                 250                 255
Cys Cys Ala Thr Gly Thr Ala Cys Thr Cys Ala Ala Cys Ala Ala Thr
            260                 265                 270
Cys Thr Ala Thr Gly Ala Gly Cys Thr Cys Cys Ala Ala Gly Ala Gly
        275                 280                 285
Ala Ala Thr Ala Ala Thr Ala Gly Thr Thr Ala Cys Ala Ala Cys Gly
        290                 295                 300
Thr Thr Ala Cys Cys Thr Cys Cys Ala Thr Cys Thr Thr Gly Gly Thr
305             310                 315                 320
Gly Ala Gly Gly Gly Ala Cys Cys Ala Gly Gly Ala Thr Cys Ala Gly
            325                 330                 335
Gly Gly Ala Thr Gly Thr Cys Gly Cys Thr Ala Cys Thr Gly Gly Ala
        340                 345                 350
Thr Thr Cys Gly Gly Ala Cys Ala Thr Cys Gly Thr Ala Cys Cys
    355                 360                 365
Ala Ala Gly Thr Thr Cys Thr Cys Gly Gly Gly Cys Cys Gly Gly Thr
        370                 375                 380
Cys Ala Gly Thr Thr Thr Ala Cys Thr Cys Gly Gly Gly Cys Ala
385                 390                 395                 400
Ala Cys Ala Thr Gly Cys Ala Cys Ala Gly Gly Thr Ala Thr Cys Cys
            405                 410                 415
Cys Cys Ala Ala Gly Thr Thr Cys Ala Ala Thr Cys Thr Thr Ala Cys
```

-continued

```
                420                 425                 430
Ala Ala Cys Gly Thr Gly Cys Ala Gly Gly Thr Gly Cys Gly Ala
            435                 440                 445
Cys Thr Ala Cys Cys Gly Ala Cys Thr Ala Cys Ala Ala Cys Cys Ala
            450                 455                 460
Ala Thr Thr Cys Gly Cys Thr Ala Thr Gly Gly Thr Gly Thr Thr Cys
465                 470                 475                 480
Thr Thr Cys Cys Gly Cys Ala Ala Ala Cys Ala Ala Gly Cys Gly
                485                 490                 495
Ala Gly Ala Ala Cys Ala Ala Gly Cys Ala Gly Thr Ala Thr Thr
                500                 505                 510
Thr Ala Ala Ala Thr Cys Ala Cys Thr Cys Thr Gly Thr Ala Cys
            515                 520                 525
Gly Gly Thr Ala Gly Ala Ala Cys Thr Ala Ala Gly Gly Ala Gly Cys
            530                 535                 540
Thr Gly Ala Gly Cys Cys Cys Thr Gly Ala Ala Cys Thr Thr Ala Ala
545                 550                 555                 560
Gly Gly Ala Gly Cys Gly Gly Thr Thr Cys Ala Cys Cys Ala Gly Ala
                565                 570                 575
Thr Thr Cys Gly Cys Thr Ala Ala Gly Thr Cys Cys Cys Thr Gly Gly
                580                 585                 590
Gly Ala Cys Thr Gly Ala Ala Gly Gly Ala Thr Gly Ala Thr Ala Ala
                595                 600                 605
Thr Ala Thr Ala Ala Thr Cys Thr Thr Thr Thr Cys Cys Gly Thr Cys
            610                 615                 620
Cys Cys Cys Ala Cys Cys Gly Ala Thr Cys Ala Gly Thr Gly Thr Ala
625                 630                 635                 640
Thr Cys Gly Ala Thr Ala Ala Thr Cys Ala Gly Cys Thr Thr Gly
                645                 650                 655
Gly Thr Cys Ala Cys Ala Thr Cys Cys Cys Cys Ala Gly Thr Thr Cys
                660                 665                 670
Gly Ala Gly Ala Ala Ala Gly Gly Ala Gly Gly Cys Gly Gly Thr Gly
            675                 680                 685
Gly Ala Thr Cys Cys Ala Thr Gly Thr Thr Cys Ala Ala Ala Ala
            690                 695                 700
Cys Cys Cys Gly Gly Cys Thr Gly Ala Gly Ala Gly Ala Cys Cys Gly
705                 710                 715                 720
Cys Gly Gly Ala Ala Gly Thr Thr Gly Cys Ala Cys Gly Ala Gly Cys
                725                 730                 735
Thr Cys Thr Cys Ala Thr Cys Cys Gly Cys Gly Cys Thr Gly Gly Ala
            740                 745                 750
Ala Ala Thr Ala Cys Cys Thr Thr Ala Thr Gly Ala Thr Gly Ala Gly
            755                 760                 765
Cys Thr Thr Cys Gly Cys Thr Thr Gly Ala Ala Thr Thr Gly Thr Gly
            770                 775                 780
Thr Gly Thr Ala Cys Thr Gly Cys Ala Ala Ala Gly Gly Cys Cys Ala
785                 790                 795                 800
Gly Cys Thr Cys Ala Cys Thr Gly Ala Gly Ala Cys Cys Gly Ala Ala
                805                 810                 815
Gly Thr Ala Cys Thr Thr Gly Ala Thr Thr Thr Gly Cys Cys Thr
            820                 825                 830
Thr Thr Ala Cys Thr Gly Ala Cys Cys Thr Gly Ala Cys Ala Ala Thr
            835                 840                 845
```

Cys Gly Thr Cys Thr Ala Thr Gly Ala Gly Ala Cys Gly Ala Cys
              850                 855                 860
Ala Cys Thr Cys Cys Ala Cys Ala Cys Gly Gly Gly Thr Cys Thr
865                 870                 875                 880
Gly Thr Ala Cys Ala Ala Ala Thr Gly Thr Cys Thr Gly Cys Gly
                885                 890                 895
Gly Thr Thr Thr Thr Ala Thr Ala Gly Thr Ala Ala Gly Thr Gly
                900                 905                 910
Ala Gly Cys Gly Ala Ala Thr Thr Cys Cys Gly Gly Thr Gly Thr
                915                 920                 925
Ala Thr Cys Gly Cys Thr Ala Thr Thr Cys Ala Gly Thr Gly Thr Ala
    930                 935                 940
Thr Gly Gly Ala Ala Cys Cys Ala Cys Ala Thr Thr Gly Gly Ala Gly
945                 950                 955                 960
Ala Ala Ala Cys Thr Cys Ala Cys Thr Ala Cys Ala Ala Ala Gly
                965                 970                 975
Gly Thr Ala Thr Cys Thr Gly Thr Gly Ala Cys Cys Thr Gly Cys Thr
    980                 985                 990
Gly Ala Thr Cys Ala Gly Gly Thr    Gly Cys Ala Thr Ala    Ala Cys Thr
        995                 1000                1005
Thr Gly Thr Cys Ala Gly Ala    Gly Gly Cys Cys Gly    Cys Thr Cys
    1010                1015                    1020
Thr Gly Cys Cys Cys Gly    Ala Gly Gly Ala Gly    Ala Ala Gly
1025                1030                    1035
Cys Ala    Gly Cys Gly Cys Cys    Ala Cys Cys Thr Gly    Gly Ala Thr
1040                1045                    1050
Ala Ala    Gly Ala Ala Gly Ala    Ala Gly Ala Gly Ala    Thr Thr Cys
1055                1060                    1065
Cys Ala Cys Ala Ala Cys Ala    Thr Thr Gly Gly Ala    Gly Gly Cys
1070                1075                    1080
Ala Gly    Ala Thr Gly Gly Ala    Cys Ala Gly Gly Cys    Cys Gly Gly
1085                1090                    1095
Thr Gly    Cys Ala Thr Thr Gly    Cys Thr Thr Gly Thr    Thr Gly Gly
1100                1105                    1110
Cys Gly    Cys Ala Gly Gly Cys    Cys Ala Ala Gly Ala    Ala Cys Cys
1115                1120                    1125
Gly Ala    Gly Ala Cys Cys Cys    Ala Ala Gly Thr Thr    Thr Gly Ala
1130                1135                    1140
Cys Gly    Gly Ala Cys Cys Gly    Cys Cys Thr Cys Thr    Cys Cys Cys
1145                1150                    1155
Thr Cys    Cys Cys
1160

<210> SEQ ID NO 65
<211> LENGTH: 1009
<212> TYPE: DNA
<213> ORGANISM: artificial
<220> FEATURE:
<223> OTHER INFORMATION: IgK-H6-murineScn-StrepII-GGGGS-E7.31

<400> SEQUENCE: 65
ctcgagacca tggagaccga cacgctcttg ttgtgggttc tcttgttgtg ggtgcctggg      60
tctacaggcg accaccacca tcatcaccac ctcgttccta gaggcagcca ggatagtacc     120
cagaatctta tcccagcacc atctttgctc acagtaccat gcaacccga ctttcggtct     180

```
gatcaatttc ggggacgctg gtacgtggtt ggactggccg gcaatgctgt acagaaaaaa      240
acagagggca gtttcaccat gtactcaaca atctatgagc tccaagagaa taatagttac      300
aacgttacct ccatcttggt gagggaccag gatcagggat gtcgctactg gattcggaca      360
ttcgtaccaa gttctcgggc cggtcagttt actctgggca acatgcacag gtatccccaa      420
gttcaatctt acaacgtgca ggtggcgact accgactaca accaattcgc tatggtgttc      480
ttccgcaaaa caagcgagaa caagcagtat tttaaaatca ctctgtacgg tagaactaag      540
gagctgagcc ctgaacttaa ggagcggttc accagattcg ctaagtccct gggactgaag      600
gatgataata taatcttttc cgtccccacc gatcagtgta tcgataattc agcttggtca      660
catccccagt tcgagaaagg aggcggtgga tccatgcggg gtgagacacc aactcttcag      720
gattatgttc tggatctgca gccagaggcc acagatctgc actgttacga gcaattgcct      780
gattccagcg acgaggagga tgtcatcgat agccctgctg ggcaggccaa gccagacact      840
tcaaattaca acattgtaac gttttgttgt cagtgcgaat ccaccctcag gctttgcgtc      900
cagagcactc aggttgacat tcgaatactc caggagctgt tgatggggag ctttggaatc      960
gtgtgcccaa attgtagtac acgactgtga cggaccgcct ctccctccc                 1009

<210> SEQ ID NO 66
<211> LENGTH: 1162
<212> TYPE: DNA
<213> ORGANISM: artificial
<220> FEATURE:
<223> OTHER INFORMATION: IgK-H6-murineScn-StrepII-GGGGS-E6.58

<400> SEQUENCE: 66
ctcgagacca tggagaccga cacgctcttg ttgtgggttc tcttgttgtg ggtgcctggg       60
tctacaggcg accaccacca tcatcaccac ctcgttccta gaggcagcca ggatagtacc      120
cagaatctta tcccagcacc atctttgctc acagtaccat gcaacccga ctttcggtct      180 gatcaatttc ggggacgctg gtacgtggtt ggactggccg gcaatgctgt acagaaaaaa      240
acagagggca gtttcaccat gtactcaaca atctatgagc tccaagagaa taatagttac      300
aacgttacct ccatcttggt gagggaccag gatcagggat gtcgctactg gattcggaca      360
ttcgtaccaa gttctcgggc cggtcagttt actctgggca acatgcacag gtatccccaa      420
gttcaatctt acaacgtgca ggtggcgact accgactaca accaattcgc tatggtgttc      480
ttccgcaaaa caagcgagaa caagcagtat tttaaaatca ctctgtacgg tagaactaag      540
gagctgagcc ctgaacttaa ggagcggttc accagattcg ctaagtccct gggactgaag      600
gatgataata taatcttttc cgtccccacc gatcagtgta tcgataattc agcttggtca      660
catccccagt tcgagaaagg aggcggtgga tccatgtttc aggacgctga ggagaagccc      720
agaactctgc acgatctgtg tcaggccttg agacgtctg tgcataaaat tgagcttaaa      780
tgtgtcgaat gtaagaagac actccagcgc agcgaagttt atgacttcgt gttcgcggat      840
ctgagaatcg tgtatcggga cggcaaccct tttgctgttt gcaaggtttg ccttaggctc      900
ctgtccaaaa ttagcgagta ccgccactat aactactctc tctacggtga tactctcgag      960
caaacactga agaagtgctt gaacgagatc ctgattagat gcatcatttg tcaaaggcca     1020
ctttgtccac aggagaagaa gaggcacgtg gacctgaata gcgctttca taacatctct     1080 ggcagatgga caggccgatg cgctgtatgt tggcgcccac ggagaaggca aacccaggtg     1140
tgacggaccg cctctccctc cc                                              1162
```

<210> SEQ ID NO 67
<211> LENGTH: 1009
<212> TYPE: DNA
<213> ORGANISM: artificial
<220> FEATURE:
<223> OTHER INFORMATION: IgK-H6-murineScn-StrepII-GGGGS-E7.58

<400> SEQUENCE: 67

| | | | | |
|---|---|---|---|---|
| ctcgagacca tggagaccga cacgctcttg ttgtgggttc tcttgttgtg ggtgcctggg | 60 |
| tctacaggcg accaccacca tcatcaccac ctcgttccta gaggcagcca ggatagtacc | 120 |
| cagaatctta tcccagcacc atctttgctc acagtaccat gcaacccga ctttcggtct | 180 |
| gatcaatttc ggggacgctg gtacgtggtt ggactggccg gcaatgctgt acagaaaaaa | 240 |
| acagagggca gtttcaccat gtactcaaca atctatgagc tccaagagaa taatagttac | 300 |
| aacgttacct ccatcttggt gagggaccag gatcagggat gtcgctactg gattcggaca | 360 |
| ttcgtaccaa gttctcgggc cggtcagttt actctgggca acatgcacag gtatccccaa | 420 |
| gttcaatctt acaacgtgca ggtggcgact accgactaca accaattcgc tatggtgttc | 480 |
| ttccgcaaaa caagcgagaa caagcagtat tttaaaatca ctctgtacgg tagaactaag | 540 |
| gagctgagcc ctgaacttaa ggagcggttc accagattcg ctaagtccct gggactgaag | 600 |
| gatgataata taatctttc cgtccccacc gatcagtgta tcgataattc agcttggtca | 660 |
| catccccagt tcgagaaagg aggcggtgga tccatgcggg ggaataaccc caccctgcgc | 720 |
| gagtacattc ttgacctgca cccagagcct acggatctgt tttgttacga caactgtgc | 780 |
| gactcctccg acgaggatga gatcgggctg atggcccag acgggcaggc acagcctgct | 840 |
| acagctaact actatattgt gacatgttgc tacacatgcg gaacgacggt cagactgtgc | 900 |
| attaatagca ctgccacaga cgtgcggacc ctgcagcaac tgctcatggg gacctgcact | 960 |
| attgtgtgtc cttcatgtgc gcagcaatga cggaccgcct ctccctccc | 1009 |

<210> SEQ ID NO 68
<211> LENGTH: 319
<212> TYPE: PRT
<213> ORGANISM: artificial
<220> FEATURE:
<223> OTHER INFORMATION: IgK-sFLAG-H6-GGS-humanScn-GGS-ENLYFQ-GG-
    Adv2E3/19K

<400> SEQUENCE: 68

Met Glu Thr Asp Thr Leu Leu Leu Trp Val Leu Leu Leu Trp Val Pro
1               5                   10                  15

Gly Ser Thr Gly Asp Tyr Lys Asp Glu His His His His His His Gly
                20                  25                  30

Gly Ser Gln Asp Ser Thr Ser Asp Leu Ile Pro Ala Pro Pro Leu Ser
            35                  40                  45

Lys Val Pro Leu Gln Gln Asn Phe Gln Asp Asn Gln Phe Gln Gly Lys
        50                  55                  60

Trp Tyr Val Val Gly Leu Ala Gly Asn Ala Ile Leu Arg Glu Asp Lys
65                  70                  75                  80

Asp Pro Gln Lys Met Tyr Ala Thr Ile Tyr Glu Leu Lys Glu Asp Lys
                85                  90                  95

Ser Tyr Asn Val Thr Ser Val Leu Phe Arg Lys Lys Lys Cys Asp Tyr
                100                 105                 110

Trp Ile Arg Thr Phe Val Pro Gly Ser Gln Pro Gly Glu Phe Thr Leu
            115                 120                 125

Gly Asn Ile Lys Ser Tyr Pro Gly Leu Thr Ser Tyr Leu Val Arg Val
            130                 135                 140

Val Ser Thr Asn Tyr Asn Gln His Ala Met Val Phe Lys Lys Val
145                 150                 155                 160

Ser Gln Asn Arg Glu Tyr Phe Lys Ile Thr Leu Tyr Gly Arg Thr Lys
                165                 170                 175

Glu Leu Thr Ser Glu Leu Lys Glu Asn Phe Ile Arg Phe Ser Lys Ser
            180                 185                 190

Leu Gly Leu Pro Glu Asn His Ile Val Phe Pro Val Pro Ile Asp Gln
        195                 200                 205

Cys Ile Asp Gly Gly Ser Glu Asn Leu Tyr Phe Gln Gly Gly Ala
210                 215                 220

Lys Lys Val Glu Phe Lys Glu Pro Ala Cys Asn Val Thr Phe Lys Ser
225                 230                 235                 240

Glu Ala Asn Glu Cys Thr Thr Leu Ile Lys Cys Thr Thr Glu His Glu
                245                 250                 255

Lys Leu Ile Ile Arg His Lys Asp Lys Ile Gly Lys Tyr Ala Val Tyr
            260                 265                 270

Ala Ile Trp Gln Pro Gly Asp Thr Asn Asp Tyr Asn Val Thr Val Phe
        275                 280                 285

Gln Gly Glu Asn Arg Lys Thr Phe Met Tyr Lys Phe Pro Phe Tyr Glu
    290                 295                 300

Met Cys Asp Ile Thr Met Tyr Met Ser Lys Gln Tyr Lys Leu Trp
305                 310                 315

<210> SEQ ID NO 69
<211> LENGTH: 704
<212> TYPE: PRT
<213> ORGANISM: artificial
<220> FEATURE:
<223> OTHER INFORMATION: IgK-sFLAG-H6-GGS-humanScn-GGS-ENLYFQ-GG-
      SF162gp120

<400> SEQUENCE: 69

Met Glu Thr Asp Thr Leu Leu Leu Trp Val Leu Leu Leu Trp Val Pro
1               5                   10                  15

Gly Ser Thr Gly Asp Tyr Lys Asp Glu His His His His His His Gly
            20                  25                  30

Gly Ser Gln Asp Ser Thr Ser Asp Leu Ile Pro Ala Pro Pro Leu Ser
        35                  40                  45

Lys Val Pro Leu Gln Gln Asn Phe Gln Asp Asn Gln Phe Gln Gly Lys
50                  55                  60

Trp Tyr Val Val Gly Leu Ala Gly Asn Ala Ile Leu Arg Glu Asp Lys
65                  70                  75                  80

Asp Pro Gln Lys Met Tyr Ala Thr Ile Tyr Glu Leu Lys Glu Asp Lys
                85                  90                  95

Ser Tyr Asn Val Thr Ser Val Leu Phe Arg Lys Lys Lys Cys Asp Tyr
            100                 105                 110

Trp Ile Arg Thr Phe Val Pro Gly Ser Gln Pro Gly Glu Phe Thr Leu
        115                 120                 125

Gly Asn Ile Lys Ser Tyr Pro Gly Leu Thr Ser Tyr Leu Val Arg Val
    130                 135                 140

Val Ser Thr Asn Tyr Asn Gln His Ala Met Val Phe Lys Lys Val
145                 150                 155                 160

Ser Gln Asn Arg Glu Tyr Phe Lys Ile Thr Leu Tyr Gly Arg Thr Lys
                165                 170                 175

```
Glu Leu Thr Ser Glu Leu Lys Glu Asn Phe Ile Arg Phe Ser Lys Ser
            180                 185                 190

Leu Gly Leu Pro Glu Asn His Ile Val Phe Pro Val Pro Ile Asp Gln
        195                 200                 205

Cys Ile Asp Gly Gly Gly Ser Glu Asn Leu Tyr Phe Gln Gly Gly Trp
210                 215                 220

Val Thr Val Tyr Tyr Gly Val Pro Val Trp Lys Glu Ala Thr Thr Thr
225                 230                 235                 240

Leu Phe Cys Ala Ser Asp Ala Lys Ala Tyr Asp Thr Glu Val His Asn
                245                 250                 255

Val Trp Ala Thr His Ala Cys Val Pro Thr Asp Pro Asn Pro Gln Glu
                260                 265                 270

Ile Val Leu Glu Asn Val Thr Glu Asn Phe Asn Met Trp Lys Asn Asn
            275                 280                 285

Met Val Glu Gln Met His Glu Asp Ile Ile Ser Leu Trp Asp Gln Ser
        290                 295                 300

Leu Lys Pro Cys Val Lys Leu Thr Pro Leu Cys Val Thr Leu His Cys
305                 310                 315                 320

Thr Asn Leu Lys Asn Ala Thr Asn Thr Lys Ser Ser Asn Trp Lys Glu
                325                 330                 335

Met Asp Arg Gly Glu Ile Lys Asn Cys Ser Phe Lys Val Thr Thr Ser
                340                 345                 350

Ile Arg Asn Lys Met Gln Lys Glu Tyr Ala Leu Phe Tyr Lys Leu Asp
            355                 360                 365

Val Val Pro Ile Asp Asn Asp Asn Thr Ser Tyr Lys Leu Ile Asn Cys
        370                 375                 380

Asn Thr Ser Val Ile Thr Gln Ala Cys Pro Lys Val Ser Phe Glu Pro
385                 390                 395                 400

Ile Pro Ile His Tyr Cys Ala Pro Ala Gly Phe Ala Ile Leu Lys Cys
                405                 410                 415

Asn Asp Lys Lys Phe Asn Gly Ser Gly Pro Cys Thr Asn Val Ser Thr
                420                 425                 430

Val Gln Cys Thr His Gly Ile Arg Pro Val Val Ser Thr Gln Leu Leu
            435                 440                 445

Leu Asn Gly Ser Leu Ala Glu Glu Gly Val Val Ile Arg Ser Glu Asn
        450                 455                 460

Phe Thr Asp Asn Ala Lys Thr Ile Ile Val Gln Leu Lys Glu Ser Val
465                 470                 475                 480

Glu Ile Asn Cys Thr Arg Pro Asn Asn Thr Arg Lys Ser Ile Thr
                485                 490                 495

Ile Gly Pro Gly Arg Ala Phe Tyr Ala Thr Gly Asp Ile Ile Gly Asp
                500                 505                 510

Ile Arg Gln Ala His Cys Asn Ile Ser Gly Glu Lys Trp Asn Asn Thr
            515                 520                 525

Leu Lys Gln Ile Val Thr Lys Leu Gln Ala Gln Phe Gly Asn Lys Thr
        530                 535                 540

Ile Val Phe Lys Gln Ser Ser Gly Gly Asp Pro Glu Ile Val Met His
545                 550                 555                 560

Ser Phe Asn Cys Gly Gly Glu Phe Phe Tyr Cys Asn Ser Thr Gln Leu
                565                 570                 575

Phe Asn Ser Thr Trp Asn Asn Thr Ile Gly Pro Asn Asn Thr Asn Gly
                580                 585                 590
```

```
Thr Ile Thr Leu Pro Cys Arg Ile Lys Gln Ile Ile Asn Arg Trp Gln
            595                 600                 605

Glu Val Gly Lys Ala Met Tyr Ala Pro Pro Ile Arg Gly Gln Ile Arg
        610                 615                 620

Cys Ser Ser Asn Ile Thr Gly Leu Leu Leu Thr Arg Asp Gly Gly Lys
625                 630                 635                 640

Glu Ile Ser Asn Thr Thr Glu Ile Phe Arg Pro Gly Gly Gly Asp Met
                645                 650                 655

Arg Asp Asn Trp Arg Ser Glu Leu Tyr Lys Tyr Lys Val Val Lys Ile
            660                 665                 670

Glu Pro Leu Gly Val Ala Pro Thr Lys Ala Lys Arg Arg Val Val Gln
        675                 680                 685

Gln Gly Leu Asn Asp Ile Phe Glu Ala Gln Lys Ile Glu Trp His Glu
    690                 695                 700
```

<210> SEQ ID NO 70
<211> LENGTH: 723
<212> TYPE: PRT
<213> ORGANISM: artificial
<220> FEATURE:
<223> OTHER INFORMATION: IgK-sFLAG-H6-GGS-humanScn-GGS-ENLYFQ-GG-QH0692gp120

<400> SEQUENCE: 70

```
Met Glu Thr Asp Thr Leu Leu Leu Trp Val Leu Leu Leu Trp Val Pro
1               5                   10                  15

Gly Ser Thr Gly Asp Tyr Lys Asp Glu His His His His His His Gly
            20                  25                  30

Gly Ser Gln Asp Ser Thr Ser Asp Leu Ile Pro Ala Pro Pro Leu Ser
        35                  40                  45

Lys Val Pro Leu Gln Gln Asn Phe Gln Asp Asn Gln Phe Gln Gly Lys
50                  55                  60

Trp Tyr Val Val Gly Leu Ala Gly Asn Ala Ile Leu Arg Glu Asp Lys
65                  70                  75                  80

Asp Pro Gln Lys Met Tyr Ala Thr Ile Tyr Glu Leu Lys Glu Asp Lys
                85                  90                  95

Ser Tyr Asn Val Thr Ser Val Leu Phe Arg Lys Lys Lys Cys Asp Tyr
            100                 105                 110

Trp Ile Arg Thr Phe Val Pro Gly Ser Gln Pro Gly Glu Phe Thr Leu
        115                 120                 125

Gly Asn Ile Lys Ser Tyr Pro Gly Leu Thr Ser Tyr Leu Val Arg Val
    130                 135                 140

Val Ser Thr Asn Tyr Asn Gln His Ala Met Val Phe Phe Lys Lys Val
145                 150                 155                 160

Ser Gln Asn Arg Glu Tyr Phe Lys Ile Thr Leu Tyr Gly Arg Thr Lys
                165                 170                 175

Glu Leu Thr Ser Glu Leu Lys Glu Asn Phe Ile Arg Phe Ser Lys Ser
            180                 185                 190

Leu Gly Leu Pro Glu Asn His Ile Val Phe Pro Val Pro Ile Asp Gln
        195                 200                 205

Cys Ile Asp Gly Gly Gly Ser Glu Asn Leu Tyr Phe Gln Gly Gly Trp
    210                 215                 220

Val Thr Val Tyr Tyr Gly Val Pro Val Trp Lys Glu Ala Thr Thr Thr
225                 230                 235                 240

Leu Phe Cys Ala Ser Asp Ala Lys Ala Tyr Glu Thr Glu Lys His Asn
                245                 250                 255
```

```
Val Trp Ala Thr His Ala Cys Val Pro Thr Asp Pro Asn Pro Gln Glu
            260                 265                 270

Val Val Leu Gly Asn Val Thr Glu Asn Phe Asn Met Trp Lys Asn Asn
            275                 280                 285

Met Val Glu Gln Met His Glu Asp Ile Ile Ser Leu Trp Asp Glu Ser
    290                 295                 300

Leu Lys Pro Cys Val Lys Leu Thr Pro Leu Cys Val Thr Leu Asn Cys
305                 310                 315                 320

Thr Asp Glu Val Lys Thr Ser Tyr Ala Asn Lys Thr Ser Asn Glu Thr
                325                 330                 335

Tyr Lys Thr Ser Asn Glu Thr Phe Gly Glu Ile Lys Asn Cys Ser Phe
            340                 345                 350

Ser Val Pro Thr Gly Ile Lys Asp Lys Val Gln Asn Val Tyr Ala Leu
            355                 360                 365

Phe Tyr Lys Leu Asp Val Ile Pro Ile Asp Asn Asn Asn Ser Ser
    370                 375                 380

Lys Asn Asn Asn Gly Ser Tyr Ser Ser Tyr Arg Leu Ile Asn Cys Asn
385                 390                 395                 400

Thr Ser Val Ile Thr Gln Ala Cys Pro Lys Val Ser Phe Glu Pro Ile
                405                 410                 415

Pro Ile His Tyr Cys Ala Pro Ala Gly Phe Ala Ile Leu Lys Cys Asn
            420                 425                 430

Asn Lys Thr Phe Asn Gly Thr Gly Pro Cys Thr Asn Val Ser Thr Val
            435                 440                 445

Gln Cys Thr His Gly Ile Arg Pro Val Val Ser Thr Gln Leu Leu Leu
    450                 455                 460

Asn Gly Ser Leu Ala Glu Glu Val Val Ile Arg Ser Glu Asn Phe
465                 470                 475                 480

Thr Asn Asn Ala Lys Thr Ile Ile Val His Leu Lys Lys Ser Val Glu
                485                 490                 495

Ile Asn Cys Thr Arg Pro Gly Asn Asn Thr Arg Lys Ser Ile His Ile
            500                 505                 510

Gly Pro Gly Arg Ala Phe Tyr Ala Thr Gly Asp Ile Ile Gly Asp Ile
            515                 520                 525

Arg Gln Ala His Cys Asn Leu Ser Ser Val Gln Trp Asn Asp Thr Leu
    530                 535                 540

Lys Gln Ile Val Ile Lys Leu Gly Glu Gln Phe Gly Thr Asn Lys Thr
545                 550                 555                 560

Ile Ala Phe Asn Gln Ser Ser Gly Gly Asp Pro Glu Ile Val Met His
                565                 570                 575

Ser Phe Asn Cys Gly Gly Glu Phe Phe Tyr Cys Asn Thr Thr Gln Leu
            580                 585                 590

Phe Asn Ser Thr Trp Glu Phe His Gly Asn Trp Thr Arg Ser Asn Phe
            595                 600                 605

Thr Glu Ser Asn Ser Thr Thr Ile Thr Leu Pro Cys Arg Ile Lys Gln
    610                 615                 620

Ile Val Asn Met Trp Gln Glu Val Gly Lys Ala Met Tyr Ala Pro Pro
625                 630                 635                 640

Ile Arg Gly Gln Ile Arg Cys Ser Ser Asn Ile Thr Gly Leu Leu Leu
                645                 650                 655

Thr Arg Asp Gly Gly Val Asn Gly Thr Arg Glu Thr Phe Arg Pro Gly
            660                 665                 670
```

```
Gly Gly Asp Met Arg Asp Asn Trp Arg Ser Glu Leu Tyr Lys Tyr Lys
            675                 680                 685

Val Val Lys Ile Glu Pro Leu Gly Val Ala Pro Thr Lys Ala Lys Arg
    690                 695                 700

Arg Val Val Gln Gly Leu Asn Asp Ile Phe Glu Ala Gln Lys Ile Glu
705                 710                 715                 720

Trp His Glu

<210> SEQ ID NO 71
<211> LENGTH: 259
<212> TYPE: PRT
<213> ORGANISM: artificial
<220> FEATURE:
<223> OTHER INFORMATION: IgK-sFLAG-H6-GGS-humanScn-GGS-ENLYFQ-GG-ITPR-1

<400> SEQUENCE: 71

Met Glu Thr Asp Thr Leu Leu Leu Trp Val Leu Leu Leu Trp Val Pro
1               5                   10                  15

Gly Ser Thr Gly Asp Tyr Lys Asp Glu His His His His His His Gly
            20                  25                  30

Gly Ser Gln Asp Ser Thr Ser Asp Leu Ile Pro Ala Pro Pro Leu Ser
        35                  40                  45

Lys Val Pro Leu Gln Gln Asn Phe Gln Asp Asn Gln Phe Gln Gly Lys
50                  55                  60

Trp Tyr Val Val Gly Leu Ala Gly Asn Ala Ile Leu Arg Glu Asp Lys
65                  70                  75                  80

Asp Pro Gln Lys Met Tyr Ala Thr Ile Tyr Glu Leu Lys Glu Asp Lys
                85                  90                  95

Ser Tyr Asn Val Thr Ser Val Leu Phe Arg Lys Lys Lys Cys Asp Tyr
            100                 105                 110

Trp Ile Arg Thr Phe Val Pro Gly Ser Gln Pro Gly Glu Phe Thr Leu
        115                 120                 125

Gly Asn Ile Lys Ser Tyr Pro Gly Leu Thr Ser Tyr Leu Val Arg Val
    130                 135                 140

Val Ser Thr Asn Tyr Asn Gln His Ala Met Val Phe Phe Lys Lys Val
145                 150                 155                 160

Ser Gln Asn Arg Glu Tyr Phe Lys Ile Thr Leu Tyr Gly Arg Thr Lys
                165                 170                 175

Glu Leu Thr Ser Glu Leu Lys Glu Asn Phe Ile Arg Phe Ser Lys Ser
            180                 185                 190

Leu Gly Leu Pro Glu Asn His Ile Val Phe Pro Val Pro Ile Asp Gln
        195                 200                 205

Cys Ile Asp Gly Gly Gly Ser Glu Asn Leu Tyr Phe Gln Gly Gly Ser
    210                 215                 220

Lys Cys Arg Val Phe Asn Thr Thr Glu Arg Asp Glu Gln Gly Ser Lys
225                 230                 235                 240

Val Asn Asp Phe Phe Gln Gln Thr Glu Asp Leu Tyr Asn Glu Met Lys
                245                 250                 255

Trp Gln Lys

<210> SEQ ID NO 72
<211> LENGTH: 259
<212> TYPE: PRT
<213> ORGANISM: artificial
<220> FEATURE:
<223> OTHER INFORMATION: IgK-sFLAG-H6-GGS-humanScn-GGS-ENLYFQ-GG-ITPR-2
```

<400> SEQUENCE: 72

```
Met Glu Thr Asp Thr Leu Leu Leu Trp Val Leu Leu Leu Trp Val Pro
1               5                   10                  15

Gly Ser Thr Gly Asp Tyr Lys Asp Glu His His His His His Gly
                20                  25                  30

Gly Ser Gln Asp Ser Thr Ser Asp Leu Ile Pro Ala Pro Pro Leu Ser
            35                  40                  45

Lys Val Pro Leu Gln Gln Asn Phe Gln Asp Asn Gln Phe Gln Gly Lys
    50                  55                  60

Trp Tyr Val Val Gly Leu Ala Gly Asn Ala Ile Leu Arg Glu Asp Lys
65                  70                  75                  80

Asp Pro Gln Lys Met Tyr Ala Thr Ile Tyr Glu Leu Lys Glu Asp Lys
                85                  90                  95

Ser Tyr Asn Val Thr Ser Val Leu Phe Arg Lys Lys Cys Asp Tyr
                100                 105                 110

Trp Ile Arg Thr Phe Val Pro Gly Ser Gln Pro Gly Glu Phe Thr Leu
            115                 120                 125

Gly Asn Ile Lys Ser Tyr Pro Gly Leu Thr Ser Tyr Leu Val Arg Val
    130                 135                 140

Val Ser Thr Asn Tyr Asn Gln His Ala Met Val Phe Phe Lys Lys Val
145                 150                 155                 160

Ser Gln Asn Arg Glu Tyr Phe Lys Ile Thr Leu Tyr Gly Arg Thr Lys
                165                 170                 175

Glu Leu Thr Ser Glu Leu Lys Glu Asn Phe Ile Arg Phe Ser Lys Ser
            180                 185                 190

Leu Gly Leu Pro Glu Asn His Ile Val Phe Pro Val Pro Ile Asp Gln
    195                 200                 205

Cys Ile Asp Gly Gly Ser Glu Asn Leu Tyr Phe Gln Gly Gly Pro
    210                 215                 220

Pro His Glu Leu Thr Glu Glu Lys Gln Gln Ile Leu His Ser Glu
225                 230                 235                 240

Glu Phe Leu Ser Phe Phe Asp His Ser Thr Arg Ile Val Glu Arg Ala
                245                 250                 255

Leu Ser Glu
```

<210> SEQ ID NO 73
<211> LENGTH: 259
<212> TYPE: PRT
<213> ORGANISM: artificial
<220> FEATURE:
<223> OTHER INFORMATION: IgK-sFLAG-H6-GGS-humanScn-GGS-ENLYFQ-GG-ITPR-3

<400> SEQUENCE: 73

```
Met Glu Thr Asp Thr Leu Leu Leu Trp Val Leu Leu Leu Trp Val Pro
1               5                   10                  15

Gly Ser Thr Gly Asp Tyr Lys Asp Glu His His His His His Gly
                20                  25                  30

Gly Ser Gln Asp Ser Thr Ser Asp Leu Ile Pro Ala Pro Pro Leu Ser
            35                  40                  45

Lys Val Pro Leu Gln Gln Asn Phe Gln Asp Asn Gln Phe Gln Gly Lys
    50                  55                  60

Trp Tyr Val Val Gly Leu Ala Gly Asn Ala Ile Leu Arg Glu Asp Lys
65                  70                  75                  80

Asp Pro Gln Lys Met Tyr Ala Thr Ile Tyr Glu Leu Lys Glu Asp Lys
                85                  90                  95
```

Ser Tyr Asn Val Thr Ser Val Leu Phe Arg Lys Lys Cys Asp Tyr
            100                 105                 110

Trp Ile Arg Thr Phe Val Pro Gly Ser Gln Pro Gly Glu Phe Thr Leu
        115                 120                 125

Gly Asn Ile Lys Ser Tyr Pro Gly Leu Thr Ser Tyr Leu Val Arg Val
130                 135                 140

Val Ser Thr Asn Tyr Asn Gln His Ala Met Val Phe Lys Lys Val
145                 150                 155                 160

Ser Gln Asn Arg Glu Tyr Phe Lys Ile Thr Leu Tyr Gly Arg Thr Lys
                165                 170                 175

Glu Leu Thr Ser Glu Leu Lys Glu Asn Phe Ile Arg Phe Ser Lys Ser
            180                 185                 190

Leu Gly Leu Pro Glu Asn His Ile Val Phe Pro Val Pro Ile Asp Gln
        195                 200                 205

Cys Ile Asp Gly Gly Ser Glu Asn Leu Tyr Phe Gln Gly Gly Pro
    210                 215                 220

Pro Pro Arg Cys Ile Ser Thr Asn Lys Cys Thr Ala Pro Glu Val Glu
225                 230                 235                 240

Asn Ala Ile Arg Val Pro Gly Asn Arg Ser Phe Phe Ser Leu Thr Glu
                245                 250                 255

Ile Val Arg

<210> SEQ ID NO 74
<211> LENGTH: 259
<212> TYPE: PRT
<213> ORGANISM: artificial
<220> FEATURE:
<223> OTHER INFORMATION: IgK-sFLAG-H6-GGS-humanScn-GGS-ENLYFQ-GG-ITPR-4

<400> SEQUENCE: 74

Met Glu Thr Asp Thr Leu Leu Leu Trp Val Leu Leu Leu Trp Val Pro
1               5                   10                  15

Gly Ser Thr Gly Asp Tyr Lys Asp Glu His His His His His His Gly
                20                  25                  30

Gly Ser Gln Asp Ser Thr Ser Asp Leu Ile Pro Ala Pro Pro Leu Ser
            35                  40                  45

Lys Val Pro Leu Gln Gln Asn Phe Gln Asp Asn Gln Phe Gln Gly Lys
        50                  55                  60

Trp Tyr Val Val Gly Leu Ala Gly Asn Ala Ile Leu Arg Glu Asp Lys
65                  70                  75                  80

Asp Pro Gln Lys Met Tyr Ala Thr Ile Tyr Glu Leu Lys Glu Asp Lys
                85                  90                  95

Ser Tyr Asn Val Thr Ser Val Leu Phe Arg Lys Lys Cys Asp Tyr
            100                 105                 110

Trp Ile Arg Thr Phe Val Pro Gly Ser Gln Pro Gly Glu Phe Thr Leu
        115                 120                 125

Gly Asn Ile Lys Ser Tyr Pro Gly Leu Thr Ser Tyr Leu Val Arg Val
130                 135                 140

Val Ser Thr Asn Tyr Asn Gln His Ala Met Val Phe Lys Lys Val
145                 150                 155                 160

Ser Gln Asn Arg Glu Tyr Phe Lys Ile Thr Leu Tyr Gly Arg Thr Lys
                165                 170                 175

Glu Leu Thr Ser Glu Leu Lys Glu Asn Phe Ile Arg Phe Ser Lys Ser
            180                 185                 190

```
Leu Gly Leu Pro Glu Asn His Ile Val Phe Pro Val Pro Ile Asp Gln
            195                 200                 205

Cys Ile Asp Gly Gly Gly Ser Glu Asn Leu Tyr Phe Gln Gly Gly Thr
210                 215                 220

Glu Arg Asp Glu Gln Gly Ser Lys Ile Asn Asp Phe Phe Leu Arg Ser
225                 230                 235                 240

Glu Asp Leu Phe Asn Glu Met Asn Trp Gln Lys Lys Leu Arg Ala Gln
            245                 250                 255

Pro Val Leu

<210> SEQ ID NO 75
<211> LENGTH: 259
<212> TYPE: PRT
<213> ORGANISM: artificial
<220> FEATURE:
<223> OTHER INFORMATION: IgK-sFLAG-H6-GGS-humanScn-GGS-ENLYFQ-GG-ITPR-5

<400> SEQUENCE: 75

Met Glu Thr Asp Thr Leu Leu Leu Trp Val Leu Leu Leu Trp Val Pro
1               5                   10                  15

Gly Ser Thr Gly Asp Tyr Lys Asp Glu His His His His His His Gly
            20                  25                  30

Gly Ser Gln Asp Ser Thr Ser Asp Leu Ile Pro Ala Pro Pro Leu Ser
        35                  40                  45

Lys Val Pro Leu Gln Gln Asn Phe Gln Asp Asn Gln Phe Gln Gly Lys
    50                  55                  60

Trp Tyr Val Val Gly Leu Ala Gly Asn Ala Ile Leu Arg Glu Asp Lys
65                  70                  75                  80

Asp Pro Gln Lys Met Tyr Ala Thr Ile Tyr Glu Leu Lys Glu Asp Lys
                85                  90                  95

Ser Tyr Asn Val Thr Ser Val Leu Phe Arg Lys Lys Lys Cys Asp Tyr
            100                 105                 110

Trp Ile Arg Thr Phe Val Pro Gly Ser Gln Pro Gly Glu Phe Thr Leu
        115                 120                 125

Gly Asn Ile Lys Ser Tyr Pro Gly Leu Thr Ser Tyr Leu Val Arg Val
    130                 135                 140

Val Ser Thr Asn Tyr Asn Gln His Ala Met Val Phe Phe Lys Lys Val
145                 150                 155                 160

Ser Gln Asn Arg Glu Tyr Phe Lys Ile Thr Leu Tyr Gly Arg Thr Lys
                165                 170                 175

Glu Leu Thr Ser Glu Leu Lys Glu Asn Phe Ile Arg Phe Ser Lys Ser
            180                 185                 190

Leu Gly Leu Pro Glu Asn His Ile Val Phe Pro Val Pro Ile Asp Gln
        195                 200                 205

Cys Ile Asp Gly Gly Gly Ser Glu Asn Leu Tyr Phe Gln Gly Gly Leu
    210                 215                 220

Thr Glu Glu Thr Lys His Arg Leu Phe Thr Thr Thr Glu Gln Asp Glu
225                 230                 235                 240

Gln Gly Ser Lys Val Ser Asp Phe Phe Asp Gln Ser Ser Phe Leu His
                245                 250                 255

Asn Glu Met

<210> SEQ ID NO 76
<211> LENGTH: 259
<212> TYPE: PRT
<213> ORGANISM: artificial
```

<220> FEATURE:
<223> OTHER INFORMATION: IgK-sFLAG-H6-GGS-humanScn-GGS-ENLYFQ-GG-ITPR-8

<400> SEQUENCE: 76

```
Met Glu Thr Asp Thr Leu Leu Leu Trp Val Leu Leu Leu Trp Val Pro
1               5                   10                  15

Gly Ser Thr Gly Asp Tyr Lys Asp Glu His His His His His Gly
                20                  25                  30

Gly Ser Gln Asp Ser Thr Ser Asp Leu Ile Pro Ala Pro Pro Leu Ser
            35                  40                  45

Lys Val Pro Leu Gln Gln Asn Phe Gln Asp Asn Gln Phe Gln Gly Lys
    50                  55                  60

Trp Tyr Val Val Gly Leu Ala Gly Asn Ala Ile Leu Arg Glu Asp Lys
65                  70                  75                  80

Asp Pro Gln Lys Met Tyr Ala Thr Ile Tyr Glu Leu Lys Glu Asp Lys
                85                  90                  95

Ser Tyr Asn Val Thr Ser Val Leu Phe Arg Lys Lys Lys Cys Asp Tyr
            100                 105                 110

Trp Ile Arg Thr Phe Val Pro Gly Ser Gln Pro Gly Glu Phe Thr Leu
        115                 120                 125

Gly Asn Ile Lys Ser Tyr Pro Gly Leu Thr Ser Tyr Leu Val Arg Val
    130                 135                 140

Val Ser Thr Asn Tyr Asn Gln His Ala Met Val Phe Phe Lys Lys Val
145                 150                 155                 160

Ser Gln Asn Arg Glu Tyr Phe Lys Ile Thr Leu Tyr Gly Arg Thr Lys
                165                 170                 175

Glu Leu Thr Ser Glu Leu Lys Glu Asn Phe Ile Arg Phe Ser Lys Ser
            180                 185                 190

Leu Gly Leu Pro Glu Asn His Ile Val Phe Pro Val Pro Ile Asp Gln
        195                 200                 205

Cys Ile Asp Gly Gly Ser Glu Asn Leu Tyr Phe Gln Gly Gly Gly
    210                 215                 220

Ala Gln Pro Pro Phe Asp Ala Gln Ser Pro Leu Asp Ser Gln Pro Gln
225                 230                 235                 240

Pro Ser Gly Gln Pro Trp Asn Phe His Ala Ser Thr Ser Trp Tyr Trp
                245                 250                 255

Arg Gln Ser
```

<210> SEQ ID NO 77
<211> LENGTH: 488
<212> TYPE: PRT
<213> ORGANISM: artificial
<220> FEATURE:
<223> OTHER INFORMATION: IgK-sFLAG-H6-GGS-humanScn-GGS-ENLYFQ-GG-
      human HMOX1

<400> SEQUENCE: 77

```
Met Glu Thr Asp Thr Leu Leu Leu Trp Val Leu Leu Leu Trp Val Pro
1               5                   10                  15

Gly Ser Thr Gly Asp Tyr Lys Asp Glu His His His His His Gly
                20                  25                  30

Gly Ser Gln Asp Ser Thr Ser Asp Leu Ile Pro Ala Pro Pro Leu Ser
            35                  40                  45

Lys Val Pro Leu Gln Gln Asn Phe Gln Asp Asn Gln Phe Gln Gly Lys
    50                  55                  60

Trp Tyr Val Val Gly Leu Ala Gly Asn Ala Ile Leu Arg Glu Asp Lys
```

-continued

```
                65                  70                  75                  80
Asp Pro Gln Lys Met Tyr Ala Thr Ile Tyr Glu Leu Lys Glu Asp Lys
                    85                  90                  95
Ser Tyr Asn Val Thr Ser Val Leu Phe Arg Lys Lys Cys Asp Tyr
                100                 105                 110
Trp Ile Arg Thr Phe Val Pro Gly Ser Gln Pro Gly Glu Phe Thr Leu
                115                 120                 125
Gly Asn Ile Lys Ser Tyr Pro Gly Leu Thr Ser Tyr Leu Val Arg Val
130                 135                 140
Val Ser Thr Asn Tyr Asn Gln His Ala Met Val Phe Phe Lys Lys Val
145                 150                 155                 160
Ser Gln Asn Arg Glu Tyr Phe Lys Ile Thr Leu Tyr Gly Arg Thr Lys
                165                 170                 175
Glu Leu Thr Ser Glu Leu Lys Glu Asn Phe Ile Arg Phe Ser Lys Ser
                180                 185                 190
Leu Gly Leu Pro Glu Asn His Ile Val Phe Pro Val Pro Ile Asp Gln
                195                 200                 205
Cys Ile Asp Gly Gly Ser Glu Asn Leu Tyr Phe Gln Gly Gly Met
        210                 215                 220
Glu Arg Pro Gln Pro Asp Ser Met Pro Gln Asp Leu Ser Glu Ala Leu
225                 230                 235                 240
Lys Glu Ala Thr Lys Glu Val His Thr Gln Ala Glu Asn Ala Glu Phe
                245                 250                 255
Met Arg Asn Phe Gln Lys Gly Gln Val Thr Arg Asp Gly Phe Lys Leu
                260                 265                 270
Val Met Ala Ser Leu Tyr His Ile Tyr Val Ala Leu Glu Glu Glu Ile
        275                 280                 285
Glu Arg Asn Lys Glu Ser Pro Val Phe Ala Pro Val Tyr Phe Pro Glu
        290                 295                 300
Glu Leu His Arg Lys Ala Ala Leu Glu Gln Asp Leu Ala Phe Trp Tyr
305                 310                 315                 320
Gly Pro Arg Trp Gln Glu Val Ile Pro Tyr Thr Pro Ala Met Gln Arg
                325                 330                 335
Tyr Val Lys Arg Leu His Glu Val Gly Arg Thr Glu Pro Glu Leu Leu
                340                 345                 350
Val Ala His Ala Tyr Thr Arg Tyr Leu Gly Asp Leu Ser Gly Gly Gln
                355                 360                 365
Val Leu Lys Lys Ile Ala Gln Lys Ala Leu Asp Leu Pro Ser Ser Gly
        370                 375                 380
Glu Gly Leu Ala Phe Phe Thr Phe Pro Asn Ile Ala Ser Ala Thr Lys
385                 390                 395                 400
Phe Lys Gln Leu Tyr Arg Ser Arg Met Asn Ser Leu Glu Met Thr Pro
                405                 410                 415
Ala Val Arg Gln Arg Val Ile Glu Glu Ala Lys Thr Ala Phe Leu Leu
                420                 425                 430
Asn Ile Gln Leu Phe Glu Glu Leu Gln Glu Leu Leu Thr His Asp Thr
                435                 440                 445
Lys Asp Gln Ser Pro Ser Arg Ala Pro Gly Leu Arg Gln Arg Ala Ser
        450                 455                 460
Asn Lys Val Gln Asp Ser Ala Pro Val Glu Thr Pro Arg Gly Lys Pro
465                 470                 475                 480
Pro Leu Asn Thr Arg Ser Gln Ala
                485
```

<210> SEQ ID NO 78
<211> LENGTH: 488
<212> TYPE: PRT
<213> ORGANISM: artificial
<220> FEATURE:
<223> OTHER INFORMATION: IgK-sFLAG-H6-GGS-humanScn-GGS-ENLYFQ-GG-murineHMOX1

<400> SEQUENCE: 78

```
Met Glu Thr Asp Thr Leu Leu Leu Trp Val Leu Leu Leu Trp Val Pro
1               5                   10                  15

Gly Ser Thr Gly Asp Tyr Lys Asp Glu His His His His His His Gly
            20                  25                  30

Gly Ser Gln Asp Ser Thr Ser Asp Leu Ile Pro Ala Pro Pro Leu Ser
        35                  40                  45

Lys Val Pro Leu Gln Gln Asn Phe Gln Asp Asn Gln Phe Gln Gly Lys
    50                  55                  60

Trp Tyr Val Val Gly Leu Ala Gly Asn Ala Ile Leu Arg Glu Asp Lys
65                  70                  75                  80

Asp Pro Gln Lys Met Tyr Ala Thr Ile Tyr Glu Leu Lys Glu Asp Lys
                85                  90                  95

Ser Tyr Asn Val Thr Ser Val Leu Phe Arg Lys Lys Lys Cys Asp Tyr
            100                 105                 110

Trp Ile Arg Thr Phe Val Pro Gly Ser Gln Pro Gly Glu Phe Thr Leu
        115                 120                 125

Gly Asn Ile Lys Ser Tyr Pro Gly Leu Thr Ser Tyr Leu Val Arg Val
    130                 135                 140

Val Ser Thr Asn Tyr Asn Gln His Ala Met Val Phe Phe Lys Lys Val
145                 150                 155                 160

Ser Gln Asn Arg Glu Tyr Phe Lys Ile Thr Leu Tyr Gly Arg Thr Lys
                165                 170                 175

Glu Leu Thr Ser Glu Leu Lys Glu Asn Phe Ile Arg Phe Ser Lys Ser
            180                 185                 190

Leu Gly Leu Pro Glu Asn His Ile Val Phe Pro Val Pro Ile Asp Gln
        195                 200                 205

Cys Ile Asp Gly Gly Gly Ser Glu Asn Leu Tyr Phe Gln Gly Gly Met
    210                 215                 220

Glu Arg Pro Gln Pro Asp Ser Met Pro Gln Asp Leu Ser Glu Ala Leu
225                 230                 235                 240

Lys Glu Ala Thr Lys Glu Val His Ile Gln Ala Glu Asn Ala Glu Phe
                245                 250                 255

Met Lys Asn Phe Gln Lys Gly Gln Val Ser Arg Glu Gly Phe Lys Leu
            260                 265                 270

Val Met Ala Ser Leu Tyr His Ile Tyr Thr Ala Leu Glu Glu Glu Ile
        275                 280                 285

Glu Arg Asn Lys Gln Asn Pro Val Tyr Ala Pro Leu Tyr Phe Pro Glu
    290                 295                 300

Glu Leu His Arg Arg Ala Ala Leu Glu Gln Asp Met Ala Phe Trp Tyr
305                 310                 315                 320

Gly Pro His Trp Gln Glu Ile Ile Pro Cys Thr Pro Ala Thr Gln His
                325                 330                 335

Tyr Val Lys Arg Leu His Glu Val Gly Arg Thr His Pro Glu Leu Leu
            340                 345                 350

Val Ala His Ala Tyr Thr Arg Tyr Leu Gly Asp Leu Ser Gly Gly Gln
```

-continued

```
                355                 360                 365
Val Leu Lys Lys Ile Ala Gln Lys Ala Met Ala Leu Pro Ser Ser Gly
            370                 375                 380
Glu Gly Leu Ala Phe Phe Thr Phe Pro Asn Ile Asp Ser Pro Thr Lys
385                 390                 395                 400
Phe Lys Gln Leu Tyr Arg Ala Arg Met Asn Thr Leu Glu Met Thr Pro
                405                 410                 415
Glu Val Lys His Arg Val Thr Glu Ala Lys Thr Ala Phe Leu Leu
            420                 425                 430
Asn Ile Glu Leu Phe Glu Leu Gln Val Met Leu Thr Glu Glu His
            435                 440                 445
Lys Asp Gln Ser Pro Ser Gln Met Ala Ser Leu Arg Gln Arg Pro Ala
    450                 455                 460
Ser Leu Val Gln Asp Thr Ala Pro Ala Glu Thr Pro Arg Gly Lys Pro
465                 470                 475                 480
Gln Ile Ser Thr Ser Ser Ser Gln
                485

<210> SEQ ID NO 79
<211> LENGTH: 489
<212> TYPE: PRT
<213> ORGANISM: artificial
<220> FEATURE:
<223> OTHER INFORMATION: humanScn-humanHMOX1

<400> SEQUENCE: 79

Met Pro Leu Gly Leu Leu Trp Leu Gly Leu Ala Leu Leu Gly Ala Leu
1               5                   10                  15
His Ala Gln Ala Gln Asp Ser Thr Ser Asp Leu Ile Pro Ala Pro Pro
            20                  25                  30
Leu Ser Lys Val Pro Leu Gln Gln Asn Phe Gln Asp Asn Gln Phe Gln
        35                  40                  45
Gly Lys Trp Tyr Val Val Gly Leu Ala Gly Asn Ala Ile Leu Arg Glu
    50                  55                  60
Asp Lys Asp Pro Gln Lys Met Tyr Ala Thr Ile Tyr Glu Leu Lys Glu
65                  70                  75                  80
Asp Lys Ser Tyr Asn Val Thr Ser Val Leu Phe Arg Lys Lys Lys Cys
                85                  90                  95
Asp Tyr Trp Ile Arg Thr Phe Val Pro Gly Ser Gln Pro Gly Glu Phe
            100                 105                 110
Thr Leu Gly Asn Ile Lys Ser Tyr Pro Gly Leu Thr Ser Tyr Leu Val
        115                 120                 125
Arg Val Val Ser Thr Asn Tyr Asn Gln His Ala Met Val Phe Phe Lys
    130                 135                 140
Lys Val Ser Gln Asn Arg Glu Tyr Phe Lys Ile Thr Leu Tyr Gly Arg
145                 150                 155                 160
Thr Lys Glu Leu Thr Ser Glu Leu Lys Glu Asn Phe Ile Arg Phe Ser
                165                 170                 175
Lys Ser Leu Gly Leu Pro Glu Asn His Ile Val Phe Pro Val Pro Ile
            180                 185                 190
Asp Gln Cys Ile Asp Gly Gly Ser Glu Asn Leu Tyr Phe Gln Gly
        195                 200                 205
Gly Gly Met Glu Arg Pro Gln Pro Asp Ser Met Pro Gln Asp Leu Ser
    210                 215                 220
Glu Ala Leu Lys Glu Ala Thr Lys Glu Val His Thr Gln Ala Glu Asn
```

```
                225                 230                 235                 240
Ala Glu Phe Met Arg Asn Phe Gln Lys Gly Gln Val Thr Arg Asp Gly
                        245                 250                 255

Phe Lys Leu Val Met Ala Ser Leu Tyr His Ile Tyr Val Ala Leu Glu
                260                 265                 270

Glu Glu Ile Glu Arg Asn Lys Glu Ser Pro Val Phe Ala Pro Val Tyr
                275                 280                 285

Phe Pro Glu Glu Leu His Arg Lys Ala Ala Leu Glu Gln Asp Leu Ala
            290                 295                 300

Phe Trp Tyr Gly Pro Arg Trp Gln Glu Val Ile Pro Tyr Thr Pro Ala
305                 310                 315                 320

Met Gln Arg Tyr Val Lys Arg Leu His Glu Val Gly Arg Thr Glu Pro
                        325                 330                 335

Glu Leu Leu Val Ala His Ala Tyr Thr Arg Tyr Leu Gly Asp Leu Ser
                340                 345                 350

Gly Gly Gln Val Leu Lys Lys Ile Ala Gln Lys Ala Leu Asp Leu Pro
            355                 360                 365

Ser Ser Gly Glu Gly Leu Ala Phe Phe Thr Phe Pro Asn Ile Ala Ser
        370                 375                 380

Ala Thr Lys Phe Lys Gln Leu Tyr Arg Ser Arg Met Asn Ser Leu Glu
385                 390                 395                 400

Met Thr Pro Ala Val Arg Gln Arg Val Ile Glu Glu Ala Lys Thr Ala
                        405                 410                 415

Phe Leu Leu Asn Ile Gln Leu Phe Glu Glu Leu Gln Glu Leu Leu Thr
                420                 425                 430

His Asp Thr Lys Asp Gln Ser Pro Ser Arg Ala Pro Gly Leu Arg Gln
            435                 440                 445

Arg Ala Ser Asn Lys Val Gln Asp Ser Ala Pro Val Glu Thr Pro Arg
        450                 455                 460

Gly Lys Pro Pro Leu Asn Thr Arg Ser Gln Ala Gly Gly Leu Val Pro
465                 470                 475                 480

Arg Gly Ser His His His His His His
                        485

<210> SEQ ID NO 80
<211> LENGTH: 387
<212> TYPE: PRT
<213> ORGANISM: artificial
<220> FEATURE:
<223> OTHER INFORMATION: humanScn-cTHAP4

<400> SEQUENCE: 80

Met Pro Leu Gly Leu Leu Trp Leu Gly Leu Ala Leu Leu Gly Ala Leu
1               5                   10                  15

His Ala Gln Ala Gln Asp Ser Thr Ser Asp Leu Ile Pro Ala Pro Pro
                20                  25                  30

Leu Ser Lys Val Pro Leu Gln Gln Asn Phe Gln Asp Asn Gln Phe Gln
            35                  40                  45

Gly Lys Trp Tyr Val Val Gly Leu Ala Gly Asn Ala Ile Leu Arg Glu
        50                  55                  60

Asp Lys Asp Pro Gln Lys Met Tyr Ala Thr Ile Tyr Glu Leu Lys Glu
65                  70                  75                  80

Asp Lys Ser Tyr Asn Val Thr Ser Val Leu Phe Arg Lys Lys Lys Cys
                85                  90                  95

Asp Tyr Trp Ile Arg Thr Phe Val Pro Gly Ser Gln Pro Gly Glu Phe
```

```
              100                 105                 110
Thr Leu Gly Asn Ile Lys Ser Tyr Pro Gly Leu Thr Ser Tyr Leu Val
            115                 120                 125

Arg Val Val Ser Thr Asn Tyr Asn Gln His Ala Met Val Phe Phe Lys
130                 135                 140

Lys Val Ser Gln Asn Arg Glu Tyr Phe Lys Ile Thr Leu Tyr Gly Arg
145                 150                 155                 160

Thr Lys Glu Leu Thr Ser Glu Leu Lys Glu Asn Phe Ile Arg Phe Ser
                165                 170                 175

Lys Ser Leu Gly Leu Pro Glu Asn His Ile Val Phe Pro Val Pro Ile
            180                 185                 190

Asp Gln Cys Ile Asp Gly Gly Ser Glu Asn Leu Tyr Phe Gln Gly
            195                 200                 205

Gly Gly Pro Pro Lys Met Asn Pro Val Val Glu Pro Leu Ser Trp Met
210                 215                 220

Leu Gly Thr Trp Leu Ser Asp Pro Pro Gly Ala Gly Thr Tyr Pro Thr
225                 230                 235                 240

Leu Gln Pro Phe Gln Tyr Leu Glu Glu Val His Ile Ser His Val Gly
                245                 250                 255

Gln Pro Met Leu Asn Phe Ser Phe Asn Ser Phe His Pro Asp Thr Arg
            260                 265                 270

Lys Pro Met His Arg Glu Cys Gly Phe Ile Arg Leu Lys Pro Asp Thr
            275                 280                 285

Asn Lys Val Ala Phe Val Ser Ala Gln Asn Thr Gly Val Val Glu Val
290                 295                 300

Glu Glu Gly Glu Val Asn Gly Gln Glu Leu Cys Ile Ala Ser His Ser
305                 310                 315                 320

Ile Ala Arg Ile Ser Phe Ala Lys Glu Pro His Val Glu Gln Ile Thr
                325                 330                 335

Arg Lys Phe Arg Leu Asn Ser Glu Gly Lys Leu Glu Gln Thr Val Ser
            340                 345                 350

Met Ala Thr Thr Thr Gln Pro Met Thr Gln His Leu His Val Thr Tyr
            355                 360                 365

Lys Lys Val Thr Pro Gly Gly Leu Val Pro Arg Gly Ser His His His
            370                 375                 380

His His His
385

<210> SEQ ID NO 81
<211> LENGTH: 295
<212> TYPE: PRT
<213> ORGANISM: artificial
<220> FEATURE:
<223> OTHER INFORMATION: IgK-sFLAG-H6-GGS-humanScn-GGS-ENLYFQ-GG-
      heptamer

<400> SEQUENCE: 81

Met Glu Thr Asp Thr Leu Leu Leu Trp Val Leu Leu Leu Trp Val Pro
1               5                   10                  15

Gly Ser Thr Gly Asp Tyr Lys Asp Glu His His His His His His Gly
            20                  25                  30

Gly Ser Gln Asp Ser Thr Ser Asp Leu Ile Pro Ala Pro Pro Leu Ser
        35                  40                  45

Lys Val Pro Leu Gln Gln Asn Phe Gln Asp Asn Gln Phe Gln Gly Lys
50                  55                  60
```

```
Trp Tyr Val Val Gly Leu Ala Gly Asn Ala Ile Leu Arg Glu Asp Lys
 65                  70                  75                  80

Asp Pro Gln Lys Met Tyr Ala Thr Ile Tyr Glu Leu Lys Glu Asp Lys
                 85                  90                  95

Ser Tyr Asn Val Thr Ser Val Leu Phe Arg Lys Lys Lys Cys Asp Tyr
            100                 105                 110

Trp Ile Arg Thr Phe Val Pro Gly Ser Gln Pro Gly Glu Phe Thr Leu
            115                 120                 125

Gly Asn Ile Lys Ser Tyr Pro Gly Leu Thr Ser Tyr Leu Val Arg Val
        130                 135                 140

Val Ser Thr Asn Tyr Asn Gln His Ala Met Val Phe Phe Lys Lys Val
145                 150                 155                 160

Ser Gln Asn Arg Glu Tyr Phe Lys Ile Thr Leu Tyr Gly Arg Thr Lys
                165                 170                 175

Glu Leu Thr Ser Glu Leu Lys Glu Asn Phe Ile Arg Phe Ser Lys Ser
            180                 185                 190

Leu Gly Leu Pro Glu Asn His Ile Val Phe Pro Val Pro Ile Asp Gln
        195                 200                 205

Cys Ile Asp Gly Gly Ser Glu Asn Leu Tyr Phe Gln Gly Gly Gly
210                 215                 220

Arg Ser Ala Gly Ala His Ala Gly Trp Glu Thr Pro Glu Gly Cys Glu
225                 230                 235                 240

Gln Val Leu Thr Gly Lys Arg Leu Met Gln Cys Leu Pro Asn Pro Glu
                245                 250                 255

Asp Val Lys Met Ala Leu Glu Val Tyr Lys Leu Ser Leu Glu Ile Glu
            260                 265                 270

Gln Leu Glu Leu Gln Arg Asp Ser Ala Arg Gln Ser Thr Leu Asp Lys
        275                 280                 285

Glu Leu Val Pro Arg Gly Ser
        290                 295

<210> SEQ ID NO 82
<211> LENGTH: 522
<212> TYPE: PRT
<213> ORGANISM: artificial
<220> FEATURE:
<223> OTHER INFORMATION: IgK-sFLAG-H6-GGS-humanScn-GGS-ENLYFQ-GG-
      CD80heptamer
<220> FEATURE:
<221> NAME/KEY: misc_feature
<222> LOCATION: (490)..(490)
<223> OTHER INFORMATION: Xaa can be any naturally occurring amino acid

<400> SEQUENCE: 82

Met Glu Thr Asp Thr Leu Leu Leu Trp Val Leu Leu Leu Trp Val Pro
  1               5                  10                  15

Gly Ser Thr Gly Asp Tyr Lys Asp Glu His His His His His His Gly
             20                  25                  30

Gly Ser Gln Asp Ser Thr Ser Asp Leu Ile Pro Ala Pro Pro Leu Ser
         35                  40                  45

Lys Val Pro Leu Gln Gln Asn Phe Gln Asp Asn Gln Phe Gln Gly Lys
 50                  55                  60

Trp Tyr Val Val Gly Leu Ala Gly Asn Ala Ile Leu Arg Glu Asp Lys
 65                  70                  75                  80

Asp Pro Gln Lys Met Tyr Ala Thr Ile Tyr Glu Leu Lys Glu Asp Lys
                 85                  90                  95

Ser Tyr Asn Val Thr Ser Val Leu Phe Arg Lys Lys Lys Cys Asp Tyr
```

```
                100                 105                 110
Trp Ile Arg Thr Phe Val Pro Gly Ser Gln Pro Gly Glu Phe Thr Leu
            115                 120                 125
Gly Asn Ile Lys Ser Tyr Pro Gly Leu Thr Ser Tyr Leu Val Arg Val
        130                 135                 140
Val Ser Thr Asn Tyr Asn Gln His Ala Met Val Phe Phe Lys Lys Val
145                 150                 155                 160
Ser Gln Asn Arg Glu Tyr Phe Lys Ile Thr Leu Tyr Gly Arg Thr Lys
                165                 170                 175
Glu Leu Thr Ser Glu Leu Lys Glu Asn Phe Ile Arg Phe Ser Lys Ser
            180                 185                 190
Leu Gly Leu Pro Glu Asn His Ile Val Phe Pro Val Pro Ile Asp Gln
        195                 200                 205
Cys Ile Asp Gly Gly Ser Glu Asn Leu Tyr Phe Gln Gly Gly Gly
210                 215                 220
Ile Ile Gln Val Asn Lys Thr Val Lys Glu Val Ala Val Leu Ser Cys
225                 230                 235                 240
Asp Tyr Asn Ile Ser Thr Thr Glu Leu Met Lys Val Arg Ile Tyr Trp
                245                 250                 255
Gln Lys Asp Asp Glu Val Val Leu Ala Val Thr Ser Gly Gln Thr Lys
            260                 265                 270
Val Trp Ser Lys Tyr Glu Asn Arg Thr Phe Ala Asp Phe Thr Asn Asn
        275                 280                 285
Leu Ser Ile Val Ile Met Ala Leu Arg Leu Ser Asp Asn Gly Lys Tyr
        290                 295                 300
Thr Cys Ile Val Gln Lys Thr Glu Lys Arg Ser Tyr Lys Val Lys His
305                 310                 315                 320
Met Thr Ser Val Met Leu Leu Val Arg Ala Asp Phe Pro Val Pro Ser
                325                 330                 335
Ile Thr Asp Leu Gly Asn Pro Ser His Asp Ile Lys Arg Ile Met Cys
            340                 345                 350
Ser Thr Ser Gly Gly Phe Pro Lys Pro His Leu Ser Trp Trp Glu Asn
        355                 360                 365
Glu Glu Glu Leu Asn Ala Ala Asn Thr Thr Val Ser Gln Asp Pro Asp
370                 375                 380
Thr Glu Leu Tyr Thr Ile Ser Ser Glu Leu Asp Phe Asn Ile Thr Ser
385                 390                 395                 400
Asn His Ser Phe Val Cys Leu Val Lys Tyr Gly Asp Leu Thr Val Ser
                405                 410                 415
Gln Ile Phe Asn Trp Gln Lys Ser Val Glu Pro His Pro Asn Asn
            420                 425                 430
Ser Ala Trp Ser His Pro Gln Phe Glu Lys Gly Gly Ser Leu Val Pro
        435                 440                 445
Arg Gly Ser Gly Ser Ala Gly Ala His Ala Gly Trp Glu Thr Pro Glu
        450                 455                 460
Gly Cys Glu Gln Val Leu Thr Gly Lys Arg Leu Met Gln Cys Leu Pro
465                 470                 475                 480
Asn Pro Glu Asp Val Lys Met Ala Leu Xaa Val Tyr Lys Leu Ser Leu
                485                 490                 495
Glu Ile Glu Gln Leu Glu Leu Gln Arg Asp Ser Ala Arg Gln Ser Thr
            500                 505                 510
Leu Asp Lys Glu Leu Val Pro Arg Gly Ser
        515                 520
```

<210> SEQ ID NO 83
<211> LENGTH: 279
<212> TYPE: PRT
<213> ORGANISM: artificial
<220> FEATURE:
<223> OTHER INFORMATION: IgK-sFLAG-H6-GGS-humanScn-GGS-ENLYFQ-GG-trimer

<400> SEQUENCE: 83

Met Glu Thr Asp Thr Leu Leu Leu Trp Val Leu Leu Leu Trp Val Pro
1               5                   10                  15

Gly Ser Thr Gly Asp Tyr Lys Asp Glu His His His His His His Gly
            20                  25                  30

Gly Ser Gln Asp Ser Thr Ser Asp Leu Ile Pro Ala Pro Pro Leu Ser
        35                  40                  45

Lys Val Pro Leu Gln Gln Asn Phe Gln Asp Asn Gln Phe Gln Gly Lys
50                  55                  60

Trp Tyr Val Val Gly Leu Ala Gly Asn Ala Ile Leu Arg Glu Asp Lys
65                  70                  75                  80

Asp Pro Gln Lys Met Tyr Ala Thr Ile Tyr Glu Leu Lys Glu Asp Lys
                85                  90                  95

Ser Tyr Asn Val Thr Ser Val Leu Phe Arg Lys Lys Lys Cys Asp Tyr
            100                 105                 110

Trp Ile Arg Thr Phe Val Pro Gly Ser Gln Pro Gly Glu Phe Thr Leu
        115                 120                 125

Gly Asn Ile Lys Ser Tyr Pro Gly Leu Thr Ser Tyr Leu Val Arg Val
    130                 135                 140

Val Ser Thr Asn Tyr Asn Gln His Ala Met Val Phe Phe Lys Lys Val
145                 150                 155                 160

Ser Gln Asn Arg Glu Tyr Phe Lys Ile Thr Leu Tyr Gly Arg Thr Lys
                165                 170                 175

Glu Leu Thr Ser Glu Leu Lys Glu Asn Phe Ile Arg Phe Ser Lys Ser
            180                 185                 190

Leu Gly Leu Pro Glu Asn His Ile Val Phe Pro Val Pro Ile Asp Gln
        195                 200                 205

Cys Ile Asp Gly Gly Gly Ser Glu Asn Leu Tyr Phe Gln Gly Gly Gly
    210                 215                 220

Arg Asn Leu Val Thr Ala Phe Ser Asn Met Asp Asp Met Leu Gln Lys
225                 230                 235                 240

Ala His Leu Val Ile Glu Gly Thr Phe Ile Tyr Leu Arg Asp Ser Thr
                245                 250                 255

Glu Phe Phe Ile Arg Val Arg Asp Gly Trp Lys Lys Leu Gln Leu Gly
            260                 265                 270

Glu Leu Ile Pro Ile Pro Ala
        275

<210> SEQ ID NO 84
<211> LENGTH: 506
<212> TYPE: PRT
<213> ORGANISM: artificial
<220> FEATURE:
<223> OTHER INFORMATION: IgK-sFLAG-H6-GGS-humanScn-GGS-ENLYFQ-GG-
    CD80trimer

<400> SEQUENCE: 84

Met Glu Thr Asp Thr Leu Leu Leu Trp Val Leu Leu Leu Trp Val Pro
1               5                   10                  15

-continued

Gly Ser Thr Gly Asp Tyr Lys Asp Glu His His His His His Gly
            20                  25                  30
Gly Ser Gln Asp Ser Thr Ser Asp Leu Ile Pro Ala Pro Pro Leu Ser
        35                  40                  45
Lys Val Pro Leu Gln Gln Asn Phe Gln Asp Asn Gln Phe Gln Gly Lys
    50                  55                  60
Trp Tyr Val Val Gly Leu Ala Gly Asn Ala Ile Leu Arg Glu Asp Lys
65                  70                  75                  80
Asp Pro Gln Lys Met Tyr Ala Thr Ile Tyr Glu Leu Lys Glu Asp Lys
                85                  90                  95
Ser Tyr Asn Val Thr Ser Val Leu Phe Arg Lys Lys Lys Cys Asp Tyr
            100                 105                 110
Trp Ile Arg Thr Phe Val Pro Gly Ser Gln Pro Gly Glu Phe Thr Leu
        115                 120                 125
Gly Asn Ile Lys Ser Tyr Pro Gly Leu Thr Ser Tyr Leu Val Arg Val
    130                 135                 140
Val Ser Thr Asn Tyr Asn Gln His Ala Met Val Phe Phe Lys Lys Val
145                 150                 155                 160
Ser Gln Asn Arg Glu Tyr Phe Lys Ile Thr Leu Tyr Gly Arg Thr Lys
                165                 170                 175
Glu Leu Thr Ser Glu Leu Lys Glu Asn Phe Ile Arg Phe Ser Lys Ser
            180                 185                 190
Leu Gly Leu Pro Glu Asn His Ile Val Phe Pro Val Pro Ile Asp Gln
        195                 200                 205
Cys Ile Asp Gly Gly Gly Ser Glu Asn Leu Tyr Phe Gln Gly Gly Gly
    210                 215                 220
Ile Ile Gln Val Asn Lys Thr Val Lys Glu Val Ala Val Leu Ser Cys
225                 230                 235                 240
Asp Tyr Asn Ile Ser Thr Thr Glu Leu Met Lys Val Arg Ile Tyr Trp
                245                 250                 255
Gln Lys Asp Asp Glu Val Val Leu Ala Val Thr Ser Gly Gln Thr Lys
            260                 265                 270
Val Trp Ser Lys Tyr Glu Asn Arg Thr Phe Ala Asp Phe Thr Asn Asn
        275                 280                 285
Leu Ser Ile Val Ile Met Ala Leu Arg Leu Ser Asp Asn Gly Lys Tyr
    290                 295                 300
Thr Cys Ile Val Gln Lys Thr Glu Lys Arg Ser Tyr Lys Val Lys His
305                 310                 315                 320
Met Thr Ser Val Met Leu Leu Val Arg Ala Asp Phe Pro Val Pro Ser
                325                 330                 335
Ile Thr Asp Leu Gly Asn Pro Ser His Asp Ile Lys Arg Ile Met Cys
            340                 345                 350
Ser Thr Ser Gly Gly Phe Pro Lys Pro His Leu Ser Trp Trp Glu Asn
        355                 360                 365
Glu Glu Glu Leu Asn Ala Ala Asn Thr Thr Val Ser Gln Asp Pro Asp
    370                 375                 380
Thr Glu Leu Tyr Thr Ile Ser Ser Glu Leu Asp Phe Asn Ile Thr Ser
385                 390                 395                 400
Asn His Ser Phe Val Cys Leu Val Lys Tyr Gly Asp Leu Thr Val Ser
                405                 410                 415
Gln Ile Phe Asn Trp Gln Lys Ser Val Glu Pro His Pro Pro Asn Asn
            420                 425                 430
Ser Ala Trp Ser His Pro Gln Phe Glu Lys Gly Gly Ser Leu Val Pro

```
                435                 440                 445
Arg Gly Ser Gly Asn Leu Val Thr Ala Phe Ser Asn Met Asp Asp Met
        450                 455                 460

Leu Gln Lys Ala His Leu Val Ile Glu Gly Thr Phe Ile Tyr Leu Arg
465                 470                 475                 480

Asp Ser Thr Glu Phe Phe Ile Arg Val Arg Asp Gly Trp Lys Lys Leu
                485                 490                 495

Gln Leu Gly Glu Leu Ile Pro Ile Pro Ala
        500                 505

<210> SEQ ID NO 85
<211> LENGTH: 278
<212> TYPE: PRT
<213> ORGANISM: artificial
<220> FEATURE:
<223> OTHER INFORMATION: IgK-sFLAG-H6-GGS-humanScn-GGS-ENLYFQ-GG-
      pentamer

<400> SEQUENCE: 85

Met Glu Thr Asp Thr Leu Leu Leu Trp Val Leu Leu Leu Trp Val Pro
1               5                   10                  15

Gly Ser Thr Gly Asp Tyr Lys Asp Glu His His His His His His Gly
            20                  25                  30

Gly Ser Gln Asp Ser Thr Ser Asp Leu Ile Pro Ala Pro Pro Leu Ser
        35                  40                  45

Lys Val Pro Leu Gln Gln Asn Phe Gln Asp Asn Gln Phe Gln Gly Lys
    50                  55                  60

Trp Tyr Val Val Gly Leu Ala Gly Asn Ala Ile Leu Arg Glu Asp Lys
65                  70                  75                  80

Asp Pro Gln Lys Met Tyr Ala Thr Ile Tyr Glu Leu Lys Glu Asp Lys
                85                  90                  95

Ser Tyr Asn Val Thr Ser Val Leu Phe Arg Lys Lys Lys Cys Asp Tyr
            100                 105                 110

Trp Ile Arg Thr Phe Val Pro Gly Ser Gln Pro Gly Glu Phe Thr Leu
        115                 120                 125

Gly Asn Ile Lys Ser Tyr Pro Gly Leu Thr Ser Tyr Leu Val Arg Val
    130                 135                 140

Val Ser Thr Asn Tyr Asn Gln His Ala Met Val Phe Phe Lys Lys Val
145                 150                 155                 160

Ser Gln Asn Arg Glu Tyr Phe Lys Ile Thr Leu Tyr Gly Arg Thr Lys
                165                 170                 175

Glu Leu Thr Ser Glu Leu Lys Glu Asn Phe Ile Arg Phe Ser Lys Ser
            180                 185                 190

Leu Gly Leu Pro Glu Asn His Ile Val Phe Pro Val Pro Ile Asp Gln
        195                 200                 205

Cys Ile Asp Gly Gly Gly Ser Glu Asn Leu Tyr Phe Gln Gly Gly Gly
    210                 215                 220

Arg Ser Ser Asn Ala Lys Trp Asp Gln Trp Ser Ser Asp Trp Gln Thr
225                 230                 235                 240

Trp Asn Ala Lys Trp Asp Gln Trp Ser Asn Asp Trp Asn Ala Trp Arg
                245                 250                 255

Ser Asp Trp Gln Ala Trp Lys Asp Asp Trp Ala Arg Trp Asn Gln Arg
            260                 265                 270

Trp Asp Asn Trp Ala Thr
        275
```

<210> SEQ ID NO 86
<211> LENGTH: 302
<212> TYPE: PRT
<213> ORGANISM: artificial
<220> FEATURE:
<223> OTHER INFORMATION: IgK-sFLAG-H6-GGS-humanScn-GGS-ENLYFQ-GG-
      ROR1Kringle

<400> SEQUENCE: 86

Met Glu Thr Asp Thr Leu Leu Leu Trp Val Leu Leu Trp Val Pro
1               5                   10                  15

Gly Ser Thr Gly Asp Tyr Lys Asp Glu His His His His His Gly
            20                  25                  30

Gly Ser Gln Asp Ser Thr Ser Asp Leu Ile Pro Ala Pro Leu Ser
        35                  40                  45

Lys Val Pro Leu Gln Gln Asn Phe Gln Asp Asn Gln Phe Gln Gly Lys
50                  55                  60

Trp Tyr Val Val Gly Leu Ala Gly Asn Ala Ile Leu Arg Glu Asp Lys
65                  70                  75                  80

Asp Pro Gln Lys Met Tyr Ala Thr Ile Tyr Glu Leu Lys Glu Asp Lys
                85                  90                  95

Ser Tyr Asn Val Thr Ser Val Leu Phe Arg Lys Lys Cys Asp Tyr
            100                 105                 110

Trp Ile Arg Thr Phe Val Pro Gly Ser Gln Pro Gly Glu Phe Thr Leu
            115                 120                 125

Gly Asn Ile Lys Ser Tyr Pro Gly Leu Thr Ser Tyr Leu Val Arg Val
        130                 135                 140

Val Ser Thr Asn Tyr Asn Gln His Ala Met Val Phe Phe Lys Lys Val
145                 150                 155                 160

Ser Gln Asn Arg Glu Tyr Phe Lys Ile Thr Leu Tyr Gly Arg Thr Lys
                165                 170                 175

Glu Leu Thr Ser Glu Leu Lys Glu Asn Phe Ile Arg Phe Ser Lys Ser
            180                 185                 190

Leu Gly Leu Pro Glu Asn His Ile Val Phe Pro Val Pro Ile Asp Gln
        195                 200                 205

Cys Ile Asp Gly Gly Gly Ser Glu Asn Leu Tyr Phe Gln Gly Gly Cys
    210                 215                 220

Tyr Asn Ser Thr Gly Val Asp Tyr Arg Gly Thr Val Ser Val Thr Lys
225                 230                 235                 240

Ser Gly Arg Gln Cys Gln Pro Trp Asn Ser Gln Tyr Pro His Thr His
                245                 250                 255

Thr Phe Thr Ala Leu Arg Phe Pro Glu Leu Asn Gly Gly His Ser Tyr
            260                 265                 270

Cys Arg Asn Pro Gly Asn Gln Lys Glu Ala Pro Trp Cys Phe Thr Leu
        275                 280                 285

Asp Glu Asn Phe Lys Ser Asp Leu Cys Asp Ile Pro Ala Cys
    290                 295                 300

<210> SEQ ID NO 87
<211> LENGTH: 343
<212> TYPE: PRT
<213> ORGANISM: artificial
<220> FEATURE:
<223> OTHER INFORMATION: IgK-sFLAG-H6-GGS-humanScn-GGS-ENLYFQ-GG-CTLA4

<400> SEQUENCE: 87

Met Glu Thr Asp Thr Leu Leu Leu Trp Val Leu Leu Trp Val Pro

```
  1               5                  10                 15
Gly Ser Thr Gly Asp Tyr Lys Asp Glu His His His His His Gly
            20                  25                  30
Gly Ser Gln Asp Ser Thr Ser Asp Leu Ile Pro Ala Pro Pro Leu Ser
            35                  40                  45
Lys Val Pro Leu Gln Gln Asn Phe Gln Asp Asn Gln Phe Gln Gly Lys
        50                  55                  60
Trp Tyr Val Val Gly Leu Ala Gly Asn Ala Ile Leu Arg Glu Asp Lys
65                  70                  75                  80
Asp Pro Gln Lys Met Tyr Ala Thr Ile Tyr Glu Leu Lys Glu Asp Lys
                85                  90                  95
Ser Tyr Asn Val Thr Ser Val Leu Phe Arg Lys Lys Cys Asp Tyr
            100                 105                 110
Trp Ile Arg Thr Phe Val Pro Gly Ser Gln Pro Gly Glu Phe Thr Leu
            115                 120                 125
Gly Asn Ile Lys Ser Tyr Pro Gly Leu Thr Ser Tyr Leu Val Arg Val
        130                 135                 140
Val Ser Thr Asn Tyr Asn Gln His Ala Met Val Phe Phe Lys Lys Val
145                 150                 155                 160
Ser Gln Asn Arg Glu Tyr Phe Lys Ile Thr Leu Tyr Gly Arg Thr Lys
                165                 170                 175
Glu Leu Thr Ser Glu Leu Lys Glu Asn Phe Ile Arg Phe Ser Lys Ser
            180                 185                 190
Leu Gly Leu Pro Glu Asn His Ile Val Phe Pro Val Pro Ile Asp Gln
        195                 200                 205
Cys Ile Asp Gly Gly Gly Ser Glu Asn Leu Tyr Phe Gln Gly Gly Met
210                 215                 220
His Val Ala Gln Pro Ala Val Val Leu Ala Ser Ser Arg Gly Val Ala
225                 230                 235                 240
Ser Phe Val Cys Glu Tyr Gly Ser Ser Gly Asn Ala Ala Glu Val Arg
                245                 250                 255
Val Thr Val Leu Arg Gln Ala Gly Ser Gln Met Thr Glu Val Cys Ala
            260                 265                 270
Ala Thr Tyr Thr Val Glu Asp Glu Leu Ala Phe Leu Asp Asp Ser Thr
        275                 280                 285
Cys Thr Gly Thr Ser Ser Gly Asn Lys Val Asn Leu Thr Ile Gln Gly
290                 295                 300
Leu Arg Ala Met Asp Thr Gly Leu Tyr Ile Cys Lys Val Glu Leu Met
305                 310                 315                 320
Tyr Pro Pro Pro Tyr Tyr Val Gly Met Gly Asn Gly Thr Gln Ile Tyr
                325                 330                 335
Val Ile Asp Pro Glu Pro Cys
            340

<210> SEQ ID NO 88
<211> LENGTH: 788
<212> TYPE: DNA
<213> ORGANISM: artificial
<220> FEATURE:
<223> OTHER INFORMATION: IgK-sFLAG-H6-GGS-humanScn-GGS-ENLYFQ-GG-
      Imperatoxin

<400> SEQUENCE: 88
ctcgagacca tggagacaga cacactcctg ctatgggtac tgctgctctg ggttccaggt    60
tccactggtg actacaagga cgagcatcac catcatcacc atggtggaag ccaggactcc   120
```

```
acctcagacc tgatcccagc cccacctctg agcaaggtcc ctctgcagca gaacttccag      180
gacaaccaat tccaggggaa gtggtatgtg gtaggcctgg cagggaatgc aattctcaga      240
gaagacaaag acccgcaaaa gatgtatgcc accatctatg agctgaaaga agacaagagc      300
tacaatgtca cctccgtcct gtttaggaaa aagaagtgtg actactggat caggactttt      360
gttccaggtt gccagcccgg cgagttcacg ctgggcaaca ttaagagtta ccctggatta      420
acgagttacc tcgtccgagt ggtgagcacc aactacaacc agcatgctat ggtgttcttc      480
aagaaagttt ctcaaaacag ggagtacttc aagatcaccc tctacgggag aaccaaggag      540
ctgacttcgg aactaaagga gaacttcatc cgcttctcca aatctctggg cctccctgaa      600
aaccacatcg tcttccctgt cccaatcgac cagtgtatcg acggcggagg tagcgaaaac      660
ctgtattttc agggaggcga ctgcctgccc cacctgagga ggtgcagggc cgacaacgac      720
tgctgcggca ggaggtgcag gaggaggggc accaacgccg agaggaggtg caggtaagct      780
aaggatcc                                                              788
```

<210> SEQ ID NO 89
<211> LENGTH: 20
<212> TYPE: PRT
<213> ORGANISM: artificial
<220> FEATURE:
<223> OTHER INFORMATION: synthesized murine IgK light chain signal
      peptide

<400> SEQUENCE: 89

Met Glu Thr Asp Thr Leu Leu Leu Trp Val Leu Leu Leu Trp Val Pro
1               5                   10                  15

Gly Ser Thr Gly
            20

<210> SEQ ID NO 90
<211> LENGTH: 60
<212> TYPE: DNA
<213> ORGANISM: artificial
<220> FEATURE:
<223> OTHER INFORMATION: coding sequence for synthesized murine IgK
      light chain signal peptide

<400> SEQUENCE: 90
atggagacag acacactcct gctatgggta ctgctgctct gggttccagg ttccactggt      60

<210> SEQ ID NO 91
<211> LENGTH: 5
<212> TYPE: PRT
<213> ORGANISM: artificial
<220> FEATURE:
<223> OTHER INFORMATION: Shortened FLAG epitope

<400> SEQUENCE: 91

Asp Tyr Lys Asp Glu
1               5

<210> SEQ ID NO 92
<211> LENGTH: 15
<212> TYPE: DNA
<213> ORGANISM: artificial
<220> FEATURE:
<223> OTHER INFORMATION: Shortened FLAG epitope coding

<400> SEQUENCE: 92
gactacaagg acgag                                                      15

<210> SEQ ID NO 93
<211> LENGTH: 6
<212> TYPE: PRT
<213> ORGANISM: artificial
<220> FEATURE:
<223> OTHER INFORMATION: 6xhistidine tag

<400> SEQUENCE: 93

His His His His His His
1               5

<210> SEQ ID NO 94
<211> LENGTH: 18
<212> TYPE: DNA
<213> ORGANISM: artificial
<220> FEATURE:
<223> OTHER INFORMATION: 6xhistidine tag coding

<400> SEQUENCE: 94
catcatcatc atcatcat                                                 18

<210> SEQ ID NO 95
<211> LENGTH: 6
<212> TYPE: PRT
<213> ORGANISM: artificial
<220> FEATURE:
<223> OTHER INFORMATION: Tobacco Etch Virus Protease recognition site

<400> SEQUENCE: 95

Glu Asn Leu Tyr Phe Gln
1               5

<210> SEQ ID NO 96
<211> LENGTH: 18
<212> TYPE: DNA
<213> ORGANISM: artificial
<220> FEATURE:
<223> OTHER INFORMATION: Coding sequencee for Tobacco Etch Virus
      Protease recognition site

<400> SEQUENCE: 96
gagaatttat attttcag                                                 18

<210> SEQ ID NO 97

<400> SEQUENCE: 97

000

<210> SEQ ID NO 98

<400> SEQUENCE: 98

000

<210> SEQ ID NO 99
<211> LENGTH: 8
<212> TYPE: PRT
<213> ORGANISM: artificial
<220> FEATURE:
<223> OTHER INFORMATION: furin cleavage site used for a BamHI site

<400> SEQUENCE: 99

Arg Ala Arg Tyr Lys Arg Gly Ser
1               5

<210> SEQ ID NO 100
<211> LENGTH: 24
<212> TYPE: DNA
<213> ORGANISM: artificial
<220> FEATURE:
<223> OTHER INFORMATION: coding sequence for furin cleavage site used
      for a BamHI site

<400> SEQUENCE: 100
cgggcccggt ataaacgggg atcc                                          24

<210> SEQ ID NO 101
<211> LENGTH: 6
<212> TYPE: PRT
<213> ORGANISM: artificial
<220> FEATURE:
<223> OTHER INFORMATION: furin cleavage site

<400> SEQUENCE: 101

Arg Ala Arg Tyr Lys Arg
1               5

<210> SEQ ID NO 102
<211> LENGTH: 4
<212> TYPE: PRT
<213> ORGANISM: artificial
<220> FEATURE:
<223> OTHER INFORMATION: 4 amino acid residues of a siderocalin right
      before a cleavage site in a siderocalin fusion construct

<400> SEQUENCE: 102

Cys Ile Asp Gly
1

<210> SEQ ID NO 103
<211> LENGTH: 198
<212> TYPE: PRT
<213> ORGANISM: artificial
<220> FEATURE:
<223> OTHER INFORMATION: a lipocalin fusion protein

<400> SEQUENCE: 103

Met Pro Leu Gly Leu Leu Trp Leu Gly Leu Ala Leu Leu Gly Ala Leu
1               5                   10                  15

His Ala Gln Ala Gln Asp Ser Thr Ser Asp Leu Ile Pro Ala Pro Pro
            20                  25                  30

Leu Ser Lys Val Pro Leu Gln Gln Asn Phe Gln Asp Asn Gln Phe Gln
        35                  40                  45

Gly Lys Trp Tyr Val Val Gly Leu Ala Gly Asn Ala Ile Leu Arg Glu
    50                  55                  60

Asp Lys Asp Pro Gln Lys Met Tyr Ala Thr Ile Tyr Glu Leu Lys Glu
65                  70                  75                  80

Asp Lys Ser Tyr Asn Val Thr Ser Val Leu Phe Arg Lys Lys Lys Cys
                85                  90                  95

Asp Tyr Trp Ile Arg Thr Phe Val Pro Gly Cys Gln Pro Gly Glu Phe
            100                 105                 110

Thr Leu Gly Asn Ile Lys Ser Tyr Pro Gly Leu Thr Ser Tyr Leu Val
        115                 120                 125

Arg Val Val Ser Thr Asn Tyr Asn Gln His Ala Met Val Phe Phe Lys
    130                 135                 140

Lys Val Ser Gln Asn Arg Glu Tyr Phe Lys Ile Thr Leu Tyr Gly Arg
145                 150                 155                 160

Thr Lys Glu Leu Thr Ser Glu Leu Lys Glu Asn Phe Ile Arg Phe Ser
            165                 170                 175

Lys Ser Leu Gly Leu Pro Glu Asn His Ile Val Phe Pro Val Pro Ile
            180                 185                 190

Asp Gln Cys Ile Asp Gly
        195

<210> SEQ ID NO 104
<211> LENGTH: 8
<212> TYPE: PRT
<213> ORGANISM: artificial
<220> FEATURE:
<223> OTHER INFORMATION: amino acid sequence in a light chain-
      siderocalin fusion

<400> SEQUENCE: 104

Gly Arg Gly Gly Ser Gly Gly Ser
1               5

<210> SEQ ID NO 105
<211> LENGTH: 5
<212> TYPE: PRT
<213> ORGANISM: artificial
<220> FEATURE:
<223> OTHER INFORMATION: amino acid sequence in a siderocalin construct
      for downstream viral fusions

<400> SEQUENCE: 105

Gly Gly Gly Gly Ser
1               5

<210> SEQ ID NO 106
<211> LENGTH: 287
<212> TYPE: PRT
<213> ORGANISM: artificial
<220> FEATURE:
<223> OTHER INFORMATION: IgK-SF-H6-GGS-lcn2C-GGS-ENLYFQ-GG-BubbleProtein
      amino acid sequence

<400> SEQUENCE: 106

Met Glu Thr Asp Thr Leu Leu Leu Trp Val Leu Leu Leu Trp Val Pro
1               5                   10                  15

Gly Ser Thr Gly Asp Tyr Lys Asp Glu His His His His His His Gly
            20                  25                  30

Gly Ser Gln Asp Ser Thr Ser Asp Leu Ile Pro Ala Pro Pro Leu Ser
        35                  40                  45

Lys Val Pro Leu Gln Gln Asn Phe Gln Asp Asn Gln Phe Gln Gly Lys
    50                  55                  60

Trp Tyr Val Val Gly Leu Ala Gly Asn Ala Ile Leu Arg Glu Asp Lys
65                  70                  75                  80

Asp Pro Gln Lys Met Tyr Ala Thr Ile Tyr Glu Leu Lys Glu Asp Lys
                85                  90                  95

Ser Tyr Asn Val Thr Ser Val Leu Phe Arg Lys Lys Lys Cys Asp Tyr
            100                 105                 110

Trp Ile Arg Thr Phe Val Pro Gly Cys Gln Pro Gly Glu Phe Thr Leu
        115                 120                 125

Gly Asn Ile Lys Ser Tyr Pro Gly Leu Thr Ser Tyr Leu Val Arg Val
    130                 135                 140

Val Ser Thr Asn Tyr Asn Gln His Ala Met Val Phe Phe Lys Lys Val
145                 150                 155                 160

```
Ser Gln Asn Arg Glu Tyr Phe Lys Ile Thr Leu Tyr Gly Arg Thr Lys
                165                 170                 175

Glu Leu Thr Ser Glu Leu Lys Glu Asn Phe Ile Arg Phe Ser Lys Ser
            180                 185                 190

Leu Gly Leu Pro Glu Asn His Ile Val Phe Pro Val Pro Ile Asp Gln
            195                 200                 205

Cys Ile Asp Gly Gly Gly Ser Glu Asn Leu Tyr Phe Gln Gly Gly Asp
            210                 215                 220

Thr Cys Gly Ser Gly Tyr Asn Val Asp Gln Arg Arg Thr Asn Ser Gly
225                 230                 235                 240

Cys Lys Ala Gly Asn Gly Asp Arg His Phe Cys Gly Cys Asp Arg Thr
                245                 250                 255

Gly Val Val Glu Cys Lys Gly Gly Lys Trp Thr Glu Val Gln Asp Cys
            260                 265                 270

Gly Ser Ser Ser Cys Lys Gly Thr Ser Asn Gly Gly Ala Thr Cys
            275                 280                 285

<210> SEQ ID NO 107
<211> LENGTH: 281
<212> TYPE: PRT
<213> ORGANISM: artificial
<220> FEATURE:
<223> OTHER INFORMATION: IgK-SF-H6-GGS-lcn2C-GGS-ENLYFQ-GG-Attractin
      amino acid sequence

<400> SEQUENCE: 107

Met Glu Thr Asp Thr Leu Leu Leu Trp Val Leu Leu Leu Trp Val Pro
1               5                   10                  15

Gly Ser Thr Gly Asp Tyr Lys Asp Glu His His His His His His Gly
                20                  25                  30

Gly Ser Gln Asp Ser Thr Ser Asp Leu Ile Pro Ala Pro Pro Leu Ser
            35                  40                  45

Lys Val Pro Leu Gln Gln Asn Phe Gln Asp Asn Gln Phe Gln Gly Lys
        50                  55                  60

Trp Tyr Val Val Gly Leu Ala Gly Asn Ala Ile Leu Arg Glu Asp Lys
65                  70                  75                  80

Asp Pro Gln Lys Met Tyr Ala Thr Ile Tyr Glu Leu Lys Glu Asp Lys
                85                  90                  95

Ser Tyr Asn Val Thr Ser Val Leu Phe Arg Lys Lys Lys Cys Asp Tyr
            100                 105                 110

Trp Ile Arg Thr Phe Val Pro Gly Cys Gln Pro Gly Glu Phe Thr Leu
        115                 120                 125

Gly Asn Ile Lys Ser Tyr Pro Gly Leu Thr Ser Tyr Leu Val Arg Val
    130                 135                 140

Val Ser Thr Asn Tyr Asn Gln His Ala Met Val Phe Phe Lys Lys Val
145                 150                 155                 160

Ser Gln Asn Arg Glu Tyr Phe Lys Ile Thr Leu Tyr Gly Arg Thr Lys
                165                 170                 175

Glu Leu Thr Ser Glu Leu Lys Glu Asn Phe Ile Arg Phe Ser Lys Ser
            180                 185                 190

Leu Gly Leu Pro Glu Asn His Ile Val Phe Pro Val Pro Ile Asp Gln
        195                 200                 205

Cys Ile Asp Gly Gly Gly Ser Glu Asn Leu Tyr Phe Gln Gly Gly Asp
    210                 215                 220

Gln Asn Cys Asp Ile Gly Asn Ile Thr Ser Gln Cys Gln Met His Gln
225                 230                 235                 240
```

```
Lys Asn Cys Glu Asp Ala Asn Gly Cys Asp Thr Ile Ile Glu Glu Cys
                245                 250                 255

Lys Thr Ser Met Val Glu Arg Cys Gln Asn Gln Glu Phe Glu Ser Ala
            260                 265                 270

Ala Gly Ser Thr Thr Leu Gly Pro Gln
        275                 280

<210> SEQ ID NO 108
<211> LENGTH: 245
<212> TYPE: PRT
<213> ORGANISM: artificial
<220> FEATURE:
<223> OTHER INFORMATION: IgK-SF-H6-GGS-lcn2C-GGS-ENLYFQ-GG-Hefutoxin
      amino acid sequence

<400> SEQUENCE: 108

Met Glu Thr Asp Thr Leu Leu Leu Trp Val Leu Leu Trp Val Pro
1               5                   10                  15

Gly Ser Thr Gly Asp Tyr Lys Asp Glu His His His His His Gly
                20                  25                  30

Gly Ser Gln Asp Ser Thr Ser Asp Leu Ile Pro Ala Pro Leu Ser
            35                  40                  45

Lys Val Pro Leu Gln Gln Asn Phe Gln Asp Asn Gln Phe Gln Gly Lys
50                  55                  60

Trp Tyr Val Val Gly Leu Ala Gly Asn Ala Ile Leu Arg Glu Asp Lys
65                  70                  75                  80

Asp Pro Gln Lys Met Tyr Ala Thr Ile Tyr Glu Leu Lys Glu Asp Lys
                85                  90                  95

Ser Tyr Asn Val Thr Ser Val Leu Phe Arg Lys Lys Lys Cys Asp Tyr
                100                 105                 110

Trp Ile Arg Thr Phe Val Pro Gly Cys Gln Pro Gly Glu Phe Thr Leu
            115                 120                 125

Gly Asn Ile Lys Ser Tyr Pro Gly Leu Thr Ser Tyr Leu Val Arg Val
        130                 135                 140

Val Ser Thr Asn Tyr Asn Gln His Ala Met Val Phe Phe Lys Lys Val
145                 150                 155                 160

Ser Gln Asn Arg Glu Tyr Phe Lys Ile Thr Leu Tyr Gly Arg Thr Lys
                165                 170                 175

Glu Leu Thr Ser Glu Leu Lys Glu Asn Phe Ile Arg Phe Ser Lys Ser
            180                 185                 190

Leu Gly Leu Pro Glu Asn His Ile Val Phe Pro Val Pro Ile Asp Gln
        195                 200                 205

Cys Ile Asp Gly Gly Gly Ser Glu Asn Leu Tyr Phe Gln Gly Gly Gly
    210                 215                 220

His Ala Cys Tyr Arg Asn Cys Trp Arg Glu Gly Asn Asp Glu Glu Thr
225                 230                 235                 240

Cys Lys Glu Arg Cys
                245

<210> SEQ ID NO 109
<211> LENGTH: 258
<212> TYPE: PRT
<213> ORGANISM: artificial
<220> FEATURE:
<223> OTHER INFORMATION: IgK-SF-H6-GGS-lcn2C-GGS-ENLYFQ-GG-Hanatoxin
      amino acid sequence

<400> SEQUENCE: 109
```

```
Met Glu Thr Asp Thr Leu Leu Leu Trp Val Leu Leu Leu Trp Val Pro
1               5                   10                  15

Gly Ser Thr Gly Asp Tyr Lys Asp Glu His His His His His Gly
                20                  25                  30

Gly Ser Gln Asp Ser Thr Ser Asp Leu Ile Pro Ala Pro Pro Leu Ser
                35                  40                  45

Lys Val Pro Leu Gln Gln Asn Phe Gln Asp Asn Gln Phe Gln Gly Lys
50                  55                  60

Trp Tyr Val Val Gly Leu Ala Gly Asn Ala Ile Leu Arg Glu Asp Lys
65                  70                  75                  80

Asp Pro Gln Lys Met Tyr Ala Thr Ile Tyr Glu Leu Lys Glu Asp Lys
                85                  90                  95

Ser Tyr Asn Val Thr Ser Val Leu Phe Arg Lys Lys Lys Cys Asp Tyr
                100                 105                 110

Trp Ile Arg Thr Phe Val Pro Gly Cys Gln Pro Gly Glu Phe Thr Leu
                115                 120                 125

Gly Asn Ile Lys Ser Tyr Pro Gly Leu Thr Ser Tyr Leu Val Arg Val
                130                 135                 140

Val Ser Thr Asn Tyr Asn Gln His Ala Met Val Phe Lys Lys Val
145                 150                 155                 160

Ser Gln Asn Arg Glu Tyr Phe Lys Ile Thr Leu Tyr Gly Arg Thr Lys
                165                 170                 175

Glu Leu Thr Ser Glu Leu Lys Glu Asn Phe Ile Arg Phe Ser Lys Ser
                180                 185                 190

Leu Gly Leu Pro Glu Asn His Ile Val Phe Pro Val Pro Ile Asp Gln
                195                 200                 205

Cys Ile Asp Gly Gly Ser Glu Asn Leu Tyr Phe Gln Gly Gly Glu
210                 215                 220

Cys Arg Tyr Leu Phe Gly Gly Cys Lys Thr Thr Ser Asp Cys Cys Lys
225                 230                 235                 240

His Leu Gly Cys Lys Phe Arg Asp Lys Tyr Cys Ala Trp Asp Phe Thr
                245                 250                 255

Phe Ser
```

<210> SEQ ID NO 110
<211> LENGTH: 259
<212> TYPE: PRT
<213> ORGANISM: artificial
<220> FEATURE:
<223> OTHER INFORMATION: IgK-SF-H6-GGS-lcn2C-GGS-ENLYFQ-GG-Chymotrypsin Inhibitor amino acid sequence

<400> SEQUENCE: 110

```
Met Glu Thr Asp Thr Leu Leu Leu Trp Val Leu Leu Leu Trp Val Pro
1               5                   10                  15

Gly Ser Thr Gly Asp Tyr Lys Asp Glu His His His His His Gly
                20                  25                  30

Gly Ser Gln Asp Ser Thr Ser Asp Leu Ile Pro Ala Pro Pro Leu Ser
                35                  40                  45

Lys Val Pro Leu Gln Gln Asn Phe Gln Asp Asn Gln Phe Gln Gly Lys
50                  55                  60

Trp Tyr Val Val Gly Leu Ala Gly Asn Ala Ile Leu Arg Glu Asp Lys
65                  70                  75                  80

Asp Pro Gln Lys Met Tyr Ala Thr Ile Tyr Glu Leu Lys Glu Asp Lys
                85                  90                  95
```

Ser Tyr Asn Val Thr Ser Val Leu Phe Arg Lys Lys Cys Asp Tyr
            100                 105                 110

Trp Ile Arg Thr Phe Val Pro Gly Cys Gln Pro Gly Glu Phe Thr Leu
            115                 120                 125

Gly Asn Ile Lys Ser Tyr Pro Gly Leu Thr Ser Tyr Leu Val Arg Val
            130                 135                 140

Val Ser Thr Asn Tyr Asn Gln His Ala Met Val Phe Lys Lys Val
145                 150                 155                 160

Ser Gln Asn Arg Glu Tyr Phe Lys Ile Thr Leu Tyr Gly Arg Thr Lys
            165                 170                 175

Glu Leu Thr Ser Glu Leu Lys Glu Asn Phe Ile Arg Phe Ser Lys Ser
            180                 185                 190

Leu Gly Leu Pro Glu Asn His Ile Val Phe Pro Val Pro Ile Asp Gln
            195                 200                 205

Cys Ile Asp Gly Gly Ser Glu Asn Leu Tyr Phe Gln Gly Gly Glu
            210                 215                 220

Ile Ser Cys Glu Pro Gly Lys Thr Phe Lys Asp Lys Cys Asn Thr Cys
225                 230                 235                 240

Arg Cys Gly Ala Asp Gly Lys Ser Ala Ala Cys Thr Leu Lys Ala Cys
            245                 250                 255

Pro Asn Gln

<210> SEQ ID NO 111
<211> LENGTH: 260
<212> TYPE: PRT
<213> ORGANISM: artificial
<220> FEATURE:
<223> OTHER INFORMATION: IgK-SF-H6-GGS-lcn2C-GGS-ENLYFQ-GG-ToxinK amino
      acid sequence

<400> SEQUENCE: 111

Met Glu Thr Asp Thr Leu Leu Leu Trp Val Leu Leu Leu Trp Val Pro
1               5                   10                  15

Gly Ser Thr Gly Asp Tyr Lys Asp Glu His His His His His His Gly
            20                  25                  30

Gly Ser Gln Asp Ser Thr Ser Asp Leu Ile Pro Ala Pro Pro Leu Ser
            35                  40                  45

Lys Val Pro Leu Gln Gln Asn Phe Gln Asp Asn Gln Phe Gln Gly Lys
            50                  55                  60

Trp Tyr Val Val Gly Leu Ala Gly Asn Ala Ile Leu Arg Glu Asp Lys
65                  70                  75                  80

Asp Pro Gln Lys Met Tyr Ala Thr Ile Tyr Glu Leu Lys Glu Asp Lys
            85                  90                  95

Ser Tyr Asn Val Thr Ser Val Leu Phe Arg Lys Lys Cys Asp Tyr
            100                 105                 110

Trp Ile Arg Thr Phe Val Pro Gly Cys Gln Pro Gly Glu Phe Thr Leu
            115                 120                 125

Gly Asn Ile Lys Ser Tyr Pro Gly Leu Thr Ser Tyr Leu Val Arg Val
            130                 135                 140

Val Ser Thr Asn Tyr Asn Gln His Ala Met Val Phe Lys Lys Val
145                 150                 155                 160

Ser Gln Asn Arg Glu Tyr Phe Lys Ile Thr Leu Tyr Gly Arg Thr Lys
            165                 170                 175

Glu Leu Thr Ser Glu Leu Lys Glu Asn Phe Ile Arg Phe Ser Lys Ser
            180                 185                 190

Leu Gly Leu Pro Glu Asn His Ile Val Phe Pro Val Pro Ile Asp Gln
        195                 200                 205

Cys Ile Asp Gly Gly Gly Ser Glu Asn Leu Tyr Phe Gln Gly Gly Val
        210                 215                 220

Cys Arg Asp Trp Phe Lys Glu Thr Ala Cys Arg His Ala Lys Ser Leu
225                 230                 235                 240

Gly Asn Cys Arg Thr Ser Gln Lys Tyr Arg Ala Asn Cys Ala Lys Thr
                245                 250                 255

Cys Glu Leu Cys
        260

<210> SEQ ID NO 112
<211> LENGTH: 269
<212> TYPE: PRT
<213> ORGANISM: artificial
<220> FEATURE:
<223> OTHER INFORMATION: IgK-SF-H6-GGS-lcn2C-GGS-ENLYFQ-GG-
      EGFepiregulinCore amino acid sequence

<400> SEQUENCE: 112

Met Glu Thr Asp Thr Leu Leu Leu Trp Val Leu Leu Leu Trp Val Pro
1               5                   10                  15

Gly Ser Thr Gly Asp Tyr Lys Asp Glu His His His His His His Gly
            20                  25                  30

Gly Ser Gln Asp Ser Thr Ser Asp Leu Ile Pro Ala Pro Pro Leu Ser
        35                  40                  45

Lys Val Pro Leu Gln Gln Asn Phe Gln Asp Asn Gln Phe Gln Gly Lys
    50                  55                  60

Trp Tyr Val Val Gly Leu Ala Gly Asn Ala Ile Leu Arg Glu Asp Lys
65                  70                  75                  80

Asp Pro Gln Lys Met Tyr Ala Thr Ile Tyr Glu Leu Lys Glu Asp Lys
                85                  90                  95

Ser Tyr Asn Val Thr Ser Val Leu Phe Arg Lys Lys Lys Cys Asp Tyr
            100                 105                 110

Trp Ile Arg Thr Phe Val Pro Gly Cys Gln Pro Gly Glu Phe Thr Leu
        115                 120                 125

Gly Asn Ile Lys Ser Tyr Pro Gly Leu Thr Ser Tyr Leu Val Arg Val
    130                 135                 140

Val Ser Thr Asn Tyr Asn Gln His Ala Met Val Phe Phe Lys Lys Val
145                 150                 155                 160

Ser Gln Asn Arg Glu Tyr Phe Lys Ile Thr Leu Tyr Gly Arg Thr Lys
                165                 170                 175

Glu Leu Thr Ser Glu Leu Lys Glu Asn Phe Ile Arg Phe Ser Lys Ser
            180                 185                 190

Leu Gly Leu Pro Glu Asn His Ile Val Phe Pro Val Pro Ile Asp Gln
        195                 200                 205

Cys Ile Asp Gly Gly Gly Ser Glu Asn Leu Tyr Phe Gln Gly Gly Val
    210                 215                 220

Ser Ile Thr Lys Cys Ser Ser Asp Met Asn Gly Tyr Cys Leu His Gly
225                 230                 235                 240

Gln Cys Ile Tyr Leu Val Asp Met Ser Gln Asn Tyr Cys Arg Cys Glu
                245                 250                 255

Val Gly Tyr Thr Gly Val Arg Cys Glu His Phe Phe Leu
            260                 265

```
<210> SEQ ID NO 113
<211> LENGTH: 253
<212> TYPE: PRT
<213> ORGANISM: artificial
<220> FEATURE:
<223> OTHER INFORMATION: IgK-SF-H6-GGS-lcn2C-GGS-ENLYFQ-GG-Circulin
      amino acid sequence

<400> SEQUENCE: 113
```

Met Glu Thr Asp Thr Leu Leu Leu Trp Val Leu Leu Leu Trp Val Pro
1               5                   10                  15

Gly Ser Thr Gly Asp Tyr Lys Asp Glu His His His His His His Gly
            20                  25                  30

Gly Ser Gln Asp Ser Thr Ser Asp Leu Ile Pro Ala Pro Pro Leu Ser
        35                  40                  45

Lys Val Pro Leu Gln Gln Asn Phe Gln Asp Asn Gln Phe Gln Gly Lys
    50                  55                  60

Trp Tyr Val Val Gly Leu Ala Gly Asn Ala Ile Leu Arg Glu Asp Lys
65                  70                  75                  80

Asp Pro Gln Lys Met Tyr Ala Thr Ile Tyr Glu Leu Lys Glu Asp Lys
                85                  90                  95

Ser Tyr Asn Val Thr Ser Val Leu Phe Arg Lys Lys Lys Cys Asp Tyr
            100                 105                 110

Trp Ile Arg Thr Phe Val Pro Gly Cys Gln Pro Gly Glu Phe Thr Leu
        115                 120                 125

Gly Asn Ile Lys Ser Tyr Pro Gly Leu Thr Ser Tyr Leu Val Arg Val
    130                 135                 140

Val Ser Thr Asn Tyr Asn Gln His Ala Met Val Phe Phe Lys Lys Val
145                 150                 155                 160

Ser Gln Asn Arg Glu Tyr Phe Lys Ile Thr Leu Tyr Gly Arg Thr Lys
                165                 170                 175

Glu Leu Thr Ser Glu Leu Lys Glu Asn Phe Ile Arg Phe Ser Lys Ser
            180                 185                 190

Leu Gly Leu Pro Glu Asn His Ile Val Phe Pro Val Pro Ile Asp Gln
        195                 200                 205

Cys Ile Asp Gly Gly Gly Ser Glu Asn Leu Tyr Phe Gln Gly Gly
    210                 215                 220

Ile Pro Cys Gly Glu Ser Cys Val Trp Ile Pro Cys Ile Ser Ala Ala
225                 230                 235                 240

Leu Gly Cys Ser Cys Lys Asn Lys Val Cys Tyr Arg Asn
                245                 250

```
<210> SEQ ID NO 114
<211> LENGTH: 277
<212> TYPE: PRT
<213> ORGANISM: artificial
<220> FEATURE:
<223> OTHER INFORMATION: IgK-SF-H6-GGS-lcn2C-GGS-ENLYFQ-GG-Brazzein
      amino acid sequence

<400> SEQUENCE: 114
```

Met Glu Thr Asp Thr Leu Leu Leu Trp Val Leu Leu Leu Trp Val Pro
1               5                   10                  15

Gly Ser Thr Gly Asp Tyr Lys Asp Glu His His His His His His Gly
            20                  25                  30

Gly Ser Gln Asp Ser Thr Ser Asp Leu Ile Pro Ala Pro Pro Leu Ser
        35                  40                  45

Lys Val Pro Leu Gln Gln Asn Phe Gln Asp Asn Gln Phe Gln Gly Lys

-continued

```
                50                  55                  60
Trp Tyr Val Val Gly Leu Ala Gly Asn Ala Ile Leu Arg Glu Asp Lys
 65                  70                  75                  80

Asp Pro Gln Lys Met Tyr Ala Thr Ile Tyr Glu Leu Lys Glu Asp Lys
                 85                  90                  95

Ser Tyr Asn Val Thr Ser Val Leu Phe Arg Lys Lys Cys Asp Tyr
                100                 105                 110

Trp Ile Arg Thr Phe Val Pro Gly Cys Gln Pro Gly Glu Phe Thr Leu
                115                 120                 125

Gly Asn Ile Lys Ser Tyr Pro Gly Leu Thr Ser Tyr Leu Val Arg Val
                130                 135                 140

Val Ser Thr Asn Tyr Asn Gln His Ala Met Val Phe Phe Lys Lys Val
145                 150                 155                 160

Ser Gln Asn Arg Glu Tyr Phe Lys Ile Thr Leu Tyr Gly Arg Thr Lys
                165                 170                 175

Glu Leu Thr Ser Glu Leu Lys Glu Asn Phe Ile Arg Phe Ser Lys Ser
                180                 185                 190

Leu Gly Leu Pro Glu Asn His Ile Val Phe Pro Val Pro Ile Asp Gln
                195                 200                 205

Cys Ile Asp Gly Gly Ser Glu Asn Leu Tyr Phe Gln Gly Gly Gln
210                 215                 220

Asp Lys Cys Lys Lys Val Tyr Glu Asn Tyr Pro Val Ser Lys Cys Gln
225                 230                 235                 240

Leu Ala Asn Gln Cys Asn Tyr Asp Cys Lys Leu Asp Lys His Ala Arg
                245                 250                 255

Ser Gly Glu Cys Phe Tyr Asp Glu Lys Arg Asn Leu Gln Cys Ile Cys
                260                 265                 270

Asp Tyr Cys Glu Tyr
                275

<210> SEQ ID NO 115
<211> LENGTH: 259
<212> TYPE: PRT
<213> ORGANISM: artificial
<220> FEATURE:
<223> OTHER INFORMATION: amino acid sequence for IgK-SF-H6-GGS-lcn2C-
      GGS-ENLYFQ-GG-fusion construct

<400> SEQUENCE: 115

Met Glu Thr Asp Thr Leu Leu Leu Trp Val Leu Leu Leu Trp Val Pro
 1                   5                  10                  15

Gly Ser Thr Gly Asp Tyr Lys Asp Glu His His His His His His Gly
                 20                  25                  30

Gly Ser Gln Asp Ser Thr Ser Asp Leu Ile Pro Ala Pro Pro Leu Ser
                 35                  40                  45

Lys Val Pro Leu Gln Gln Asn Phe Gln Asp Asn Gln Phe Gln Gly Lys
                 50                  55                  60

Trp Tyr Val Val Gly Leu Ala Gly Asn Ala Ile Leu Arg Glu Asp Lys
 65                  70                  75                  80

Asp Pro Gln Lys Met Tyr Ala Thr Ile Tyr Glu Leu Lys Glu Asp Lys
                 85                  90                  95

Ser Tyr Asn Val Thr Ser Val Leu Phe Arg Lys Lys Cys Asp Tyr
                100                 105                 110

Trp Ile Arg Thr Phe Val Pro Gly Cys Gln Pro Gly Glu Phe Thr Leu
                115                 120                 125
```

Gly Asn Ile Lys Ser Tyr Pro Gly Leu Thr Ser Tyr Leu Val Arg Val
            130                 135                 140

Val Ser Thr Asn Tyr Asn Gln His Ala Met Val Phe Phe Lys Lys Val
145                 150                 155                 160

Ser Gln Asn Arg Glu Tyr Phe Lys Ile Thr Leu Tyr Gly Arg Thr Lys
                165                 170                 175

Glu Leu Thr Ser Glu Leu Lys Glu Asn Phe Ile Arg Phe Ser Lys Ser
            180                 185                 190

Leu Gly Leu Pro Glu Asn His Ile Val Phe Pro Val Pro Ile Asp Gln
                195                 200                 205

Cys Ile Asp Gly Gly Ser Glu Asn Leu Tyr Phe Gln Gly Gly Met
210                 215                 220

Cys Met Pro Cys Phe Thr Thr Asp His Gln Met Ala Arg Lys Cys Asp
225                 230                 235                 240

Asp Cys Cys Gly Gly Lys Gly Arg Gly Lys Cys Tyr Gly Pro Gln Cys
                245                 250                 255

Leu Cys Arg

<210> SEQ ID NO 116
<211> LENGTH: 7
<212> TYPE: PRT
<213> ORGANISM: artificial
<220> FEATURE:
<223> OTHER INFORMATION: idealized furin cut site

<400> SEQUENCE: 116

Arg Ala Arg Tyr Lys Arg Ser
1               5

<210> SEQ ID NO 117
<211> LENGTH: 266
<212> TYPE: PRT
<213> ORGANISM: artificial
<220> FEATURE:
<223> OTHER INFORMATION: IgK-SF-H6-GGS-lcn2C-GGS-ENLYFQ-GS-MIDKINE amino
      acid sequence

<400> SEQUENCE: 117

Met Glu Thr Asp Thr Leu Leu Leu Trp Val Leu Leu Leu Trp Val Pro
1               5                   10                  15

Gly Ser Thr Gly Asp Tyr Lys Asp Glu His His His His His His Gly
            20                  25                  30

Gly Ser Gln Asp Ser Thr Ser Asp Leu Ile Pro Ala Pro Pro Leu Ser
        35                  40                  45

Lys Val Pro Leu Gln Gln Asn Phe Gln Asp Asn Gln Phe Gln Gly Lys
50                  55                  60

Trp Tyr Val Val Gly Leu Ala Gly Asn Ala Ile Leu Arg Glu Asp Lys
65                  70                  75                  80

Asp Pro Gln Lys Met Tyr Ala Thr Ile Tyr Glu Leu Lys Glu Asp Lys
                85                  90                  95

Ser Tyr Asn Val Thr Ser Val Leu Phe Arg Lys Lys Lys Cys Asp Tyr
            100                 105                 110

Trp Ile Arg Thr Phe Val Pro Gly Cys Gln Pro Gly Glu Phe Thr Leu
        115                 120                 125

Gly Asn Ile Lys Ser Tyr Pro Gly Leu Thr Ser Tyr Leu Val Arg Val
            130                 135                 140

Val Ser Thr Asn Tyr Asn Gln His Ala Met Val Phe Phe Lys Lys Val
145                 150                 155                 160

```
Ser Gln Asn Arg Glu Tyr Phe Lys Ile Thr Leu Tyr Gly Arg Thr Lys
                165                 170                 175

Glu Leu Thr Ser Glu Leu Lys Glu Asn Phe Ile Arg Phe Ser Lys Ser
            180                 185                 190

Leu Gly Leu Pro Glu Asn His Ile Val Phe Pro Val Pro Ile Asp Gln
        195                 200                 205

Cys Ile Asp Gly Gly Ser Glu Asn Leu Tyr Phe Gln Ser Asp Cys
    210                 215                 220

Lys Tyr Lys Phe Glu Asn Trp Gly Ala Cys Asp Gly Gly Thr Gly Thr
225                 230                 235                 240

Lys Val Arg Gln Gly Thr Leu Lys Lys Ala Arg Tyr Asn Ala Gln Cys
                245                 250                 255

Gln Glu Thr Ile Arg Val Thr Lys Pro Cys
            260                 265

<210> SEQ ID NO 118
<211> LENGTH: 250
<212> TYPE: PRT
<213> ORGANISM: artificial
<220> FEATURE:
<223> OTHER INFORMATION: IgK-SF-H6-GGS-lcn2C-GGS-ENLYFQ-GG-Violacin A
      amino acid sequence

<400> SEQUENCE: 118

Met Glu Thr Asp Thr Leu Leu Leu Trp Val Leu Leu Leu Trp Val Pro
1               5                   10                  15

Gly Ser Thr Gly Asp Tyr Lys Asp Glu His His His His His His Gly
            20                  25                  30

Gly Ser Gln Asp Ser Thr Ser Asp Leu Ile Pro Ala Pro Pro Leu Ser
        35                  40                  45

Lys Val Pro Leu Gln Gln Asn Phe Gln Asp Asn Gln Phe Gln Gly Lys
50                  55                  60

Trp Tyr Val Val Gly Leu Ala Gly Asn Ala Ile Leu Arg Glu Asp Lys
65                  70                  75                  80

Asp Pro Gln Lys Met Tyr Ala Thr Ile Tyr Glu Leu Lys Glu Asp Lys
                85                  90                  95

Ser Tyr Asn Val Thr Ser Val Leu Phe Arg Lys Lys Lys Cys Asp Tyr
            100                 105                 110

Trp Ile Arg Thr Phe Val Pro Gly Cys Gln Pro Gly Glu Phe Thr Leu
        115                 120                 125

Gly Asn Ile Lys Ser Tyr Pro Gly Leu Thr Ser Tyr Leu Val Arg Val
    130                 135                 140

Val Ser Thr Asn Tyr Asn Gln His Ala Met Val Phe Phe Lys Lys Val
145                 150                 155                 160

Ser Gln Asn Arg Glu Tyr Phe Lys Ile Thr Leu Tyr Gly Arg Thr Lys
                165                 170                 175

Glu Leu Thr Ser Glu Leu Lys Glu Asn Phe Ile Arg Phe Ser Lys Ser
            180                 185                 190

Leu Gly Leu Pro Glu Asn His Ile Val Phe Pro Val Pro Ile Asp Gln
        195                 200                 205

Cys Ile Asp Gly Gly Ser Glu Asn Leu Tyr Phe Gln Gly Gly Ser
    210                 215                 220

Ala Ile Ser Cys Gly Glu Thr Cys Phe Lys Phe Lys Cys Tyr Thr Pro
225                 230                 235                 240

Arg Cys Ser Cys Ser Tyr Pro Val Cys Lys
                245                 250
```

<210> SEQ ID NO 119
<211> LENGTH: 234
<212> TYPE: PRT
<213> ORGANISM: artificial
<220> FEATURE:
<223> OTHER INFORMATION: IgK-SF-H6-GGS-lcn2C-GGS-ENLYFQ-GG-Lambda Toxin
      amino acid sequence

<400> SEQUENCE: 119

Met Glu Thr Asp Thr Leu Leu Leu Trp Val Leu Leu Leu Trp Val Pro
1               5                   10                  15

Gly Ser Thr Gly Asp Tyr Lys Asp Glu His His His His His His Gly
                20                  25                  30

Gly Ser Gln Asp Ser Thr Ser Asp Leu Ile Pro Ala Pro Pro Leu Ser
            35                  40                  45

Lys Val Pro Leu Gln Gln Asn Phe Gln Asp Asn Gln Phe Gln Gly Lys
        50                  55                  60

Trp Tyr Val Val Gly Leu Ala Gly Asn Ala Ile Leu Arg Glu Asp Lys
65                  70                  75                  80

Asp Pro Gln Lys Met Tyr Ala Thr Ile Tyr Glu Leu Lys Glu Asp Lys
                85                  90                  95

Ser Tyr Asn Val Thr Ser Val Leu Phe Arg Lys Lys Lys Cys Asp Tyr
            100                 105                 110

Trp Ile Arg Thr Phe Val Pro Gly Cys Gln Pro Gly Glu Phe Thr Leu
        115                 120                 125

Gly Asn Ile Lys Ser Tyr Pro Gly Leu Thr Ser Tyr Leu Val Arg Val
    130                 135                 140

Val Ser Thr Asn Tyr Asn Gln His Ala Met Val Phe Phe Lys Lys Val
145                 150                 155                 160

Ser Gln Asn Arg Glu Tyr Phe Lys Ile Thr Leu Tyr Gly Arg Thr Lys
                165                 170                 175

Glu Leu Thr Ser Glu Leu Lys Glu Asn Phe Ile Arg Phe Ser Lys Ser
            180                 185                 190

Leu Gly Leu Pro Glu Asn His Ile Val Phe Pro Val Pro Ile Asp Gln
        195                 200                 205

Cys Ile Asp Gly Gly Gly Ser Glu Asn Leu Tyr Phe Gln Gly Gly Val
    210                 215                 220

Cys Cys Gly Tyr Lys Leu Cys His Pro Cys
225                 230

<210> SEQ ID NO 120
<211> LENGTH: 236
<212> TYPE: PRT
<213> ORGANISM: artificial
<220> FEATURE:
<223> OTHER INFORMATION: IgK-SF-H6-GGS-lcn2C-GGS-ENLYFQ-GG-Lambda Toxin
      NG amino acid sequence

<400> SEQUENCE: 120

Met Glu Thr Asp Thr Leu Leu Leu Trp Val Leu Leu Leu Trp Val Pro
1               5                   10                  15

Gly Ser Thr Gly Asp Tyr Lys Asp Glu His His His His His His Gly
                20                  25                  30

Gly Ser Gln Asp Ser Thr Ser Asp Leu Ile Pro Ala Pro Pro Leu Ser
            35                  40                  45

Lys Val Pro Leu Gln Gln Asn Phe Gln Asp Asn Gln Phe Gln Gly Lys

```
              50                  55                  60
Trp Tyr Val Val Gly Leu Ala Gly Asn Ala Ile Leu Arg Glu Asp Lys
 65                  70                  75                  80

Asp Pro Gln Lys Met Tyr Ala Thr Ile Tyr Glu Leu Lys Glu Asp Lys
                     85                  90                  95

Ser Tyr Asn Val Thr Ser Val Leu Phe Arg Lys Lys Lys Cys Asp Tyr
                    100                 105                 110

Trp Ile Arg Thr Phe Val Pro Gly Cys Gln Pro Gly Glu Phe Thr Leu
                115                 120                 125

Gly Asn Ile Lys Ser Tyr Pro Gly Leu Thr Ser Tyr Leu Val Arg Val
                130                 135                 140

Val Ser Thr Asn Tyr Asn Gln His Ala Met Val Phe Phe Lys Lys Val
145                 150                 155                 160

Ser Gln Asn Arg Glu Tyr Phe Lys Ile Thr Leu Tyr Gly Arg Thr Lys
                165                 170                 175

Glu Leu Thr Ser Glu Leu Lys Glu Asn Phe Ile Arg Phe Ser Lys Ser
                180                 185                 190

Leu Gly Leu Pro Glu Asn His Ile Val Phe Pro Val Pro Ile Asp Gln
                195                 200                 205

Cys Ile Asp Gly Gly Ser Glu Asn Leu Tyr Phe Gln Gly Gly Asn
    210                 215                 220

Gly Val Cys Cys Gly Tyr Lys Leu Cys His Pro Cys
225                 230                 235

<210> SEQ ID NO 121
<211> LENGTH: 262
<212> TYPE: PRT
<213> ORGANISM: artificial
<220> FEATURE:
<223> OTHER INFORMATION: IgK-SF-H6-GGS-lcn2C-GGS-ENLYFQ-GG-Potato
      Carboxypeptidase Inhibitor amino acid sequence

<400> SEQUENCE: 121

Met Glu Thr Asp Thr Leu Leu Leu Trp Val Leu Leu Leu Trp Val Pro
 1               5                  10                  15

Gly Ser Thr Gly Asp Tyr Lys Asp Glu His His His His His His Gly
                 20                  25                  30

Gly Ser Gln Asp Ser Thr Ser Asp Leu Ile Pro Ala Pro Pro Leu Ser
             35                  40                  45

Lys Val Pro Leu Gln Gln Asn Phe Gln Asp Asn Gln Phe Gln Gly Lys
 50                  55                  60

Trp Tyr Val Val Gly Leu Ala Gly Asn Ala Ile Leu Arg Glu Asp Lys
 65                  70                  75                  80

Asp Pro Gln Lys Met Tyr Ala Thr Ile Tyr Glu Leu Lys Glu Asp Lys
                     85                  90                  95

Ser Tyr Asn Val Thr Ser Val Leu Phe Arg Lys Lys Lys Cys Asp Tyr
                    100                 105                 110

Trp Ile Arg Thr Phe Val Pro Gly Cys Gln Pro Gly Glu Phe Thr Leu
                115                 120                 125

Gly Asn Ile Lys Ser Tyr Pro Gly Leu Thr Ser Tyr Leu Val Arg Val
                130                 135                 140

Val Ser Thr Asn Tyr Asn Gln His Ala Met Val Phe Phe Lys Lys Val
145                 150                 155                 160

Ser Gln Asn Arg Glu Tyr Phe Lys Ile Thr Leu Tyr Gly Arg Thr Lys
                165                 170                 175
```

```
Glu Leu Thr Ser Glu Leu Lys Glu Asn Phe Ile Arg Phe Ser Lys Ser
            180                 185                 190

Leu Gly Leu Pro Glu Asn His Ile Val Phe Pro Val Pro Ile Asp Gln
        195                 200                 205

Cys Ile Asp Gly Gly Gly Ser Glu Asn Leu Tyr Phe Gln Gly Gly Gln
        210                 215                 220

Gln His Ala Asp Pro Ile Cys Asn Lys Pro Cys Lys Thr His Asp Asp
225                 230                 235                 240

Cys Ser Gly Ala Trp Phe Cys Gln Ala Cys Trp Asn Ser Ala Arg Thr
                245                 250                 255

Cys Gly Pro Tyr Val Gly
            260
```

<210> SEQ ID NO 122
<211> LENGTH: 191
<212> TYPE: DNA
<213> ORGANISM: artificial
<220> FEATURE:
<223> OTHER INFORMATION: sequence of an oligonucleotide coding for a
      knottin variant in a libary vector

<400> SEQUENCE: 122

```
ctgtaacctg atcctgctag cgggtctcaa ggtggatcca tgtgcatgcc gtgcttcacc     60
accgataacg aaatggcggc gaactgcgat cgctgctgcg gtggccgtgg ccgtggccgc    120
tgctatggcc cgcagtgcct gtgccgctaa tgcggccgct agtgagaccg cttgcatggc    180
tagtacctac g                                                        191
```

<210> SEQ ID NO 123
<211> LENGTH: 191
<212> TYPE: DNA
<213> ORGANISM: artificial
<220> FEATURE:
<223> OTHER INFORMATION: sequence of an oligonucleotide coding for a
      knottin variant in a libary vector

<400> SEQUENCE: 123

```
ctgtaacctg atcctgctag cgggtctcaa ggtggatcca tgtgcatgcc gtgcttcacc     60
accgataacg atatggcgga tgaatgcgat cgctgctgcg gtggccgtgg ccgtggccgc    120
tgctatggcc cgcagtgcct gtgccgctaa tgcggccgct agtgagaccg cttgcatggc    180
tagtacctac g                                                        191
```

<210> SEQ ID NO 124
<211> LENGTH: 36
<212> TYPE: PRT
<213> ORGANISM: artificial
<220> FEATURE:
<223> OTHER INFORMATION: unique tryptic peptide of a knottin
<220> FEATURE:
<221> NAME/KEY: MISC_FEATURE
<222> LOCATION: (21)..(27)
<223> OTHER INFORMATION: Xaa can be any amino acid
<220> FEATURE:
<221> NAME/KEY: MISC_FEATURE
<222> LOCATION: (29)..(32)
<223> OTHER INFORMATION: Xaa can be any amino acid
<220> FEATURE:
<221> NAME/KEY: MISC_FEATURE
<222> LOCATION: (34)..(34)
<223> OTHER INFORMATION: Xaa can be any amino acid
<220> FEATURE:
<221> NAME/KEY: MISC_FEATURE
<222> LOCATION: (36)..(36)
<223> OTHER INFORMATION: Xaa can be any amino acid

<400> SEQUENCE: 124

Met Cys Met Pro Cys Phe Thr Thr Asp Asn Glu Met Ala Ala Asn Cys
1               5                   10                  15

Asp Arg Cys Cys Xaa Xaa Xaa Xaa Xaa Xaa Cys Xaa Xaa Xaa Xaa
            20                  25                  30

Cys Xaa Cys Xaa
        35

<210> SEQ ID NO 125
<211> LENGTH: 36
<212> TYPE: PRT
<213> ORGANISM: artificial
<220> FEATURE:
<223> OTHER INFORMATION: unique tryptic peptide of a knottin
<220> FEATURE:
<221> NAME/KEY: MISC_FEATURE
<222> LOCATION: (21)..(27)
<223> OTHER INFORMATION: Xaa can be any amino acid
<220> FEATURE:
<221> NAME/KEY: MISC_FEATURE
<222> LOCATION: (29)..(32)
<223> OTHER INFORMATION: Xaa can be any amino acid
<220> FEATURE:
<221> NAME/KEY: MISC_FEATURE
<222> LOCATION: (34)..(34)
<223> OTHER INFORMATION: Xaa can be any amino acid
<220> FEATURE:
<221> NAME/KEY: MISC_FEATURE
<222> LOCATION: (36)..(36)
<223> OTHER INFORMATION: Xaa can be any amino acid

<400> SEQUENCE: 125

Met Cys Met Pro Cys Phe Thr Thr Asp Asn Asp Met Ala Asp Glu Cys
1               5                   10                  15

Asp Arg Cys Cys Xaa Xaa Xaa Xaa Xaa Xaa Cys Xaa Xaa Xaa Xaa
            20                  25                  30

Cys Xaa Cys Xaa
        35

<210> SEQ ID NO 126
<211> LENGTH: 112
<212> TYPE: DNA
<213> ORGANISM: artificial
<220> FEATURE:
<223> OTHER INFORMATION: sequence of an oligonucleotide coding for a
      knottin variant in a libary vector

<400> SEQUENCE: 126
atgtgcatgc cgtgcttcac caccgataac gaaatggcgg cgaactgcga tcgctgctgc        60
ggtggccgtg ccgtggccg ctgctatggc ccgcagtgcc tgtgccgcta at                 112

<210> SEQ ID NO 127
<211> LENGTH: 36
<212> TYPE: PRT
<213> ORGANISM: artificial
<220> FEATURE:
<223> OTHER INFORMATION: unique tryptic peptide of a knottin
<220> FEATURE:
<221> NAME/KEY: MISC_FEATURE
<222> LOCATION: (21)..(27)
<223> OTHER INFORMATION: Xaa can be any amino acid
<220> FEATURE:
<221> NAME/KEY: MISC_FEATURE
<222> LOCATION: (29)..(32)
<223> OTHER INFORMATION: Xaa can be any amino acid
<220> FEATURE:
<221> NAME/KEY: MISC_FEATURE

```
<222> LOCATION: (34)..(34)
<223> OTHER INFORMATION: Xaa can be any amino acid

<400> SEQUENCE: 127

Met Cys Met Pro Cys Phe Thr Thr Asp Asn Glu Met Ala Ala Asn Cys
1               5                   10                  15

Asp Arg Cys Cys Xaa Xaa Xaa Xaa Xaa Xaa Cys Xaa Xaa Xaa Xaa
            20                  25                  30

Cys Xaa Cys Arg
        35

<210> SEQ ID NO 128
<211> LENGTH: 38
<212> TYPE: PRT
<213> ORGANISM: artificial
<220> FEATURE:
<223> OTHER INFORMATION: representative sequence from a cloned knottin
      library

<400> SEQUENCE: 128

Gly Ser Glu Ile Ser Cys Glu Pro Gly Arg Thr Phe Arg Asp Arg Cys
1               5                   10                  15

Asn Gln Cys Phe Cys Gly Phe Asp Gly Arg Arg Ala Ala Cys Thr Ile
            20                  25                  30

Arg Ala Cys Pro Asn Gln
        35

<210> SEQ ID NO 129
<211> LENGTH: 38
<212> TYPE: PRT
<213> ORGANISM: artificial
<220> FEATURE:
<223> OTHER INFORMATION: representative sequence from a cloned knottin
      library

<400> SEQUENCE: 129

Gly Ser Glu Ile His Cys Gln Pro Gly Arg Thr Phe Arg Asp Arg Cys
1               5                   10                  15

Asn Thr Cys Tyr Cys Gly Trp Tyr Gly Arg Ser Ala Ala Cys Thr Leu
            20                  25                  30

Arg Ala Cys Pro Asn Gln
        35

<210> SEQ ID NO 130
<211> LENGTH: 38
<212> TYPE: PRT
<213> ORGANISM: artificial
<220> FEATURE:
<223> OTHER INFORMATION: representative sequence from a cloned knottin
      library

<400> SEQUENCE: 130

Gly Ser Glu Ile Ser Cys Glu Pro Gly Gly Thr Phe Glu Asp Arg Cys
1               5                   10                  15

Asn Val Cys Arg Cys Gly Ala Asp Gly Arg Ser Ala Gly Cys Thr Leu
            20                  25                  30

Arg Ala Cys Pro Asn Gln
        35

<210> SEQ ID NO 131
<211> LENGTH: 38
<212> TYPE: PRT
<213> ORGANISM: artificial
```

```
<220> FEATURE:
<223> OTHER INFORMATION: representative sequence from a cloned knottin
      library

<400> SEQUENCE: 131

Gly Ser Arg Ile Asp Cys Arg Pro Gly Arg Thr Phe Arg Asp Arg Cys
1               5                   10                  15

Asn Thr Cys Met Cys Gly Trp Thr Gly His Ser Ala Ala Cys Thr Leu
            20                  25                  30

Arg Ala Cys Pro Asn Gln
        35

<210> SEQ ID NO 132
<211> LENGTH: 38
<212> TYPE: PRT
<213> ORGANISM: artificial
<220> FEATURE:
<223> OTHER INFORMATION: representative sequence from a cloned knottin
      library

<400> SEQUENCE: 132

Gly Ser Glu Ile Ser Cys Glu Pro Gly Arg Thr Phe Arg Asp Arg Cys
1               5                   10                  15

Asn Thr Cys His Cys Trp Ala Asp Gly Arg Gly Ala Ala Cys Thr Glu
            20                  25                  30

Arg Ala Cys Pro Asn Gln
        35

<210> SEQ ID NO 133
<211> LENGTH: 38
<212> TYPE: PRT
<213> ORGANISM: artificial
<220> FEATURE:
<223> OTHER INFORMATION: representative sequence from a cloned knottin
      library

<400> SEQUENCE: 133

Gly Ser Glu Ser Ser Cys Glu Pro Gly Ala Thr Trp Arg Asp Arg Cys
1               5                   10                  15

Asn Thr Cys Arg Cys Arg Ala Asp Gly Arg Ser Ala Ala Cys Thr Val
            20                  25                  30

Arg Gln Cys Pro Asn Gln
        35

<210> SEQ ID NO 134
<211> LENGTH: 38
<212> TYPE: PRT
<213> ORGANISM: artificial
<220> FEATURE:
<223> OTHER INFORMATION: representative sequence from a cloned knottin
      library

<400> SEQUENCE: 134

Gly Ser Glu Ile Phe Cys Ile Pro Gly Arg Thr Phe Arg Asp Arg Cys
1               5                   10                  15

Asn Thr Cys Arg Cys Gly Arg Arg Gly Ile Ser Ala Ala Cys Thr Leu
            20                  25                  30

Arg Ala Cys Pro Asn Gln
        35

<210> SEQ ID NO 135
<211> LENGTH: 38
<212> TYPE: PRT
```

```
<213> ORGANISM: artificial
<220> FEATURE:
<223> OTHER INFORMATION: representative sequence from a cloned knottin
      library

<400> SEQUENCE: 135

Gly Ser Glu Ile Ser Cys Glu Pro Gly Arg Thr Phe Arg Asp Arg Cys
1               5                   10                  15

Asn Thr Cys Arg Cys Gly Ala Asp Gly Arg Ser Ala Ala Cys Thr Leu
            20                  25                  30

Phe Asp Cys Ser Leu Gln
        35

<210> SEQ ID NO 136
<211> LENGTH: 38
<212> TYPE: PRT
<213> ORGANISM: artificial
<220> FEATURE:
<223> OTHER INFORMATION: representative sequence from a cloned knottin
      library

<400> SEQUENCE: 136

Gly Ser Glu Ile Ser Cys Glu Pro Gly Arg Thr Ser Arg Asp Arg Cys
1               5                   10                  15

Asn Thr Cys Arg Cys Gly Ala Asp Gly Arg Ser Ala Ala Cys Thr Leu
            20                  25                  30

Ile Asp Cys Pro Gly Gln
        35

<210> SEQ ID NO 137
<211> LENGTH: 38
<212> TYPE: PRT
<213> ORGANISM: artificial
<220> FEATURE:
<223> OTHER INFORMATION: representative sequence from a cloned knottin
      library

<400> SEQUENCE: 137

Gly Ser Glu Ile Ser Cys Glu Pro Gly Arg Thr Phe Arg Asp Arg Cys
1               5                   10                  15

Asn Thr Cys Arg Cys Gly Ala Asp Gly Arg Asp Ala Ala Cys Thr Leu
            20                  25                  30

Gly His Cys Phe Phe Tyr
        35

<210> SEQ ID NO 138
<211> LENGTH: 38
<212> TYPE: PRT
<213> ORGANISM: artificial
<220> FEATURE:
<223> OTHER INFORMATION: representative sequence from a cloned knottin
      library

<400> SEQUENCE: 138

Gly Ser Glu Ile Ser Cys Glu Pro Gly Phe Thr Glu Gln Asp Arg Cys
1               5                   10                  15

Asn Thr Cys Arg Cys Gly Ala Ile Gly Arg Ser Ala Ala Cys Thr Leu
            20                  25                  30

Arg Ala Cys Pro Asn Gln
        35

<210> SEQ ID NO 139
<211> LENGTH: 38
```

```
<212> TYPE: PRT
<213> ORGANISM: artificial
<220> FEATURE:
<223> OTHER INFORMATION: representative sequence from a cloned knottin
      library

<400> SEQUENCE: 139

Gly Ser Glu Ile Ser Cys Glu Pro Tyr Ser Thr Phe Arg Asp Arg Cys
1               5                   10                  15

Asn Thr Cys Ser Cys Gly Ala Asp Gly Arg Gly Ala Ala Cys Thr Met
            20                  25                  30

Arg Ala Cys Pro Asn Gln
        35

<210> SEQ ID NO 140
<211> LENGTH: 38
<212> TYPE: PRT
<213> ORGANISM: artificial
<220> FEATURE:
<223> OTHER INFORMATION: representative sequence from a cloned knottin
      library

<400> SEQUENCE: 140

Gly Ser Glu Ile Ser Cys Glu Pro Gly Arg Thr Phe Arg Asp Arg Cys
1               5                   10                  15

Asn Thr Cys Arg Cys Gly Ala Asp Gly Arg Ser Ala Ala Cys Thr Leu
            20                  25                  30

Val Ala Cys Leu Ile Thr
        35

<210> SEQ ID NO 141
<211> LENGTH: 38
<212> TYPE: PRT
<213> ORGANISM: artificial
<220> FEATURE:
<223> OTHER INFORMATION: representative sequence from a cloned knottin
      library

<400> SEQUENCE: 141

Gly Ser Glu Ile Phe Cys Ile Pro Gly Val Thr Phe Arg Phe Arg Cys
1               5                   10                  15

Asn Thr Cys Arg Cys Gly Met Asp Gly Arg Ser Ala Ala Cys Thr Leu
            20                  25                  30

Arg Ala Cys Pro Asn Gln
        35

<210> SEQ ID NO 142
<211> LENGTH: 38
<212> TYPE: PRT
<213> ORGANISM: artificial
<220> FEATURE:
<223> OTHER INFORMATION: representative sequence from a cloned knottin
      library

<400> SEQUENCE: 142

Gly Ser Glu Asn Asp Cys His Pro Gly Thr Thr Phe Arg Asp Arg Cys
1               5                   10                  15

Asn Thr Cys Arg Cys Gly Gly Glu Gly Arg Ser Ala Ala Cys Thr Leu
            20                  25                  30

Arg Ala Cys Pro Asn Gln
        35

<210> SEQ ID NO 143
```

```
<211> LENGTH: 38
<212> TYPE: PRT
<213> ORGANISM: artificial
<220> FEATURE:
<223> OTHER INFORMATION: representative sequence from a cloned knottin
      library

<400> SEQUENCE: 143

Gly Ser Gln Arg Ser Cys Glu Pro Gly Arg Thr Phe Arg Asp Arg Cys
1               5                   10                  15

Asn Thr Cys Arg Cys Gly Ala Asp Gly Arg Ser Ala Ala Cys Thr Leu
            20                  25                  30

Phe Ile Cys Pro Phe Gln
            35

<210> SEQ ID NO 144
<211> LENGTH: 38
<212> TYPE: PRT
<213> ORGANISM: artificial
<220> FEATURE:
<223> OTHER INFORMATION: representative sequence from a cloned knottin
      library

<400> SEQUENCE: 144

Gly Ser Glu Ile Ser Cys Glu Pro Gly Arg Thr Phe Arg Asp Arg Cys
1               5                   10                  15

Asn Thr Cys Arg Cys Gly Ala Asp Gly Arg Ser Ala Ala Cys Thr Leu
            20                  25                  30

Phe Leu Cys Gly Phe Ile
            35

<210> SEQ ID NO 145
<211> LENGTH: 38
<212> TYPE: PRT
<213> ORGANISM: artificial
<220> FEATURE:
<223> OTHER INFORMATION: representative sequence from a cloned knottin
      library

<400> SEQUENCE: 145

Gly Ser Glu Ile Ser Cys Glu Pro Asp Ser Thr Thr Arg Asp Arg Cys
1               5                   10                  15

Asn Ser Cys Arg Cys Gly Asn Asp Gly Arg Ser Ala Ala Cys Thr Leu
            20                  25                  30

Arg Ala Cys Pro Asn Gln
            35

<210> SEQ ID NO 146
<211> LENGTH: 38
<212> TYPE: PRT
<213> ORGANISM: artificial
<220> FEATURE:
<223> OTHER INFORMATION: representative sequence from a cloned knottin
      library

<400> SEQUENCE: 146

Gly Ser Glu Ile Ser Cys Glu Pro Gly Arg Thr Phe Arg Asp Arg Cys
1               5                   10                  15

Asn Thr Cys Arg Cys Gly Ala Asp Gly Arg Ser Glu Ala Cys Thr Leu
            20                  25                  30

His Asn Cys Arg Glu Gln
            35
```

```
<210> SEQ ID NO 147
<211> LENGTH: 38
<212> TYPE: PRT
<213> ORGANISM: artificial
<220> FEATURE:
<223> OTHER INFORMATION: representative sequence from a cloned knottin
      library

<400> SEQUENCE: 147

Gly Ser Asp Ile Ser Cys Glu Pro Gly Ser Thr His Arg Asp Arg Cys
1               5                   10                  15

Asn Thr Cys Arg Cys Ser Ala Asp Gly Arg Ser Arg Ala Cys Thr Leu
            20                  25                  30

Arg Ala Cys Pro Asn Gln
        35

<210> SEQ ID NO 148
<211> LENGTH: 38
<212> TYPE: PRT
<213> ORGANISM: artificial
<220> FEATURE:
<223> OTHER INFORMATION: representative sequence from a cloned knottin
      library

<400> SEQUENCE: 148

Gly Ser Glu Asp Ser Cys Glu Pro Gly Trp Thr Gln Arg Met Arg Cys
1               5                   10                  15

Asn Thr Cys Arg Cys Thr Ala Asp Gly Arg Ser Ala Ala Cys Thr Leu
            20                  25                  30

Arg Ala Cys Pro Asn Gln
        35

<210> SEQ ID NO 149
<211> LENGTH: 38
<212> TYPE: PRT
<213> ORGANISM: artificial
<220> FEATURE:
<223> OTHER INFORMATION: representative sequence from a cloned knottin
      library

<400> SEQUENCE: 149

Gly Ser Glu Ile Ser Cys Glu Pro Gly Arg Thr Phe Arg Asp Arg Cys
1               5                   10                  15

Asn Thr Cys Arg Cys Gly Ala Asp Gly Arg Ser Ala Ala Cys Thr Leu
            20                  25                  30

His His Cys Ile Tyr Trp
        35

<210> SEQ ID NO 150
<211> LENGTH: 38
<212> TYPE: PRT
<213> ORGANISM: artificial
<220> FEATURE:
<223> OTHER INFORMATION: representative sequence from a cloned knottin
      library

<400> SEQUENCE: 150

Gly Ser Glu Val Ser Cys Glu Pro Gly Arg Thr Phe Arg Ser Arg Cys
1               5                   10                  15

Asn Asp Cys Val Cys Gly Ala Asp Gly Arg His Ala Ala Cys Thr Ile
            20                  25                  30

Arg Ala Cys Pro Asn Gln
        35
```

<210> SEQ ID NO 151
<211> LENGTH: 38
<212> TYPE: PRT
<213> ORGANISM: artificial
<220> FEATURE:
<223> OTHER INFORMATION: representative sequence from a cloned knottin
      library

<400> SEQUENCE: 151

Gly Ser Glu Ile Ser Cys Glu Pro Gly Arg Thr Phe Arg Asp Arg Cys
1               5                   10                  15

Asn Thr Cys Arg Cys Gly Ala Asp Gly Arg Ser Ala Ala Cys Thr Leu
            20                  25                  30

Val Phe Cys His Glu Asp
        35

<210> SEQ ID NO 152
<211> LENGTH: 38
<212> TYPE: PRT
<213> ORGANISM: artificial
<220> FEATURE:
<223> OTHER INFORMATION: representative sequence from a cloned knottin
      library

<400> SEQUENCE: 152

Gly Ser Glu Ile Ser Cys Glu Pro Trp Arg Thr Phe Arg Asp Arg Cys
1               5                   10                  15

Asn Thr Cys Arg Cys Gly Ala Asp Gly Arg Gly Ala Ala Cys Thr Leu
            20                  25                  30

Val Ile Cys Gly Met Gln
        35

<210> SEQ ID NO 153
<211> LENGTH: 38
<212> TYPE: PRT
<213> ORGANISM: artificial
<220> FEATURE:
<223> OTHER INFORMATION: representative sequence from a cloned knottin
      library

<400> SEQUENCE: 153

Gly Ser Glu Ile Ser Cys Glu Pro Gly Arg Thr Phe Arg Asp Arg Cys
1               5                   10                  15

Asn Met Cys Gly Cys Gly Ala Asp Gly Arg Trp Ala Arg Cys Thr Arg
            20                  25                  30

Arg Ala Cys Pro Asn Gln
        35

<210> SEQ ID NO 154
<211> LENGTH: 38
<212> TYPE: PRT
<213> ORGANISM: artificial
<220> FEATURE:
<223> OTHER INFORMATION: representative sequence from a cloned knottin
      library

<400> SEQUENCE: 154

Gly Ser Glu Ile Ser Cys Glu Pro Gly Arg Thr Phe Arg Asp Arg Cys
1               5                   10                  15

Asn Thr Cys Arg Cys Gly Ala Asp Gly Arg Ser Ala Ala Cys Thr Leu
            20                  25                  30

Phe Thr Cys Thr Tyr Phe
        35

<210> SEQ ID NO 155
<211> LENGTH: 38
<212> TYPE: PRT
<213> ORGANISM: artificial
<220> FEATURE:
<223> OTHER INFORMATION: representative sequence from a cloned knottin
      library

<400> SEQUENCE: 155

Gly Ser Glu Ile Ser Cys Glu Pro Gly Arg Thr Trp Arg Asp Arg Cys
1               5                   10                  15

Asn Thr Cys Arg Cys Gly Ala Asp Gly Arg Ser Ala Ala Cys Thr Leu
            20                  25                  30

Asn Gly Cys Leu Leu Gln
            35

<210> SEQ ID NO 156
<211> LENGTH: 38
<212> TYPE: PRT
<213> ORGANISM: artificial
<220> FEATURE:
<223> OTHER INFORMATION: representative sequence from a cloned knottin
      library

<400> SEQUENCE: 156

Gly Ser Glu Ile Ser Cys Glu Pro Gly Arg Thr Phe Arg Asp Arg Cys
1               5                   10                  15

Asn Thr Cys Arg Cys Gly Ala Asp Gly Arg Ser Ala Ala Cys Thr Leu
            20                  25                  30

Ala Asn Cys Phe Phe Ala
            35

<210> SEQ ID NO 157
<211> LENGTH: 178
<212> TYPE: PRT
<213> ORGANISM: Homo sapiens

<400> SEQUENCE: 157

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

```
Leu Pro Glu Asn His Ile Val Phe Pro Val Pro Ile Asp Gln Cys Ile
                165                 170                 175

Asp Gly

<210> SEQ ID NO 158
<211> LENGTH: 178
<212> TYPE: PRT
<213> ORGANISM: Pan troglodytes

<400> SEQUENCE: 158

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
        50                  55                  60

Asn Val Thr Ser Val Leu Phe Arg Lys Lys Lys Cys Asp Tyr Trp Ile
65                  70                  75                  80

Arg Thr Phe Val Pro Gly Arg Gln Pro Gly Glu Phe Thr Leu Gly Asn
                85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
        130                 135                 140

Thr Ser Glu Leu Gln Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 159
<211> LENGTH: 180
<212> TYPE: PRT
<213> ORGANISM: Gorilla gorilla

<400> SEQUENCE: 159

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
        50                  55                  60

Asn Val Thr Ser Val Leu Phe Arg Glu Lys Ala Gln Lys Cys Asp Tyr
65                  70                  75                  80

Trp Ile Arg Thr Phe Val Pro Gly Ser Gln Pro Gly Glu Phe Thr Leu
                85                  90                  95

Gly Asn Ile Lys Ser Tyr Pro Gly Leu Thr Ser Tyr Leu Val Arg Val
                100                 105                 110

Val Ser Thr Asn Tyr Asn Gln His Ala Met Val Phe Phe Lys Lys Val
            115                 120                 125
```

Ser Gln Asn Arg Glu Tyr Phe Lys Ile Thr Leu Tyr Gly Arg Thr Lys
    130                 135                 140

Glu Leu Thr Ser Glu Leu Lys Glu Asn Phe Ile Arg Phe Ser Lys Ser
145                 150                 155                 160

Leu Gly Leu Pro Glu Asn His Ile Val Phe Pro Val Pro Ile Asp Gln
                165                 170                 175

Cys Ile Asp Gly
            180

<210> SEQ ID NO 160
<211> LENGTH: 178
<212> TYPE: PRT
<213> ORGANISM: Pongo pygmaeus

<400> SEQUENCE: 160

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Arg Arg Glu Asp Lys Asp Ser
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Ser Gln Pro Gly Glu Phe Thr Leu Gly Asn
                85                  90                  95

Thr Lys Gly Tyr Pro Gly Leu Thr Ser Tyr Leu Val Arg Val Val Ser
            100                 105                 110

Thr Asn Tyr Asn Gln Tyr Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Ala Pro Ile Asp Gln Cys Ile
                165                 170                 175

Asp Gly

<210> SEQ ID NO 161
<211> LENGTH: 178
<212> TYPE: PRT
<213> ORGANISM: Macaca mulatta

<400> SEQUENCE: 161

Gln Asp Ser Ser Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ser Gly Asn Ala Val Gly Arg Lys Asp Glu Ala Pro
        35                  40                  45

Leu Lys Met Tyr Ala Thr Ile Tyr Glu Leu Lys Glu Asp Lys Ser Tyr
    50                  55                  60

Asn Val Thr Ser Ile Leu Phe Arg Lys Glu Lys Cys Asp Tyr Trp Ile
65                  70                  75                  80

-continued

Arg Thr Phe Val Pro Gly Ser Gln Pro Gly Glu Phe Thr Leu Gly Asn
                85                  90                  95

Ile Gln Asn His Pro Gly Leu Thr Ser Tyr Val Val Arg Val Val Ser
            100                 105                 110

Thr Asn Tyr Lys Gln Tyr Ala Met Val Phe Phe Lys Lys Val Ser Gln
        115                 120                 125

Asn Lys Glu Tyr Phe Lys Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Ser Val Pro Ile Asp Gln Cys Ile
                165                 170                 175

Asn Gly

<210> SEQ ID NO 162
<211> LENGTH: 179
<212> TYPE: PRT
<213> ORGANISM: Callithrix jacchus

<400> SEQUENCE: 162

Gln Asp Ser Pro Ser Pro Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Arg Arg Glu Asp Gln Asp Ser
        35                  40                  45

Leu Lys Met Tyr Ala Thr Ile Tyr Glu Leu Lys Glu Asp Lys Ser Tyr
50                  55                  60

Asn Val Thr Ser Val Leu Phe Arg Lys Ala Gln Lys Cys Asp Tyr Trp
65                  70                  75                  80

Ile Arg Thr Phe Val Pro Ser Ser Arg Pro Gly Glu Phe Lys Leu Gly
                85                  90                  95

Asn Ile Glu Ser His Pro Gly Leu Thr Ser Tyr Ile Val Arg Val Val
            100                 105                 110

Asn Thr Asp Tyr Lys Gln His Ala Met Val Phe Phe Met Lys Ala Ser
        115                 120                 125

His Asn Arg Lys Tyr Phe Lys Val Thr Leu Tyr Gly Arg Thr Lys Glu
130                 135                 140

Leu Thr Ser Asp Leu Lys Glu Asn Phe Thr Ser Phe Ser Lys Ser Leu
145                 150                 155                 160

Gly Leu Thr Glu Asn His Ile Ile Phe Pro Val Pro Ile Asp Gln Cys
                165                 170                 175

Ile Asp Gly

<210> SEQ ID NO 163
<211> LENGTH: 180
<212> TYPE: PRT
<213> ORGANISM: Mus musculus

<400> SEQUENCE: 163

Gln Asp Ser Thr Gln Asn Leu Ile Pro Ala Pro Ser Leu Leu Thr Val
1               5                   10                  15

Pro Leu Gln Pro Asp Phe Arg Ser Asp Gln Phe Arg Gly Arg Trp Tyr
            20                  25                  30

Val Val Gly Leu Ala Gly Asn Ala Val Gln Lys Lys Thr Glu Gly Ser
        35                  40                  45

```
Phe Thr Met Tyr Ser Thr Ile Tyr Glu Leu Gln Glu Asn Asn Ser Tyr
        50                  55                  60

Asn Val Thr Ser Ile Leu Val Arg Asp Gln Asp Gln Gly Cys Arg Tyr
 65                  70                  75                  80

Trp Ile Arg Thr Phe Val Pro Ser Ser Arg Ala Gly Gln Phe Thr Leu
                    85                  90                  95

Gly Asn Met His Arg Tyr Pro Gln Val Gln Ser Tyr Asn Val Gln Val
                100                 105                 110

Ala Thr Thr Asp Tyr Asn Gln Phe Ala Met Val Phe Arg Lys Thr
                115                 120                 125

Ser Glu Asn Lys Gln Tyr Phe Lys Ile Thr Leu Tyr Gly Arg Thr Lys
        130                 135                 140

Glu Leu Ser Pro Glu Leu Lys Glu Arg Phe Thr Arg Phe Ala Lys Ser
145                 150                 155                 160

Leu Gly Leu Lys Asp Asp Asn Ile Ile Phe Ser Val Pro Thr Asp Gln
                165                 170                 175

Cys Ile Asp Asn
            180

<210> SEQ ID NO 164
<211> LENGTH: 178
<212> TYPE: PRT
<213> ORGANISM: Rattus norvegicus

<400> SEQUENCE: 164

Gln Asp Ser Thr Gln Asn Leu Ile Pro Ala Pro Pro Leu Ile Ser Val
 1               5                  10                  15

Pro Leu Gln Pro Gly Phe Trp Thr Glu Arg Phe Gln Gly Arg Trp Phe
                20                  25                  30

Val Val Gly Leu Ala Ala Asn Ala Val Gln Lys Glu Arg Gln Ser Arg
            35                  40                  45

Phe Thr Met Tyr Ser Thr Ile Tyr Glu Leu Gln Glu Asp Asn Ser Tyr
        50                  55                  60

Asn Val Thr Ser Ile Leu Val Arg Gly Gln Gly Cys Arg Tyr Trp Ile
 65                  70                  75                  80

Arg Thr Phe Val Pro Ser Ser Arg Pro Gly Gln Phe Thr Leu Gly Asn
                85                  90                  95

Ile His Ser Tyr Pro Gln Ile Gln Ser Tyr Asp Val Gln Val Ala Asp
                100                 105                 110

Thr Asp Tyr Asp Gln Phe Ala Met Val Phe Phe Gln Lys Thr Ser Glu
            115                 120                 125

Asn Lys Gln Tyr Phe Lys Val Thr Leu Tyr Gly Arg Thr Lys Gly Leu
        130                 135                 140

Ser Asp Glu Leu Lys Glu Arg Phe Val Ser Phe Ala Lys Ser Leu Gly
145                 150                 155                 160

Leu Lys Asp Asn Asn Ile Val Phe Ser Val Pro Thr Asp Gln Cys Ile
                165                 170                 175

Asp Asn

<210> SEQ ID NO 165
<211> LENGTH: 181
<212> TYPE: PRT
<213> ORGANISM: Ochotona princeps

<400> SEQUENCE: 165
```

Gln Glu Leu Thr Thr Asp Leu Ile Pro Val Pro Ser Leu Arg Lys Ile
1               5                   10                  15

His Val Gln Lys Asn Phe Gln Ser Asp Gln Phe Gln Gly Lys Trp Tyr
            20                  25                  30

Val Val Gly Leu Ala Gly Asn Asn Ile His Asn Ser Asp Gln Glu His
            35                  40                  45

Gln Gln Met Tyr Ser Thr Thr Tyr Glu Leu Lys Glu Asp Gly Ser Tyr
        50                  55                  60

Asn Val Thr Ser Thr Leu Leu Arg Gln Arg Asn Gln Gln Cys Asp His
65                  70                  75                  80

Trp Ile Arg Thr Phe Val Pro Gly Ser Lys Leu Gly His Phe Asn Leu
                85                  90                  95

Gly Asn Ile Lys Ser Tyr Pro Thr Leu Lys Ser Tyr Leu Ile Arg Val
            100                 105                 110

Val Thr Thr Asp Tyr Asn Gln Phe Ala Ile Val Phe Phe Arg Lys Val
            115                 120                 125

Tyr Lys Asn Asn Lys Lys Phe Phe Lys Ile Val Leu Tyr Gly Arg Thr
130                 135                 140

Lys Glu Leu Ser Pro Glu Leu Arg Gly Arg Phe Thr Ser Phe Ala Lys
145                 150                 155                 160

Thr Leu Gly Leu Thr Asp Asn His Ile Val Phe Pro Ala Pro Ile Gly
                165                 170                 175

Gln Cys Ile Asp Asp
            180

<210> SEQ ID NO 166
<211> LENGTH: 178
<212> TYPE: PRT
<213> ORGANISM: Oryctolagus cuniculus

<400> SEQUENCE: 166

Gln Asp Pro Thr Pro Lys Leu Ile Pro Ala Pro Ser Leu Arg Arg Val
1               5                   10                  15

Pro Leu Gln Arg Asn Phe Gln Asp Glu Gln Phe Gln Gly Lys Trp Tyr
            20                  25                  30

Val Val Gly Leu Ala Gly Asn Ala Val Gln Lys Arg Glu Glu Gly Gln
            35                  40                  45

Glu Pro Met Tyr Ser Thr Thr Tyr Glu Leu Asn Glu Asp Arg Ser Phe
        50                  55                  60

Asn Val Thr Ser Thr Leu Leu Arg Asp Gln Arg Cys Asp His Trp Ile
65                  70                  75                  80

Arg Thr Phe Val Pro Thr Ser Arg Pro Gly Gln Tyr Asn Leu Gly Asn
                85                  90                  95

Ile Lys Ser Tyr Pro Gly Val Lys Asn Tyr Ile Val Arg Val Val Ala
            100                 105                 110

Thr Asp Tyr Ser Gln Tyr Ala Met Met Phe Phe Arg Lys Gly Ser Arg
            115                 120                 125

Asn Lys Gln Phe Phe Lys Thr Thr Leu Tyr Gly Arg Thr Lys Glu Leu
130                 135                 140

Ser Pro Glu Leu Arg Glu Arg Phe Thr Arg Phe Ala Lys Ser Leu Gly
145                 150                 155                 160

Leu Pro Asp Asp Arg Ile Val Phe Pro Thr Pro Ile Asp Gln Cys Ile
                165                 170                 175

Asp Asp

```
<210> SEQ ID NO 167
<211> LENGTH: 179
<212> TYPE: PRT
<213> ORGANISM: Bos taurus

<400> SEQUENCE: 167

Arg Ser Ser Ser Ser Arg Leu Leu Arg Ala Pro Pro Leu Ser Arg Ile
1               5                   10                  15

Pro Leu Gln Pro Asn Phe Gln Ala Asp Gln Phe Gln Gly Lys Trp Tyr
            20                  25                  30

Thr Val Gly Val Ala Gly Asn Ala Ile Lys Lys Glu Glu Gln Asp Pro
        35                  40                  45

Leu Lys Met Tyr Ser Ser Asn Tyr Glu Leu Lys Glu Asp Gly Ser Tyr
    50                  55                  60

Asn Val Thr Ser Ile Leu Leu Lys Asp Asp Leu Cys Asp Tyr Trp Ile
65                  70                  75                  80

Arg Thr Phe Val Pro Ser Ser Gln Pro Gly Gln Phe Thr Leu Gly Asn
                85                  90                  95

Ile Lys Ser Tyr Arg Gly Ile Arg Ser Tyr Thr Val Arg Val Val Asn
            100                 105                 110

Thr Asp Tyr Asn Gln Phe Ala Ile Val Tyr Phe Lys Lys Val Gln Arg
        115                 120                 125

Lys Lys Thr Tyr Phe Lys Ile Thr Leu Tyr Gly Arg Thr Lys Glu Leu
    130                 135                 140

Thr Pro Glu Val Arg Glu Asn Phe Ile Asn Phe Ala Lys Ser Leu Gly
145                 150                 155                 160

Leu Thr Asp Asp His Ile Val Phe Thr Val Pro Ile Asp Arg Cys Ile
                165                 170                 175

Asp Asp Gln

<210> SEQ ID NO 168
<211> LENGTH: 179
<212> TYPE: PRT
<213> ORGANISM: Sus scrofa

<400> SEQUENCE: 168

Gln Gly Thr Ile Pro Asn Trp Ile Pro Ala Pro Pro Leu Ser Lys Val
1               5                   10                  15

Pro Leu Gln Pro Asn Phe Gln Ala Asp Gln Phe Gln Gly Lys Trp Tyr
            20                  25                  30

Val Val Gly Leu Ala Gly Asn Ala Val Lys Lys Glu Glu Gln Gly Arg
        35                  40                  45

Phe Lys Met Tyr Thr Thr Thr Tyr Glu Leu Lys Glu Asp Gly Ser Tyr
    50                  55                  60

Asn Val Ile Ser Thr Leu Leu Arg Gly Gln Leu Cys Asp Asn Trp Ile
65                  70                  75                  80

Arg Thr Phe Val Pro Ser Leu Gln Pro Gly Gln Phe Lys Leu Gly Asp
                85                  90                  95

Ile Lys Lys Tyr Ser Gly Leu Gln Ser Tyr Val Val Arg Val Val Ser
            100                 105                 110

Thr Asn Tyr Ser Gln Phe Ala Ile Val Phe Phe Lys Lys Val Ser Asn
        115                 120                 125

Asn Gln Glu Tyr Phe Lys Thr Thr Leu Tyr Gly Arg Thr Lys Val Leu
    130                 135                 140

Ser Pro Glu Leu Lys Glu Asn Phe Val Arg Phe Ala Lys Ser Leu Gly
```

```
                145                 150                 155                 160
Leu Ser Asp Asp Asn Ile Ile Phe Pro Val Ala Ile Asp Gln Cys Ile
                165                 170                 175

Asp Gly Gln

<210> SEQ ID NO 169
<211> LENGTH: 181
<212> TYPE: PRT
<213> ORGANISM: Tursiops truncatus

<400> SEQUENCE: 169

Gln Asp Ser Thr Pro Asn Leu Ile Pro Ala Pro Leu Phe Arg Val
1               5                   10                  15

Pro Leu Gln Pro Asn Phe Gln Pro Asp Gln Phe Gln Gly Lys Trp Tyr
                20                  25                  30

Ile Val Gly Leu Ala Gly Asn Ala Phe Lys Lys Glu Lys Gln Gly Gln
            35                  40                  45

Phe Lys Met Tyr Ala Thr Thr Tyr Glu Leu Lys Glu Asp Arg Ser Tyr
50                  55                  60

Asn Val Thr Ser Ala Leu Leu Arg Gly Lys Thr Gln Arg Cys Asp His
65                  70                  75                  80

Trp Ile Arg Thr Phe Val Pro Ser Ser Arg Pro Gly Gln Phe Thr Leu
                85                  90                  95

Gly Asn Ile Lys Gly Phe Pro Gly Val Gln Ser Tyr Thr Val Arg Val
                100                 105                 110

Ala Thr Thr Asn Tyr Asn Gln Phe Ala Ile Val Tyr Phe Lys Lys Val
            115                 120                 125

Tyr Lys Asn Gln Glu Tyr Phe Lys Thr Thr Leu Tyr Gly Arg Thr Lys
130                 135                 140

Glu Leu Thr Pro Gln Leu Lys Glu Asn Phe Ile His Phe Ala Lys Ser
145                 150                 155                 160

Leu Gly Leu Thr Asp Glu Tyr Ile Leu Phe Pro Val Pro Ile Asp Lys
                165                 170                 175

Cys Ile Asp Asp Gln
            180

<210> SEQ ID NO 170
<211> LENGTH: 179
<212> TYPE: PRT
<213> ORGANISM: Equus caballus

<400> SEQUENCE: 170

Arg Asp Pro Ala Pro Lys Leu Ile Pro Ala Pro Leu Asp Arg Val
1               5                   10                  15

Pro Leu Gln Pro Asp Phe Lys Asp Gln Phe Gln Gly Lys Trp Tyr
                20                  25                  30

Val Val Gly Val Ala Gly Asn Ala Phe Lys Lys Glu Glu Gln Gly Gln
            35                  40                  45

Phe Thr Met Tyr Thr Thr Thr Tyr Glu Leu Lys Glu Asp His Ser Tyr
50                  55                  60

Asn Val Thr Ser Ile Leu Leu Arg Asp Gln Asn Cys Asp His Trp Ile
65                  70                  75                  80

Arg Thr Phe Ile Pro Ser Ser Gln Pro Gly Gln Phe Asn Leu Gly Asp
                85                  90                  95

Ile Lys Arg Tyr Phe Gly Val Gln Ser Tyr Ile Val Arg Val Ala Asp
                100                 105                 110
```

```
Thr Asp Tyr Asn Gln Phe Ala Ile Val Phe Arg Lys Val Tyr Lys
            115                 120                 125

Asn Gln Glu Tyr Phe Lys Thr Thr Leu Tyr Arg Arg Thr Lys Glu Leu
        130                 135                 140

Thr Pro Glu Leu Arg Glu Lys Phe Ile Ser Phe Ala Lys Ser Leu Gly
145                 150                 155                 160

Leu Thr Asp Asp His Ile Ile Phe Pro Val Pro Ile Asp Gln Cys Ile
                165                 170                 175

Asp Glu Glu

<210> SEQ ID NO 171
<211> LENGTH: 178
<212> TYPE: PRT
<213> ORGANISM: Microcebus murinus

<400> SEQUENCE: 171

Gln Asp Ser Lys Glu Lys Leu Ile Pro Ala Pro Leu Leu Arg Val
1               5                   10                  15

Pro Leu Gln Pro Asp Phe Gln Asp Asp Gln Phe Arg Glu Thr Ser Trp
            20                  25                  30

Pro Arg Gly Ser Lys Met Lys Glu Thr Pro Ala Gly Ser Arg Asp Ala
        35                  40                  45

Gly Thr Gly Trp Ala Thr Thr Tyr Glu Leu Lys Asp His Ser Tyr Asn
    50                  55                  60

Val Thr Ser Thr Leu Leu Arg Gln Asn Gly Lys Cys Asp Tyr Trp Ile
65                  70                  75                  80

Arg Thr Phe Val Leu Thr Ser Gln Pro Gly Gln Phe Ala Leu Gly Asn
                85                  90                  95

Ile Asn Arg Tyr Pro Gly Ile Gln Ser Tyr Thr Val Arg Val Val Thr
            100                 105                 110

Thr Asn Tyr Asn Gln Phe Ala Ile Val Phe Lys Lys Val Ser Glu
        115                 120                 125

Asn Lys Glu Tyr Phe Lys Thr Thr Leu Tyr Gly Arg Thr Lys Glu Leu
    130                 135                 140

Pro Pro Glu Leu Lys Glu Asn Phe Ile Arg Phe Ala Lys Ser Leu Gly
145                 150                 155                 160

Leu Thr Glu Asp His Ile Ile Tyr Pro Val Pro Ile Asp Gln Cys Ile
                165                 170                 175

Asp Asp

<210> SEQ ID NO 172
<211> LENGTH: 178
<212> TYPE: PRT
<213> ORGANISM: Loxodonta africana

<400> SEQUENCE: 172

Gln Thr His Ser Pro Thr Leu Ile Pro Ala Pro Leu Leu Arg Val
1               5                   10                  15

Pro Leu Gln Pro Asp Phe Gln Asp Asp Lys Phe Gln Gly Lys Trp Tyr
            20                  25                  30

Val Ile Gly Leu Ala Gly Asn Ala Val Glu Lys Lys Gln Gly Gln
        35                  40                  45

Phe Lys Met Tyr Thr Thr Thr Tyr Glu Leu Lys Glu Asp Gly Ser Tyr
    50                  55                  60

Asn Val Thr Ser Thr Leu Leu Gln Glu Asp Gly Lys Cys Ser Tyr Trp
```

```
            65                  70                  75                  80
Ile Arg Thr Phe Val Pro Ser Phe Gln Pro Gly Gln Phe Asn Leu Gly
                85                  90                  95

Asn Ile Lys Asn Phe Pro Gly Leu Gln Ser Tyr Thr Val Arg Val Thr
            100                 105                 110

Ala Thr Asn Tyr Asn Gln Phe Ala Ile Val Phe Lys Lys Val Ser
        115                 120                 125

Lys Asn Gly Glu Tyr Phe Lys Thr Thr Leu Tyr Gly Arg Thr Lys Glu
130                 135                 140

Leu Thr Pro Glu Leu Lys Glu Arg Phe Ile Arg Phe Ala Lys Ser Leu
145                 150                 155                 160

Gly Leu Ser Asp His Ile Ile Phe Pro Val Pro Ile Asp Arg Cys Ile
                165                 170                 175

Asp Asp

<210> SEQ ID NO 173
<211> LENGTH: 179
<212> TYPE: PRT
<213> ORGANISM: Procavia capensis

<400> SEQUENCE: 173

Gln Glu Pro Thr Pro Thr Leu Ile Pro Ala Pro Pro Leu Ser Ser Ile
1               5                   10                  15

Pro Leu Lys Pro Asn Phe His Asn Asp Lys Phe Gln Gly Lys Trp Tyr
            20                  25                  30

Val Val Gly Val Ala Gly Asn Ala Ile Thr Lys Glu Lys Asp Pro Ser
        35                  40                  45

Leu Met Tyr Thr Thr Thr Tyr Glu Leu Arg Asp Asp Gly Ser Tyr Asn
    50                  55                  60

Val Thr Ser Thr Gln Phe Arg Glu Lys Ile Asn Cys Thr His Trp Thr
65                  70                  75                  80

Arg Thr Phe Val Pro Thr Ser Gln Pro Gly Gln Phe Ser Leu Gly Asn
                85                  90                  95

Ile Asp Lys Tyr Pro His Leu Ser Ser Tyr Thr Val Arg Val Thr Ala
            100                 105                 110

Thr Asn Tyr Asn Tyr Phe Ala Ile Val Tyr Phe Lys Lys Val Ser Lys
        115                 120                 125

Asn Gln Glu Tyr Phe Lys Thr Thr Leu Tyr Lys Arg Ile Lys Lys Leu
    130                 135                 140

Thr His Gly Leu Lys Lys His Phe Ile Gln Phe Ala Lys Ser Leu Gly
145                 150                 155                 160

Leu Pro Asp Asn His Ile Thr Phe Leu Val Pro Thr Asp Arg Cys Ile
                165                 170                 175

Asp Asp Ala

<210> SEQ ID NO 174
<211> LENGTH: 178
<212> TYPE: PRT
<213> ORGANISM: Canis familiaris

<400> SEQUENCE: 174

Gln Asp Ser Thr Pro Ser Leu Ile Pro Ala Pro Pro Leu Lys Val
1               5                   10                  15

Pro Leu Gln Pro Asp Phe Gln Asp Gln Phe Gln Gly Lys Trp Tyr
            20                  25                  30
```

```
Val Ile Gly Ile Ala Gly Asn Ile Leu Lys Lys Glu Gly His Gly Gln
         35                  40                  45

Leu Lys Met Tyr Thr Thr Thr Tyr Glu Leu Lys Asp Asp Gln Ser Tyr
     50                  55                  60

Asn Val Thr Ser Thr Leu Leu Arg Asn Glu Arg Cys Asp Tyr Trp Asn
 65                  70                  75                  80

Arg Asp Phe Val Pro Ser Phe Gln Pro Gly Gln Phe Ser Leu Gly Asp
                 85                  90                  95

Ile Gln Leu Tyr Pro Gly Val Gln Ser Tyr Leu Val Gln Val Val Ala
                100                 105                 110

Thr Asn Tyr Asn Gln Tyr Ala Leu Val Tyr Phe Arg Lys Val Tyr Lys
            115                 120                 125

Ser Gln Glu Tyr Phe Lys Ile Thr Leu Tyr Gly Arg Thr Lys Glu Leu
130                 135                 140

Pro Leu Glu Leu Lys Lys Glu Phe Ile Arg Phe Ala Lys Ser Ile Gly
145                 150                 155                 160

Leu Thr Glu Asp His Ile Ile Phe Pro Val Pro Ile Asp Gln Cys Ile
                165                 170                 175

Asp Glu

<210> SEQ ID NO 175
<211> LENGTH: 427
<212> TYPE: PRT
<213> ORGANISM: artificial
<220> FEATURE:
<223> OTHER INFORMATION: amino acid sequence of a light chain antibody
      fusion with Scn

<400> SEQUENCE: 175

Met Asp Phe Gln Val Gln Ile Phe Ser Phe Leu Leu Ile Ser Ala Ser
 1               5                  10                  15

Val Ile Met Ser Arg Gly Asp Ile Val Met Thr Gln Ala Ala Pro Ser
                20                  25                  30

Val Pro Val Thr Pro Gly Glu Ser Val Ser Ile Ser Cys Arg Ser Thr
             35                  40                  45

Lys Ser Leu Leu His Ser Asn Gly Asn Thr Tyr Leu Tyr Trp Phe Leu
 50                  55                  60

Gln Arg Pro Gly Gln Ser Pro Gln Arg Leu Ile Tyr Tyr Met Ser Asn
 65                  70                  75                  80

Leu Ala Ser Gly Val Pro Asp Arg Phe Ser Arg Gly Ser Gly Thr
                 85                  90                  95

Asp Phe Thr Leu Arg Ile Ser Arg Val Glu Ala Glu Asp Ala Gly Val
                100                 105                 110

Tyr Tyr Cys Met Gln Ser Leu Glu Tyr Pro Tyr Thr Phe Gly Gly Gly
            115                 120                 125

Thr Lys Leu Glu Ile Lys Arg Ala Asp Ala Ala Pro Thr Val Ser Ile
130                 135                 140

Phe Pro Pro Ser Ser Glu Gln Leu Thr Ser Gly Gly Ala Ser Val Val
145                 150                 155                 160

Cys Phe Leu Asn Asn Phe Tyr Pro Lys Asp Ile Asn Val Lys Trp Lys
                165                 170                 175

Ile Asp Gly Ser Glu Arg Gln Asn Gly Val Leu Asn Ser Trp Thr Asp
                180                 185                 190

Gln Asp Ser Lys Asp Ser Thr Tyr Ser Met Ser Ser Thr Leu Thr Leu
            195                 200                 205
```

```
Thr Lys Asp Glu Tyr Glu Arg His Asn Ser Tyr Thr Cys Glu Ala Thr
    210                 215                 220

His Lys Thr Ser Thr Ser Pro Ile Val Lys Ser Phe Asn Arg Asn Glu
225             230                 235                 240

Cys Gly Arg Gly Gly Ser Gly Gly Ser Gln Asp Ser Thr Ser Asp Leu
            245                 250                 255

Ile Pro Ala Pro Pro Leu Ser Lys Val Pro Leu Gln Gln Asn Phe Gln
            260                 265                 270

Asp Asn Gln Phe Gln Gly Lys Trp Tyr Val Val Gly Leu Ala Gly Asn
            275                 280                 285

Ala Ile Leu Arg Glu Asp Lys Asp Pro Gln Lys Met Tyr Ala Thr Ile
290                 295                 300

Tyr Glu Leu Lys Glu Asp Lys Ser Tyr Asn Val Thr Ser Val Leu Phe
305                 310                 315                 320

Arg Lys Lys Lys Cys Asp Tyr Trp Ile Arg Thr Phe Val Pro Gly Ser
                325                 330                 335

Gln Pro Gly Glu Phe Thr Leu Gly Asn Ile Lys Ser Tyr Pro Gly Leu
            340                 345                 350

Thr Ser Tyr Leu Val Arg Val Val Ser Thr Asn Tyr Asn Gln His Ala
            355                 360                 365

Met Val Phe Phe Lys Lys Val Ser Gln Asn Arg Glu Tyr Phe Lys Ile
            370                 375                 380

Thr Leu Tyr Gly Arg Thr Lys Glu Leu Thr Ser Glu Leu Lys Glu Asn
385                 390                 395                 400

Phe Ile Arg Phe Ser Lys Ser Leu Gly Leu Pro Glu Asn His Ile Val
                405                 410                 415

Phe Pro Val Pro Ile Asp Gln Cys Ile Asp Gly
            420                 425

<210> SEQ ID NO 176
<211> LENGTH: 46
<212> TYPE: DNA
<213> ORGANISM: artificial
<220> FEATURE:
<223> OTHER INFORMATION: sequence showing NotI cut for SEQ ID NO: 1

<400> SEQUENCE: 176
aacctgtatt ttcagggagg cgctaaggat cccggaccgc ctctcc                46
```

LIPOCALIN FUSION PARTNERS

CROSS-REFERENCE TO RELATED APPLICATIONS

This application is a national phase of International Application No. PCT/US2013/074215, filed Dec. 10, 2013, which claims the benefit of U.S. Provisional Application Ser. No. 61/794,685, filed Mar. 15, 2013, and 61/735,516 filed Dec. 10, 2012, all of which are hereby incorporated by reference in their entirety.

STATEMENT OF GOVERNMENT SUPPORT AS TO FEDERALLY SPONSORED RESEARCH

This invention was made with government support under grants CA135491, AI1094419, and AI097786 awarded by the National Institutes of Health. The government has certain rights in the invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is F053-0071US_SeqList_ST25.TXT. The text file is about 259 KB, was created on Nov. 20, 2017, and is being submitted electronically via EFS-Web.

BACKGROUND OF THE INVENTION

Efforts toward drug discovery continue to use vast technical and financial resources to identify and develop new and useful drugs. Unfortunately, finding new drugs has continued to be difficult. For example, development of less damaging, more precisely targeted cancer therapies is essential. But even after decades of research, scientists still struggle to identify therapeutic compounds with the right mix of medicinal and cancer-targeting properties which not only reduce the likelihood that a therapeutic compound could serve as a treatment strategy but creates a need for successful methods of surgical resection.

A wide variety of types of compounds have been studied and pursued for a large breadth of therapeutic purposes. For example, small chemical molecules and larger biologics (e.g., antibodies) have been used for a plethora of therapeutic applications with varied success. Some smaller peptides have also been shown to be useful as drugs, e.g., by virtue of their natural potency.

A lack of methods for rapid and efficient production of peptides and proteins for clinical applications has limited the discovery of peptides and proteins that might serve as therapeutic compounds. Creating fusions of peptides, protein domains, or proteins, to a different protein to enhance production of peptides and proteins has been explored in bacterial expression systems, e.g., *E. coli* gene expression. However, bacterial protein expression systems are generally limited due to errors in protein folding efficiency. Thus, there is still a need for methods enabling the rapid and efficient production of peptides, protein domains, and proteins.

SUMMARY OF THE INVENTION

The present invention relates to methods for the production of siderocalin fusion proteins. In various aspects, the present invention relates to the fusion proteins produced according to those methods. In certain aspects, the fusion protein is cleaved, thereby producing a peptide according to the present disclosure. The present invention further relates to methods for producing a fusion protein, the methods comprising expressing, in a cell, a fusion protein, the fusion protein comprising a peptide or protein domain and a lipocalin protein, thereby producing the fusion protein. In some embodiments, the present invention further relates to a method of producing a peptide, the method comprising: expressing, in a cell, a fusion protein comprising a peptide and a lipocalin protein; and separating the peptide from the lipocalin protein, thereby producing the peptide.

In some embodiments, the present invention relates to a composition of a fusion protein, the composition comprising; a peptide or protein domain, and; a lipocalin protein. In some embodiments, the present invention further relates to a composition comprising a peptide library, the peptide library further comprising a plurality of peptides lacking at least one native lysine residue. The present invention further relates to a composition comprising a fusion protein comprising a peptide and a lipocalin protein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 7B shows an expanded view of FIG. 7A.

FIG. 8 describes representative sequencing data (SEQ ID NOs: 128-156) from a cloned knottin library, in accordance with an embodiment of the present invention.

FIG. 21 depicts the expression of a Scn fusion with a knottin protein, Imperatoxin, and the corresponding SDS PAGE analysis according to one aspect of the present disclosure.

DETAILED DESCRIPTION OF THE INVENTION

Figure 1:
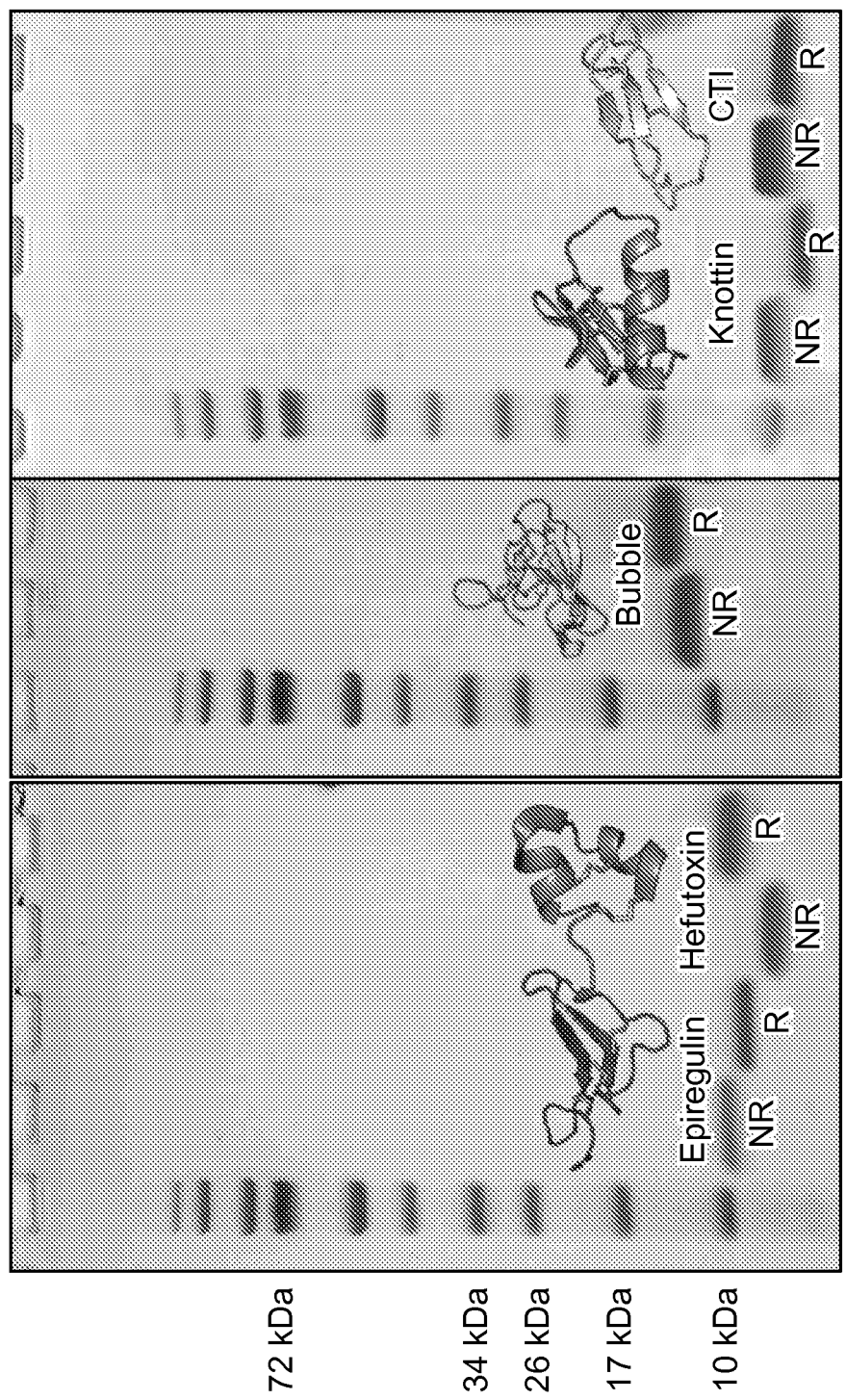
FIG. 1 provides a gel image showing a variety of scaffolds, in accordance with an embodiment of the present invention.

The methods and systems of the present disclosure relate to fusion proteins and methods of producing them. According to certain aspects, the peptides produced using the present methods can be used as components of drug discovery platforms. In some aspects, the methods relate to creating a fusion of a first protein, or of a peptide, that has potential therapeutic value, with a second protein such that the second protein enhances production and folding of the first protein by an expression system. In some aspects, after expression and purification of the fusion protein, the fusion protein is cleaved such that the first protein and the second protein are separate proteins. In some aspects, the second protein may be a lipocalin. For example, the second protein may be a specific lipocalin such as siderocalin.

Conjugates

In some aspects, the present invention includes fusion proteins, peptides, or conjugates thereof as described herein. For example, some or all of the fusion proteins or peptides can be conjugated to a moiety selected to modify a property of the peptides.

In certain aspects, the present invention includes fusion proteins or peptides conjugated at the N-terminus to hydrophobic (e.g., lipophilic) moieties. All or some of the fusion proteins or peptides of the present disclosure can be lacking internal lysines, e.g., to avoid conjugation at the internal lysine positions, thereby allowing conjugation to the amino terminus of the peptide. In some embodiments, the attachment of a hydrophobic moiety to the N-terminus can be used to extend half-life of the fusion protein or peptide of the present disclosure. In some embodiments, simple carbon chains (e.g., by myristoylation and/or palmitylation) can be conjugated to the fusion proteins or peptides. In some aspects, the simple carbon chains may render the fusion proteins or peptides easily separable from the unconjugated material. For example, methods that may be used to separate the fusion proteins or peptides from the unconjugated material include, but are not limited to, solvent extraction and reverse phase chromatography. The lipophilic moieties can extend half-life through reversible binding to serum albumin. In certain embodiments, attachment of a near infrared dye to the N-terminus of the fusion protein or peptide can also be performed to allow for tracing of the conjugated fusion protein or peptide. In certain embodiments, attachment of a near infrared dye to a lysine of the peptide can also be performed to allow for tracing of the conjugated peptide. An antibody to the dye can further allow the dye to fill a dual role of both a tracking marker and a retrieval handle. The conjugated fusion proteins or peptides can also be conjugated to other moieties that can serve other roles, such as providing an affinity handle (e.g., biotin) for retrieval of the peptides from tissues or fluids.

Other modifications can be used. For example, the fusion proteins, peptides, or conjugates thereof can include post-translational modifications (e.g., methylation and/or amidation). In some embodiments, the fusion proteins or peptides of the present disclosure can be conjugated to other moieties that, e.g., can modify or effect changes to the properties of the peptides. The conjugated moieties can, e.g., be lipophilic moieties that extend half-life of the peptides through reversible binding to serum albumin. In some embodiments, the lipophilic moiety can be cholesterol or a cholesterol derivative including cholestenes, cholestanes, cholestadienes and oxysterols. In some embodiments, the peptides can be conjugated to myristic acid (tetradecanoic acid) or a derivative thereof.

In some embodiments, the fusion proteins or peptides of the present disclosure can be conjugated to detectable labels to enable tracking detecting or visualizing of the biodistribution of a conjugated peptide. The detectable labels can be fluorescent labels (e.g., fluorescent dyes). In certain embodiments, the fluorescent label can have emission characteristics that are desired for a particular application. For example, the fluorescent label can be a fluorescent dye that has an emission wavelength maximum between a range of 500 nm to 1100 nm, between a range of 600 nm to 1000 nm, between a range of 600 to 800 nm, between a range of 650 nm to 850 nm, between a range of 700 nm to 800 nm, between a range of 720 to 780 nm, or between a range of 720 to 750 nm. For example, under certain conditions, cyanine 5.5 can have an emission maximum around 695 nm, IRdye 800 can have an emission maximum around 800 nm, and indocyanine green can have an emission maximum around 820 nm. One of ordinary skill in the art will appreciate the various dyes that can be used as detectable labels and that have the emission characteristics above.

As used herein, the term "detectable label" means a tag or modification that can be attached to a small chemical molecule, peptide, protein, or a fragment or a portion thereof such that the small chemical molecule, peptide, protein, or a fragment thereof is recognizable using a device, apparatus or method that permits the detection of the tag or modification.

In some aspects, the detectable label is a fluorescent dye. Non limiting examples of fluorescent dyes that could be used as a conjugating molecule in the present disclosure include rhodamine, rhodol, fluorescein, thiofluorescein, aminofluorescein, carboxyfluorescein, chlorofluorescein, methylfluorescein, sulfofluorescein, aminorhodol, carboxyrhodol, chlororhodol, methylrhodol, sulforhodol; aminorhodamine, carboxyrhodamine, chlororhodamine, methylrhodamine, sulforhodamine, and thiorhodamine, cyanine, indocarbocyanine, oxacarbocyanine, thiacarbocyanine, merocyanine, a cyanine dye (e.g., cyanine 2, cyanine 3, cyanine 3.5, cyanine 5, cyanine 5.5, cyanine 7), oxadiazole derivatives, pyridyloxazole, nitrobenzoxadiazole, benzoxadiazole, pyrene derivatives, cascade blue, oxazine derivatives, Nile red, Nile blue, cresyl violet, oxazine 170, acridine derivatives, proflavin, acridine orange, acridine yellow, arylmethine derivatives, xanthene dyes, sulfonated xanthenes dyes, Alexa Fluors (e.g., Alexa Fluor 594, Alexa Fluor 633, Alexa Fluor 647, Alexa Fluor 700), auramine, crystal violet, malachite green, tetrapyrrole derivatives, porphyrin, phtalocyanine, and bilirubin. In some embodiments, the dyes can be near-infrared dyes including, e.g., Cy5.5, IRdye 800, DyLight 750 or indocyanine green (ICG). In some embodiments, near infrared dyes can include cyanine dyes (e.g., cyanine 2, cyanine 3, cyanine 3.5, cyanine 5, cyanine 5.5, cyanine 7). In certain embodiments, the detectable label can include xanthene dyes or sulfonated xanthenes dyes, such as Alexa Fluors (e.g., Alexa Fluor 594, Alexa Fluor 633, Alexa Fluor 647, Alexa Fluor 700). If an antibody to the dye could be found the conjugated dyes could be used both as a tracking, detecting or visualizing marker and as a retrieval handle.

The fusion proteins or peptides of the present invention can also be conjugated to biotin. In addition of extension of half-life, biotin could also act as an affinity handle for retrieval of the peptides from tissues or other locations. In one embodiment, the peptides can be conjugated, e.g., to a biotinidase resistant biotin with a PEG linker (e.g., NHS-dPEG$_4$-Biotinidase resistant biotin). In some embodiments, fluorescent biotin conjugates that can act both as a detectable label and an affinity handle can be used. Non limiting examples of commercially available fluorescent biotin conjugates include Atto 425-Biotin, Atto 488-Biotin, Atto 520-Biotin, Atto-550 Biotin, Atto 565-Biotin, Atto 590-Biotin, Atto 610-Biotin, Atto 620-Biotin, Atto 655-Biotin, Atto 680-Biotin, Atto 700-Biotin, Atto 725-Biotin, Atto 740-Biotin, fluorescein biotin, biotin-4-fluorescein, biotin-(5-fluorescein) conjugate, and biotin-B-phycoerythrin, alexa fluor 488 biocytin, alexa flour 546, alexa fluor 549, *lucifer* yellow cadaverine biotin-X, *Lucifer* yellow biocytin, Oregon green 488 biocytin, biotin-rhodamine and tetramethylrhodamine biocytin. In some other examples, the conjugates could include chemiluminescent compounds, colloidal metals, luminescent compounds, enzymes, radioisotopes, and paramagnetic labels.

In some aspects, the fusion proteins and peptides of the present invention can be conjugated to vitamins or other molecules typically found in foods that are absorbed into the bloodstream from the stomach, small intestine, or colon. Examples include, but are not limited to, vitamin A, vitamin C, vitamin $B_2$, vitamin $B_3$, vitamin $B_6$, vitamin $B_{12}$, vitamin D, vitamin E, vitamin K. The goal of these conjugations is to improve oral bioavailability or absorption of the peptide from the gastrointestinal system.

In some instances, selected series of amino acids that appear to help certain peptides cross biologic barriers such as the gastrointestinal tract, the blood brain barrier, the cell membrane, the nuclear membrane can be identified and genetically or physically grafted onto other peptides for the purpose of helping the new peptide cross the same biologic barriers. In other cases, the same approach might be used to graft sequences onto peptides that would prevent the new peptide from crossing certain biological barriers. For example, a drug could be modified in this manner to prevent BBB penetration and thus reduce the likelihood of central nervous system side effects.

In certain embodiments, the fluorescent label can have emission characteristics that are desired for a particular application. For example, the fluorescent label can be a fluorescent dye that has a emission wavelength maximum between a range of 500 nm to 1100 nm, between a range of 600 nm to 1000 nm, between a range of 600 to 800 nm, between a range of 650 nm to 850 nm, between a range of 700 nm to 800 nm, between a range of 720 to 780 nm, or between a range of 720 to 750 nm. One of ordinary skill in the art will appreciate the various dyes that can be used as detectable labels and that have the emission characteristics above. For example, under certain conditions, cyanine 5.5 can have an emission maximum around 695 nm, IRdye can have an emission maximum around 800 nm, and indocyanine green can have an emission maximum around 820 nm.

Non-limiting examples of fluorescent dyes that could be used as a conjugating molecule in the present disclosure include rhodamine, rhodol, fluorescein, thiofluorescein, aminofluorescein, carboxyfluorescein, chlorofluorescein, methylfluorescein, sulfofluorescein, aminorhodol, carboxyrhodol, chlororhodol, methylrhodol, sulforhodol; aminorhodamine, carboxyrhodamine, chlororhodamine, methylrhodamine, sulforhodamine, and thiorhodamine, cyanine, indocarbocyanine, oxacarbocyanine, thiacarbocyanine, merocyanine, oxadiazole derivatives, pyridyloxazole, nitrobenzoxadiazole, benzoxadiazole, pyrene derivatives, cascade blue, oxazine derivatives, Nile red, Nile blue, cresyl violet, oxazine 170, acridine derivatives, proflavin, acridine orange, acridine yellow, arylmethine derivatives, auramine, crystal violet, malachite green, tetrapyrrole derivatives, porphyrin, phtalocyanine, and bilirubin. In some embodiments, the detectable label can include near-infrared dyes, such as, but not limited to, Cy5.5, indocyanine green (ICG), DyLight 750 or IRdye 800. In some embodiments, near infrared dyes can include a cyanine dye (e.g., cyanine 2, cyanine 3, cyanine 3.5, cyanine 5, cyanine 5.5, cyanine 7). In certain embodiments, the detectable label can include xanthene dyes or sulfonated xanthenes dyes, such as Alexa Fluors (e.g., Alexa Fluor 594, Alexa Fluor 633, Alexa Fluor 647, Alexa Fluor 700). In addition, if an antibody to the dyes can be identified, then conjugated dyes could be used both as a tracking, detecting or visualizing marker and as a retrieval handle.

Other modifications to fusion proteins, peptides, or conjugates thereof of the present disclosure can be used. For example, the fusion proteins or peptides of the present disclosure can include post-translational modifications (e.g., methylation and/or amidation), which can affect, e.g., serum half-life. In some embodiments, the fusion proteins or peptides can be conjugated to other moieties that, e.g., can modify or effect changes to the properties of the peptides. The conjugated moieties can, e.g., be lipophilic moieties that extend half-life of the peptides through reversible binding to serum albumin. In some embodiments, simple carbon chains (e.g., by myristoylation) can be conjugated to the peptides. In some embodiments, the lipophilic moiety can be cholesterol or a cholesterol derivative including cholestenes, cholestanes, cholestadienes and oxysterols. In some embodiments, the peptides can be conjugated to myristic acid (tetradecanoic acid) or a derivative thereof.

The fusion proteins or peptides of the present disclosure can also be conjugated to other moieties that can serve other roles, such as providing an affinity handle (e.g., biotin) for retrieval of the peptides from tissues or fluids. For example, the peptides of the present invention can also be conjugated to biotin. In addition to extension of half-life, biotin could also act as an affinity handle for retrieval of the peptides from tissues or other locations. In some embodiments, fluorescent biotin conjugates that can act both as a detectable label and an affinity handle can be used. Non limiting examples of commercially available fluorescent biotin conjugates include Atto 425-Biotin, Atto 488-Biotin, Atto 520-Biotin, Atto-550 Biotin, Atto 565-Biotin, Atto 590-Biotin, Atto 610-Biotin, Atto 620-Biotin, Atto 655-Biotin, Atto 680-Biotin, Atto 700-Biotin, Atto 725-Biotin, Atto 740-Biotin, fluorescein biotin, biotin-4-fluorescein, biotin-(5-fluorescein) conjugate, and biotin-B-phycoerythrin, Alexa fluor 488 biocytin, Alexa flour 546, Alexa Fluor 549, *lucifer* yellow cadaverine biotin-X, *Lucifer* yellow biocytin, Oregon green 488 biocytin, biotin-rhodamine and tetramethylrhodamine biocytin. In some other examples, the conjugates could include chemiluminescent compounds, colloidal metals, luminescent compounds, enzymes, radioisotopes, and paramagnetic labels.

Methods of Making Fusion Proteins and Peptides

In yet another aspect, the present invention includes methods for making fusion proteins or peptides according to the present disclosure.

In some embodiments, the present invention includes methods of making fusion proteins or peptides according to the present disclosure. As described further herein, the present invention includes scaffolds that can be used as a starting point for generating fusion proteins or peptides according to the present disclosure. These scaffolds as well as a large diversity of scaffold variants can be made using several different approaches. In some aspects, the fusion proteins or peptides according to the present disclosure can be produced using peptide synthesis techniques generally well known in the art. Conventional oligonucleotide synthesis techniques (e.g., chip-based oligonucleotide synthesis) can also be used. In some instances, the synthetic approaches can be combined with a variety of expression systems. In one example embodiment, particular residue positions in a scaffold can be targeted for random mutagenesis using degenerate codons to generate a diverse set of DNAs that can be made using, e.g., chip-based oligonucleotide synthesis and can code for a large library of scaffold variants.

In some embodiments, the molecules coding for the scaffolds and scaffold variants can be expressed in various expression systems, and can, in some embodiments, be combined as part of a fusion system. The DNA molecules encoding the scaffolds and scaffold variants, e.g., can be combined with fusion systems that can be expressed in several different cell types, e.g., 293 HEK or *E. coli*. Fusions for 293 HEK cells, e.g., can include but are not limited to, IgK leader sequences and/or secreted fusion proteins, such as siderocalin, lipocalin 2, and human serum albumin.

In some embodiments, the peptides described herein (e.g., knotted peptides) can be expressed as fusions with lipocalin proteins. In one aspect, the present invention includes a method for producing a peptide that can include expressing, in a cell, a fusion protein including a peptide (e.g., a knotted peptide) and a lipocalin protein. The method can further include separating the peptide from the lipocalin protein, thereby producing the peptide (e.g., the knotted peptide). The present invention further includes compositions of the fusion protein including the lipocalin protein and the peptide (e.g., the knotted peptide). This fusion system offers a variety of advantages for producing peptides (e.g., knotted-peptides) over traditional fusion systems. By way of background, and not to be limiting in any way, the lipocalins are a class of proteins that can have a conserved fold characterized by an eight-stranded beta barrel with a flanking alpha helix. The expression levels of lipocalin proteins, like Lcn2, NGAL and Siderocalin, in mammalian cells equal or surpass many other fusion systems, including Fc fusions. The present invention relates to methods for producing a fusion protein, the methods comprising expressing, in a cell, a fusion protein, the fusion protein comprising a peptide or protein domain and a lipocalin protein, thereby producing the fusion protein. In some embodiments, the methods further comprise separating the peptide or protein domain from the lipocalin protein, thereby producing a peptide or protein domain. In certain embodiments, the peptide or protein domain is an antibody fragment. In certain embodiments, the antibody is trastuzumab, infliximab, adalimumab, OKT3, or Fc.

In some embodiments, the peptide or protein domain is human heme oxygenase 1 or murine heme oxygenase 1. In some embodiments, the fusion protein further comprises a cleavage site. In certain embodiments, the cleavage site is a furin cleavage site, a trypsin cleavage site or a TEV cleavage site. In some embodiments, the separating of the peptide or protein domain from the lipocalin protein results from cleavage at the cleavage site in the fusion protein. In certain embodiments, the separating of the peptide or protein domain from the lipocalin protein occurs following secretion of the fusion protein from a cell. In certain embodiments, the cell is a mammalian cell.

The present invention relates to methods of producing a peptide, the method comprising: expressing, in a cell, a fusion protein comprising a peptide and a lipocalin protein; and separating the peptide from the lipocalin protein, thereby producing the peptide. In some embodiments, the peptide is separated from the lipocalin protein by proteolysis or by cleavage of a furin cleavage site in the fusion protein such that the peptide is cleaved from the lipocalin protein upon secretion from the cell. In certain embodiments, the cell is a mammalian cell. In some embodiments, the peptide is produced at a concentration less than about 200 mg/liter.

In some embodiments, the present invention relates to compositions comprising a fusion protein comprising a peptide and a lipocalin protein. In some embodiments, the peptide comprises a knotted peptide. In some embodiments, the knotted-peptide is selected from the group consisting of chymotrypsin inhibitor, hefutoxin, bubble protein, the C-terminal domain of midkine, potato carboxypeptidase inhibitor, and epiregulin. In certain embodiments, the lipocalin protein is siderocalin. In certain embodiments, the knotted-peptide includes at least two disulfide bonds The peptides described herein (e.g., knotted peptides) can be expressed using a variety of lipocalin proteins. As used herein, the term "lipocalin" refers to a protein as defined in "Structure and sequence relationships in the lipocalins and related proteins", Darren R. Flower, Anthony C. T. North, Teresa K. Attwood, *Protein Science* (1993) 2:5, 753-761. Lipocalins may include, but are not limited to, the numbered lipocalins (e.g., Lcn2 (also NGAL, Siderocalin, 24p3), and the like, chicken Ex-FABP and quail Q83.

In various aspects of the present disclosure, siderocalin is used as a secretion partner. As used herein, the term "siderocalin" refers to a lipocalin that is capable of binding a small chelator. In some aspects, a chelator may be natural or engineered. In some aspects, siderocalin binds to siderophores and ferric siderophore complexes. For example, a siderocalin can be, but is not limited to, a siderocalin or Ex-FABP. As used herein, the term "Siderocalin," (as a proper noun), refers to the orthologous family of proteins related to the human archetype Siderocalin.

Siderocalin advantageously can be used for the secretion of a variety of peptides, proteins, and protein domains, including intracellular peptides, proteins, and peptide domains when used as a secretion partner.

Siderocalin is useful as a fusion partner for larger proteins because, e.g., of the small size of siderocalin relative to larger proteins (the mature protein is 178 amino acids and has a molecular weight of 20547 Da). Also, a C87S mutation in siderocalin can prevent dimerization and yields pure monomeric fusion protein (see Goetz, D. H., et al. 'The Neutrophil Lipocalin NGAL is a Bacteriostatic Agent that Interferes with Siderophore-mediated Iron Acquisition' *Molecular Cell* (2002) 10: 1033-43). A single intramolecular disulfide bond present in siderocalin increases its stability. Also, siderocalin only has a single N-linked glycosylation site, which involves correct processing in the ER before secretion. In some aspects, the peptides can also be expressed as fusion peptides with Murine SCN (also known as 24p3), which also works very well as a secretion partner.

Other homologs can also be used. In addition, the peptides (e.g., knotted peptides) provided herein can also be expressed as fusion systems with the other members of the lipocalin family including Lcn1, Lcn6, Lcn8, Lcn9, Lcn10, Lcn12, Lcn15. In some embodiments, the peptide comprises a disulfide knotted-peptide. In certain embodiments, the knotted-peptide is PMP-D2, potato carboxypeptidase, huwentoxin, imperatoxin, epiregulin, midkine, bubble protein or conotoxin CVIC. In other embodiments, the peptide comprises a knottin. In some embodiments, the lipocalin protein comprises siderocalin. In some embodiments, the lipocalin protein is siderocalin. In certain embodiments, the lipocalin protein is human siderocalin, murine siderocalin, chicken Ex-FABP, or quail Q83.

In some embodiments, the expression of peptides (e.g., knotted peptides) as fusions with SCN can be utilized with an endogenously cleaving SCN, with RARYKR (SEQ ID NO: 101) right after the CIDG (SEQ ID NO: 102), and an exogenously cleaved one, with ENLYFQ (SEQ ID NO: 95) in that position. The former can be cleaved by the mammalian cells during protein export (e.g., by furin), and the free SCN and knotted peptide can be secreted into surrounding media. ENLYFQ (SEQ ID NO: 95) is a tobacco etch virus (TEV) protease site, which is not found endogenously in mammalian cells. The constructs in this system can be secreted as fusions, allowing for the knotted peptide to be cleaved off later by adding exogenous TEV protease. This can be useful for recovering the knottins. In some embodiments, purification "handles" such as poly-histidine or poly-arginine can be added to the SCN and subsequently removed by proteolysis. In addition to the knotted peptides, these fusion systems can also used for difficult-to-express proteins of medical interest such as chemokines, interleukins, and peptide hormones.

In some embodiments, the peptide comprises a knotted-peptide. In certain embodiments, the knotted-peptide is selected from the group consisting of chymotrypsin inhibitor, hefutoxin, bubble protein, the C-terminal domain of midkine, and epiregulin. In some embodiments, the lipocalin protein comprises siderocalin.

The lipocalin fusions (e.g., siderocalin and/or Lcn2 fused with a knotted peptide) can be used in several ways different ways. It could be used to increase the size of the target protein (for example a potential therapeutic) in order to increase its half-life. It could be used to secrete the target protein where the target protein is naturally expressed in the cytoplasm. SCN also has unique ligand specificity and tightly binds catecholate siderophores (bacterial iron chelators). This opens the possibility of loading the SCN fusion with specific ligands, such as a chemotherapeutic or radioactive reagent or some type or a compound that has beneficial properties. SCN, when loaded with siderophores and iron, has a deep red color that can aid in chromatography or other purification steps.

The lipocalin fusions of the present disclosure (e.g., SCN fused with HO-1) can be used in a variety of ways. For example, fusions can be used to increase the size of the target protein (e.g., a potential therapeutic) in order to increase its biological half-life. Fusions can be used to secrete the target protein where the target protein is naturally expressed in the cytoplasm. Fusions can also be used to target the fusion partner protein to specific locations to maximize therapeutic effects. SCN also has unique ligand specificity, tightly binding catecholate siderophores (bacterial iron chelators), and has kidney protective effects. Combining SCN with other kidney protective agents, like HO-1, which could generate synergistic functional effects. This also opens the possibility of loading the SCN fusion with specific ligands, such as radioactive metal atoms (e.g., $^{55}$Fe or Th) to allow in vivo tracking or specific cytotoxic activities. In addition to several other advantages, the lipocalin fusion systems can be used to make large amounts of protein over relatively short time frames. In some embodiments, the amount of peptide obtained can be less than about 10 mg/L, less than about 20 mg/L, less than about 40 mg/L, less than about 50 mg/L, less than about 100 mg/L, less than about 150 mg/L, less than about 180 mg/L, or less than about 200 mg/L. In some embodiments, the amount of peptide obtained can be between about 10 mg/L and 200 mg/L, between about 50 mg/L and 200 mg/L, between about 100 mg/L and 200 mg/L, and between about 150 mg/L and 200 mg/L In some embodiments, the peptide is produced at a concentration less than about 500 mg/liter, less than about 400 mg/liter, less than about 300 mg/liter, less than about 200 mg/liter, less than about 100 mg/liter, or less than about 50 mg/liter.

In other embodiments, some of the peptides described herein can be expressed in a variety of ways known in the literature. For example, the peptides are expressed in bacterial systems including *E. coli, Corynebacterium,* and *Pseudomonas* fluoresceins. Expression platforms for *E. coli* can include periplasmic expression or cytoplasmic expression. For periplasmic expression, fusions can include pelB, dsbA, and ExFABP fusion. The peptides can also be expressed in insect cell systems and eukaryotic systems including mammalian systems.

In some aspects, the peptides disclosed herein can be introduced by transfection, a technique that involves introduction of foreign DNA into the nucleus of the eukaryotic cells. In some aspects, the peptides can be synthesized by transient transfection (DNA does not integrate with the genome of the eukaryotic cells, but the genes are expressed for 24-96 hours). Various methods can be used to introduce the foreign DNA into the host cells, and transfection can be achieved by chemical-based means including by the calcium phosphate, by dendrimers, by liposomes, and by the use of cationic polymers. Non-chemical methods of transfection include electroporation, sono-poration, optical transfection, protoplast fusion, impalefection, and hydrodynamic delivery. In some embodiments, transfection can be achieved by particle-based methods including gene gun where the DNA is coupled to a nanoparticle of an inert solid which is then "shot" directly into the target cell's nucleus. Other particle-based transfection methods include magnet assisted transfection and impalefection.

DNA can also be introduced into cells using virus as a carrier (viral transduction) using reteroviruses or lentiviruses. In some embodiments, the peptides of the present invention can be prepared using a Daedalus expression system. Ashok D. Bandaranayake et al., *Nucleic Acids Res.* 2011 November; 39(21): e143, which is incorporated herein by reference in its entirety. This technique may also be combined with a serum free mammalian culture system. And, it is also possible to express tagless proteins, which can be purified in a single size exclusion step directly from the media, at high levels.

Figure 2:
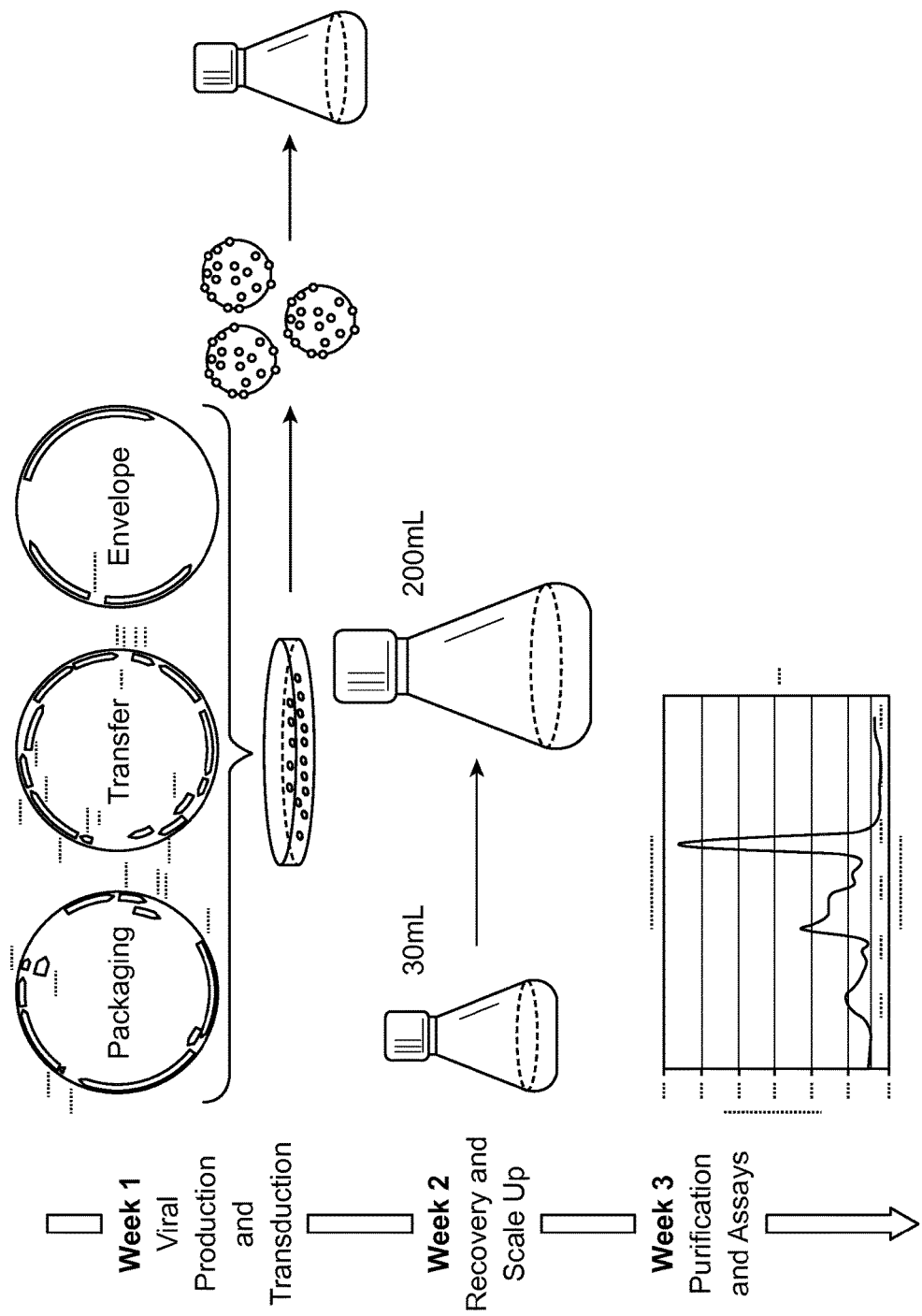
FIG. 2 shows an example method of producing peptide libraries, in accordance with an embodiment of the present invention.

In one aspect, the present invention provides a method of making hundreds to thousands or more of peptide variants at high levels. Conventional methods of making knotted peptides can be limited in that activity of knotted peptides can depend on proper folding of the peptides. There has been limited success in making knotted peptides that fold properly during manufacture. The present invention overcomes these problems with other techniques known in the art. FIG. 2 shows an example method for making the peptide libraries of the present invention. As shown, viruses can be produced by packaging of specific oligonucleotides sequences, transferring the sequences to the viruses, and expressing the peptides. Recovery and scale up of the peptides can be conducted, and then the sample can be purified and assayed. The process can be conducted efficiently (e.g., in three weeks) and large amounts of peptide can be produced (e.g., 200 mg/liter). In some instances, purification by chromatography may not be needed due to the purity of manufacture according the methods described herein.

Figure 3:
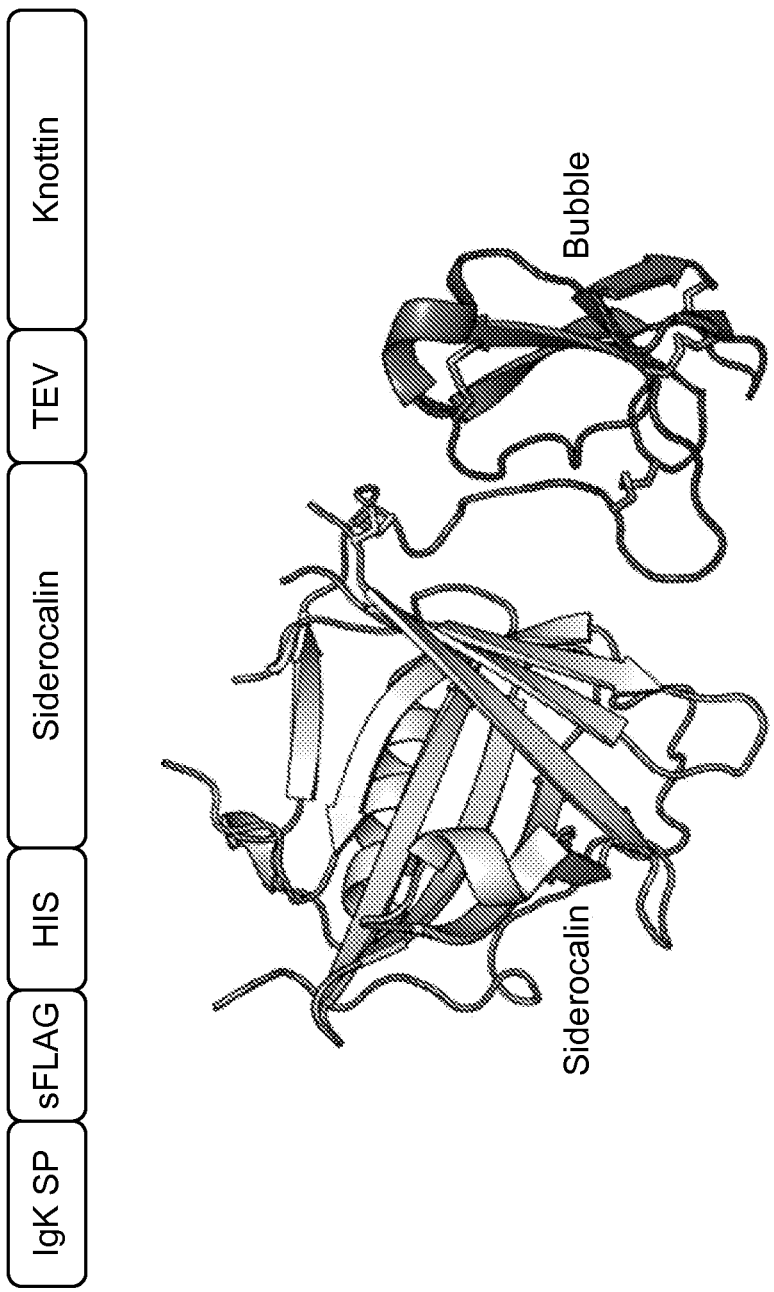
FIG. 3 depicts an example fusion system that can be used to make knottins (e.g., bubble protein), in accordance with an embodiment of the present invention.
Figure 4:
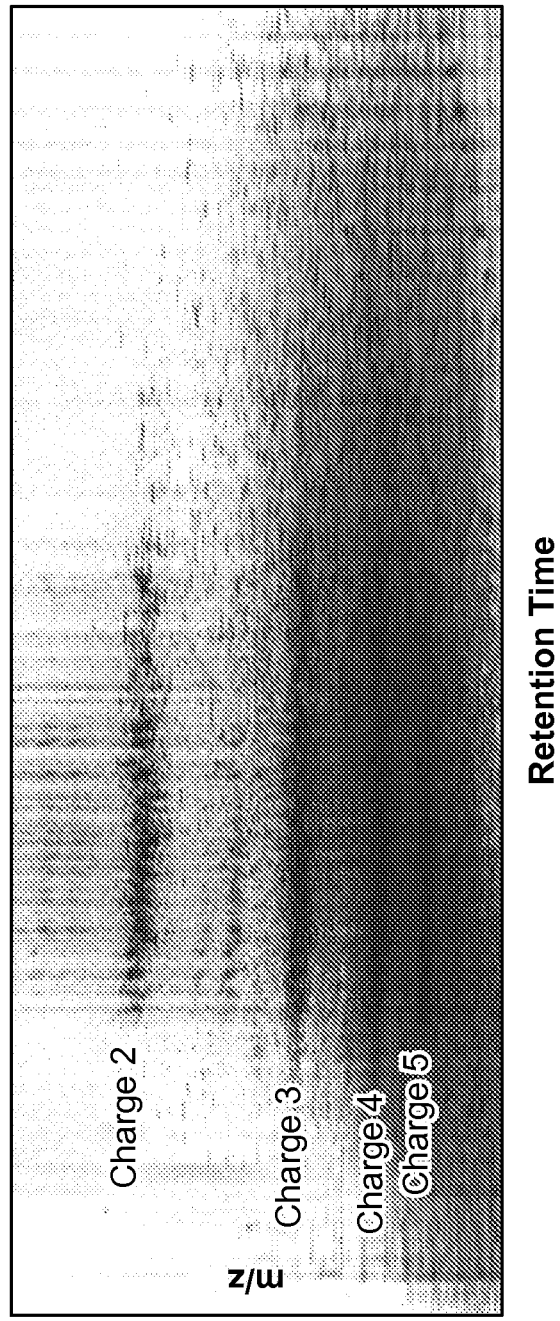
FIG. 4 shows analysis of a large peptide library using mass spectrometry, in accordance with an embodiment of the present invention.

In an example embodiment, the present invention includes fusion proteins of a knotted peptide fused to siderocalin via a cleavable linker. FIG. 3 shows an example fusion system that can be used to make the knotted peptide libraries. As shown, the fusion system includes a sequence including an IgK SP, sFLAG, HIS, siderocalin, TEV, and the knotted peptide sequence of interest. In some embodiments, these fusions can be combined with the Daedalus expression systems. Ashok D. Bandaranayake et al., *Nucleic Acids Res.* 2011 November; 39(21): e143, which is incorporated herein by reference in its entirety. A lentivirus can be used to gain rapid, stable expression in HEK293 cells, a human kidney cell line. The siderocalin can be highly expressed in this system and, e.g., serves to help the knotted peptide to be expressed as well. The nature of the cleavable linker allows the fusion to be cleaved as the protein is being expressed or later via an exogenously added protease. The siderocalin fusion partner can, e.g., be a generalizable expression enhancement system for any difficult-to-express protein, can be used as a tag to increase the size of a smaller peptide, and/or to improve a peptide's serum half-life (e.g., by increasing the size of the final fusion protein above the glomerular filtration limit. In some embodiments, the fusion protein further comprises at least one of an IgK starter sequence, a sFLAG, a HIS, and a TEV. In certain embodiments, the fusion protein comprises the following construct: IgK SP-sFLAG-HIS-siderocalin-TEP-peptide. In some embodiments, the peptide comprises a knotted-peptide.

Although HEK293 cells are robust and used for general protein expression, the lentivirus can infect a wide variety of cells. Combining this with a system that allows proteins to be cleaved as they are expressed enables a set of powerful assays that rely upon the secreted peptide to act in an autocrine or paracrine manner (i.e., they act on the cell that is secreting them or on nearby cells). An example of this would be to infect cancer target cells with a library of peptide-expressing lentiviruses and then screen those cells by flow cytometry for those that showed signs of apoptosis (e.g., Annexin V expression). The cells showing signs of apoptotic stress could be sorted out and the viruses sequenced, essentially looking for cells that were expressing a peptide that was inducing apoptosis in an autocrine fashion. A related set of screens could be done in a diffusion-limited matrix (e.g., soft agar), where peptide-expressing cells were mixed with target cells and the agar limited diffusion of the peptide. Areas of target cell death would be an indication of an active secreted peptide. Screens done in this manner could employ very large libraries, as the deconvolution would be as simple as sequencing the gene from which the peptide came.

In some embodiments, the present invention can include methods for producing knottins such that the knottin protein can remain tethered to the surface of the mammalian cell for use in conventional binding screens (e.g., those in which the target molecule is tethered to a column or beads and candidate drugs are identified by affinity to the target). In contrast to other known methods (e.g., phage or yeast display), the methods described herein use fusion systems (e.g., a siderocalin system of the present invention) to express libraries of peptides that have been designed according to the "rules" described above (e.g., ratio of acid/basic amino acids in a peptide) and that can be established through the in vivo drug discovery process and/or that have already been prescreened for specific biophysical and pharmacological properties. In these methods, e.g., all DNA sequences and protein products are already known and have already been validated (e.g., the peptides all fold properly and have improved serum half lives). The methods of present invention are in direct contrast to other known display technologies where the displayed proteins are not known and previously validated, and instead have their sequences randomized (using mutagenic oligonucleotides and degenerate NNN codons) yielding libraries of immense size (generally greater than 10$^7$), where many of the proteins do not fold properly due to deleterious mutations.

Methods of Making Knotted Peptides and Related Compositions

The fusion systems of the present disclosure can be used in various aspects for the production of peptides, knottins, and cytoplasmic and secreted proteins. In some aspects, the methods and compositions described herein include fusion of target proteins and/or peptides to lipocalin such that lipocalin facilitates the expression and secretion of the target protein by a cell. For example, lipocalins have a conserved fold characterized by an eight-stranded beta barrel with a flanking alpha helix and supports a versatile scaffold. In some aspects, lipocalin fusion protein systems result in greater fusion protein expression in mammalian cells compared to systems without the use of a lipocalin fusion protein. For example, lipocalin fusion protein systems result in less than 0.5 times greater, 1 times greater, 2 times greater, 3 times greater, 4 times greater, 5 times greater, 6 times greater, 7 times greater, 8 times greater, 9 times greater, 10 times greater, 11 times greater, 12 times greater, 13 times greater, 14 times greater, 15 times greater, 16 times greater, 17 times greater, 18 times greater, 19 times greater, 20 times greater, 25 times greater, 30 times greater, 35 times greater, 40 times greater, 45 times greater, 50 times greater, 55 times greater, 60 times greater, 65 times greater, 70 times greater, 75 times greater, 80 times greater, 85 times greater, 90 times greater, 95 times greater, 100 times greater, 200 times greater, 300 times greater, 400 times greater, 500 times greater, 600 times greater, 700 times greater, 800 times greater, 900 times greater, or 1000 times fusion protein expression in mammalian cells compared to systems lacking the lipocalin fusion protein.

In some aspects, lipocalin (e.g., SCN) may be used as a fusion partner to stabilize proteins or peptides of interest as immunogens. In aspects, the species from which the lipocalin sequence is derived is different than the recipient species. In some aspects, the species from which the lipocalin sequence is derived is the same as the recipient species.

SCN, and related proteins, when used as a secretion partner advantageously improve the production of secreted proteins and peptides. Moreover, SCN, and related proteins, advantageously are small, thereby improving their bioavailability. For example, the mature protein is 178 amino acids and has a molecular weight of 20547 Da. SCN has a single intramolecular disulfide bond, which increases its stability and a single N-linked glycosylation site.

In some aspects, at least one of the amino acids in the native sequence of lipocalin 2 (SCN) may be substituted for a non-native amino acid. In some aspects, the mutations may be generated to prevent SCN from dimerizing. For example, one SCN protein may dimerize with another SCN protein at cysteine residues or one SCN protein may dimerize with different proteins at cysteine residues. For example, generating a C87S mutation in SCN may prevent dimerization at a cysteine residue (see Goetz, D. H., et al., 'The Neutrophil Lipocalin NGAL is a Bacteriostatic Agent that Interferes with Siderophore-mediated Iron Acquisition' *Molecular Cell* (2002) 10: 1033-43).

In some aspects, at least one of the amino acids in the native sequence of the non-human lipocalin protein orthologous to the human SCN may be substituted for a non-native amino acid. For example, non-human orthologs of the human lipocalin protein that may be used with the methods and compositions described herein include, but are not limited to, murine Lcn2 (e.g., 24p3), Lcn1, Lcn6, Lcn8, Lcn9, Lcn10, Lcn12 and Lcn15 (see FIG. 14). In some aspects, the mutations may be generated to prevent non-human lipocalin protein orthologous to the human SCN from dimerizing. For example, one non-human lipocalin protein orthologous to the human SCN protein may dimerize with another non-human lipocalin protein orthologous to the human SCN protein at cysteine residues or one non-human lipocalin protein orthologous to the human SCN protein may dimerize with a different protein at cysteine residues. For example, generating a mutation at a site orthologous to the C87S mutation in human lipocalin protein may prevent dimerization at a cysteine residue (see Goetz, D. H., et al., 'The Neutrophil Lipocalin NGAL is a Bacteriostatic Agent that Interferes with Siderophore-mediated Iron Acquisition' *Molecular Cell* (2002) 10: 1033-43).

In an exemplary aspect, a lipocalin fusion protein may contain the following protein sequence:

MPLGLLWLGLALLGALHAQAQDSTSDLIPAPPLSKVPLQQNFQDNQFQGK

WYVVGLAGNAILREDKDPQKMYATIYELKEDKSYNVTSVLFRKKKCDYWI

RTFVPGCQPGEFTLGNIKSYPGLTSYLVRVVSTNYNQHAMVFFKKVSQNR

EYFKITLYGRTKELTSELKENFIRFSKSLGLPENHIVFPVPIDQCIDG

In this sequence, the annotations indicate, a signal peptide, glycosylation site, disulfide bond and the C87S mutation.

In some aspects, fusion of a protein or peptide of interest to lipocalin may improve the biological properties of the target protein (e.g., a potential therapeutic). For example, fusion of a protein or peptide of interest to lipocalin may increase the half-life of the protein or peptide of interest by increasing the size of the overall protein. For example, the increased size of the protein may prevent glomerular filtration of the protein or peptide of interest. In some aspects, fusions of small proteins, such as antibody fragments, exhibit decreased glomerular filtration. These effects are observed with both enzymes and Fab antibody fragments. In some embodiments, the fusion protein further comprises a peptide selected from the group consisting of: an IgK starter sequence, a sFLAG, a HIS, siderocalin, a TEV and the knotted peptide sequence of interest. In certain embodiments, the fusion protein comprises the following construct: IgK SP-sFLAG-HIS-siderocalin-TEV-peptide. In some embodiments, the knotted-peptide includes at least two disulfide bonds.

In some embodiments, the fusion protein further comprises at least one of an IgK starter sequence, a sFLAG, a HIS, and a TEV. In certain embodiments, the fusion protein comprises the following construct: IgK SP-sFLAG-HISsiderocalin-TEV-peptide. In some embodiments, the fusion protein is generated by direct fusion of each subunit to the adjacent subunits. In certain embodiments, the composition further comprises a linker sequence between the peptide or protein domain and the lipocalin protein. In some embodiments, the peptide comprises a knotted-peptide.

In some embodiments, the fusion protein further comprises at least one of an IgK starter sequence, a sFLAG, a HIS, and a TEV. In certain embodiments, the fusion protein comprises the following construct: IgK SP-sFLAG-HIS-siderocalin-TEV-peptide. In other embodiments, the peptide comprises a knotted-peptide In some aspects, fusion of the protein or peptide of interest to lipocalin may enhance the purification of the protein or peptide of interest after production. For example, the protein or peptide of interest fused to lipocalin may be produced from a protein expression system (e.g., fusion protein expression system). For example, proteins or peptides of interest may be retained in a compartment of a cell during production if proteins or peptides of interest are not fused to lipocalin.

In some aspects, SCN has protective properties in vivo that are imparted to a fusion partner as the basis of in vivo therapeutics fusion partners. In some aspects, these therapeutics can be stabilized for use as immunogens, matching the species donating the lipocalin sequence to that of the recipient species to focus elicited immune responses to the fusion partner. SCN also has unique ligand specificity and tightly binds siderophores (ferric iron chelators).

The methods and compositions described herein include fusion proteins of a protein or peptide of interest coupled to SCN and a SCN ligand. In some aspects, the ligands for SCN may include, but are not limited to, a siderophore or an organizing metal. In some aspects, fusion proteins including the SCN ligands may be coupled to a fluorphore. For example, the coupling may be covalently coupled. In some aspects, fusion proteins including the SCN ligands may be coupled to a luminescent siderophore. In some aspects, the luminescent siderophore may include a metal complex.

In some aspects, the addition of SCN ligands to the fusion proteins could be used to detect or localize the target protein, or target peptide, of the fusion protein. For example, the detection and localization could be performed either in vitro or in vivo. In some aspects, the addition of SCN ligands to the fusion proteins could be used to purify fusion proteins from mixtures. For example, an SCN ligand (e.g., a siderophore/metal complex) could be contacted with at least one purification resin metal other than, including but not limited to, aluminum, gadolinium, indium, vanadium, plutonium or thorium, and any related isotopes.

In some aspect, the addition of SCN ligands to the fusion proteins could be used for the delivery of radionuclides to a target tissue. In some aspects, the addition of SCN ligands to the fusion proteins could be used to deliver iron to a target. In addition, SCN bound to siderophores and iron can be a dark red color. For example, the dark red color can be combined with methods and compositions of chromatography or other steps in a method of purification.

In an exemplary aspect, a self-cleaving SCN isoform may be added to a peptide or protein of interest to generate a fusion protein. For example, the self-cleaving SCN isoform may contain the RARYKR (SEQ ID NO: 101) amino acid sequence immediately following the CIDG (SEQ ID NO: 102) amino acid sequence. In this case, the RARYKR (SEQ ID NO: 101) sequence may be cleaved by an endogenous enzyme to the cells of the protein expression system (e.g., the mammalian cells) during export of the fusion protein. For example, furin may cleave the RARYKR (SEQ ID NO: 101) sequence. In this case, SCN and the peptide or protein of interest may be free and located in the extracellular space.

In an exemplary aspect, an exogenously cleaved SCN isoform may be added to a peptide or protein of interest to generate a fusion protein. For example, the exogenously cleaved SCN isoform may contain the ENLYFQ (SEQ ID NO: 95) amino acid sequence immediately following the CIDG (SEQ ID NO: 102) amino acid sequence. In this case, the ENLYFQ (SEQ ID NO: 95) sequence may be cleaved by an exogenous enzyme to the cells of the protein expression system (e.g., the mammalian cells) during export or after export of the fusion protein. For example, a tobacco etch protease may cleave the ENLYFQ (SEQ ID NO: 95) site.

In some aspects, the fusion proteins may be secreted from the cells of the protein expression system (e.g., the mammalian cells) as fusion proteins. In this case, the peptide or protein of interest may be cleaved from the SCN protein by TEV protease. For example, the TEV protease may be added to the cells of the protein expression system (e.g., the mammalian cells) or added after removal of the fusion protein from the cells.

In some aspects, the SCN peptide may be modified to include compounds for purification or isolation. In some aspects, the compounds may be an amino acid or more than one amino acid. For example, the compounds may be poly-histidine or poly-arginine and may be located between Lcn2 and a signal peptide in the fusion protein. In some aspects, the compounds may be removed from Lcn2 using an enzyme or proteolysis.

The present invention relates to compositions comprising a peptide library, the peptide library further comprising a plurality of peptides lacking at least one native lysine residue. In some embodiments, the peptides are conjugated to an adaptor molecule. In certain embodiments, the adaptor molecule is a peptide. In some embodiments, the peptide has a unique signature determined by mass spectroscopy.

Methods of Use

The fusion proteins, peptides, or conjugates thereof of the present disclosure can be used for a variety of other applications, such as therapeutic and/or diagnostic applications. In some embodiments, the fusion proteins, peptides, or conjugates thereof of the present disclosure can be used for methods of treating diseases. In some embodiments, the fusion proteins, peptides, or conjugates thereof of the present disclosure can be used to deliver drugs to, e.g., tumors in the brain of a subject.

The present invention also provides compositions for administering the [ ]fusion proteins, peptides, or conjugates thereof described herein to a subject to facilitate diagnostic and/or therapeutic applications.

In certain embodiments, the compositions can include a pharmaceutically acceptable excipient. Pharmaceutical excipients useful in the present invention include, but are not limited to, binders, fillers, disintegrants, lubricants, coatings, sweeteners, flavors and colors. One of skill in the art will recognize that other pharmaceutical excipients are useful in the present invention. The term "pharmaceutical composition" as used herein includes, e.g., solid and/or liquid dosage forms such as tablet, capsule, pill and the like.

The fusion proteins, peptides, or conjugates thereof of the present disclosure may be administered by any suitable technique available in the art, e.g., as compositions. For example, they can be administered as frequently as necessary, including hourly, daily, weekly or monthly. The fusion proteins, peptides, or conjugates thereof, can be utilized in the methods of the invention can be, e.g., administered at dosages that may be varied depending upon the requirements of the method being employed. The fusion proteins, peptides, or conjugates thereof described herein can be administered to the subject in a variety of ways, including parenterally, subcutaneously, intravenously, intratracheally, intranasally, intradermally, intramuscularly, colonically, rectally, urethrally or intraperitoneally. In some embodiments, the pharmaceutical compositions can be administered parenterally, intravenously, intramuscularly or orally. In some embodiments, the fusion proteins, peptides, or conjugates thereof of the present disclosure, can be administered systemically. In some embodiments, the compositions can be administered intratumorally and/or intranodally, such as delivery to a subject's lymph node(s). In certain embodiments, administration can include enteral administration including oral administration, rectal administration, and administration by gastric feeding tube or duodenal feeding tube. Administration can include intravenous injection, intra-arterial injection, intra-muscular injection, intracerebral, intracerebroventricular or subcutaneous (under the skin) administration. In some embodiments, administration can be achieved by topical means including epicutaneous (application to skin) and inhalation.

The oral agents comprising fusion proteins, peptides, or conjugates thereof of the present disclosure can be in any suitable form for oral administration, such as liquid, tablets, capsules, or the like. The oral formulations can be further coated or treated to prevent or reduce dissolution in stomach. The compositions of the present invention can be administered to a subject using any suitable methods known in the art. Suitable formulations for use in the present invention and methods of delivery are generally well known in the art. For example, the fusion proteins, peptides, or conjugates thereof of the present disclosure can be formulated as pharmaceutical compositions with a pharmaceutically acceptable diluent, carrier or excipient. The compositions may contain pharmaceutically acceptable auxiliary substances as required to approximate physiological conditions including pH adjusting and buffering agents, tonicity adjusting agents, wetting agents and the like, such as, for example, sodium acetate, sodium lactate, sodium chloride, potassium chloride, calcium chloride, sorbitan monolaurate, triethanolamine oleate, etc.

As used herein, a "subject" is a human or non-human animal. In some embodiments, a subject can include, but is not limited to, a mouse, a rat, a rabbit, a human, or other animal. In another embodiment, a subject is a human, such as a human having or at risk of having a cancer. In some embodiments, a subject or biological source may be suspected of having or being at risk for having a disease, disorder or condition, including a malignant disease, disorder or condition (e.g., cancer). In certain embodiments, a subject or biological source may be suspected of having or being at risk for having a hyperproliferative disease (e.g., carcinoma, sarcoma), and in certain other embodiments of this disclosure a subject or biological source may be known to be free of a risk or presence of such disease, disorder, or condition.

"Treatment," "treating" or "ameliorating" refers to either a therapeutic treatment or prophylactic/preventative treatment. A treatment is therapeutic if at least one symptom of disease (e.g., a hyperproliferative disorder, such as cancer) in an individual receiving treatment improves or a treatment may delay worsening of a progressive disease in an individual, or prevent onset of additional associated diseases (e.g., metastases from cancer).

A "therapeutically effective amount (or dose)" or "effective amount (or dose)" of a composition including fusion proteins, peptides, or conjugates thereof of the present disclosure, refers to that amount of compound sufficient to result in amelioration of one or more symptoms of the disease being in a statistically significant manner. When referring to an individual active ingredient, administered alone, a therapeutically effective dose refers to that ingredient alone (e.g., a fusion proteins, peptides, or conjugates thereof of the present disclosure). When referring to a combination, a therapeutically effective dose refers to combined amounts of the active ingredients that result in the therapeutic effect, whether administered serially or simultaneously (in the same formulation or in separate formulations).

The term "pharmaceutically acceptable" refers to molecular entities and compositions that do not produce allergic or other serious adverse reactions when administered to a subject using routes well known in the art.

A "patient in need" or "subject in need" refers to a patient or subject at risk of, or suffering from, a disease, disorder or condition (e.g., cancer) that is amenable to treatment or amelioration with a fusion proteins, peptides, or conjugates thereof of the present disclosure described herein.

In some embodiments, the fusion proteins, peptides, or conjugates thereof of the present disclosure can further include other agents to facilitate treatment. For example, a fusion proteins, peptides, or conjugates thereof of the present disclosure can further include cytotoxic agents (e.g., mitotic inhibitors), toxins, antisense nucleotides, cancer treatment drugs (e.g., alkylating agents), nucleotide drugs, [ ]anti-metabolites, metabolic modulators, radiosensitizers, peptide therapeutics, peptide-drug conjugates, radionuclides, or a combination thereof.

Cytotoxic agents can include drugs that can be used to treat cancer, e.g., by inhibiting cell proliferation. Some example cytotoxic agents can include, e.g., the *vinca* alkaloids, mitomycins, bleomycins, cytotoxic nucleosides, taxanes, and epothilones, Members of those classes include, for example, doxorubicin, carminomycin, daunorubicin, aminopterin, methotrexate, methopterin, dichloromethotrexate, mitomycin C, porfiromycin, 5-fluorouracil, 6-mercaptopurine, gemcitabine, cytosine arabinoside, podophyllotoxin or podo-phyllotoxin derivatives, such as etoposide, etoposide phosphate or teniposide, melphalan, vinblastine, vincristine, leurosidine, vindesine, leurosine, paclitaxel and therapeutically effective analogs and derivatives of the same. Other useful antineoplastic agents include estramustine, cisplatin, carboplatin, cyclophosphamide, bleomycin, gemcitibine, ifosamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons and interleukins.

Suitable metabolic modulators can include, but are not limited to, lonidamine, dichloroacetate, alpha-tocopheryl succinate, methyl jasmonate, betulinic acid, and resveratrol Radiosensitizers are known to increase the sensitivity of cancerous cells to the toxic effects of electromagnetic radiation, e.g., x-rays. Examples of x-ray activated radiosensitizers include, but are not limited to, metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

In some embodiments, the fusion proteins, peptides, or conjugates thereof of the present disclosure can include radionuclides and/or complexed radionuclides. Suitable radionuclides can include, but are not limited to, Sc-47, Ga-67, Y-90, Ag-111, In-111, Sm-153, Tb-166, Lu-177, Bi-213, Ac-225, Cu-64, Cu-67, Pd-109, Ag-111, Re-186, Re-188, Pt-197, Bi-212, Bi-213, Pb-212 or Ra-223.

In certain embodiments, the present invention can include treating diseases, disorders, and/or conditions, such as gliomas, astrocytomas medulloblastomas, choroids plexus carcinomas, ependymomas, other brain tumors, neuroblastoma, head and neck cancer, lung cancer, breast cancer, intestinal cancer, pancreatic cancer, liver cancer, kidney cancer, sarcomas, osteosarcoma, rhabdomyosarcoma, Ewing's sarcoma, carcinomas, melanomas, ovarian cancer, cervical cancer, lymphoma, thyroid cancer, anal cancer, colo-rectal cancer, endometrial cancer, germ cell tumors, laryngeal cancer, multiple myeloma, prostate cancer, retinoblastoma, gastric cancer, testicular cancer, and Wilm's tumor. In some embodiments, the methods can include treating a disease, disorder and/or condition including a glioma, a skin cancer, a lung cancer, a lymphoma, a medulloblastoma, a prostate cancer, a pancreatic cancer, or a combination thereof. In certain embodiments, the methods can be used to treat breast and mammary cancers, colon, skin, lung, lymphoma, glioma, medulloblastoma prostate, pancreatic cancers, oral squamous cell carcinoma, and/or hemangiopericytoma.

The present invention further includes methods of administering a fusion proteins, peptides, or conjugates thereof of the present disclosure. For example, in one aspect, the present invention includes a method comprising a step of administering an effective dose of a fusion proteins, peptides, or conjugates thereof of the present disclosure or a composition including fusion proteins, peptides, or conjugates thereof of the present disclosure to a subject with a tumor such that the peptide selectively targets tumor tissue over normal tissue.

The methods can further include facilitating surgical removal of cancerous tissue (e.g., a tumor) in a subject. For example, the present invention can include a method comprising administering an effective dose of fusion proteins, peptides, or conjugates thereof of the present disclosure or a composition including fusion proteins, peptides, or conjugates thereof of the present disclosure to a subject with cancerous tissue (e.g., a tumor) such that the peptide selectively targets cancerous tissue (e.g., tumor tissue) over normal tissue. The methods can include imaging the cancerous tissue by, e.g., detecting the tissue that shows elevated binding of the peptides, thereby indicating the location of the cancerous tissue. Identification of the location can provide a step of surgically removing the cancerous tissue from the subject. The surgically removing can include, e.g., intraoperative visualization of the cancerous tissue as identified by binding of the fusion proteins, peptides, or conjugates thereof of the present disclosure.

The present invention also provides compositions for administering fusion proteins, peptides, or conjugates thereof of the present disclosure to a subject to facilitate diagnostic and/or therapeutic applications. In certain embodiments, the compositions can include a pharmaceutically acceptable excipient. Pharmaceutical excipients useful in the present invention include, but are not limited to, binders, fillers, disintegrants, lubricants, coatings, sweeteners, flavors and colors. One of skill in the art will recognize that other pharmaceutical excipients are useful in the present invention. The term "pharmaceutical composition" as used herein includes, e.g., solid and/or liquid dosage forms such as tablet, capsule, pill and the like.

The fusion proteins, peptides, or conjugates thereof of the present disclosure can be administered as frequently as necessary, including hourly, daily, weekly or monthly. The fusion proteins, peptides, or conjugates thereof of the present disclosure utilized in the methods of the invention can be, e.g., administered at dosages that may be varied depending upon the requirements of the method being employed. The fusion proteins, peptides, or conjugates thereof of the present disclosure can be administered to the subject in a variety of ways, including parenterally, subcutaneously, intravenously, intratracheally, intranasally, intradermally, intramuscularly, colonically, rectally, urethrally or intraperitoneally. In some embodiments, the pharmaceutical compositions can be administered parenterally, intravenously, intramuscularly or orally. In some embodiments, the compositions can be administered intratumorally and/or intranodally, such as delivery to a subject's lymph node(s). In certain embodiments, administration can include enteral administration including oral administration, rectal administration, and administration by gastric feeding tube or duodenal feeding tube. Administration can also include intravenous injection, intra-arterial injection, intra-muscular injection, intracerebral, intracerebroventricular or subcutaneous (under the skin) administration.

The oral agents comprising peptides or protein fusions described herein can be in any suitable form for oral administration, such as liquid, tablets, capsules, or the like. The oral formulations can be further coated or treated to prevent or reduce dissolution in stomach. The compositions of the present invention can be administered to a subject using any suitable methods known in the art. Suitable formulations for use in the present invention and methods of delivery are generally well known in the art. For example, the peptides or fusion proteins described herein can be formulated as pharmaceutical compositions with a pharmaceutically acceptable diluent, carrier or excipient. The compositions may contain pharmaceutically acceptable auxiliary substances as required to approximate physiological conditions including pH adjusting and buffering agents, tonicity adjusting agents, wetting agents and the like, such as, for example, sodium acetate, sodium lactate, sodium chloride, potassium chloride, calcium chloride, sorbitan monolaurate, triethanolamine oleate, etc.

The present invention further includes functional assays of fusion proteins, peptides, or conjugates thereof of the present disclosure. The capacity of fusion proteins, peptides, or conjugates thereof of the present disclosure, to bind to tumor or cancerous tissue can be assayed by in vitro binding, ex vivo imaging, animal models, and other assays known in the art and as previously described. See, for example, US Patent Publication Number US20080279780 and WO 2011/142858, both of which are incorporated by reference herein for the description of functional assays to detect and measure binding to tumor cells and tumor tissue.

One skilled in the art will be knowledgeable about animal models that are useful for measuring the in vivo activity of fusion proteins, peptides, or conjugates thereof of the present disclosure. For example, the National Cancer Institute maintains a database of specific cancer models. See the "Cancer Models Database" at the National Cancer Institute website. All animals are handled in strict accordance with the National Institutes of Health Guide for the Care and Use of Laboratory Animals. ND2:SmoA1 medulloblastoma mice, TRAMP prostate cancer mice and Apc$^{1638N}$ intestinal adenoma and adenocarcinoma mice have been previously described. See, Fodde, R., et al., A targeted chain-termination mutation in the mouse Apc gene results in multiple intestinal tumors. Proc. Natl. Acad. Sci. U.S.A., 1994. 91(19): p. 8969-73; Greenberg, N. M., et al., Prostate cancer in a transgenic mouse. Proc. Natl. Acad. Sci. U.S.A., 1995. 92(8): p. 3439-43; Kaplan-Lefko, P. J., et al., Pathobiology of autochthonous prostate cancer in a pre-clinical transgenic mouse model. Prostate, 2003. 55(3): p. 219-37; Hallahan, A. R., et al., The SmoA1 mouse model reveals that notch signaling is critical for the growth and survival of sonic hedgehog-induced medulloblastomas. Cancer Res., 2004. 64(21): p. 7794-800; each expressly incorporated herein by reference in its entirety.

The fusion proteins, peptides, and conjugates thereof generated and produced by the methods and systems described herein can be used for a range of applications. For example, the proteins and peptides can be used for therapeutic and/or diagnostic purposes. Some example uses include, but are not limited to, conjugating the fusion proteins or peptides to radiolabels and/or fluorescent molecules for bioimaging, linking the peptides to cytotoxic agents, using the peptides for in vitro diagnostics for biochemical assays, as well as, e.g., for veterinary uses, insecticides, antibiotics, herbicides, antifreeze compositions, and antivenoms.

As will be appreciated by one of ordinary skill in the art, the fusion proteins and peptides described herein can be tailored for a wide range of targets (e.g., therapeutic targets). In some embodiments, the targets are associated with a variety of diseases or disorders. Some targets, for example, can include but are not limited to glypican-2 (GPC2), protocadherin (1α(PCDHA1), $Ca_v2.2$, $K_v1.3$, $Na_v1.2$, NaV1.1, NaV1.7, NaV1.8, ClC-3, nAChR, NMDA-R, NPRA, GLP-1R, $α_{1B}$-AR, NT-R-1, ACE, NET mTor, cMet, VEGF/VEGFR, c-Kit, PDGF/PDGFR, PI3K, HER2, EGFR, Orai1, CD47, Raf, NFκB, Bromodomains, HATS, HDAC, LDH, IDH2, CD22, MIC, c-Myc, n-Myc, PHF5A, BUB1B, Bcl-2, k-Ras, Notch1, p53, α5β3, NKG2D, CTLA4/CD28, and/or Mcl-1.

The present invention also provides compositions for administering the fusion peptides, peptides, or conjugates thereof according to the present disclosure to a subject to facilitate diagnostic and/or therapeutic applications. In certain embodiments, the compositions can include a pharmaceutically acceptable excipient. Pharmaceutical excipients useful in the present invention include, but are not limited to, binders, fillers, disintegrants, lubricants, coatings, sweeteners, flavors and colors. One of skill in the art will recognize that other pharmaceutical excipients are useful in the present invention. The term "pharmaceutical composition" as used herein includes, e.g., solid and/or liquid dosage forms such as tablet, capsule, pill and the like.

The fusion peptides, peptides, or conjugates thereof according to the present disclosure can be administered as frequently as necessary, including hourly, daily, weekly or monthly. The fusion peptides, peptides, or conjugates thereof according to the present disclosure utilized in the methods of the invention can be, e.g., administered at dosages that may be varied depending upon the requirements of the method being employed. The fusion peptides, peptides, or conjugates thereof according to the present disclosure can be administered to the subject in a variety of ways, including parenterally, subcutaneously, intravenously, intratracheally, intranasally, intradermally, intramuscularly, colonically, rectally, urethrally or intraperitoneally. In some embodiments, the pharmaceutical compositions can be administered parenterally, intravenously, intramuscularly or orally. In some embodiments, the [ ]fusion peptides, peptides, or conjugates thereof according to the present disclosure can be administered systemically. In some embodiments, the compositions can be administered intratumorally and/or intranodally, such as delivery to a subject's lymph node(s). In certain embodiments, administration can include enteral administration including oral administration, rectal administration, and administration by gastric feeding tube or duodenal feeding tube. Administration can also include intravenous injection, intra-arterial injection, intra-muscular injection, intracerebral, intracerebroventricular or subcutaneous (under the skin) administration. In some embodiments, administration can be achieved by topical means including epicutaneous (application to skin) and inhalation.

The oral agents comprising fusion peptides, peptides, or conjugates thereof according to the present disclosure described herein can be in any suitable form for oral administration, such as liquid, tablets, capsules, or the like. The oral formulations can be further coated or treated to prevent or reduce dissolution in stomach. The compositions of the present invention can be administered to a subject using any suitable methods known in the art. Suitable formulations for use in the present invention and methods of delivery are generally well known in the art. For example, the fusion peptides, peptides, or conjugates thereof according to the present disclosure can be formulated as pharmaceutical compositions with a pharmaceutically acceptable diluent, carrier or excipient. The compositions may contain pharmaceutically acceptable auxiliary substances as required to approximate physiological conditions including pH adjusting and buffering agents, tonicity adjusting agents, wetting agents and the like, such as, for example, sodium acetate, sodium lactate, sodium chloride, potassium chloride, calcium chloride, sorbitan monolaurate, triethanolamine oleate, etc.

EXEMPLARY ASPECTS

Example 1

Expressing Peptide Constructs for Knottin Generation

This example describes a method for expressing peptide constructs in culture and greatly facilitating their development, particularly as drugs.

Figure 5:
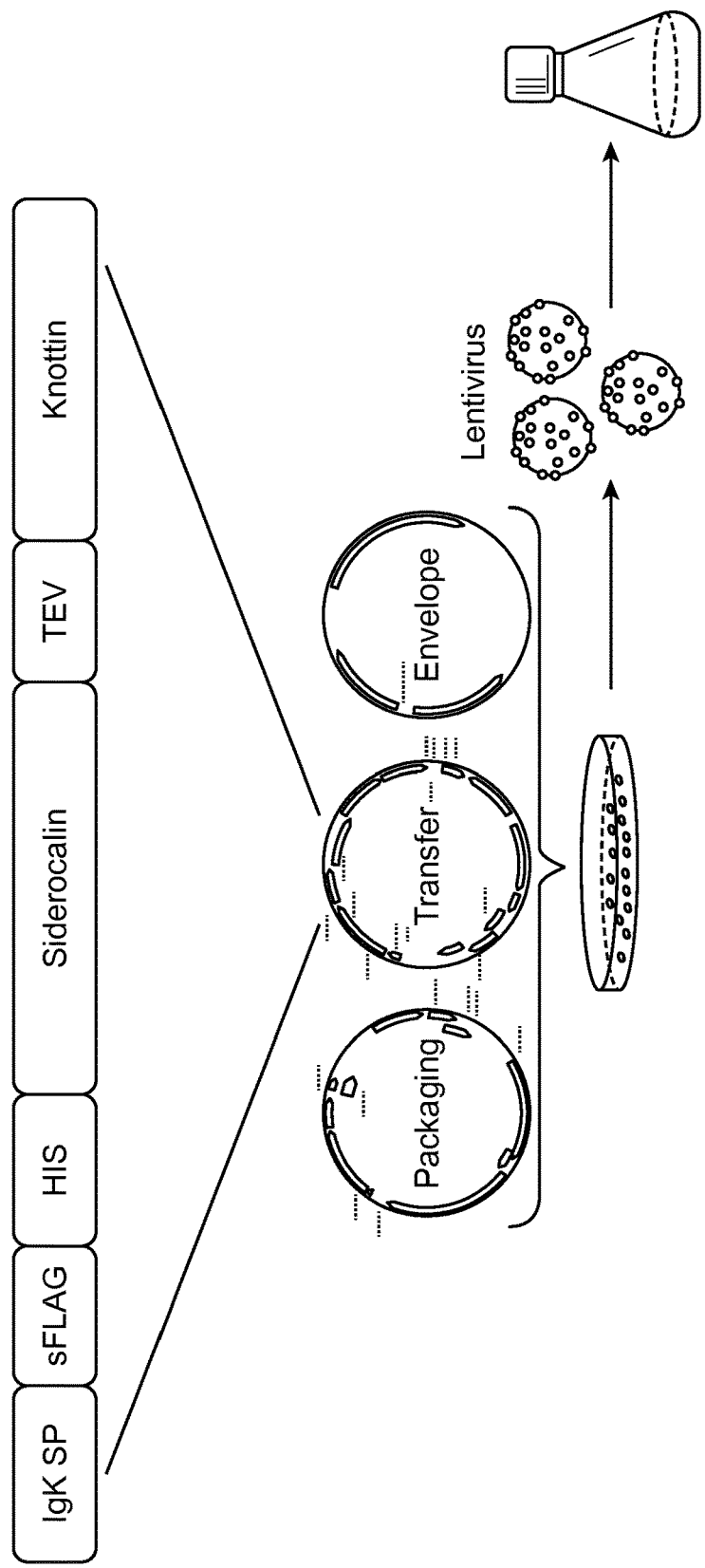
FIG. 5 shows an example method of using siderocalin fusions to express knottin variants, in accordance with an embodiment of the present invention.
Figure 6:
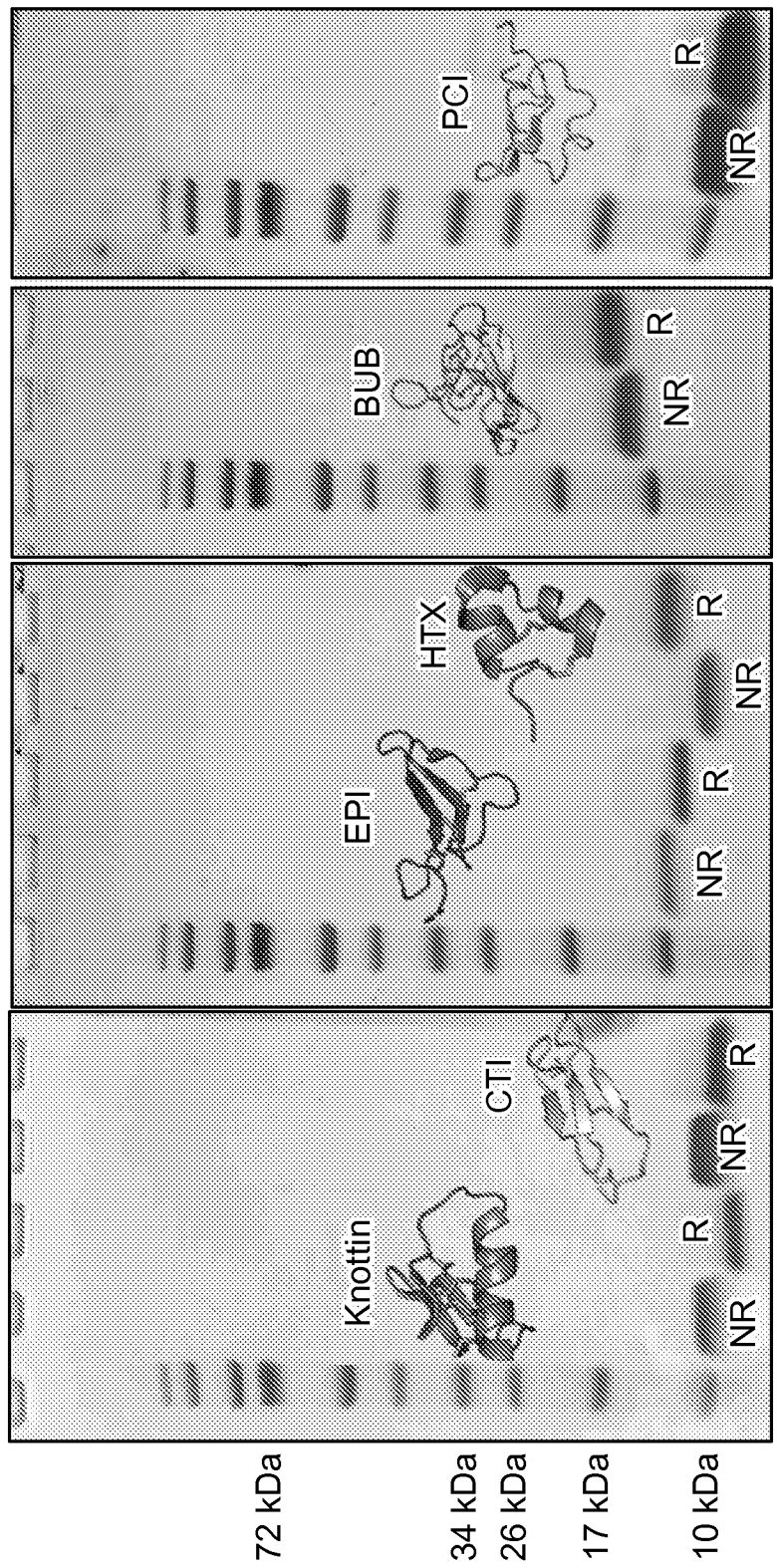
FIG. 6 depicts SDS-PAGE analysis of expressing knottin scaffolds, in accordance with embodiments of the present invention.

As shown in FIG. 5, the various knottins can be expressed, e.g., in a lentivirus expression-based method that can include packaging, transfer, and then expression followed by isolation and/or purification of the expressed knottin peptides. Several coding constructs can be used. In this example, the encoding of the knottin peptides included a polynucleotide construct including IgK SP-sFLAG-HIS-Siderocalin-TEV-Knottin. Specific sequences of some example constructs are disclosed in the "SEQUENCE" section below. FIG. 6 shows gel data of a number of example knottins that were made according to the method described in FIG. 5. As shown, chymotrypsin inhibitor (CTI), epiregulin (EPI), hefutoxin (HTX), bubble protein (BUB), potato carboxypeptidase inhibitor (PCI) were properly folded.

Figure 7A:
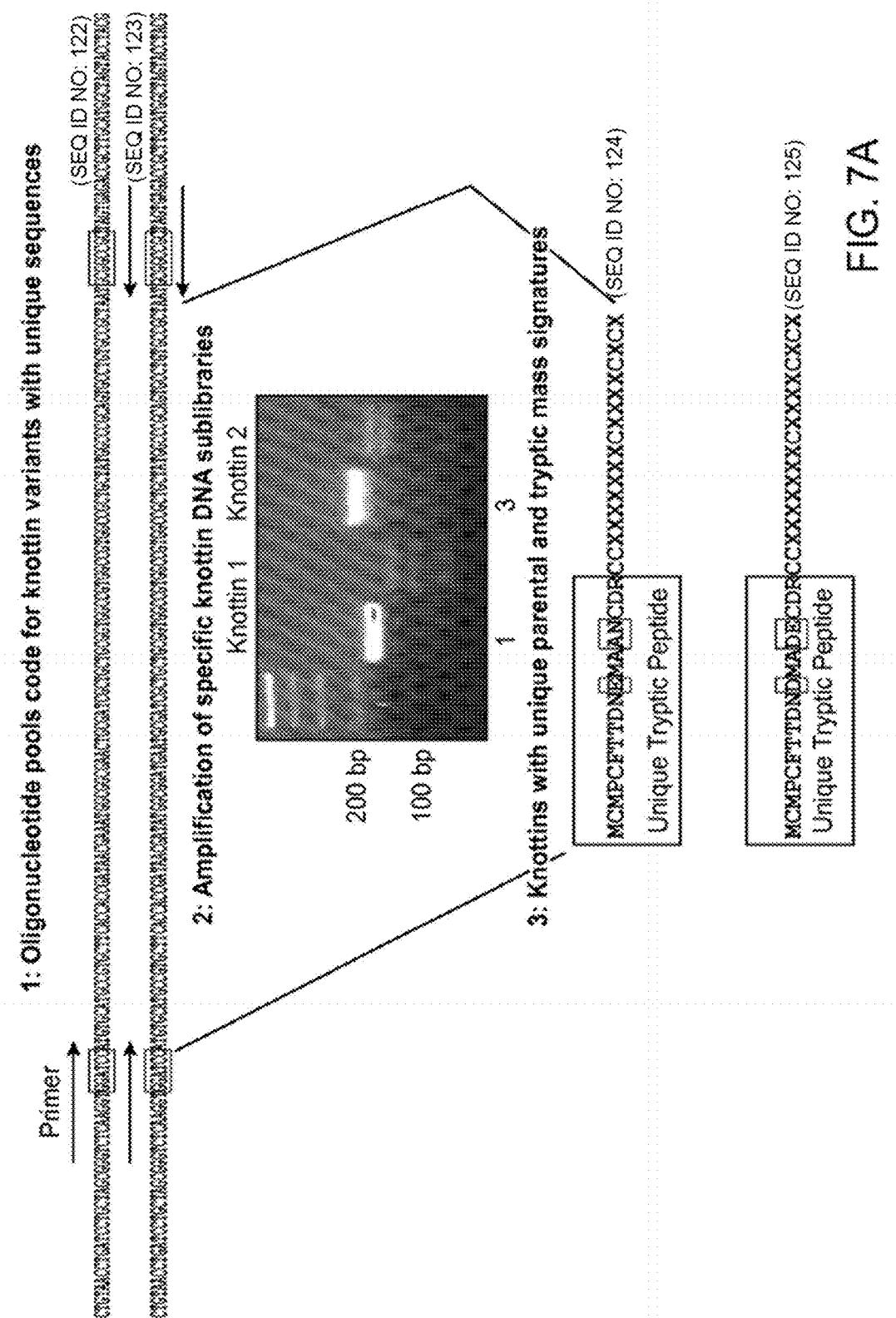
FIGS. 7A-7B provides a schematic of pooled library production, in accordance with an embodiment of the present invention.
Figure 7B:
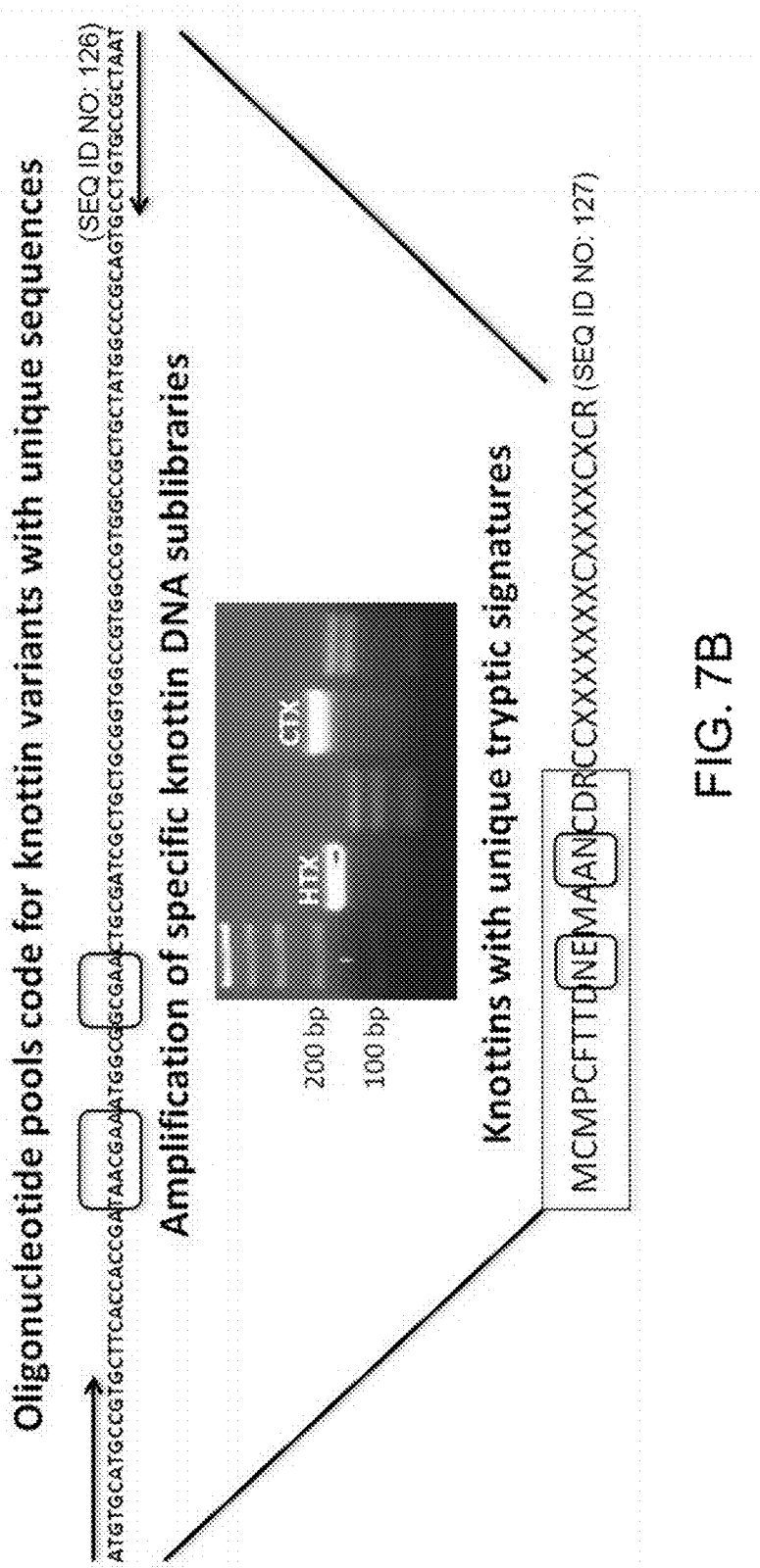

FIGS. 7A-7B shows a schematic describing production of a pooled library of knottins. In this example, sequences of thousands of knottins can be encoded in an oligonucleotide pool (1) and selectively amplified using unique primer pairs (2). DNA sublibraries can be cloned into the expression vector, which results in the knottin variants that can, e.g., have unique parental mass signatures and unique tryptic fragment mass signatures that can be resolvable using current techniques, such as mass spectroscopy.

FIG. 8 includes example knottin variants that describe representative sequencing from a cloned knottin library. The sequences show raw sequencing data (SEQ ID NOs: 128-156) from a single round of library cloning. The sequence portions highlighted in grey are full length knottin variants, and the errors in oligonucleotide synthesis can explain the truncated and extended peptide sequences.

Figure 9:
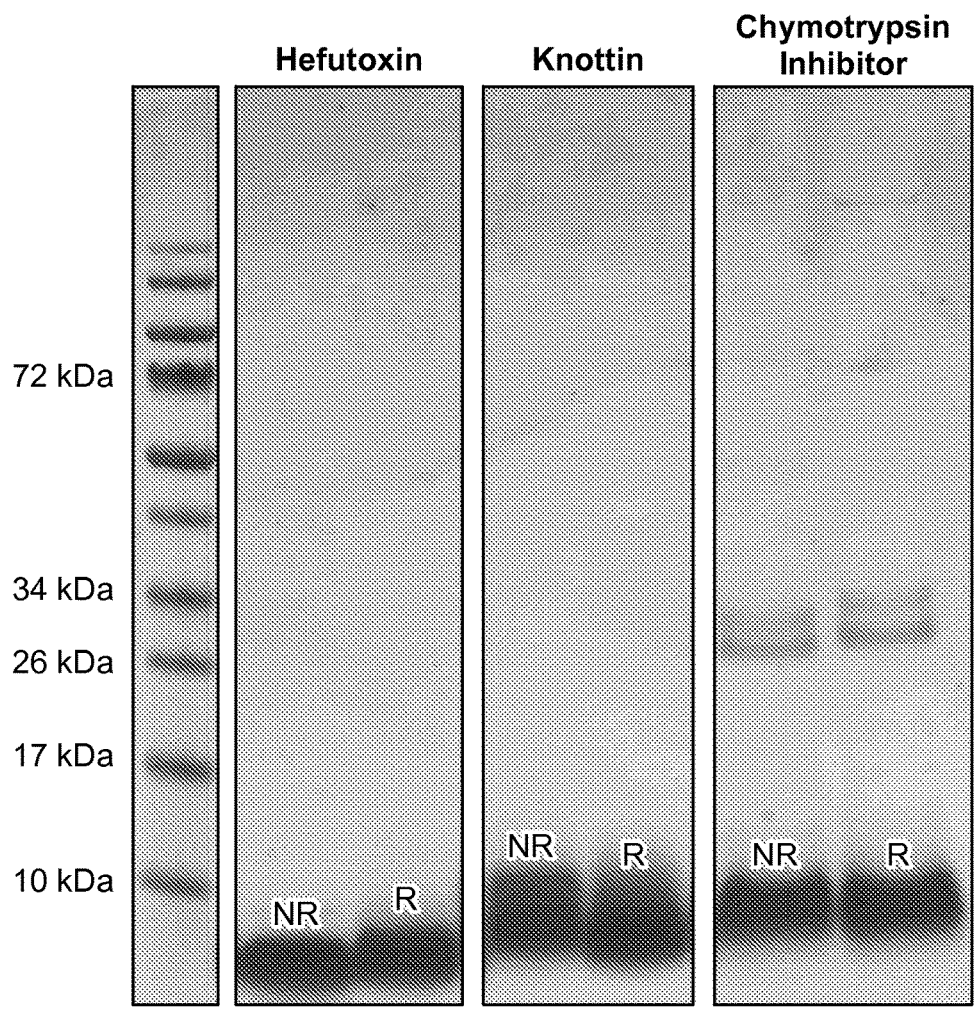
FIG. 9 shows SDS-PAGE analysis of 3000-member knottin libraries, in accordance with embodiments of the present invention.

Using the methods described in this example, variants of several knottin scaffolds were generated and analyzed. FIG. 9 shows an SDS-PAGE analysis of 3000 member knottin libraries for, e.g., hefutoxin, knottin and chymotrypsin inhibitor. Each column of the SDS-PAGE gel shows a purified sample of a pool of 3000 knottin protein variants run under native and reducing conditions. The migration shift between the paired bands indicates disulfide formation.

Four scaffolds were selected for the generation of defined libraries: hefutoxin, CTI, knottin, and epiregulin. A list of target amino acid sequences was generated in silico such that every member of each library would have a tryptic fragment with a unique mass; mutations were selected to be structurally adjacent in order to generate binding epitopes. The cysteines were not mutated, and lysine was specifically avoided in order to make N-terminal conjugation unambiguous. 3000 variants of each scaffold were generated, and each scaffold was flanked by a unique set of PCR primer sites so that each of the four sublibraries could be amplified independently. All constructs had an N-terminal BamHI site and a C-terminal NotI site, and following PCR amplification of each sublibrary from the pool of 12000 oligonucleotides, each sublibrary was restriction digested and cloned into cut parental vector (both the furin-cleaved and TEV-cleaved versions) as an SCN fusion protein using standard techniques. HEK293 cells were transfected with this plasmid library as well as the accessory plasmids needed for Daedalus expression, and the virus in the media harvested 3-4 days later. Virus was concentrated by centrifugation and used to infect HEK293 cells for protein production using standard procedures. We have found that the TEV-cleavable construct is technically easier to handle when producing libraries because it allows for facile recovery of the fusion by IMAC on nickel resin. Following IMAC, the fusion protein was dialyzed into PBS and allowed to cleave overnight with 6×His (SEQ ID NO: 93) tagged TEV protease, and the SCN and protease were subsequently removed by running the material through nickel resin again. The flow-through containing the cleaved peptide libraries was further purified and buffer exchanged by size exclusion chromatography (SEC) into 10 mM ammonium formate, and the fractions containing the peptides were pooled and lyophilized.

There were two approaches taken to cloning, Seamless Cloning (Invitrogen) and restriction/ligation based methods. Seamless cloning was employed for making single constructs, typically using synthesized "gBlocks" from IDT. The manufacturer's instructions were followed. Restriction/ligation methods were standard and were used for cloning libraries as follows: the pooled oligonucleotides from CustomArray were subjected to PCR in order to amplify the relevant sublibrary. The amplified pool was agarose gel purified and cleaned of agarose using a Qiagen column. The purified fragment was digested with FaastDigest (Fermentas) BamHI and NotI and ligated into the parental vector which had been cut with the same two restriction endonucleases. Singleton clones were sequence verified, and 48 members of each library were sequenced in order to verify library quality.

The cloned knottin or library was cotransfected into HEK293 cells and media was collected as described ("Daedalus: A Robust, Turnkey Platform for Rapid Production of Decigram Quantities of Active Recombinant Proteins in Human Cell Lines Using Novel Lentiviral Vectors." Bandaranayake A. D., et al., *Nucleic Acids Res.* (2011) 39(21): e143). Fusion protein was isolated using nickel IMAC and cleaved with recombinant TEV protease. Excess siderocalin was removed via size exclusion chromatography, a process which also allowed the buffer to be switched to 10 mM ammonium formate. The knottin containing fractions were then lyophilized. Proper folding and peptide uniformity was demonstrated via SEC chromatography, reverse-phase HPLC, mass spectrometry, and a gel shift in reduced versus non-reduced samples in SDS-PAGE.

Conjugation to palmitic acid, ICG, or biotinidase-resistant biotin was performed using a 3-10 fold excess of commercially available, activated ester conjugate in PBS. Acetonitrile was added when there were solubility problems. The final material was purified by RP-HPLC for singletons, and excess conjugate was removed from libraries by dialysis.

Example 2

Fusion Protein Systems

This example describes expression systems for the efficient production of various peptides, including knotted peptides. Advantageously, the peptides produced according to these methods are secreted and stable.

Figure 24:
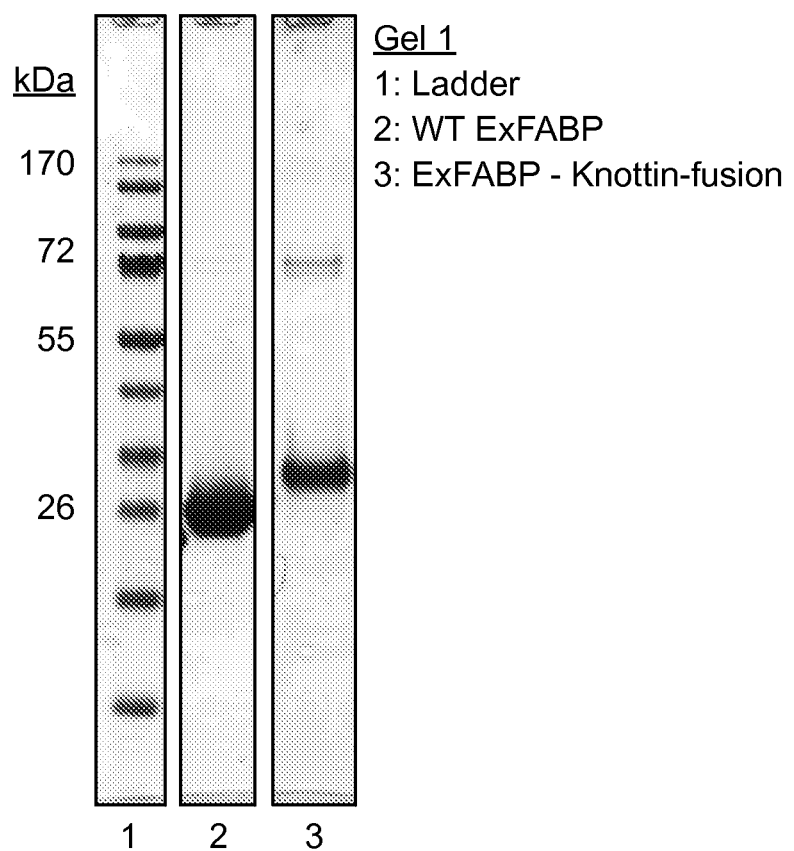
FIG. 24 depicts the expression of an ExFABP fusion with a knottin and corresponding SDS PAGE analysis according to one aspect of the present disclosure. ExFABP is another functional Scn. According to the present disclosure, this construct can be used in a periplasmic bacterial system to secrete a variety of client proteins.
Figure 25:
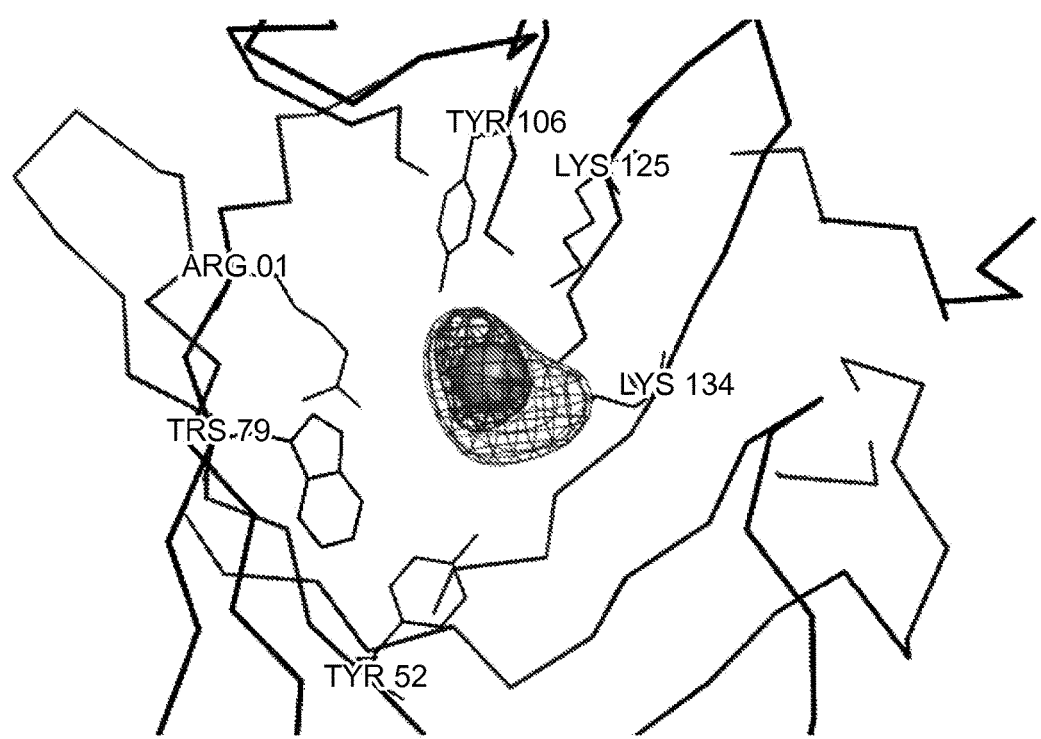
FIG. 25 depicts the crystal structure of Scn with a Th ligand.
Figure 26:
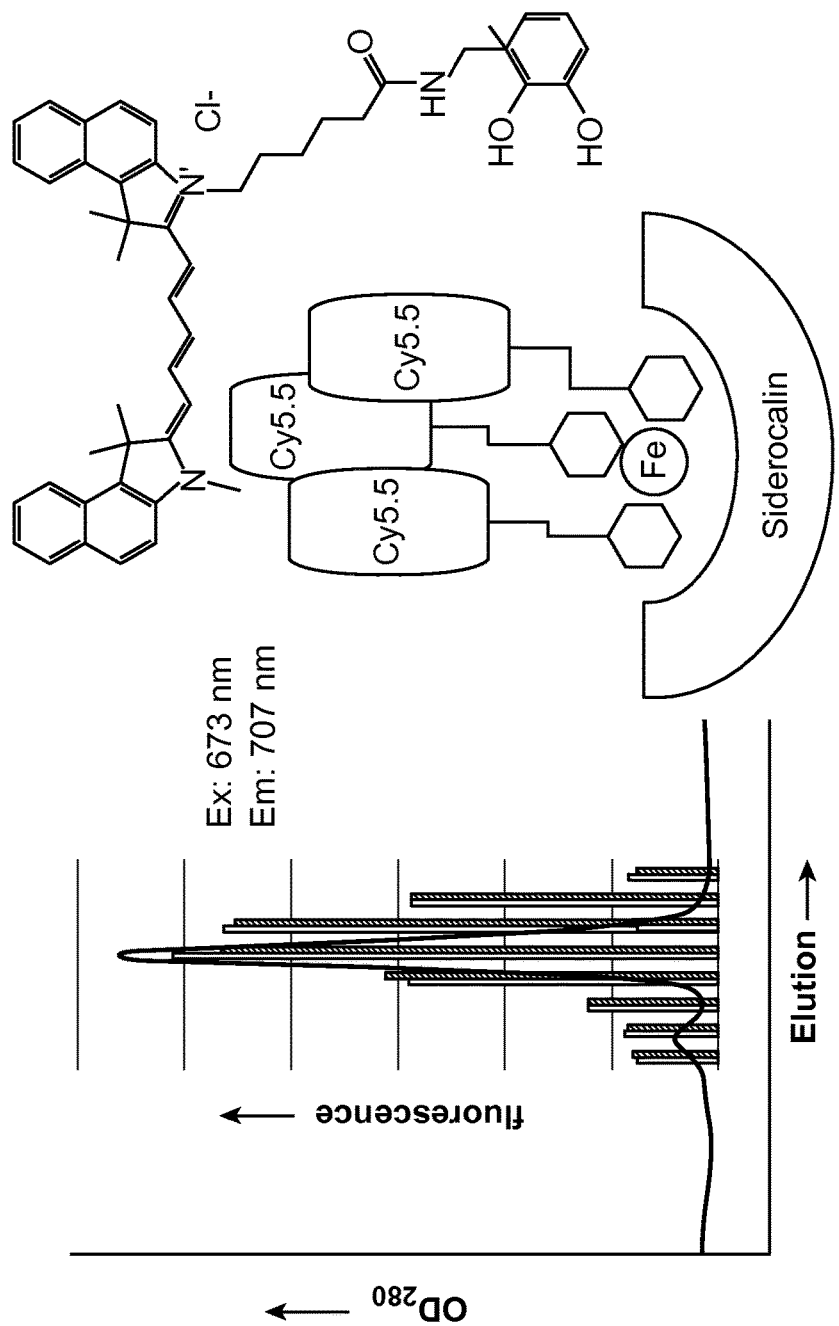
FIG. 26 depicts a captured fluorescent siderophore. The left frame depicts a size-exclusion purification of the protein siderophore complex. The right frame is a schematic.

Siderocalin can be used according to the present disclosure for construction of a Scn-peptide fusion, which can be secreted and cleaved for the efficient production of excreted peptides. FIG. 24 depicts the crystal structure of Scn with a Th ligand.

Figure 14:
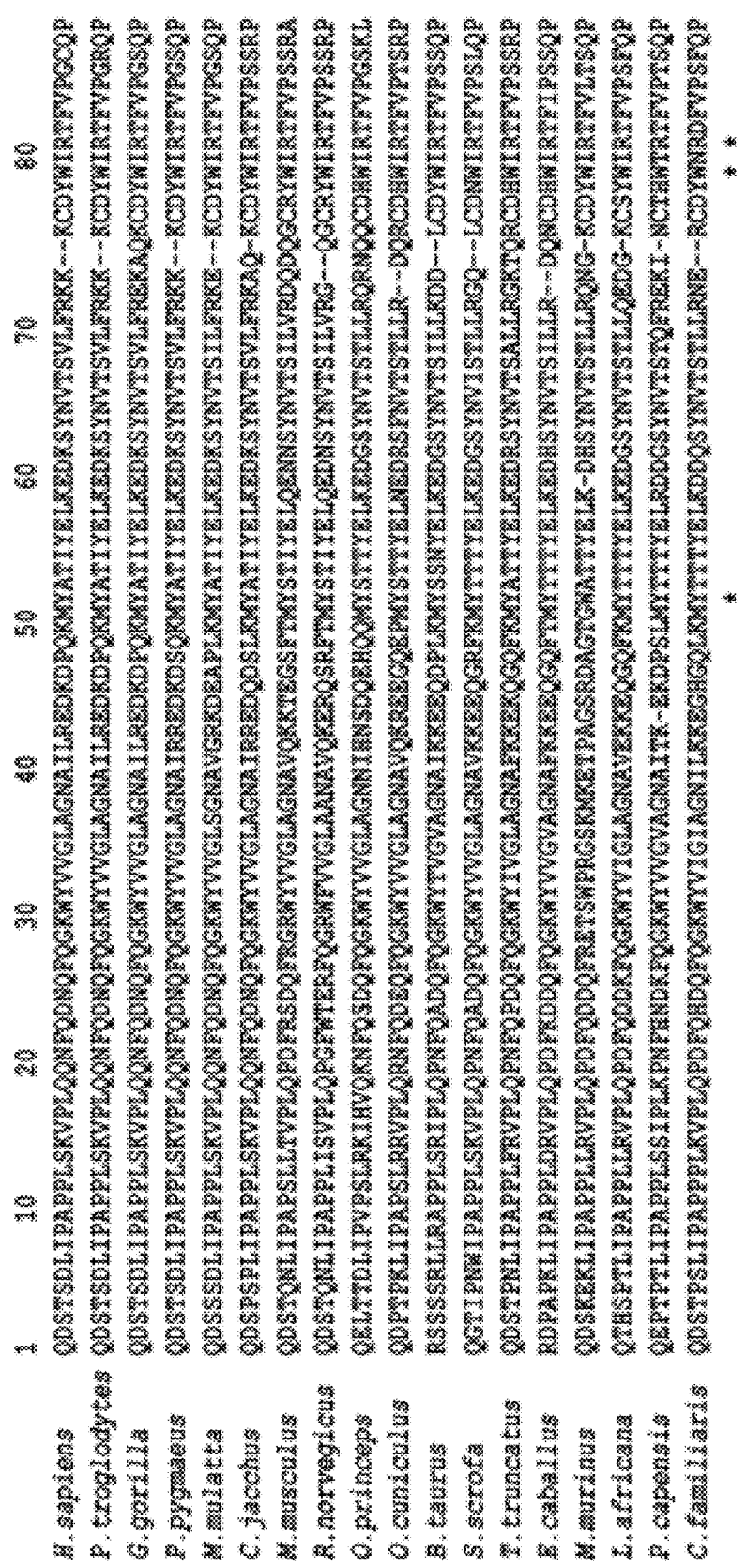
FIG. 14 shows the alignment of Scn sequences (SEQ ID NOs: 157-174) from 18 species. The alignment shows a high level of sequence conservation between the 18 species with recognizable orthologs. Positions with an asterisk are possible sites for ligand binding. Correnti, C. & Strong, R. K. (2013) 'Iron sequestration in immunity' In *Metals in Cells; Encyclopedia of Inorganic and Bioinorganic Chemistry.* (Culotta, V. & Scott, R. A., eds.) John Wiley & Sons, pp. 349-59

FIG. 14 shows the alignment of Scn sequences (SEQ ID NOs: 157-174) from 18 species. The alignment shows a high level of sequence conservation between the 18 species with recognizable orthologs. Positions with an asterisk are possible sites for ligand binding.

Figure 15:
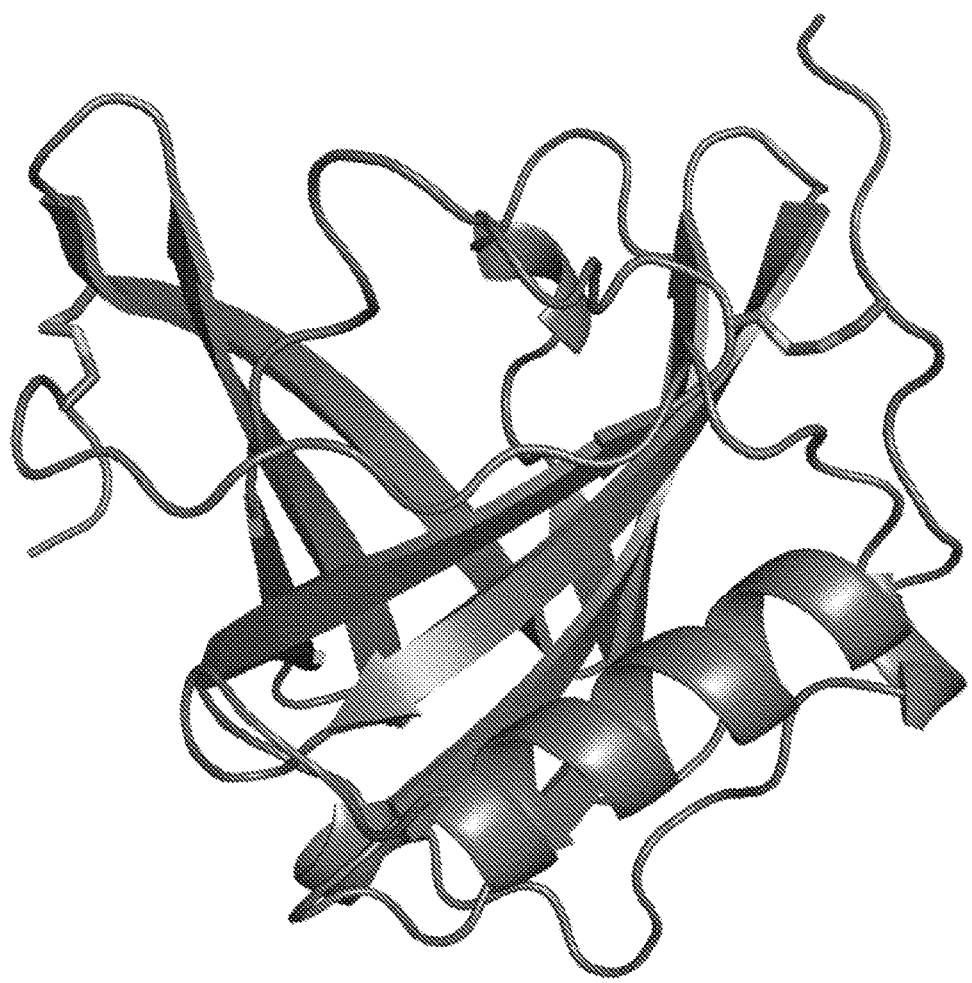
FIG. 15 depicts a 3D model of super-stable Scn in accordance with an aspect of the present disclosure. In this form of Scn, a second disulfide bond was engineered in order to secure the N-terminus and increase thermal stability.

FIG. 15 depicts a 3D model of super-stable Scn in accordance with an aspect of the present disclosure. In this form of Scn, a second disulfide bond was engineered in order to secure the N-terminus and increase thermal stability.

Figure 10:
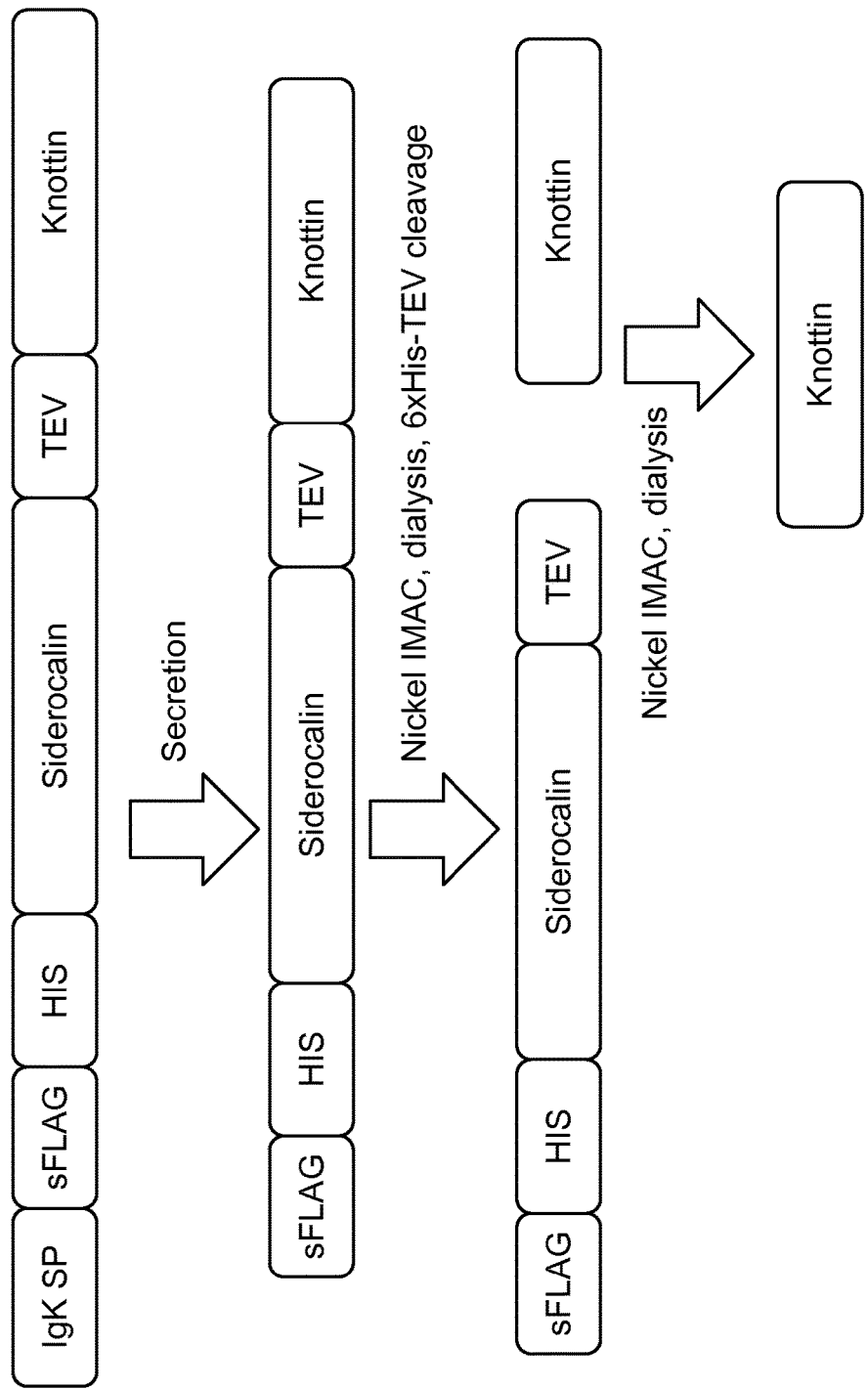
FIG. 10 shows a generalized process for manufacturing knottins, in accordance with an aspect of the present disclosure.
Figure 11:
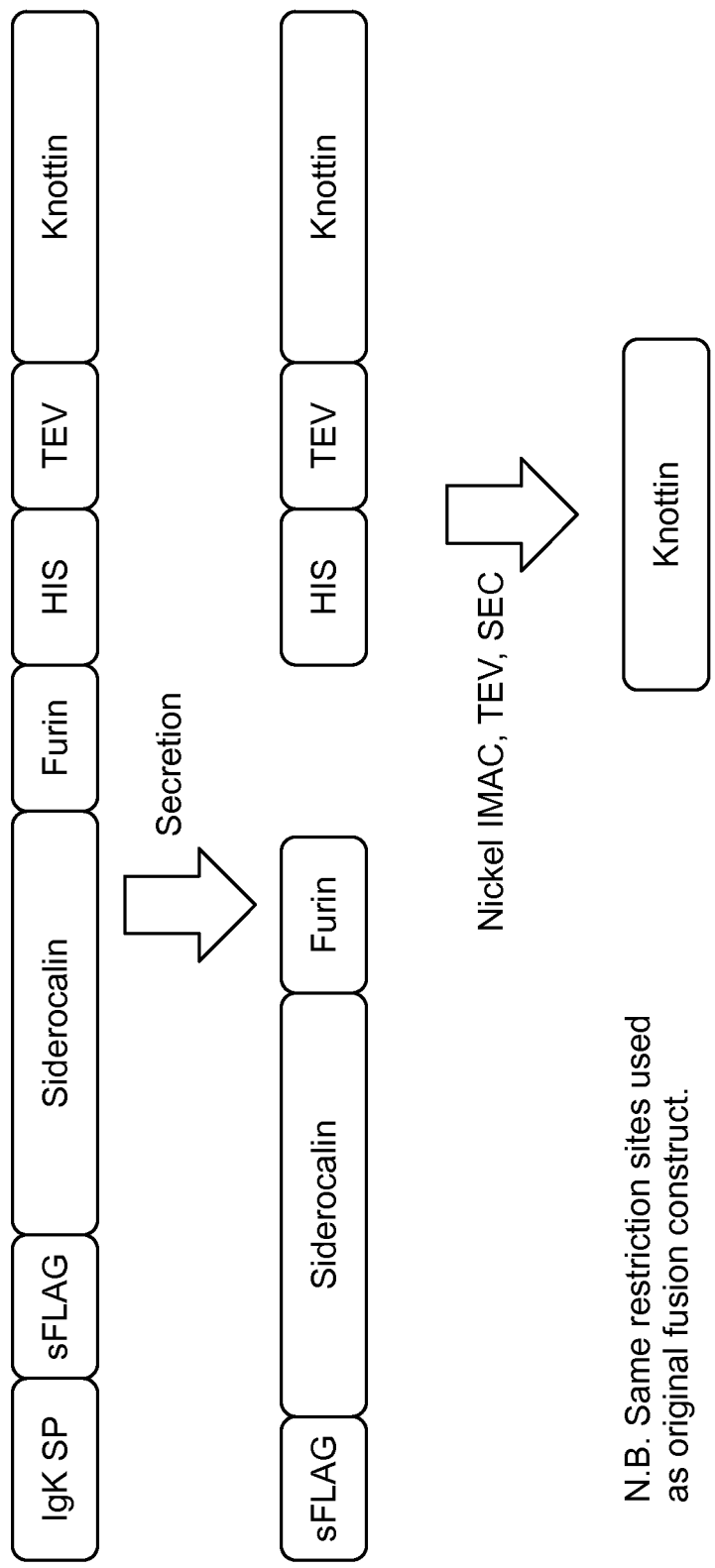
FIG. 11 shows a generalized process for manufacturing knottins, in accordance with an aspect of the present disclosure.
Figure 12:
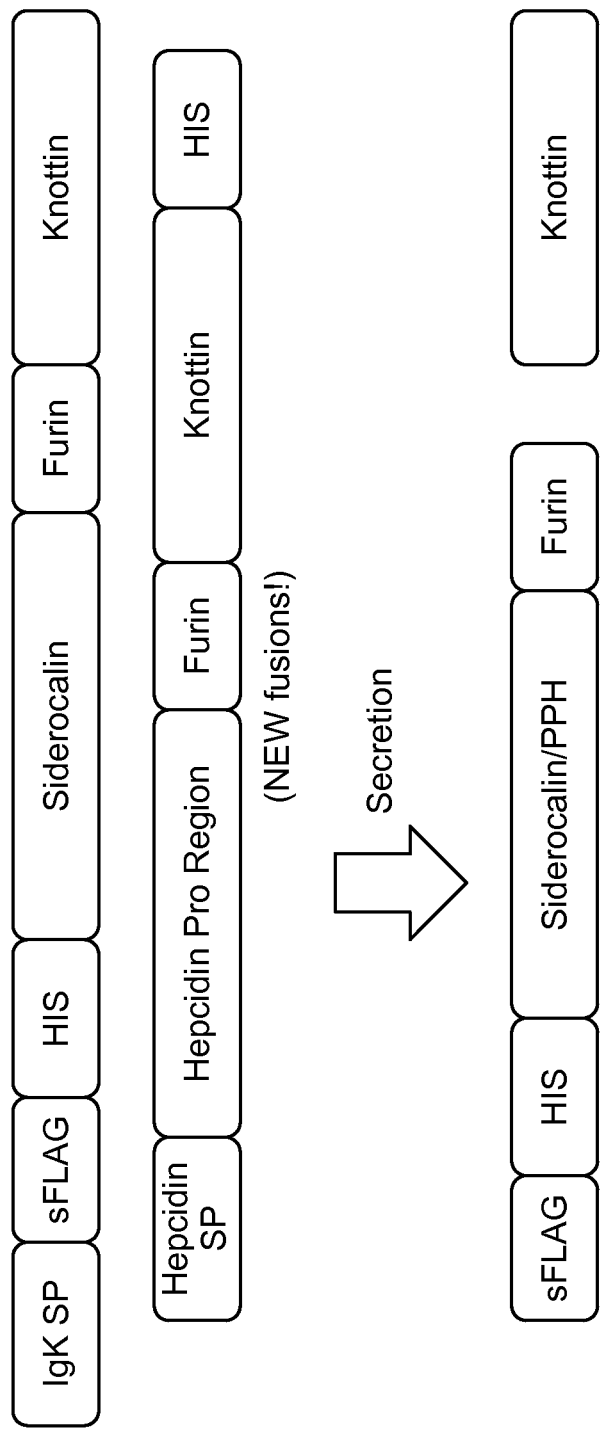
FIG. 12 a generalized process for manufacturing knottins, in accordance with an aspect of the present disclosure. According to this aspect, cleavage occurs at the furin-knottin interface.

FIGS. 10-12 depict various manufacturing methods according to the present disclosure, which enable the efficient production of knottin peptides. FIG. 10 depicts the elements of the siderocalin fusion protein and use thereof for the production of knottin peptides. In this example, the knottin is secreted as a fusion protein to the siderocalin. The IgK signal peptide is derived from the mouse Light Chain IgG. The sFLAG is the short FLAG (DYKDE, SEQ ID NO: 91) for enhanced cleavage of the signal peptide relative to the long FLAG signal peptide. The His is a histidine tag (HHHHHH, SEQ ID NO: 93) and TEV is the tobacco etch virus protease site (ENLYFQ, SEQ ID NO: 95). According to this method, and as depicted in FIG. 12, the fusion protein is secreted, followed by cleavage and isolation. IgK SP is Murine IgK light chain signal peptide, sFLAG: Shortened FLAG epitope, HIS: 6× histidine (SEQ ID NO: 93) tag, TEV: Tobacco Etch Virus Protease recognition site and Furin-furin cleavage site with BamHI site.

FIG. 10 depicts the elements of the siderocalin fusion protein and the use thereof for the production of knottin peptides. In this example, the knottin is secreted as a fusion protein to HIS-tagged siderocalin. The HIS tag is six histidines (HHHHHH, SEQ ID NO: 93) that will reversibly bind nickel and is therefore a useful purification tag for Immobilized Metal Chromatography (IMAC). Following isolation of the fusion protein by IMAC, the fusion is cleaved with TEV protease and the cleaved siderocalin removed by another round of IMAC, leaving pure knottin.

FIG. 11 depicts the elements of the siderocalin fusion protein and use thereof for the production of knottin peptides. This method includes the secretion of a siderocalin fusion with concomitant, intracellular cleavage at the Furin-His junction and purification by IMAC. The HIS tag can then be removed from the knottin with TEV protease. The secretion method depicted in FIG. 11 utilizes the same restriction sites as the method depicted in FIG. 10.

FIG. 12 depicts the elements of a system for the secretion of cleaved knottin peptides. The siderocalin in this case is present during translation but is cleaved off by intracellular furin during protein. The secretion method depicted in FIG. 12 utilizes the same restriction sites as the method depicted in FIG. 10.

Figure 16:
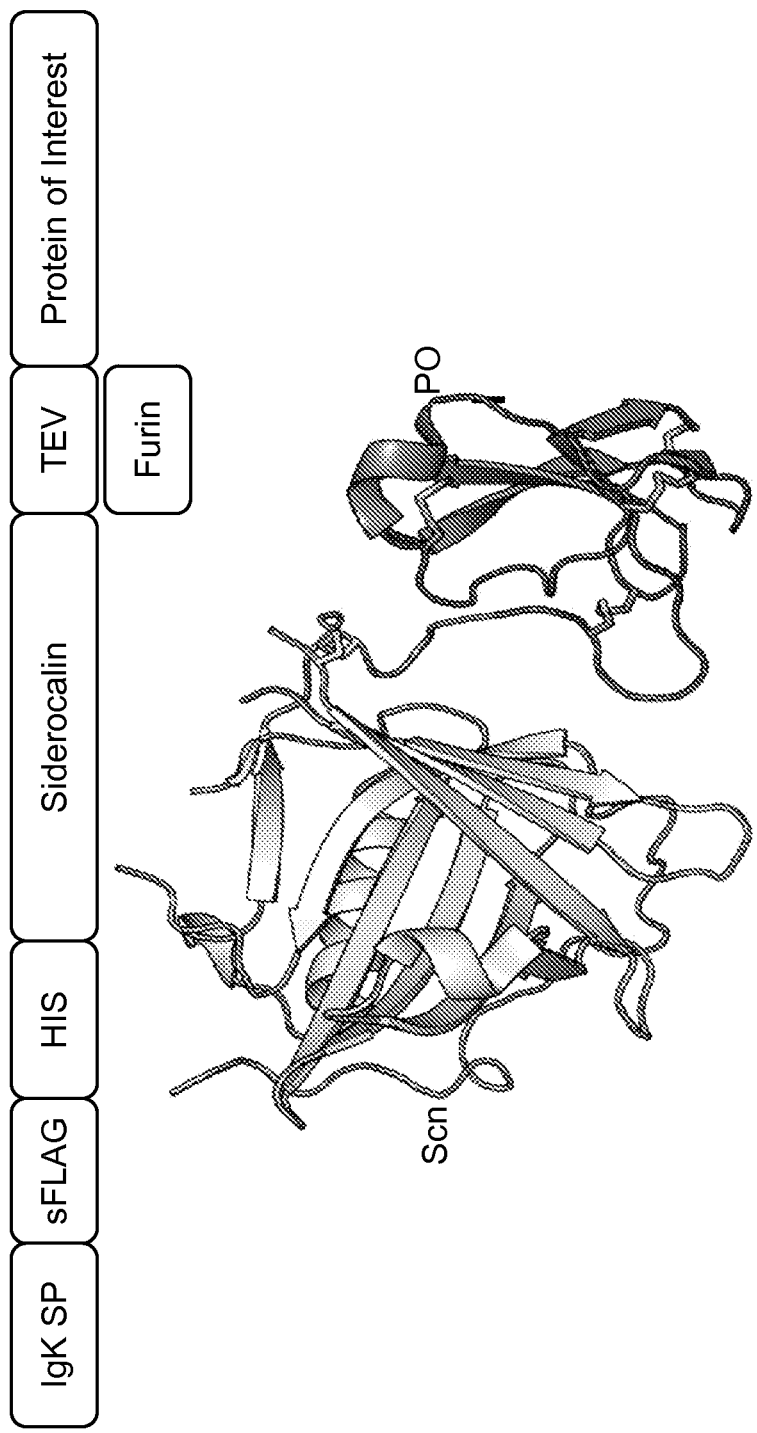
FIG. 16 shows a schematic of a generic Scn fusion that can be used in various aspects of the present disclosure. The native signal peptide was removed and an exogenous sFLAG and HIS tag were added to facilitate purification. These modifications are optionally present in various aspects of the disclosure.

FIG. 16 shows a schematic of a generic Scn fusion that can be used in various aspects of the present disclosure. The native signal peptide was removed and an exogenous sFLAG and HIS tag were added to facilitate purification. These modifications are optionally present in various aspects of the disclosure.

Figure 13:
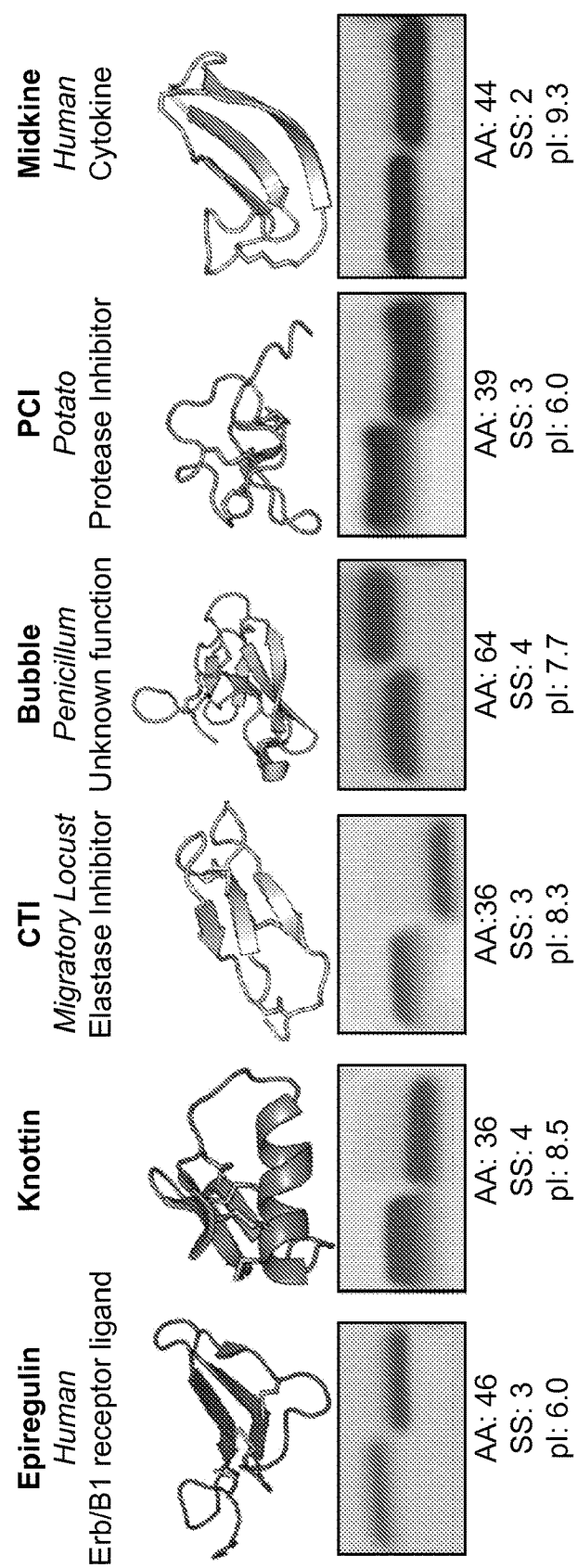
FIG. 13 shows examples of knottins made with the Daedalus system and corresponding SDS PAGE analyses in accordance with an aspect of the present disclosure. The Daedalus system is described in Bandaranayake A. D., et al., *Nucleic Acids Res.* (2011) 39(21):e143.

FIG. 13 depicts exemplary knottins made using the Daedalus system and the corresponding SDS PAGE analyses in accordance with an aspect of the present disclosure. The Dadalus system is described in Bandaranayake A. D., et al., *Nucleic Acids Res.* (2011) 39(21):e143. SDS PAGE analyses were performed under reducing (left) and non-reducing (right) conditions. As shown in FIG. 13, a number of challenging peptides can be produced according to the presently described methods.

Figure 17:
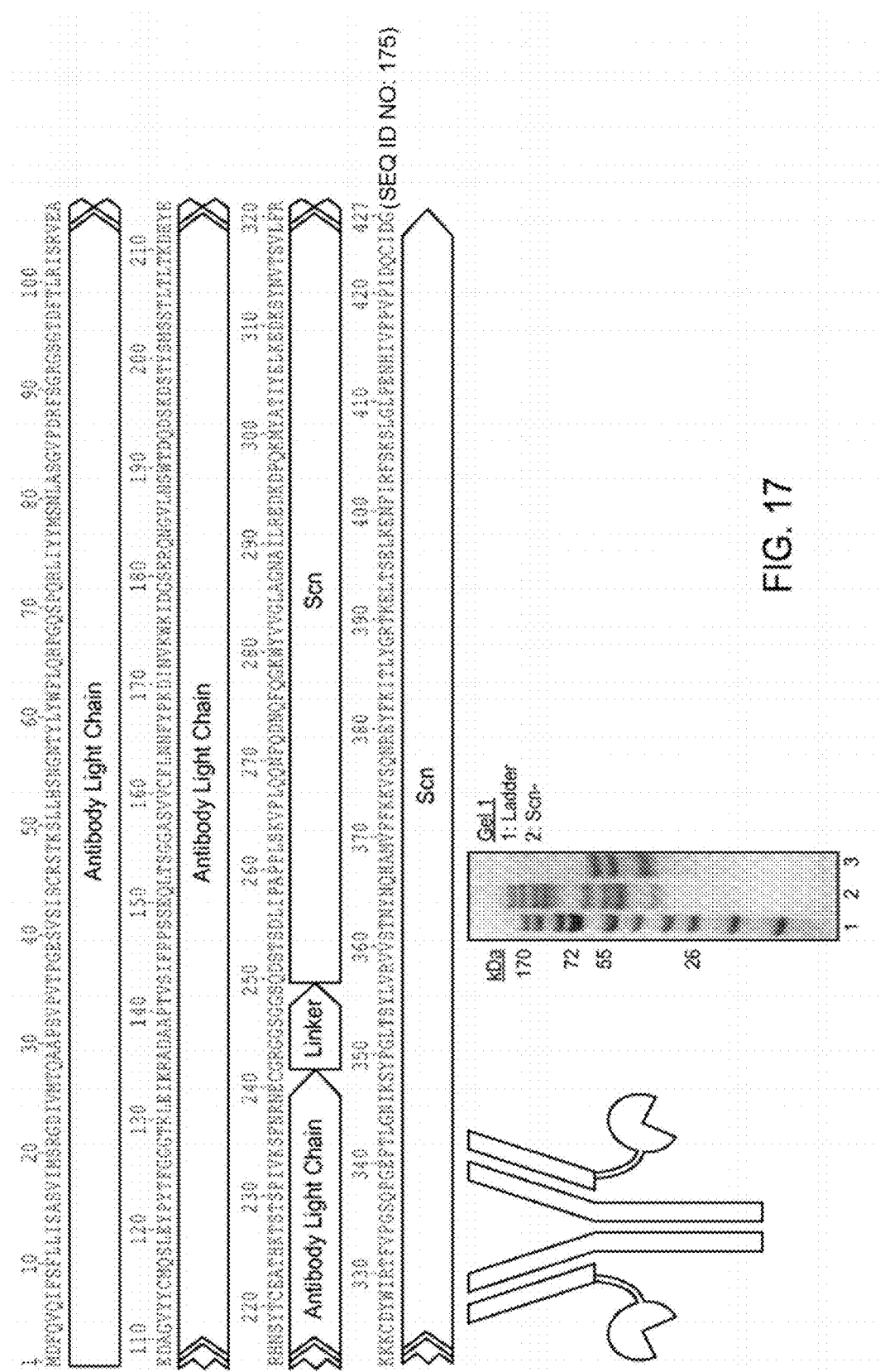
FIG. 17 depicts a schematic of a light chain antibody fusion with Scn (SEQ ID NO: 175) and corresponding SDS PAGE analysis according to an aspect of the present disclosure.

FIG. 17 depicts a schematic of a light chain antibody fusion with Scn (SEQ ID NO: 175) and a corresponding SDS PAGE analysis according to an aspect of the present disclosure. The Scn fusion enables the generation of Fab fragments that have an increased molecular weight (~75 kDa) and improved serum half-life. The addition of the Scn moiety also enables the delivery of an exogenous ligand through the Scn ligand binding site. Also depicted is the SDS PAGE analysis under non-reducing and reducing conditions of a construct according to one aspect of the present disclosure.

Figure 18:
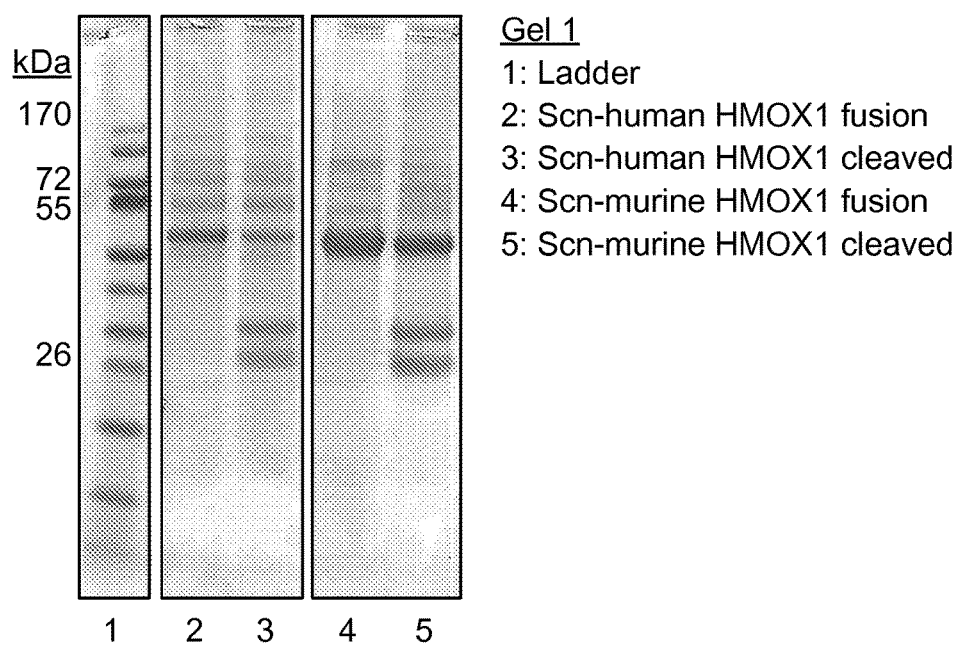
FIG. 18 shows the SDS PAGE analysis comparing the expression of a Scn fusion with a cytoplasmic enzyme, HMOX1, both before and after cleavage according to an aspect of the present disclosure.

FIG. 18 shows the SDS PAGE analysis comparing the expression of a Scn fusion with a cytoplasmic enzyme, HMOX1, both before and after cleavage according to an aspect of the present disclosure. By cleaving the fusion protein as shown in FIG. 18, it is demonstrated that the HMOX1 protein is stable even after separation from Scn. This result further suggests that, using the presently described methods, it is possible to express enzymes in a mammalian cell culture system where they are secreted out of the cell.

Figure 19:
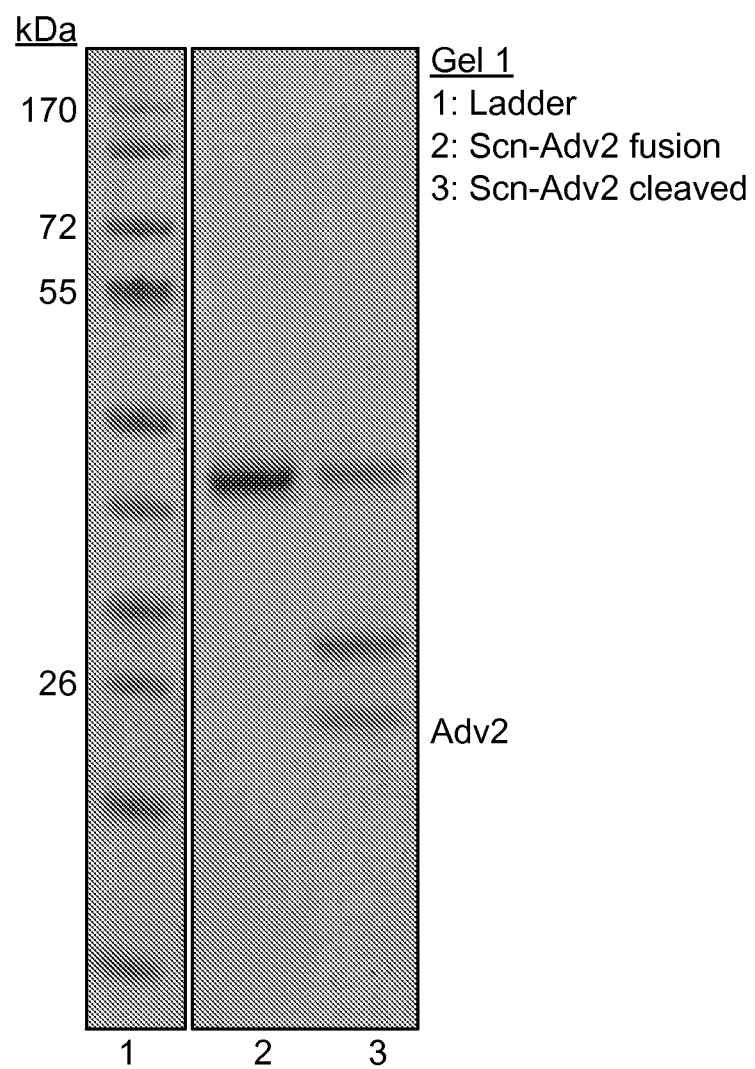
FIG. 19 depicts the expression of a Scn fusion with a cytoplasmic viral protein Adv2 and the corresponding SDS PAGE analysis according to one aspect of the present disclosure.

FIG. 19 depicts the expression of a Scn fusion with a cytoplasmic viral protein Adv2 and the corresponding SDS PAGE analysis according to one aspect of the present disclosure. By cleaving the fusion protein as shown in FIG. 19, it is demonstrated that the Adv2 protein is stable even after separation from Scn. This result further suggests that, using the presently described methods, it is possible to express difficult viral proteins in a mammalian cell culture system where they are secreted out of the cell. Additionally this fusion protein has further utility because it can be used to raise antibodies against the viral antigen in rats, mice or rabbits using the corresponding Scn ortholog.

Figure 20:
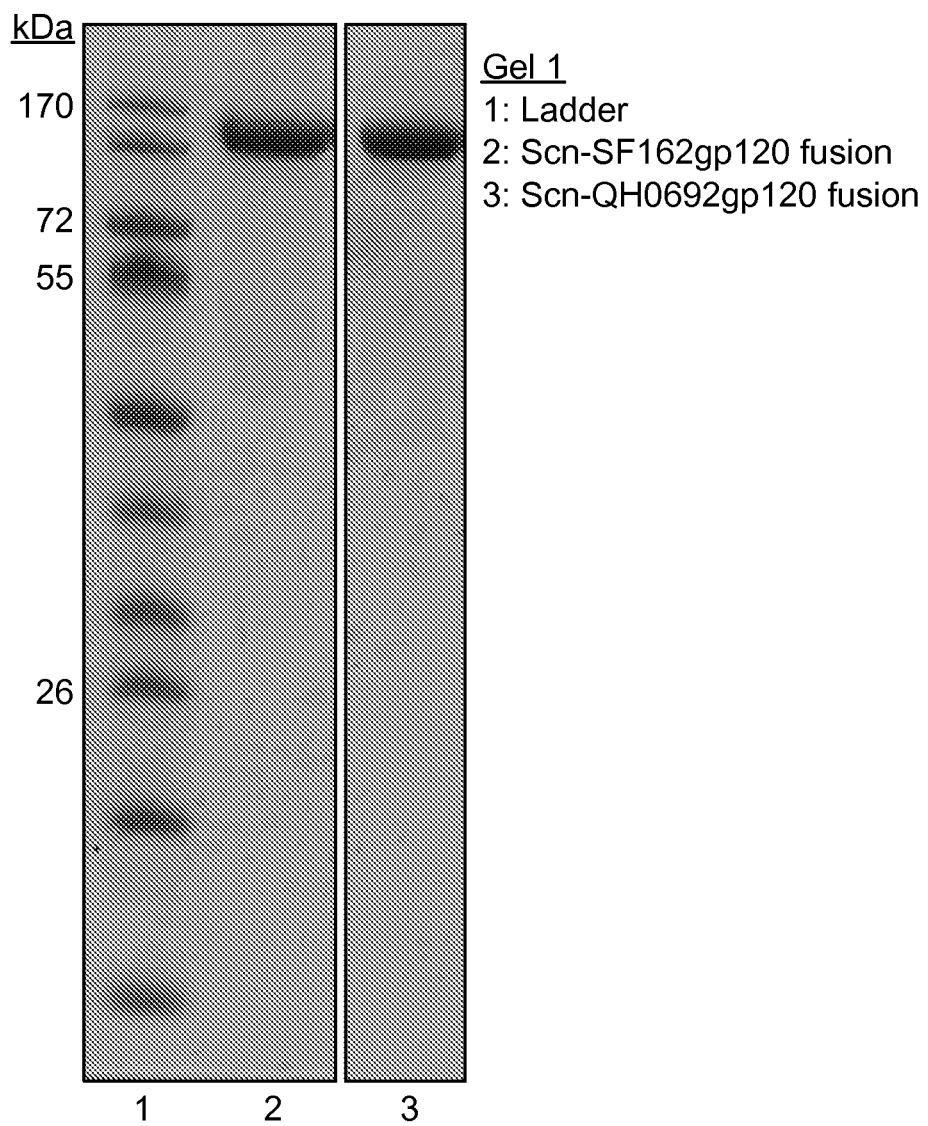
FIG. 20 depicts the expression of a Scn fusion with an extracellular viral glycoprotein HIV gp120 and the corresponding SDS PAGE analysis according to one aspect of the present disclosure.

FIG. 20 depicts the expression of a Scn fusion with an extracellular viral glycoprotein HIV gp120 and the corresponding SDS PAGE analysis according to one aspect of the present disclosure. The results in FIG. 20 demonstrate that stabilized glycoproteins can be expressed according to one aspect of the present disclosure. Additionally this fusion protein has further utility because it can be used to raise antibodies against the viral antigen in rats, mice or rabbits using the corresponding Scn ortholog.

FIG. 21 depicts the expression of a Scn fusion with a knottin protein, Imperatoxin, and the corresponding SDS PAGE analysis according to one aspect of the present disclosure. The results in FIG. 21 show that the knottin protein, Imperatoxin, is stable even after separation from Scn. These results show that knottins can be expressed in a mammalian cell culture system where they are secreted out of the cell according to an aspect of the present disclosure. Although knottins are known to be incredibly difficult to secrete in a properly folded state, the results of FIG. 21 demonstrate that it is possible to do so using the presently described methods. Additionally, this fusion protein has further utility because it can be used to raise antibodies against the viral antigen in rats, mice or rabbits using the corresponding Scn ortholog.

Figure 22:
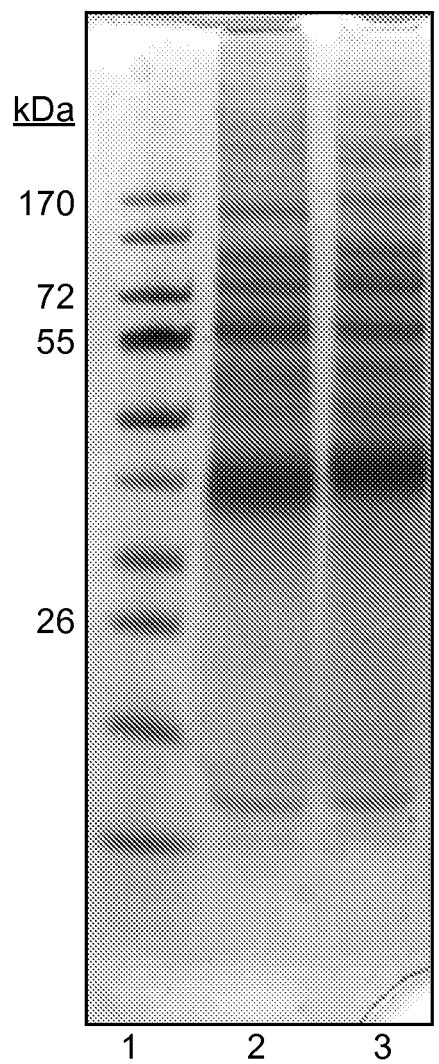
FIG. 22 depicts the expression of a Scn fusion with a small subdomain (i.e., Kringle domain) of the extracellular tyrosine kinase receptor ROR1 and corresponding SDS PAGE analysis according to one aspect of the present disclosure.

FIG. 22 depicts the expression of a Scn fusion with a small subdomain (i.e., Kringle domain) of the extracellular tyrosine kinase receptor ROR1 and corresponding SDS PAGE analysis according to one aspect of the present disclosure. The results in FIG. 22 show that the Kringle domain failed to express when alone, while it was successfully expressed as part of a Scn fusion. These results show that the Kringle domain of the extracellular tyrosine kinase receptor ROR1 can be efficiently prepared according to one aspect of the present disclosure. Additionally, this fusion protein has further utility because it can be used to raise antibodies against the viral antigen in rats, mice or rabbits using the corresponding Scn ortholog.

Figure 23:
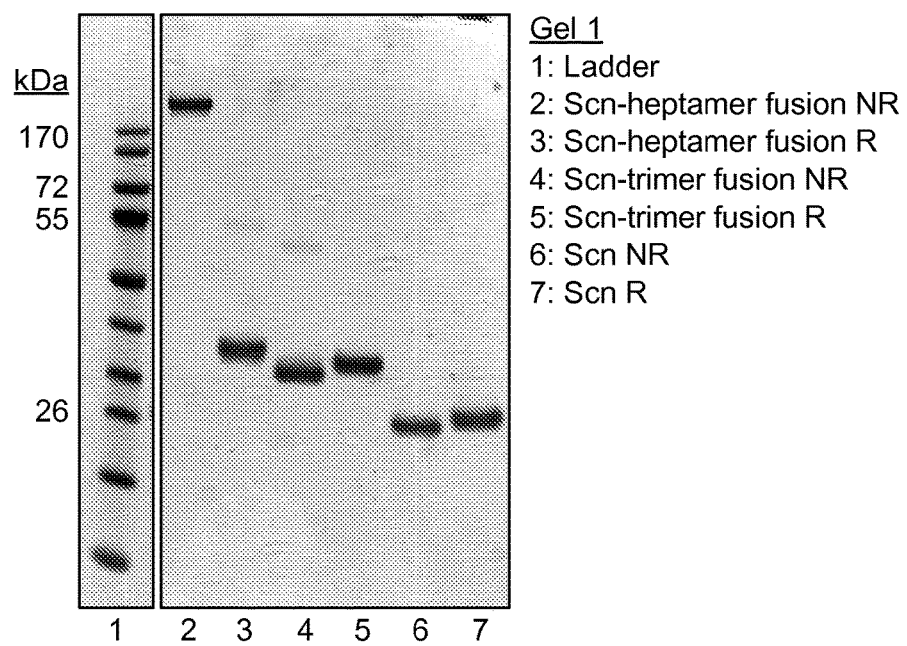
FIG. 23 depicts the expression of a Scn fusion with heptameric and trimeric subdomains and corresponding SDS PAGE analysis according to one aspect of the present disclosure.

FIG. 23 depicts the expression of a Scn fusion with heptameric and trimeric subdomains and corresponding SDS PAGE analysis according to one aspect of the present disclosure. As demonstrated in FIG. 23, the presently described methods enable the expression of multimeric protein constructs in a mammalian cell culture system, where the proteins are secreted out of the cell.

FIG. 24 depicts the expression of an ExFABP fusion with a knottin and corresponding SDS PAGE analysis according to one aspect of the present disclosure. ExFABP is another functional Scn. According to the present disclosure, this construct can be used in a periplasmic bacterial system to secrete a variety of client proteins.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

SEQUENCES

The following are DNA and/or amino acid sequences of genes of interest and constructs identified herein.

Construction of Parental Construct for Seamless Cloning:

IgK-SF-H6-GGS-lcn2C-GGS-ENLYFQ-GG-<u>PARENTAL</u>
for Xho/Bam cut from pUC57 and ligation into pCVL
SEQ ID NO: 1
GACTGAGTCGCCCGCTCGAGACCATGGAGACAGACACACTCCTGCTATGG

GTACTGCTGCTCTGGGTTCCAGGTTCCACTGGTGACTACAAGGACGAGCA

TCACCATCATCACCATGGTGGAAGCCAGGACTCCACCTCAGACCTGATCC

CAGCCCCACCTCTGAGCAAGGTCCCTCTGCAGCAGAACTTCCAGGACAAC

CAATTCCAGGGGAAGTGGTATGTGGTAGGCCTGGCAGGGAATGCAATTCT

CAGAGAAGACAAAGACCCGCAAAAGATGTATGCCACCATCTATGAGCTGA

AAGAAGACAAGAGCTACAATGTCACCTCCGTCCTGTTTAGGAAAAAGAAG

TGTGACTACTGGATCAGGACTTTTGTTCCAGGTTGCCAGCCCGGCGAGTT

CACGCTGGGCAACATTAAGAGTTACCCTGGATTAACGAGTTACCTCGTCC

GAGTGGTGAGCACCAACTACAACCAGCATGCTATGGTGTTCTTCAAGAAA

GTTTCTCAAAACAGGGAGTACTTCAAGATCACCCTCTACGGGAGAACCAA

GGAGCTGACTTCGGAACTAAAGGAGAACTTCATCCGCTTCTCCAAATCTC

TGGGCCTCCCTGAAAACCACATCGTCTTCCCTGTCCCAATCGACCAGTGT

ATCGACGGCGGAGGTAGCGAAAACCTGTATTTTCAGGGAGGCGGCCGCTA

AGGATCCCGGACCGCCTCTCC

NotI cut is AACCTGTATTTTCAGGGAGGC -
GCTAAGGATCCCGGACCGCCTCTCC
Fusion protein Sequences - original set of 10 -
cloned into NotI cut parent above by seamless
cloning:
IgK-SF-H6-GGS-lcn2C-GGS-ENLYFQ-GG-<u>BubbleProtein</u>
SEQ ID NO: 2
GACTGAGTCGCCCGCTCGAGACCATGGAGACAGACACACTCCTGCTATGG

GTACTGCTGCTCTGGGTTCCAGGTTCCACTGGTGACTACAAGGACGAGCA

TCACCATCATCACCATGGTGGAAGCCAGGACTCCACCTCAGACCTGATCC

CAGCCCCACCTCTGAGCAAGGTCCCTCTGCAGCAGAACTTCCAGGACAAC

CAATTCCAGGGGAAGTGGTATGTGGTAGGCCTGGCAGGGAATGCAATTCT

CAGAGAAGACAAAGACCCGCAAAAGATGTATGCCACCATCTATGAGCTGA

AAGAAGACAAGAGCTACAATGTCACCTCCGTCCTGTTTAGGAAAAAGAAG

TGTGACTACTGGATCAGGACTTTTGTTCCAGGTTGCCAGCCCGGCGAGTT

CACGCTGGGCAACATTAAGAGTTACCCTGGATTAACGAGTTACCTCGTCC

GAGTGGTGAGCACCAACTACAACCAGCATGCTATGGTGTTCTTCAAGAAA

GTTTCTCAAAA CAGGGAGTACTTCAAGATCACCCTCTACGGGAGAACCAA

AGGAGCTGACTTCGGAACTAAAGGAGAACTTCATCCGCTTCTCCAAATCT

CTGGGCCTCCCTGAAAACCACATCGTCTTCCCTGTCCCAATCGACCAGTG

TATCGACGGCGGAGGTAGCGAAAACCTGTATTTTCAGGGA<u>GGCGATACCT</u>

<u>GCGGCAGCGGCTATAATGTGGATCAGCGTCGTACCAATAGCGGCTGCAAA</u>

<u>GCGGGCAATGGCGATCGTCATTTTTGCGGCTGCGATCGTACCGGCGTGGT</u>

<u>GGAATGCAAAGGCGGCAAATGGACCGAAGTGCAGGATTGCGGCAGCAGCA</u>

<u>GCTGCAAAGGCACCAGCAATGGCGGCGCGACCTGCT</u>AATGCTAAGGATCC

CGGA

SEQ ID NO: 3
atggagacagacacactcctgctatgggtactgctgctctgggttccagg
M  E  T  D  T  L  L  L  W  V  L  L  L  W  V  P  G ttccactggtgactacaaggacgagcatcaccatcatcaccatggtggaa
S  T  G  D  Y  K  D  E  H  H  H  H  H  H  G  G gccaggactccacctcagacctgatcccagccccacctctgagcaaggtc
S  Q  D  S  T  S  D  L  I  P  A  P  P  L  S  K  V cctctgcagcagaacttccaggacaaccaattccaggggaagtggtatgt
D  N  Q  P  L  Q  Q  N  F  Q  F  Q  G  K  W  Y  V ggtaggcctggcagggaatgcaattctcagagaagacaaagacccgcaaa
V  G  L  A  G  N  A  I  L  R  E  D  K  D  P  Q agatgtatgccaccatctatgagctgaaagaagacaagagctacaatgtc
K  M  Y  A  T  I  Y  E  L  K  E  D  K  S  Y  N  V acctccgtcctgtttaggaaaaagaagtgtgactactggatcaggacttt
T  S  V  L  F  R  K  K  K  C  D  Y  W  I  R  T  F tgttccaggttgccagcccggcgagttcacgctgggcaacattaagagtt
V  P  G  C  Q  P  G  E  F  T  L  G  N  I  K  S accctggattaacgagttacctcgtccgagtggtgagcaccaactacaac
Y  P  G  L  T  S  Y  L  V  R  V  V  S  T  N  Y  N cagcatgctatggtgttcttcaagaaagtttctcaaaacagggagtactt
Q  H  A  M  V  F  F  K  K  V  S  Q  N  R  E  Y  F caagatcaccctctacggggagaaccaaggagctgacttcggaactaaagg
K  I  T  L  Y  G  R  T  K  E  L  T  S  E  L  K agaacttcatccgcttctccaaatctctgggcctccctgaaaaccacatc
E  N  F  I  R  F  S  K  S  L  G  L  P  E  N  H  I gtcttccctgtcccaatcgaccagtgtatcgacggcggaggtagcgaaaa
V  F  P  V  P  I  D  Q  C  I  D  G  G  G  S  E  N cctgtattttcagggaggcgatacctgcggcagcggctataatgtggatc
L  Y  F  Q  G  G  D  T  C  G  S  G  Y  N  V  D agcgtcgtaccaatagcggctgcaaagcgggcaatggcgatcgtcatttt
Q  R  R  T  N  S  G  C  K  A  G  N  G  D  R  H  F tgcggctgcgatcgtaccggcgtggtggaatgcaaaggcggcaaatggac
C  G  C  D  R  T  G  V  V  E  C  K  G  G  K  W  T cgaagtgcaggattgcggcagcagcagctgcaaaggcaccagcaatggcg
E  V  Q  D  C  G  S  S  S  C  K  G  T  S  N  G gcgcgacctgc
G  A  T  C IgK-SF-H6-GGS-lcn2C-GGS-ENLYFQ-GG-<u>Attractin</u>
SEQ ID NO: 4
GACTGAGTCGCCCGCTCGAGACCATGGAGACAGACACACTCCTGCTATGG

GTACTGCTGCTCTGGGTTCCAGGTTCCACTGGTGACTACAAGGACGAGCA

TCACCATCATCACCATGGTGGAAGCCAGGACTCCACCTCAGACCTGATCC

CAGCCCCACCTCTGAGCAAGGTCCCTCTGCAGCAGAACTTCCAGGACAAC

CAATTCCAGGGGAAGTGGTATGTGGTAGGCCTGGCAGGGAATGCAATTCT

CAGAGAAGACAAAGACCCGCAAAAGATGTATGCCACCATCTATGAGCTGA

AAGAAGACAAGAGCTACAATGTCACCTCCGTCCTGTTTAGGAAAAAGAAG

TGTGACTACTGGATCAGGACTTTTGTTCCAGGTTGCCAGCCCGGCGAGTT

CACGCTGGGCAACATTAAGAGTTACCCTGGATTAACGAGTTACCTCGTCC

GAGTGGTGAGCACCAACTACAACCAGCATGCTATGGTGTTCTTCAAGAAA

GTTTCTCAAAACAGGGAGTACTTCAAGATCACCCTCTACGGGAGAACCAA

GGAGCTGACTTCGGAACTAAAGGAGAACTTCATCCGCTTCTCCAAATCTC

-continued

TGGGCCTCCCTGAAAACCACATCGTCTTCCCTGTCCCAATCGACCAGTGT

ATCGACGGCGGAGGTAGCGAAAACCTGTATTTTCAGGGAGGCGATCAGAA

TTGCGATATTGGCAATATTACCAGCCAGTGCCAGATGCAGCATAAAAATT

GCGAAGATGCGAATGGCTGCGATACCATTATTGAAGAATGCAAAACCAGC

ATGGTGGAACGTTGCCAGAATCAGGAATTTGAAAGCGCGGCGGGCAGCAC

CACCCTGGGCCCGCAGTAATGCTAAGGATCCCGGA

SEQ ID NO: 5 atggagacagacacactcctgctatgggtactgctgctctgggttccagg
M E T D T L L L W V L L L W V P G ttccactggtgactacaaggacgagcatcaccatcatcaccatggtggaa
S T G D Y L D E H H H H H H G G gccaggactccacctcagacctgatcccagccccacctctgagcaaggtc
S Q D S T S D L I P A P P L S K V cctctgcagcagaacttccaggacaaccaattccaggggaagtggtatgt
P L Q Q N F Q D N Q F Q G K W Y V ggtaggcctggcagggaatgcaattctcagagaagacaaagacccgcaaa
V G L A G N A I L R E D K D P Q agatgtatgccaccatctatgagctgaaagaagacaagagctacaatgtc
K M Y A T I Y E L K E D K S Y N V acctccgtcctgtttaggaaaaagaagtgtgactactggatcaggacttt
T S V L F R K K K C D Y W I R T F tgttccaggttgccagcccggcgagttcacgctgggcaacattaagagtt
V P G C Q P G E F T L G N I K S accctggattaacgagttacctcgtccgagtggtgagcaccaactacaac
Y P G L T S Y L V R V V S T N Y N cagcatgctatggtgttcttcaagaaagtttctcaaaacagggagtactt
Q H A M V F F K K V S Q N R E Y F caagatcaccctctacgggagaaccaaggagctgacttcggaactaaagg
K I T L Y G R T K E L T S E L K E agaacttcatccgcttctccaaatctctgggcctccctgaaaaccacatc
N F I R F S K S L G L P E N H I gtcttccctgtcccaatcgaccagtgtatcgacggcggaggtagcgaaaa
V F P V P I D Q C I D G G G S E N cctgtattttcagggaggcgatcagaattgcgatattggcaatattacca
L Y F Q G G D Q N C D I G N I T gccagtgccagatgcagcataaaaattgcgaagatgcgaatggctgcgat
S Q C Q M Q H K N C E D A N G C D accattattgaagaatgcaaaaccagcatggtggaacgttgccagaatca
T I I E E C K T S M V E R C Q N Q ggaatttgaaagcgcggcgggcagcaccaccctgggcccgcag
E F E S A A G S T T L G P Q IgK-SF-H6-GGS-lcn2C-GGS-ENLYFQ-GG-Hefutoxin

SEQ ID NO: 6

GACTGAGTCGCCCGCTCGAGACCATGGAGACAGACACACTCCTGCTATGG

GTACTGCTGCTCTGGGTTCCAGGTTCCACTGGTGACTACAAGGACGAGCA

TCACCATCATCACCATGGTGGAAGCCAGGACTCCACCTCAGACCTGATCC

CAGCCCCACCTCTGAGCAAGGTCCCTCTGCAGCAGAACTTCCAGGACAAC

CAATTCCAGGGGAAGTGGTATGTGGTAGGCCTGGCAGGGAATGCAATTCT

CAGAGAAGACAAAGACCCGCAAAAGATGTATGCCACCATCTATGAGCTGA

AAGAAGACAAGAGCTACAATGTCACCTCCGTCCTGTTTAGGAAAAAGAAG

TGTGACTACTGGATCAGGACTTTTGTTCCAGGTTGCCAGCCCGGCGAGTT

-continued

CACGCTGGGCAACATTAAGAGTTACCCTGGATTAACGAGTTACCTCGTCC

GAGTGGTGAGCACCAACTACAACCAGCATGCTATGGTGTTCTTCAAGAAA

GTTTCTCAAAACAGGGAGTACTTCAAGATCACCCTCTACGGGAGAACCAA

GGAGCTGACTTCGGAACTAAAGGAGAACTTCATCCGCTTCTCCAAATCTC

TGGGCCTCCCTGAAAACCACATCGTCTTCCCTGTCCCAATCGACCAGTGT

ATCGACGGCGGAGGTAGCGAAAACCTGTATTTTCAGGGAGGCGGCCATGC

GTGCTATCGTAATTGCTGGCGTGAAGGCAATGATGAAGAAACCTGCAAAG

AACGTTGCTAATGCTAAGGATCCCGGACCGCC

SEQ ID NO: 7 atggagacagacacactcctgctatgggtactgctgctctgggttccagg
M E T D T L L L W V L L L W V P G ttccactggtgactacaaggacgagcatcaccatcatcaccatggtggaa
S T G D Y K D E H H H H H H G G gccaggactccacctcagacctgatcccagccccacctctgagcaaggtc
S Q D S T S D L I P A P P L S K V cctctgcagcagaacttccaggacaaccaattccaggggaagtggtatgt
P L Q Q N F Q D N Q F Q G K W Y V ggtaggcctggcagggaatgcaattctcagagaagacaaagacccgcaaa
V G L A G N A I L R E D K D P Q agatgtatgccaccatctatgagctgaaagaagacaagagctacaatgtc
K M Y A T I Y E L K E D K S Y N V acctccgtcctgtttaggaaaaagaagtgtgactactggatcaggacttt
T S V L F R K K K C D Y W I R T F tgttccaggttgccagcccggcgagttcacgctgggcaacattaagagtt
V P G C Q P G E F T L G N I K S accctggattaacgagttacctcgtccgagtggtgagcaccaactacaac
Y P G L T S Y L V R V V S T N Y N cagcatgctatggtgttcttcaagaaagtttctcaaaacagggagtactt
Q H A M V F F K K V S Q N R E Y F caagatcaccctctacgggagaaccaaggagctgacttcggaactaaagg
K I T L Y G R T K E L T S E L K agaacttcatccgcttctccaaatctctgggcctccctgaaaaccacatc
E N F I R F S K S L G L P E N H I gtcttccctgtcccaatcgaccagtgtatcgacggcggaggtagcgaaaa
V F P V P I D Q C I D G G G S E N cctgtattttcagggaggcggccatgcgtgctatcgtaattgctggcgtg
L Y F Q G G G H A C Y R N C W R aaggcaatgatgaagaaacctgcaaagaacgttgc
E G N D E E T C K E R C IgK-SF-H6-GGS-lcn2C-GGS-ENLYFQ-GG-Hanatoxin

SEQ ID NO: 8

GACTGAGTCGCCCGCTCGAGACCATGGAGACAGACACACTCCTGCTATGG

GTACTGCTGCTCTGGGTTCCAGGTTCCACTGGTGACTACAAGGACGAGCA

TCACCATCATCACCATGGTGGAAGCCAGGACTCCACCTCAGACCTGATCC

CAGCCCCACCTCTGAGCAAGGTCCCTCTGCAGCAGAACTTCCAGGACAAC

CAATTCCAGGGGAAGTGGTATGTGGTAGGCCTGGCAGGGAATGCAATTCT

CAGAGAAGACAAAGACCCGCAAAAGATGTATGCCACCATCTATGAGCTGA

AAGAAGACAAGAGCTACAATGTCACCTCCGTCCTGTTTAGGAAAAAGAAG

TGTGACTACTGGATCAGGACTTTTGTTCCAGGTTGCCAGCCCGGCGAGTT

```
                                           -continued
CACGCTGGGCAACATTAAGAGTTACCCTGGATTAACGAGTTACCTCGTCC

GAGTGGTGAGCACCAACTACAACCAGCATGCTATGGTGTTCTTCAAGAAA

GTTTCTCAAAACAGGGAGTACTTCAAGATCACCCTCTACGGGAGAACCAA

GGAGCTGACTTCGGAACTAAAGGAGAACTTCATCCGCTTCTCCAAATCTC

TGGGCCTCCCTGAAAACCACATCGTCTTCCCTGTCCCAATCGACCAGTGT

ATCGACGGCGGAGGTAGCGAAAACCTGTATTTTCAGGGAGGCGAATGCCG

TTATCTGTTTGGCGGCTGCAAAACCACCAGCGATTGCTGCAAACATCTGG

GCTGCAAATTTCGTGATAAATATTGCGCGTGGGATTTTACCTTTAGCTAA

TGCTAAGGATCCCGGA
                                              SEQ ID NO: 9
atggagacagacacactcctgctatgggtactgctgctctgggttccagg
 M  E  D  T  L  L  L  W  V  L  L  L  W  V  P  G ttccactggtgactacaaggacgagcatcaccatcatcaccatggtggaa
  S  T  G  D  Y  K  D  E  H  H  H  H  H  H  G  G gccaggactccacctcagacctgatcccagccccacctctgagcaaggtc
 S  Q  D  S  T  S  D  L  I  P  A  P  P  L  S  K  V cctctgcagcagaacttccaggacaaccaattccaggggaagtggtatgt
 P  L  Q  Q  N  F  Q  D  N  Q  F  Q  G  K  W  Y  V ggtaggcctggcagggaatgcaattctcagagaagacaaagacccgcaaa
  V  G  L  A  G  N  A  I  L  R  E  D  K  D  P  Q agatgtatgccaccatctatgagctgaaagaagacaagagctacaatgtc
 K  M  Y  A  T  I  Y  E  L  K  E  D  K  S  Y  N  V acctccgtcctgtttaggaaaaagaagtgtgactactggatcaggactt t
 T  S  V  L  F  R  K  K  K  C  D  Y  W  I  R  T  F tgttccaggt tgccagcccggcgagttcacgctgggcaacattaagagt
 V  P  G  C  Q  P  G  E  F  T  L  G  N  I  K  S taccctggattaacgagttacctcgtccgagtggtgagcaccaactacaa
  Y  P  G  L  T  S  Y  L  V  R  V  V  S  T  N  Y  N ccagcatgctatggtgttcttcaagaaagtttctcaaaacagggagtact
 Q  H  A  M  V  F  F  K  K  V  S  Q  N  R  E  Y  F tcaagatcaccctctacgggagaaccaaggagctgacttcggaactaaag
  K  I  T  L  Y  G  R  T  K  E  L  T  S  E  L  K gagaacttcatccgcttctccaaatctctgggcctccctgaaaaccacat
 E  N  F  I  R  F  S  K  S  L  G  L  P  E  N  H  I cgtcttccctgtcccaatcgaccagtgtatcgacggcggaggtagcgaaa
 V  F  P  V  P  I  D  Q  C  I  D  G  G  S  E  N acctgtattttcagggaggcgaatgccgttatctgtttggcggctgcaaa
  L  Y  F  Q  G  G  E  C  R  Y  L  F  G  G  C  K accaccagcgattgctgcaaacatctgggctgcaaatttcgtgataaata
 T  T  S  D  C  C  K  H  L  G  C  K  F  R  D  K  Y ttgcgcgtgggattttacctttagc
 C  A  W  D  F  T  F  S IgK-SF-H6-GGS-lcn2C-GGS-ENLYFQ-GG-
ChymotrypsinInhibitor
                                              SEQ ID NO: 10
GACTGAGTCGCCCGCTCGAGACCATGGAGACAGACACACTCCTGCTATGG

GTACTGCTGCTCTGGGTTCCAGGTTCCACTGGTGACTACAAGGACGAGCA

TCACCATCATCACCATGGTGGAAGCCAGGACTCCACCTCAGACCTGATCC

CAGCCCCACCTCTGAGCAAGGTCCCTCTGCAGCAGAACTTCCAGGACAAC

CAATTCCAGGGGAAGTGGTATGTGGTAGGCCTGGCAGGGAATGCAATTCT

CAGAGAAGACAAAGACCCGCAAAAGATGTATGCCACCATCTATGAGCTGA
```

```
                                           -continued
AAGAAGACAAGAGCTACAATGTCACCTCCGTCCTGTTTAGGAAAAAGAAG

TGTGACTACTGGATCAGGACTTTTGTTCCAGGTTGCCAGCCCGGCGAGTT

CACGCTGGGCAACATTAAGAGTTACCCTGGATTAACGAGTTACCTCGTCC

GAGTGGTGAGCACCAACTACAACCAGCATGCTATGGTGTTCTTCAAGAAA

GTTTCTCAAAACAGGGAGTACTTCAAGATCACCCTCTACGGGAGAACCAA

GGAGCTGACTTCGGAACTAAAGGAGAACTTCATCCGCTTCTCCAAATCTC

TGGGCCTCCCTGAAAACCACATCGTCTTCCCTGTCCCAATCGACCAGTGT

ATCGACGGCGGAGGTAGCGAAAACCTGTATTTTCAGGGAGGCGAAATTAG

CTGCGAACCGGGCAAAACCTTTAAAGATAAATGCAATACCTGCCGTTGCG

GCGCGGATGGCAAAAGCGCGGCGTGCACCCTGAAAGCGTGCCCGAATCAG

TAATGCTAAGGATCCCGGA
                                             SEQ ID NO: 11
atggagacagacacactcctgctatgggtactgctgctctgggttccagg
 M  E  D  T  L  L  L  W  V  L  L  L  W  V  P  G ttccactggtgactacaaggacgagcatcaccatcatcaccatggtggaa
  S  T  G  D  Y  K  D  E  H  H  H  H  H  H  G  G gccaggactccacctcagacctgatcccagccccacctctgagcaaggtc
 S  Q  D  S  T  S  D  L  I  P  A  P  P  L  S  K  V cctctgcagcagaacttccaggacaaccaattccaggggaagtggtatgt
 P  L  Q  Q  N  F  Q  D  N  Q  F  Q  G  K  W  Y  V ggtaggcctggcagggaatgcaattctcagagaagacaaagacccgcaaa
  V  G  L  A  G  N  A  I  L  R  E  D  K  D  P  Q agatgtatgccaccatctatgagctgaaagaagacaagagctacaatgtc
 K  M  Y  A  T  I  Y  E  L  K  E  D  K  S  Y  N  V acctccgtcctgtttaggaaaaagaagtgtgactactggatcaggacttt
 T  S  V  L  F  R  K  K  K  C  D  Y  W  I  R  T  F tgttccaggttgccagcccggcgagttcacgctgggcaacattaagagtt
 V  P  G  C  Q  P  G  E  F  T  L  G  N  I  K  S acccctggattaacgagttacctcgtccgagtggtgagcaccaactacaac
  Y  P  G  L  T  S  Y  L  V  R  V  V  S  T  N  Y  N cagcatgctatggtgttcttcaagaaagtttctcaaaacagggagtactt
 Q  H  A  M  V  F  F  K  K  V  S  Q  N  R  E  Y  F caagatcaccctctacgggagaaccaaggagctgacttcggaactaaagg
  K  I  T  L  Y  G  R  T  K  E  L  T  S  E  L  K agaacttcatccgcttctccaaatctctgggcctccctgaaaaccacatc
 E  N  F  I  R  F  S  K  S  L  G  L  P  E  N  H  I gtcttccctgtcccaatcgaccagtgtatcgacggcggaggtagcgaaaa
 V  F  P  V  P  I  D  Q  C  I  D  G  G  S  E  N cctgtattttcagggaggcgaaattagctgcgaaccgggcaaaaccttta
  L  Y  F  Q  G  G  E  I  S  C  E  P  G  K  I  F aagataaatgcaatacctgccgttgcggcgcggatggcaaaagcgcggcg
 K  D  K  C  N  T  C  R  C  G  A  D  G  K  S  A  A tgcaccctgaaagcgtgcccgaatcag
 C  T  L  K  A  C  P  N  Q IgK-SF-H6-GGS-lcn2C-GGS-ENLYFQ-GG-ToxinK
                                             SEQ ID NO: 12
GACTGAGTCGCCCGCTCGAGACCATGGAGACAGACACACTCCTGCTATGG

GTACTGCTGCTCTGGGTTCCAGGTTCCACTGGTGACTACAAGGACGAGCA

TCACCATCATCACCATGGTGGAAGCCAGGACTCCACCTCAGACCTGATCC

CAGCCCCACCTCTGAGCAAGGTCCCTCTGCAGCAGAACTTCCAGGACAAC
```

```
CAATTCCAGGGGAAGTGGTATGTGGTAGGCCTGGCAGGGAATGCAATTCT

CAGAGAAGACAAAGACCCGCAAAAGATGTATGCCACCATCTATGAGCTGA

AAGAAGACAAGAGCTACAATGTCACCTCCGTCCTGTTTAGGAAAAAGAAG

TGTGACTACTGGATCAGGACTTTTGTTCCAGGTTGCCAGCCCGGCGAGTT

CACGCTGGGAACATTAAGAGTTACCCTGGATTAACGAGTTACCTCGTCC

GAGTGGTGAGCACCAACTACAACCAGCATGCTATGGTGTTCTTCAAGAAA

GTTTCTCAAAACAGGGAGTACTTCAAGATCACCCTCTACGGGAGAACCAA

GGAGCTGACTTCGGAACTAAAGGAGAACTTCATCCGCTTCTCCAAATCTC

TGGGCCTCCCTGAAAACCACATCGTCTTCCCTGTCCCAATCGACCAGTGT

ATCGACGGCGGAGGTAGCGAAAACCTGTATTTTCAGGGAGGCGTGTGCCG
TGATTGGTTTAAAGAAACCGCGTGCCGTCATGCGAAAAGCCTGGGCAATT
GCCGTACCAGCCAGAAATATCGTGCGAATTGCGCGAAAACCTGCGAACTG
TGCTAATGCTAAGGATCCCGGA

SEQ ID NO: 13
atggagacagacacactcctgctatgggtactgctgctctgggttccagg
 M  E  T  D  T  L  L  L  W  V  L  L  L  W  V  P  G ttccactggtgactacaaggacgagcatcaccatcatccatggtggaa
 S  T  G  D  Y  K  D  E  H  H  H  H  H  G  G gccaggactccacctcagacctgatcccagccccacctctgagcaaggtc
 S  Q  D  S  T  S  D  L  I  P  A  P  P  L  S  K  V cctctgcagcagaacttccaggacaaccaattccaggggaagtggtatgt
 P  L  Q  Q  N  F  Q  D  N  Q  F  Q  G  K  W  Y  V ggtaggcctggcagggaatgcaattctcagagaagacaaagacccgcaaa
 V  G  L  A  G  N  A  I  L  R  E  D  K  D  P  Q agatgtatgccaccatctatgagctgaaagaagacaagagctacaatgtc
 K  M  Y  A  T  I  Y  E  L  K  E  D  K  S  Y  N  V acctccgtcctgtttaggaaaaagaagtgtgactactggatcaggacttt
 T  S  V  L  F  R  K  K  K  C  D  Y  W  I  R  T  F tgttccaggttgccagcccggcgagttcacgctgggaacattaagagtt
 V  P  G  C  Q  P  G  E  F  T  L  G  N  I  K  S accctggattaacgagttacctcgtccgagtggtgagcaccaactacaac
 Y  P  G  L  T  S  Y  L  V  R  V  V  S  T  N  Y  N cagcatgctatggtgttcttcaagaaagtttctcaaaacagggagtactt
 Q  H  A  M  V  F  F  K  K  V  S  Q  N  R  E  Y  F caagatcaccctctacgggagaaccaaggagctgacttcggaactaaagg
 K  I  T  L  Y  G  R  T  K  E  L  T  S  E  L  K agaacttcatccgcttctccaaatctctgggcctccctgaaaaccacatc
 E  N  F  I  R  F  S  K  S  L  G  L  P  E  N  H  I gtcttccctgtcccaatcgaccagtgtatcgacggcggaggtagcgaaaa
 V  F  P  V  P  I  D  Q  C  I  D  G  G  G  S  E  N cctgtattttcagggaggcgtgtgccgtgattggtttaaagaaaccgcgt
 L  Y  F  Q  G  G  V  C  R  D  W  F  K  E  T  A gccgtcatgcgaaaagcctgggcaattgccgtaccagccagaaatatcgt
 C  R  H  A  K  S  L  G  N  C  R  T  S  Q  K  Y  R gcgaattgcgcgaaaacctgcgaactgtgc
 A  N  C  A  K  T  C  E  L  C
```

IgK-SF-H6-GGS-lcn2C-GGS-ENLYFQ-GG-
EGFepiregulinCore
SEQ ID NO: 14

```
GACTGAGTCGCCCGCTCGAGACCATGGAGACAGACACACTCCTGCTATGG

GTACTGCTGCTCTGGGTTCCAGGTTCCACTGGTGACTACAAGGACGAGCA

TCACCATCATCACCATGGTGGAAGCCAGGACTCCACCTCAGACCTGATCC

CAGCCCCACCTCTGAGCAAGGTCCCTCTGCAGCAGAACTTCCAGGACAAC

CAATTCCAGGGGAAGTGGTATGTGGTAGGCCTGGCAGGGAATGCAATTCT

CAGAGAAGACAAAGACCCGCAAAAGATGTATGCCACCATCTATGAGCTGA

AAGAAGACAAGAGCTACAATGTCACCTCCGTCCTGTTTAGGAAAAAGAAG

TGTGACTACTGGATCAGGACTTTTGTTCCAGGTTGCCAGCCCGGCGAGTT

CACGCTGGGAACATTAAGAGTTACCCTGGATTAACGAGTTACCTCGTCC

GAGTGGTGAGCACCAACTACAACCAGCATGCTATGGTGTTCTTCAAGAAA

GTTTCTCAAAACAGGGAGTACTTCAAGATCACCCTCTACGGGAGAACCAA

GGAGCTGACTTCGGAACTAAAGGAGAACTTCATCCGCTTCTCCAAATCTC

TGGGCCTCCCTGAAAACCACATCGTCTTCCCTGTCCCAATCGACCAGTGT

ATCGACGGCGGAGGTAGCGAAAACCTGTATTTTCAGGGAGGCGTGAGCAT
TGTACCAAATGCAGCAGCGATATGAATGGCTATTGCCCATGGCCAGTGCA
TTTATCTGGTGGATATGAGCCAGAATTATTGCCGTTGCGAAGTGGGCTAT
ACCGGCGTGCGTTGCGAACATTTTTTTCTGTAATGCTAAGGATCCCGGA

SEQ ID NO: 15
atggagacagacacactcctgctatgggtactgctgctctgggttccagg
 K  E  T  D  T  L  L  L  W  V  L  L  L  W  V  P  G ttccactggtgactacaaggacgagcatcaccatcatccatggtggaa
 S  T  G  D  Y  K  D  E  H  H  H  H  H  G  G gccaggactccacctcagacctgatcccagccccacctctgagcaaggtc
 S  Q  D  S  T  S  D  L  I  P  A  P  P  L  S  K  V cctctgcagcagaacttccaggacaaccaattccaggggaagtggtatgt
 P  L  Q  Q  N  F  Q  D  X  Q  F  Q  G  K  W  Y  V ggtaggcctggcagggaatgcaattctcagagaagacaaagacccgcaaa
 V  G  L  A  G  N  A  I  L  R  E  D  K  D  P  Q agatgtatgccaccatctatgagctgaaagaagacaagagctacaatgtc
 K  M  Y  A  T  I  Y  Z  L  K  E  D  K  S  Y  N  V acctccgtcctgtttaggaaaaagaagtgtgactactggatcaggacttt
 T  S  V  L  F  R  K  K  K  C  D  Y  W  I  R  T  F tgttccaggttgccagcccggcgagttcacgctgggaacattaagagtt
 V  P  G  C  Q  P  G  E  F  T  L  G  N  I  K  S accctggattaacgagttacctcgtccgagtggtgagcaccaactacaac
 Y  P  G  L  T  S  Y  L  V  R  V  V  S  T  N  Y  N cagcatgctatggtgttcttcaagaaagtttctcaaaacagggagtactt
 Q  H  A  M  V  F  F  K  K  V  S  Q  N  R  E  Y  F caagatcaccctctacgggagaaccaaggagctgacttcggaactaaagg
 K  I  T  L  Y  G  R  T  K  E  L  T  S  E  L  K agaacttcatccgcttctccaaatctctgggcctccctgaaaaccacatc
 E  N  F  I  R  F  S  K  S  L  G  L  P  E  N  H  I gtcttccctgtcccaatcgaccagtgtatcgacggcggaggtagcgaaaa
 V  F  P  V  P  I  D  Q  C  I  D  G  G  G  S  E  N cctgtattttcagggaggcgtgagcattaccaaatgcagcagcgatatga
 L  Y  F  Q  G  G  V  S  I  T  K  C  S  S  D  M
```

```
                                  -continued
atggctattgcctgcatggccagtgcatttatctggtggatatgagccag
 N  G  Y  C  L  H  G  Q  C  I  Y  L  V  D  M  S  Q aattattgccgttgcgaagtgggctataccggcgtgcgttgcgaacattt
 N  Y  C  R  C  E  V  G  Y  T  G  V  R  C  E  H  F ttttctg
 F  L
```

IgK-SF-H6-GGS-lcn2C-GGS-ENLYFQ-GG-Circulin

SEQ ID NO: 16

```
GACTGAGTCGCCCGCTCGAGACCATGGAGACAGACACACTCCTGCTATGG
GTACTGCTGCTCTGGGTTCCAGGTTCCACTGGTGACTACAAGGACGAGCA
TCACCATCATCACCATGGTGGAAGCCAGGACTCCACCTCAGACCTGATCC
CAGCCCCACCTCTGAGCAAGGTCCCTCTGCAGCAGAACTTCCAGGACAAC
CAATTCCAGGGGAAGTGGTATGTGGTAGGCCTGGCAGGGAATGCAATTCT
CAGAGAAGACAAAGACCCGCAAAAGATGTATGCCACCATCTATGAGCTGA
AAGAAGACAAGAGCTACAATGTCACCTCCGTCCTGTTTAGGAAAAAGAAG
TGTGACTACTGGATCAGGACTTTTGTTCCAGGTTGCCAGCCCGGCGAGTT
CACGCTGGGCAACATTAAGAGTTACCCTGGATTAACGAGTTACCTCGTCC
GAGTGGTGAGCACCAACTACAACCAGCATGCTATGGTGTTCTTCAAGAAA
GTTTCTCAAAACAGGGAGTACTTCAAGATCACCCTCTACGGGAGAACCAA
GGAGCTGACTTCGGAACTAAAGGAGAACTTCATCCGCTTCTCCAAATCTC
TGGGCCTCCCTGAAAACCACATCGTCTTCCCTGTCCCAATCGACCAGTGT
ATCGACGGCGGAGGTAGCGAAAACCTGTATTTTCAGGGAGGCGGCATTCC
GTGCGGCGAAAGCTGCGTGTGGATTCCGTGCATTAGCGCGGCGCTGGGCT
GCAGCTGCAAAAATAAAGTGTGCTATCGTAATTAATGCTAAGGATCCCGG
A
```

SEQ ID NO: 17

```
atggagacagacacactcctgctatgggtactgctgctctgggttccagg
 M  E  T  D  T  L  L  L  W  V  L  L  L  W  V  P  G ttccactggtgactacaaggacgagcatcaccatcatcaccatggtggaa
 S  T  G  D  Y  K  D  E  H  H  H  H  H  H  G  G gccaggactccacctcagacctgatcccagcccccacctctgagcaaggtc
 S  Q  D  S  T  S  D  L  I  P  A  P  P  L  S  K  V cctctgcagcagaacttccaggacaaccaattccaggggaagtggtatgt
 P  L  Q  Q  N  F  Q  D  N  Q  F  Q  G  K  W  Y  V ggtaggcctggcagggaatgcaattctcagagaagacaaagacccgcaaa
 V  G  L  A  G  N  A  I  L  R  E  D  K  D  P  Q agatgtatgccaccatctatgagctgaaagaagacaagagctacaatgtc
 K  M  Y  A  T  I  Y  E  L  K  E  D  K  S  Y  N  V acctccgtcctgtttaggaaaaagaagtgtgactactggatcaggacttt
 T  S  V  L  F  R  K  K  K  C  D  Y  W  I  R  T  F tgttccaggttgccagcccggcgagttcacgctgggcaacattaagagtt
 V  P  G  C  Q  P  G  E  F  T  L  G  N  I  K  S accctggattaacgagttacctcgtccgagtggtgagcaccaactacaac
 Y  P  G  L  T  S  Y  L  V  R  V  V  S  T  N  Y  N cagcatgctatggtgttcttcaagaaagtttctcaaaacagggagtactt
 Q  H  A  M  V  F  F  K  K  V  S  Q  N  R  E  Y  F caagatcaccctctacgggagaaccaaggagctgacttcggaactaaagg
 K  I  T  L  Y  G  R  T  K  E  L  T  S  E  L  K agaacttcatccgcttctccaaatctctgggcctccctgaaaaccacatc
 E  N  F  I  R  F  S  K  S  L  G  L  P  E  N  H  I
```

-continued
```
gtcttccctgtcccaatcgaccagtgtatcgacggcggaggtagcgaaaa
 V  F  P  V  P  I  D  Q  C  I  D  G  G  G  S  E  N cctgtattttcagggaggcggcattccgtgcggcgaaagctgcgtgtgga
  L  Y  F  Q  G  G  G  I  P  C  G  E  S  C  V  W ttccgtgcattagcgcggcgctgggctgcagctgcaaaaataaagtgtgc
 I  P  C  I  S  A  A  L  G  C  S  C  K  N  K  V  C tatcgtaat
 Y  R  N
```

IgK-SF-H6-GGS-lcn2C-GGS-ENLYFQ-GG-Brazzein

SEQ ID NO: 18

```
GACTGAGTCGCCCGCTCGAGACCATGGAGACAGACACACTCCTGCTATGG
GTACTGCTGCTCTGGGTTCCAGGTTCCACTGGTGACTACAAGGACGAGCA
TCACCATCATCACCATGGTGGAAGCCAGGACTCCACCTCAGACCTGATCC
CAGCCCCACCTCTGAGCAAGGTCCCTCTGCAGCAGAACTTCCAGGACAAC
CAATTCCAGGGGAAGTGGTATGTGGTAGGCCTGGCAGGGAATGCAATTCT
CAGAGAAGACAAAGACCCGCAAAAGATGTATGCCACCATCTATGAGCTGA
AAGAAGACAAGAGCTACAATGTCACCTCCGTCCTGTTTAGGAAAAAGAAG
TGTGACTACTGGATCAGGACTTTTGTTCCAGGTTGCCAGCCCGGCGAGTT
CACGCTGGGCAACATTAAGAGTTACCCTGGATTAACGAGTTACCTCGTCC
GAGTGGTGAGCACCAACTACAACCAGCATGCTATGGTGTTCTTCAAGAAA
GTTTCTCAAAACAGGGAGTACTTCAAGATCACCCTCTACGGGAGAACCAA
GGAGCTGACTTCGGAACTAAAGGAGAACTTCATCCGCTTCTCCAAATCTC
TGGGCCTCCCTGAAAACCACATCGTCTTCCCTGTCCCAATCGACCAGTGT
ATCGACGGCGGAGGTAGCGAAAACCTGTATTTTCAGGGAGGCCAGGATAA
ATGCAAAAAAGTGTATGAAAATTATCCGGTGAGCAAATGCCAGCTGGCGA
ATCAGTGCAATTATGATTGCAAACTGGATAAACATGCGCGTAGCGGCGAA
TGCTTTTATGATGAAAAACGTAATCTGCAGTGCATTTGCGATTATTGCGA
ATATTAATGCTAAGGATCCCGGA
```

SEQ ID NO: 19

```
atggagacagacacactcctgctatgggtactgctgctctgggttccagg
 M  E  T  D  T  L  L  L  W  V  L  L  L  W  V  P  G ttccactggtgactacaaggacgagcatcaccatcatcaccatggtggaa
 S  T  G  D  Y  K  D  E  H  H  H  H  H  H  G  G gccaggactccacctcagacctgatcccagcccccacctctgagcaaggtc
 S  Q  D  S  T  S  D  L  I  P  A  P  P  L  S  K  V cctctgcagcagaacttccaggacaaccaattccaggggaagtggtatgt
 P  L  Q  Q  N  F  Q  D  N  Q  F  Q  G  K  W  Y  V ggtaggcctggcagggaatgcaattctcagagaagacaaagacccgcaaa
 V  G  L  A  G  N  A  I  L  R  E  D  K  D  P  Q agatgtatgccaccatctatgagctgaaagaagacaagagctacaatgtc
 K  M  Y  A  T  I  Y  E  L  K  E  D  K  S  Y  N  V acctccgtcctgtttaggaaaaagaagtgtgactactggatcaggacttt
 T  S  V  L  F  R  K  K  K  C  D  Y  W  I  R  T  F tgttccaggttgccagcccggcgagttcacgctgggcaacattaagagtt
 V  P  G  C  Q  P  G  E  F  T  L  G  N  I  K  S accctggattaacgagttacctcgtccgagtggtgagcaccaactacaac
 Y  P  G  L  T  S  L  V  R  V  V  S  T  N  Y  N cagcatgctatggtgttcttcaagaaagtttctcaaaacagggagtactt
 Q  H  A  M  V  F  F  K  K  V  S  Q  N  R  E  Y  F
```

```
caagatcaccctctacgggagaaccaaggagctgacttcggaactaaagg
 K  I  T  L  Y  G  R  T  K  E  L  T  S  E  L  K agaacttcatccgcttctccaaatctctgggcctccctgaaaaccacatc
 E  N  F  I  R  F  S  K  S  L  G  L  P  E  N  H  I gtcttccctgtcccaatcgaccagtgtatcgacggcggaggtagcgaaaa
 V  F  P  V  P  I  D  Q  C  I  D  G  G  S  E  N cctgtattttcagggaggccaggataaatgcaaaaagtgtatgaaaatt
 L  Y  F  Q  G  G  Q  D  K  C  K  K  V  Y  E  N atccggtgagcaaatgccagctggcgaatcagtgcaattatgattgcaaa
 Y  P  V  S  K  C  Q  L  A  N  Q  C  N  Y  D  C  K ctggataaacatgcgcgtagcggcgaatgcttttatgatgaaaaacgtaa
 L  D  K  H  A  R  S  G  E  C  F  Y  D  E  K  R  N tctgcagtgcatttgcgattattgcgaatat
 L  Q  C  I  C  D  Y  C  E  Y
```

SEQ ID NO: 20
```
atggagacagacacactcctgctatgggtactgctgctctgggttccagg
 M  E  T  D  T  L  L  L  W  V  L  L  L  W  V  P  G ttccactggtgactacaaggacgagcatcaccatcatcaccatggtggaa
 S  T  G  D  Y  K  D  E  H  H  H  H  H  H  G  G gccaggactccacctcagacctgatcccagccccacctctgagcaaggtc
 S  Q  D  S  T  S  D  L  I  P  A  P  P  L  S  K  V cctctgcagcagaacttccaggacaaccaattccaggggaagtggtatgt
 P  L  Q  Q  N  F  Q  D  N  Q  F  Q  G  K  W  Y  V ggtaggcctggcagggaatgcaattctcagagaagacaaagacccgcaaa
 V  G  L  A  G  N  A  I  L  R  E  D  K  D  P  Q agatgtatgccaccatctatgagctgaaagaagacaagagctacaatgtc
 K  M  Y  A  T  I  Y  E  L  K  E  D  K  S  Y  N  V acctccgtcctgtttaggaaaaagaagtgtgactactggatcaggacttt
 T  S  V  L  F  R  K  K  K  C  D  Y  W  I  R  T  F tgttccaggttgccagcccggcgagttcacgctgggcaacattaagagtt
 V  P  G  C  Q  P  G  E  F  T  L  G  N  I  K  S accctggattaacgagttacctcgtccgagtggtgagcaccaactacaac
 Y  P  G  L  T  S  Y  L  V  R  V  V  S  T  N  Y  N cagcatgctatggtgttcttcaagaaagtttctcaaaacagggagtactt
 Q  H  A  M  V  F  F  K  K  V  S  Q  N  R  E  Y  F caagatcaccctctacgggagaaccaaggagctgacttcggaactaaagg
 K  I  T  L  Y  G  R  T  K  E  L  T  S  E  L  K agaacttcatccgcttctccaaatctctgggcctccctgaaaaccacatc
 E  N  F  I  R  F  S  K  S  L  G  L  P  E  N  H  I gtcttccctgtcccaatcgaccagtgtatcgacggcggaggtagcgaaaa
 V  F  P  V  P  I  D  Q  C  I  D  G  G  S  E  N cctgtattttcagggaggcatgtgcatgccgtgctttaccaccgatcatc
 L  Y  F  Q  G  G  M  C  M  P  C  F  T  T  D  H agatggcgcgtaaatgcgatgattgctgcggcggcaaaggccgtggcaaa
 Q  M  A  R  K  C  D  D  C  C  G  G  K  G  R  G  K tgctatggcccgcagtgcctgtgccgt
 C  Y  G  P  Q  C  L  C  R
```

Construction of Parental Construct for BamH1/NotI Cloning:

IgK-SF-H6-GGS-lcn2C-GGS-ENLYFQ (SEQ ID NO: 95)-GS-PARENTAL

SEQ ID NO: 21
```
GACTGAGTCGCCCGCTCGAGACCATGGAGACAGACACACTCCTGCTATG

GGTACTGCTGCTCTGGGTTCCAGGTTCCACTGGTGACTACAAGGACGAG

CATCACCATCATCACCATGGTGGAAGCCAGGACTCCACCTCAGACCTGA

TCCCAGCCCCACCTCTGAGCAAGGTCCCTCTGCAGCAGAACTTCCAGGA

CAACCAATTCCAGGGGAAGTGGTATGTGGTAGGCCTGGCAGGGAATGCA

ATTCTCAGAGAAGACAAAGACCCGCAAAAGATGTATGCCACCATCTATG

AGCTGAAAGAAGACAAGAGCTACAATGTCACCTCCGTCCTGTTTAGGAA

AAAGAAGTGTGACTACTGGATCAGGACTTTTGTTCCAGGTTGCCAGCCC

GGCGAGTTCACGCTGGGCAACATTAAGAGTTACCCTGGATTAACGAGTT

ACCTCGTCCGAGTGGTGAGCACCAACTACAACCAGCATGCTATGGTGTT

CTTCAAGAAAGTTTCTCAAAACAGGGAGTACTTCAAGATCACCCTCTAC

GGGAGAACCAAGGAGCTGACTTCGGAACTAAAGGAGAACTTCATCCGCT

TCTCCAAATCTCTGGGCCTCCCTGAAAACCACATCGTCTTCCCTGTCCC

AATCGACCAGTGTATCGACGGCGGAGGTAGCGAAAACCTGTATTTTCAG

GGATCCTAATGTTGGCCATGATGTTAGGCGGCCGCTAAGGATCCCGGA
```

BamHI site: GGATCC
NotI site: GCGGCCGC

A BamHI site adds "GS" before a knottin. This construct can be used for cloning libraries.
Construction of parental construct for furin cleavage, BamHI/NotI cloning can include an idealized furin cut site is RARYKRS (SEQ ID NO: 116) -RARYKRGS (SEQ ID NO: 99) can be used for a Bam HI site.

IgK-SF-H6-GGS-lcn2C-GGS-furin-GS-PARENTAL

SEQ ID NO: 22
```
GACTGAGTCGCCCGCTCGAGACCATGGAGACAGACACACTCCTGCTATGGGTACTGCT-
GCTCTGGG

TTCCAGGTTCCACTGGTGACTACAAGGACGAGCATCACCATCATCACCATGGTGGAAGC-
CAGGACT

CCACCTCAGACCTGATCCCAGCCCCACCTCTGAGCAAGGTCCCTCTGCAGCAGAACTTC-
CAGGACA

ACCAATTCCAGGGGAAGTGGTATGTGGTAGGCCTGGCAGGGAATGCAATTCTCAGA-
GAAGACAAAG

ACCCGCAAAAGATGTATGCCACCATCTATGAGCTGAAAGAAGACAAGAGCTACAATGT-
CACCTCCG

TCCTGTTTAGGAAAAAGAAGTGTGACTACTGGATCAGGACTTTTGTTCCAGGTTGCCAGC-
CCGGCG
```

AGTTCACGCTGGGCAACATTAAGAGTTACCCTGGATTAACGAGTTACCTCGTCCGAGTG-
GTGAGCA

CCAACTACAACCAGCATGCTATGGTGTTCTTCAAGAAAGTTTCTCAAAACAGGGAGTACT-
TCAAGA

TCACCCTCTACGGGAGAACCAAGGAGCTGACTTCGGAACTAAAGGAGAACTTCATCCGCT-
TCTCCA

AATCTCTGGGCCTCCCTGAAAACCACATCGTCTTCCCTGTCCCAATCGACCAGTGTATC-
GACGGCG

GAGGTAGCcgcgcgcgctataaacgcGGATCCTAATGTTGGCCATGATGTTAG**GCGGC-
CGC**TAAGG

ATCCCGGA

IgK-SF-H6-GGS-lcn2C-GGS-ENLYFQ (SEQ ID NO: 95)-GS-MIDKINE

SEQ ID NO: 23

GACTGAGTCGCCCG*CTCGAG*ACCATGGAGACAGACACACTCCTGCTATGGGTACTGCT-
GCTCTGGG

TTCCAGGTTCCACTGGTGACTACAAGGACGAGCATCACCATCATCACCATGGTGGAAGC-
CAGGACT

CCACCTCAGACCTGATCCCAGCCCCACCTCTGAGCAAGGTCCCTCTGCAGCAGAACTTC-
CAGGACA

ACCAATTCCAGGGGAAGTGGTATGTGGTAGGCCTGGCAGGGAATGCAATTCTCAGA-
GAAGACAAAG

ACCCGCAAAAGATGTATGCCACCATCTATGAGCTGAAAGAAGACAAGAGCTACAATGT-
CACCTCCG

TCCTGTTTAGGAAAAAGAAGTGTGACTACTGGATCAGGACTTTTGTTCCAGGTTGCCAGC-
CCGGCG

AGTTCACGCTGGGCAACATTAAGAGTTACCCTGGATTAACGAGTTACCTCGTCCGAGTG-
GTGAGCA

CCAACTACAACCAGCATGCTATGGTGTTCTTCAAGAAAGTTTCTCAAAACAGGGAGTACT-
TCAAGA

TCACCCTCTACGGGAGAACCAAGGAGCTGACTTCGGAACTAAAGGAGAACTTCATCCGCT-
TCTCCA

AATCTCTGGGCCTCCCTGAAAACCACATCGTCTTCCCTGTCCCAATCGACCAGTGTATC-
GACGGCG

GAGGTAGCGAAAACCTGTATTTTCAGAGCGATTGCAAATATAAATTT-
GAAAACTGGGGCGCGTGCG

ATGGCGGCACCGGCACCAAAGTGCGCCAGGGCACCCTGAAAAAAGCGCGC-
TATAACGCGCAGTGCC

AGGAAACCATTCGCGTGACCAAACCGTGCTAATGCTGGATCCCGGACCGCCTCTCC

SEQ ID NO: 24 atggagacagacacactcctgctatgggtactgctgctctgggttccaggttccactggt gactacaaggacgagcatcaccatcatcaccatggtggaagccaggactccacctcagac ctgatcccagccccacctctgagcaaggtccctctgcagcagaacttccaggacaaccaa ttccaggggaagtggtatgtggtaggcctggcagggaatgcaattctcagagaagacaaa gacccgcaaaagatgtatgccaccatctatgagctgaaagaagacaagagctacaatgtc acctccgtcctgtttaggaaaaagaagtgtgactactggatcaggacttttgttccaggt tgccagcccggcgagttcacgctgggcaacattaagagttaccctggattaacgagttac ctcgtccgagtggtgagcaccaactacaaccagcatgctatggtgttcttcaagaaagtt tctcaaaacagggagtacttcaagatcaccctctacgggagaaccaaggagctgacttcg gaactaaaggagaacttcatccgcttctccaaatctctgggcctccctgaaaaccacatc gtcttccctgtcccaatcgaccagtgtatcgacggcggaggtagcgaaaacctgtatttt cagagcgattgcaaatataaatttgaaaactggggcgcgtgcgatggcggcaccggcacc -continued aaagtgcgccagggcaccctgaaaaaagcgcgctataacgcgcagtgccaggaaaccatt cgcgtgaccaaaccgtgc IgK-SF-H6-GGS-lcn2C-GGS-ENLYFQ (SEQ ID NO: 95)-GG-Violacin A

SEQ ID NO: 25

GACTGAGTCGCCCGCTCGAGACCATGGAGACAGACACACTCCTGCTATGGGTACTGCT-
GCTCTGGG

TTCCAGGTTCCACTGGTGACTACAAGGACGAGCATCACCATCATCACCATGGTGGAAGC-
CAGGACT

CCACCTCAGACCTGATCCCAGCCCCACCTCTGAGCAAGGTCCCTCTGCAGCAGAACTTC-
CAGGGCC

GACAACCAATTCCAGGGGAAGTGGTATGTGGTATGGCAGGGAATGCAATTCTCAGA-
GAAGACAAAG

ACCCGCAAAAGATGTATGCCACCATCTATGAGCTGAAAGAAGACAAGAGCTACAATGT-
CACCTCCG

TCCTGTTTAGGAAAAAGAAGTGTGACTACTGGATCAGGACTTTTGTTCCAGGTTGCCAGC-
CCGGCG

AGTTCACGCTGGGCAACATTAAGAGTTACCCTGGATTAACGAGTTACCTCGTCCGAGTG-
GTGAGCA

CCAACTACAACCAGCATGCTATGGTGTTCTTCAAGAAAGTTTCTCAAAACAGGGAGTACT-
TCAAGA

TCACCCTCTACGGGAGAACCAAGGAGCTGACTTCGGAACTAAAGGAGAACTTCATCCGCT-
TCTCCA

AATCTCTGGGCCTCCCTGAAAACCACATCGTCTTCCCTGTCCCAATCGACCAGTGTATC-
GACGGCG

GAGGTAGCGAAAACCTGTATTTTCAGGGAGGCAGCGCCATCAGCTGCGGCGAGACCTGCT-
TCAAGT

TCAAGTGCTACACCCCAGATGCAGCTGCAGCTACCCCGTGTGCAAGTAAGCTAAGGATC-
CCGGAC

CGCC

SEQ ID NO: 26 atggagacagacacactcctgctatgggtactgctgctctgggttccaggttccactggt gactacaaggacgagcatcaccatcatcaccatggtggaagccaggactccacctcagac ctgatcccagccccacctctgagcaaggtccctctgcagcagaacttccaggacaaccaa ttccaggggaagtggtatgtggtaggcctggcagggaatgcaattctcagagaagacaaa gacccgcaaaagatgtatgccaccatctatgagctgaaagaagacaagagctacaatgtc acctccgtcctgtttaggaaaaagaagtgtgactactggatcaggacttttgttccaggt tgccagcccggcgagttcacgctgggcaacattaagagttaccctggattaacgagttac ctcgtccgagtggtgagcaccaactacaaccagcatgctatggtgttcttcaagaaagtt tctcaaaacagggagtacttcaagatcaccctctacgggagaaccaaggagctgacttcg gaactaaaggagaacttcatccgcttctccaaatctctgggcctccctgaaaaccacatc gtcttccctgtcccaatcgaccagtgtatcgacggcggaggtagcgaaaacctgtattt cagggaggcagcgccatcagctgcggcgagacctgcttcaagttcaagtgctacaccccc agatgcagctgcagctaccccgtgtgcaag

SEQ ID NO: 27

IgK-SF-H6-GGS-lcn2C-GGS-ENLYFQ (SEQ ID NO: 95)-GG-Lambda Toxin
GACTGAGTCGCCCGCTCGAGACCATGGAGACAGACACACTCCTGCTATGGGTACTGCT-
GCTCTGGG

TTCCAGGTTCCACTGGTGACTACAAGGACGAGCATCACCATCATCACCATGGTGGAAGC-
CAGGACT

CCACCTCAGACCTGATCCCAGCCCCACCTCTGAGCAAGGTCCCTCTGCAGCAGAACTTC-
CAGGACA

-continued

ACCAATTCCAGGGGAAGTGGTATGTGGTAGGCCTGGCAGGGAATGCAATTCTCAGAGAAGACAAAG

ACCCGCAAAAGATGTATGCCACCATCTATGAGCTGAAAGAAGACAAGAGCTACAATGTCACCTCCG

TCCTGTTTAGGAAAAAGAAGTGTGACTACTGGATCAGGACTTTTGTTCCAGGTTGCCAGCCCGGCG

AGTTCACGCTGGGCAACATTAAGAGTTACCCTGGATTAACGAGTTACCTCGTCCGAGTGGTGAGCA

CCAACTACAACCAGCATGCTATGGTGTTCTTCAAGAAAGTTTCTCAAAACAGGGAGTACTTCAAGA

TCACCCTCTACGGGAGAACCAAGGAGCTGACTTCGGAACTAAAGGAGAACTTCATCCGCTTCTCCA

AATCTCTGGGCCTCCCTGAAAACCACATCGTCTTCCCTGTCCCAATCGACCAGTGTATCGACGGCG

GAGGTAGCGAAAACCTGTATTTTCAGGGAGGCGTGTGCTGCGGCTACAAGCTGTGCCACCCCTGCT

AAGCTAAGGATCCCGGACC

SEQ ID NO: 28
atggagacagacacactcctgctatgggtactgctgctctgggttccaggttccactggt gactacaaggacgagcatcaccatcatcaccatggtggaagccaggactccacctcagac ctgatcccagcccccacctctgagcaaggtccctctgcagcagaacttccaggacaaccaa ttccaggggaagtggtatgtggtaggcctggcagggaatgcaattctcagagaagacaaa gacccgcaaaagatgtatgccaccatctatgagctgaaagaagacaagagctacaatgtc acctccgtcctgtttaggaaaaagaagtgtgactactggatcaggacttttgttccaggt tgccagcccggcgagttcacgctgggcaacattaagagttaccctggattaacgagttac ctcgtccgagtggtgagcaccaactacaaccagcatgctatggtgttcttcaagaaagtt tctcaaaacagggagtacttcaagatcaccctctacgggagaaccaaggagctgacttcg gaactaaaggagaacttcatccgcttctccaaatctctgggcctccctgaaaaccacatc gtcttccctgtcccaatcgaccagtgtatcgacggcggaggtagcgaaaacctgtattttt cagggaggcgtgtgctgcggctacaagctgtgccacccctgc IgK-SF-H6-GGS-lcn2C-GGS-ENLYFQ (SEQ ID NO: 95)-GG-Lambda Toxin NG
SEQ ID NO: 29
GACTGAGTCGCCCGCTCGAGACCATGGAGACAGACACACTCCTGCTATGGGTACTGCTGCTCTGGG

TTCCAGGTTCCACTGGTGACTACAAGGACGAGCATCACCATCATCACCATGGTGGAAGCCAGGACT

CCACCTCAGACCTGATCCCAGCCCCCACCTCTGAGCAAGGTCCCTCTGCAGCAGAACTTCCAGGACA

ACCAATTCCAGGGGAAGTGGTATGTGGTAGGCCTGGCAGGGAATGCAATTCTCAGAGAAGACAAAG

ACCCGCAAAAGATGTATGCCACCATCTATGAGCTGAAAGAAGACAAGAGCTACAATGTCACCTCCG

TCCTGTTTAGGAAAAAGAAGTGTGACTACTGGATCAGGACTTTTGTTCCAGGTTGCCAGCCCGGCG

AGTTCACGCTGGGCAACATTAAGAGTTACCCTGGATTAACGAGTTACCTCGTCCGAGTGGTGAGCA

CCAACTACAACCAGCATGCTATGGTGTTCTTCAAGAAAGTTTCTCAAAACAGGGAGTACTTCAAGA

TCACCCTCTACGGGAGAACCAAGGAGCTGACTTCGGAACTAAAGGAGAACTTCATCCGCTTCTCCA

AATCTCTGGGCCTCCCTGAAAACCACATCGTCTTCCCTGTCCCAATCGACCAGTGTATCGACGGCG

```
GAGGTAGCGAAAACCTGTATTTTCAGGGAGGCAACGGCGTGTGCTGCGGCTACAAGCTGT-
GCCACC

CCTGCTAAGCTAAGGATCCCGGACC
```

SEQ ID NO: 30
```
atggagacagacacactcctgctatgggtactgctgctctgggttccaggttccactggt gactacaaggacgagcatcaccatcatcaccatggtggaagccaggactccacctcagac ctgatcccagccccacctctgagcaaggtccctctgcagcagaacttccaggacaaccaa ttccaggggaagtggtatgtggtaggcctggcagggaatgcaattctcagagaagacaaa gacccgcaaaagatgtatgccaccatctatgagctgaaagaagacaagagctacaatgtc acctccgtcctgtttaggaaaaagaagtgtgactactggatcaggacttttgttccaggt tgccagcccggcgagttcacgctgggcaacattaagagttaccctggattaacgagttac ctcgtccgagtggtgagcaccaactacaaccagcatgctatggtgttcttcaagaaagtt tctcaaaacagggagtacttcaagatcaccctctacgggagaaccaaggagctgacttcg gaactaaaggagaacttcatccgcttctccaaatctctgggcctccctgaaaaccacatc gtcttccctgtcccaatcgaccagtgtatcgacggcggaggtagcgaaaacctgtatttt cagggaggcaacggcgtgtgctgcggctacaagctgtgccacccctgc
```

IgK-SF-H6-GGS-lcn2C-GGS-ENLYFQ (SEQ ID NO: 95)-GG-Potato
Carboxypeptidase Inhibitor SEQ ID NO: 31
```
GACTGAGTCGCCCGCTCGAGACCATGGAGACAGACACACTCCTGCTATGGGTACTGCT-
GCTCTGGG

TTCCAGGTTCCACTGGTGACTACAAGGACGAGCATCACCATCATCACCATGGTGGAAGC-
CAGGACT

CCACCTCAGACCTGATCCCAGCCCCACCTCTGAGCAAGGTCCCTCTGCAGCAGAACTTC-
CAGGACA

ACCAATTCCAGGGGAAGTGGTATGTGGTAGGCCTGGCAGGGAATGCAATTCTCAGA-
GAAGACAAAG

ACCCGCAAAAGATGTATGCCACCATCTATGAGCTGAAAGAAGACAAGAGCTACAATGT-
CACCTCCG

TCCTGTTTAGGAAAAAGAAGTGTGACTACTGGATCAGGACTTTTGTTCCAGGTTGCCAGC-
CCGGCG

AGTTCACGCTGGGCAACATTAAGAGTTACCCTGGATTAACGAGTTACCTCGTCCGAGTG-
GTGAGCA

CCAACTACAACCAGCATGCTATGGTGTTCTTCAAGAAAGTTTCTCAAAACAGGGAGTACT-
TCAAGA

TCACCCTCTACGGGAGAACCAAGGAGCTGACTTCGGAACTAAAGGAGAACTTCATCCGCT-
TCTCCA

AATCTCTGGGCCTCCCTGAAAACCACATCGTCTTCCCTGTCCCAATCGACCAGTGTATC-
GACGGCG

GAGGTAGCGAAAACCTGTATTALTTCAGGGAGGCcagcagcatgcggatccgatttg-
caacaaacc gtgcaaaacccatgatgattgcagcggcgcgtggttttgccaggcgtgctggaaca-
gcgcgcgcac ctgcggcccgtatgtgggcTAATGCTAAGGATCCCGGACCG
```

SEQ ID NO: 32
```
atggagacagacacactcctgctatgggtactgctgctctgggttccaggttccactggt gactacaaggacgagcatcaccatcatcaccatggtggaagccaggactccacctcagac ctgatcccagccccacctctgagcaaggtccctctgcagcagaacttccaggacaaccaa ttccaggggaagtggtatgtggtaggcctggcagggaatgcaattctcagagaagacaaa gacccgcaaaagatgtatgccaccatctatgagctgaaagaagacaagagctacaatgtc acctccgtcctgtttaggaaaaagaagtgtgactactggatcaggacttttgttccaggt
```

-continued

```
tgccagcccggcgagttcacgctgggcaacattaagagttaccctggattaacgagttac ctcgtccgagtggtgagcaccaactacaaccagcatgctatggtgttcttcaagaaagtt tctcaaaacagggagtacttcaagatcaccctctacgggagaaccaaggagctgacttcg gaactaaaggagaacttcatccgcttctccaaatctctgggcctccctgaaaaccacatc gtcttccctgtcccaatcgaccagtgtatcgacggcggaggtagcgaaaacctgtatttt cagggaggccagcagcatgcggatccgatttgcaacaaaccgtgcaaaacccatgatgat tgcagcggcgcgtggttttgccaggcgtgctggaacagcgcgcgcacctgcggcccgtat gtgggctaa
```

Anti-CD3-STa Bispecific

The anti-CD3 is an OKT3 variant from the C-terminus of U.S. Pat. No. 7,635,462. It is supposed to work as either N- or C-terminal.

SEQ ID NO: 33
GSDIKLQQSGAELARPGASVKMSCKTSGYTFTRYTMHWVKQRPGQGLEW

IGYINPSRGYTNYNQKFKDKATLTTDKSSSTAYMQLSSLTSEDSAVYYC

ARYYDDHYCLDYWGQGTTLTVSSVEGGSGGSGGSGGSGGVDDIQLTQSP

AIMSASPGEKVTMTCRASSSVSYMNWYQQKSGTSPKRWIYDTSKVASGV

PYRFSGSGSGTSYSLTISSMEAEDAATYYCQQWSSNPLTFGAGTKLELK

GGGGSNSSNYCCELCCNPACTGCY

This is designed to be dropped into the Bam/Not cut library vector as a TEV-cleavable siderocalin fusion:

SEQ ID NO: 34
ACCTGTATTTTCAGGGATCCgatattaaactgcagcagagcggcgcgga actggcgcgcccgggcgcgagcgtgaaaatattaacccgagccgcggct ataccaactataaccagaaatttaaagataaagcgaccctgaccaccga taaaagcagcagcaccgcgtatatgcagctgagcagcctgaccagcgaa gatagcgcggtgtattattgcgcgcgctattatgatgatcattattgcc tggattattgggccagggcaccaccctgaccgtgagcagcgtggaagg cggcagcggcggcagcggcggcagcggcggcagcggcggcgtggatgat attcagctgacccagagcccggcgattatgagcgcgagcccgggcgaaa aagtgaccatgacctgccgcgcgagcagcagcgtgagctatatgaactg gtatcagcagaaagcggcaccagcccgaaacgctggatttatgatacc agcaaagtggcgagcggcgtgccgtatcgctttagcggcagcggcagcg gcaccagctatagcctgaccattagcagcatggaagcggaagatgcggc gacctattattgccagcagtggagcagcaaccgctgacctttggcgcg ggcaccaaactggaactgaaaggcggcggcggcagcaacagcagcaact attgctgcgaactgtgctgcaacccggcgtgcaccggctgctatTAATG

CGGCCGCTCATCACCATTAATC
```

Parental Cloning Construct 1 for Downstream Fusions:

IgK-sFLAG-H6-GGS-humanScn-GGS-
ENLYFQ (SEQ ID NO: 95)-GG-NotI

SEQ ID NO: 35
```
CTCGAGACCATGGAGACAGACACACTCCTGCTATGGGTACTGCTGCTCT

GGGTTCCAGGTTCCACTGGTGACTACAAGGACGAGCATCACCATCATCA

CCATGGTGGAAGCCAGGACTCCACCTCAGACCTGATCCCAGCCCCACCT

CTGAGCAAGGTCCCTCTGCAGCAGAACTTCCAGGACAACCAATTCCAGG

GGAAGTGGTATGTGGTAGGCCTGGCAGGGAATGCAATTCTCAGAGAAGA

CAAAGACCCGCAAAAGATGTATGCCACCATCTATGAGCTGAAAGAAGAC

AAGAGCTACAATGTCACCTCCGTCCTGTTTAGGAAAAAGAAGTGTGACT

ACTGGATCAGGACTTTTGTTCCAGGTTGCCAGCCCGGCGAGTTCACGCT

GGGCAACATTAAGAGTTACCCTGGATTAACGAGTTACCTCGTCCGAGTG

GTGAGCACCAACTACAACCAGCATGCTATGGTGTTCTTCAAGAAAGTTT

CTCAAAACAGGGAGTACTTCAAGATCACCCTCTACGGGAGAACCAAGGA

GCTGACTTCGGAACTAAAGGAGAACTTCATCCGCTTCTCCAAATCTCTG

GGCCTCCCTGAAAACCACATCGTCTTCCCTGTCCCAATCGACCAGTGTA

TCGACGGCGGAGGTAGCGAAAACCTGTATTTTCAGGGAGGCGGCCGC
```

Parental Cloning Construct 2 for Downstream Fusions:

IgK-sFLAG-H6-GGS-humanScnC87S-GGS-
ENLYFQ (SEQ ID NO: 95)-GS-STUFFER

SEQ ID NO: 36
```
CTCGAGACCATGGAGACAGACACACTCCTGCTATGGGTACTGCTGCTC

TGGGTTCCAGGTTCCACTGGTGACTACAAGGACGAGCATCACCATCATC

ACCATGGTGGAAGCCAGGACTCCACCTCAGACCTGATCCCAGCCCCACC

TCTGAGCAAGGTCCCTCTGCAGCAGAACTTCCAGGACAACCAATTCCAG

GGGAAGTGGTATGTGGTAGGCCTGGCAGGGAATGCAATTCTCAGAGAAG

ACAAAGACCCGCAAAAGATGTATGCCACCATCTATGAGCTGAAAGAAGA

CAAGAGCTACAATGTCACCTCCGTCCTGTTTAGGAAAAAGAAGTGTGAC

TACTGGATCAGGACTTTTGTTCCAGGTTCCCAGCCCGGCGAGTTCACGC

TGGGCAACATTAAGAGTTACCCTGGATTAACGAGTTACCTCGTCCGAGT

GGTGAGCACCAACTACAACCAGCATGCTATGGTGTTCTTCAAGAAAGTT

TCTCAAAACAGGGAGTACTTCAAGATCACCCTCTACGGGAGAACCAAGG
```

```
AGCTGACTTCGGAACTAAAGGAGAACTTCATCCGCTTCTCCAAATCTCT

GGGCCTCCCTGAAAACCACATCGTCTTCCCTGTCCCAATCGACCAGTGT

ATCGACGGCGGAGGTAGCGAAAACCTGTATTTTCAGGGATCCATGTACG

GTCTTAAGGGACCCGACATTTACAAAGGAGTTTACCAATTTAAGTCAGT

GGAGTTTGATATGTCACATCTGAACCTGACCATGCCCAACGCATGTTCA

GCCAACAACTCCCACCATTACATCAGTATGGGGACTTCTGGACTAGAAT

TGACCTTCACCAATGATTCCATCATCAGTCACAACTTTTGCAATCTGAC

CTCTGCCTTCAACAAAAAGACCTTTGACCACACACTCATGAGTATAGTT

TCGAGCCTACACCTCAGTATCAGAGGGAACTCCAACTATAAGGCAGTAT

CCTGCGACTTCAACAATGGCATAACCATCCAATACAACTTGACATTCTC

AGATCGACAAAGTGCTCAGAGCCAGTGTAGAACCTTCAGAGGTAGAGTC

CTAGATATGTTTAGAACTGCCTTCGGGGGGAAATACATGAGGAGTGGCT

GGGGCTGGACAGGCTCAGATGGCAAGACCACCTGGTGTAGCCAGACGAG

TTACCAATACCTGATTATACAAAATAGAACCTGGGAAAACCACTGCACA

TATGCAGGTCCTTTTGGGATGTCCAGGATTCTCCTTTCCCAAGAGAAGA

CTAAGTTCTTCACTAGGAGACTGGTGCCCAGGGGCAGCGGCCTGAACGA

CATCTTCGAGGCCCAGAAGATCGAGTGGCACGAGTAATGCGGCCGCTCA

TCACCATTAATCATCACCATTAATCGGACCG
```

Parental Cloning Construct 3 for Light Chain Fusions: LightChain-GRGGSGGS (SEQ ID NO: 104)-humanScnC87S

SEQ ID NO: 37
```
CTCGAGACCATGGATTTCCAGGTGCAGATTTTTAGCTTTCTGCTGATTT

CCGCTTCCGTGATTATGAGCCGAGGCGACATTGTGATGACCCAGGCAGC

TCCTAGCGTGCCAGTCACCCCAGGAGAGTCAGTGAGCATCTCCTGCAGA

AGTACTAAGTCACTGCTGCACAGCAACGGCAATACCTACCTGTATTGGT

TCCTGCAGAGACCTGGGCAGTCCCCACAGAGGCTGATCTACTATATGAG

TAACCTGGCATCAGGAGTGCCTGACAGGTTCAGCGGACGAGGCAGCGGC

ACTGATTTTACCCTGCGGATTTCTAGAGTGGAGGCAGAAGACGCCGGCG

TCTACTATTGCATGCAGAGTCTGGAGTACCCTTATACTTTCGGCGGGGG

AACCAAACTGGAAATCAAGAGGGCCGATGCCGCTCCAACCGTGTCCATT

TTTCCCCCTAGCTCCGAGCAGCTGACATCTGGCGGGGCTAGTGTGGTCT

GTTTCCTGAACAATTTTTACCCAAAGGACATCAACGTGAAATGGAAGAT

TGATGGAAGTGAAAGGCAGAACGGCGTCCTGAATTCATGGACAGACCAG

GATAGCAAAGACTCCACTTATTCTATGTCTAGTACCCTGACACTGACTA

AGGATGAGTACGAACGCCACAATTCTTATACATGCGAGGCAACTCATAA

AACCTCTACAAGTCCCATCGTGAAGAGCTTTAACCGAAATGAATGCGGC

CGCGGAGGCTCCGGAGGCTCCCAGGACTCAACAAGCGATCTGATTCCAG

CCCCACCCCTGAGCAAAGTGCCCCTGCAGCAGAACTTCCAGGACAATCA

GTTTCAGGGCAAGTGGTACGTGGTCGGGCTGGCTGGAAACGCAATCCTG

CGGGAGGACAAAGATCCCCAGAAGATGTACGCCACTATCTACGAGCTGA

AAGAAGACAAGTCATACAATGTGACCAGCGTCCTGTTCCGCAAGAAAAA

GTGTGATTATTGGATCAGAACATTCGTGCCCGGCTCCCAGCCTGGGGAG

TTTACTCTGGGGAATATTAAGTCCTACCCTGGACTGACCTCTTATCTGG

TGCGAGTGGTCTCTACAAACTACAATCAGCATGCTATGGTGTTCTTTAA

AAAGGTCAGCCAGAACCGGGAGTACTTTAAAATCACCCTGTATGGCAGA

ACCAAAGAACTGACAAGCGAGCTGAAGGAAAATTTCATTCGCTTTTCCA

AGTCTCTGGGGCTGCCAGAGAATCATATTGTGTTCCCAGTCCCCATTGA

CCAGTGTATTGACGGGTGAGGATCC
```

Super stable ScnC87S
humanScn-I8C-N39C-C87S

SEQ ID NO: 38
```
CTCGAGATGCCCCTGGGCCTGCTGTGGCTGGGCCTGGCCCTGCTGGGCGCCCTGCACGCCCAGGCCCAGGAC

TCCACCTCAGAC

-continued

Pantroglodytes
SEQ ID NO: 40
QDSTSDLIPAPPLSKVPLQQNFQDNQFQGKWYVVGLAGNAILREDKDPQKMYATIYELKEDKSYNVTSVLFR

KKKCDYWIRTFVPGRQPGEFTLGNIKSYPGLTSYLVRVVSTNYNQHAMVFFKKVSQNREYFKITLYGRTKEL

TSELQENFIRFSKSLGLPENHIVFPVPIDQCIDG

Canisfamiliaris
SEQ ID NO: 41
QDSTPSLIPAPPPLKVPLQPDFQHDQFQGKWYVIGIAGNILKKEGHGQLKMYTTTYELKDDQSYNVTSTLLR

NERCDYWNRDFVPSFQPGQFSLGDIQLYPGVQSYLVQVVATNYNQYALVYFRKVYKSQEYFKITLYGRTKEL

PLELKKEFIRFAKSIGLTEDHIIFPVPIDQCIDE

Bostaurus
SEQ ID NO: 42
RSSSSRLLRAPPLSRIPLQPNFQADQFQGKWYTVGVAGNAIKKEEQDPLKMYSSNYELKEDGSYNVTSILLK

DDLCDYWIRTFVPSSQPGQFTLGNIKSYRGIRSYTVRVVNTDYNQFAIVYFKKVQRKKTYFKITLYGRTKEL

TPEVRENFINFAKSLGLTDDHIVFTVPIDRCIDDQ

Musmusculus
SEQ ID NO: 43
QDSTQNLIPAPSLLTVPLQPDFRSDQFRGRWYVVGLAGNAVQKKTEGSFTMYSTIYELQENNSYNVTSILVR

DQDQGCRYWIRTFVPSSRAGQFTLGNMHRYPQVQSYNVQVATTDYNQFAMVFFRKTSENKQYFKITLYGRTK

ELSPELKERFTRFAKSLGLKDDNIIFSVPTDQCIDN

Rattusnorvegicus
SEQ ID NO: 44
QDSTQNLIPAPPLISVPLQPGFWTERFQGRWFVVGLAANAVQKERQSRFTMYSTIYELQEDNSYNVTSILVR

GQGCRYWIRTFVPSSRPGQFTLGNIHSYPQIQSYDVQVADTDYDQFAMVFFQKTSENKQYFKVTLYGRTKGL

SDELKERFVSFAKSLGLKDNNIVFSVPTDQCIDN

Macacamulatta
SEQ ID NO: 45
QDSSSDLIPAPPLSKVPLQQNFQDNQFQGKWYVVGLSGNAVGRKDEAPLKMYATIYELKEDKSYNVTSILFR

KEKCDYWIRTFVPGSQPGEFTLGNIQNHPGLTSYVVRVVSTNYKQYAMVFFKKVSQNKEYFKITLYGRTKEL

TSELKENFIRFSKSLGLPENHIVFSVPIDQCING

Tursiopstruncatus
SEQ ID NO: 46
QDSTPNLIPAPPLFRVPLQPNFQPDQFQGKWYIVGLAGNAFKKEKQGQFKMYATTYELKEDRSYNVTSALLR

GKTQRCDHWIRTFVPSSRPGQFTLGNIKGFPGVQSYTVRVATTNYNQFAIVYFKKVYKNQEYFKTTLYGRTK

ELTPQLKENFIHFAKSLGLTDEYILFPVPIDKCIDDQ

Gorillagorilla
SEQ ID NO: 47
QDSTSDLIPAPPLSKVPLQQNFQDNQFQGKWYVVGLAGNAILREDKDPQKMYATIYELKEDKSYNVTSVLFR

EKAQKCDYWIRTFVPGSQPGEFTLGNIKSYPGLTSYLVRVVSTNYNQHAMVFFKKVSQNREYFKITLYGRTK

ELTSELKENFIRFSKSLGLPENHIVFPVPIDQCIDG

Procaviacapensis
SEQ ID NO: 48
QEPTPTLIPAPPLSSIPLKPNFHNDKFQGKWYVVGVAGNAITKEKDPSLMYTTTYELRDDGSYNVTSTQFRE

KINCTHWTRTFVPTSQPGQFSLGNIDKYPHLSSYTVRVTATNYNYFAIVYFKKVSKNQEYFKTTLYKRIKKL

THGLKKHFIQFAKSLGLPDNHITFLVPTDRCIDDA

Callithrixjacchus
SEQ ID NO: 49
QDSPSPLIPAPPLSKVPLQQNFQDNQFQGKWYVVGLAGNAIRREDQDSLKMYATIYELKEDKSYNVTSVLFR

KAQKCDYWIRTFVPSSRPGEFKLGNIESHPGLTSYIVRVVNTDYKQHAMVFFMKASHNRKYFKVTLYGRTKE

LTSDLKENFTSFSKSLGLTENHIIFPVPIDQCIDG

*Microcebusmurinus*

SEQ ID NO: 50

QDSKEKLIPAPPLLRVPLQPDFQDDQFRETSWPRGSKMKETPAGSRDAGTGWATTYELKDHSYNVTSTLLRQ

NGKCDYWIRTFVLTSQPGQFALGNINRYPGIQSYTVRVVTTNYNQFAIVFFKKVSENKEYFKTTLYGRTKEL

PPELKENFIRFAKSLGLTEDHIIYPVPIDQCIDD

SEQ ID NO: 51

QDSTSDLIPAPPLSKVPLQQNFQDNQFQGKWYVVGLAGNAIRREDKDSQKMYATIYELKEDKSYNVTSVLFR

KKKCDYWIRTFVPGSQPGEFTLGNTKGYPGLTSYLVRVVSTNYNQYAMVFFKKVSQNREYFKITLYGRTKEL

TSELKENFIRFSKSLGLPENHIVFPAPIDQCIDG

*Ochotonaprinceps*

SEQ ID NO: 52

QELTTDLIPVPSLRKIHVQKNFQSDQFQGKWYVVGLAGNNIHNSDQEHQQMYSTTYELKEDGSYNVTSTLLR

QRNQQCDHWIRTFVPGSKLGHFNLGNIKSYPTLKSYLIRVVTTDYNQFAIVFFRKVYKNNKKFFKIVLYGRT

KELSPELRGRFTSFAKTLGLTDNHIVFPAPIGQCIDD

*Loxodontaafricana*

SEQ ID NO: 53

QTHSPTLIPAPPLLRVPLQPDFQDDKFQGKWYVIGLAGNAVEKKEQGQFKMYTTTYELKEDGSYNVTSTLLQ

EDGKCSYWIRTFVPSFQPGQFNLGNIKNFPGLQSYTVRVTATNYNQFAIVFFKKVSKNGEYFKTTLYGRTKE

LTPELKERFIRFAKSLGLSDHIIFPVPIDRCIDD

*Oryctolaguscuniculus*

SEQ ID NO: 54

QDPTPKLIPAPSLRRVPLQRNFQDEQFQGKWYVVGLAGNAVQKREEGQEPMYSTTYELNEDRSFNVTSTLLR

DQRCDHWIRTFVPTSRPGQYNLGNIKSYPGVKNYIVRVVATDYSQYAMMFFRKGSRNKQFFKTTLYGRTKEL

SPELRERFTRFAKSLGLPDDRIVFPTPIDQCIDD

Murine Scn construct for downstream viral fusions:
IgK-H6-murineScn-StrepII-GGGGS (SEQ ID NO: 105)-E7.16
gi|29468134|gb|AA085409.1|AF402678_2 E7 [HPV16]

SEQ ID NO: 55
CTCGAGACCATGGAGACCGACACGCTCTTGTTGTGGGTTCTCTTGTTGTGGGTGCCTGGGTCTACAGGCGAC

CACCACCATCATCACCACCTCGTTCCTAGAGGCAGCCAGGATAGTACCCAGAATCTTATCCCAGCACCATCT

TTGCTCACAGTACCATTGCAACCCGACTTTCGGTCTGATCAATTTCGGGGACGCTGGTACGTGGTTGGACTG

GCCGGCAATGCTGTACAGAAAAAAACAGAGGGCAGTTTCACCATGTACTCAACAATCTATGAGCTCCAAGAG

AATAATAGTTACAACGTTACCTCCATCTTGGTGAGGGACCAGGATCAGGGATGTCGCTACTGGATTCGGACA

TTCGTACCAAGTTCTCGGGCCGGTCAGTTTACTCTGGGCAACATGCACAGGTATCCCCAAGTTCAATCTTAC

AACGTGCAGGTGGCGACTACCGACTACAACCAATTCGCTATGGTGTTCTTCCGCAAAACAAGCGAGAACAAG

CAGTATTTTAAAATCACTCTGTACGGTAGAACTAAGGAGCTGAGCCCTGAACTTAAGGAGCGGTTCACCAGA

TTCGCTAAGTCCCTGGGACTGAAGGATGATAATATAATCTTTTCCGTCCCCACCGATCAGTGTATCGATAAT

TCAGCTTGGTCACATCCCCAGTTCGAGAAAGGAGGCGGTGGATCCATGCATGGCGACACTCCGACCCTGCAC

GAATACATGCTGGACCTGCAGCCCGAAACCACTGACCTGTATTGTTACGAGCAACTCAACGATTCTAGCGAG

GAGGAGGACGAGATCGATGGACCGGCAGGCCAGGCCGAACCAGACCGCGCACATTATAACATTGTTACCTTC

TGTTGCAAATGTGATTCAACTCTTAGACTTTGTGTCCAGAGTACACACGTGGACATCCGCACCCTGGAAGAT

CTGCTGATGGGAACTCTGGGTATCGTGTGTCCTATATGTAGCCAGAAACCCTGACGGACCG

SEQ ID NO: 56
METDTLLLWVLLLWVPGSTGDHHHHHHLVPRGSQDSTQNLIPAPSLLTVPLQPDFRSDQFRGRWYVVGLAGN

AVQKKTEGSFTMYSTIYELQENNSYNVTSILVRDQDQGCRYWIRTFVPSSRAGQFTLGNMHRYPQVQSYNVQ

VATTDYNQFAMVFFRKTSENKQYFKITLYGRTKELSPELKERFTRFAKSLGLKDDNIIFSVPTDQCIDN

```
SAKSDPQPEKSGGGGSMGDTPTLHEYMLDLQPETTD

LYCYEQLNDSSEEEDEIDSFAGQAEPDRAHYNIVTFCCKCDSTLRLCVQSTHVDIRTLEDLLMG

TLGIVCPICSQKP
```

IgK-H6-murineScn-StrepII-GGGGS (SEQ ID NO: 105)-E6.16
gi|4927720|gb|AAD33252.1|AF125673_1 E6 [HPV16]

SEQ ID NO: 57

```
CTCGAGACCATGGAGACCGACACGCTCTTGTTGTGGGTTCTCTTGTTGTGGGTGCCTGGGTCTACAGGCGAC
CACCACCATCATCACCACCTCGTTCCTAGAGGCAGCCAGGATAGTACCCAGAATCTTATCCCAGCACCATCT
TTGCTCACAGTACCATTGCAACCCGACTTTCGGTCTGATCAATTTCGGGGACGCTGGTACGTGGTTGGACTG
GCCGGCAATGCTGTACAGAAAAAAACAGAGGGCAGTTTCACCATGTACTCAACAATCTATGAGCTCCAAGAG
AATAATAGTTACAACGTTACCTCCATCTTGGTGAGGGACCAGGATCAGGGATGTCGCTACTGGATTCGGACA
TTCGTACCAAGTTCTCGGGCCGGTCAGTTTACTCTGGGCAACATGCACAGGTATCCCCAAGTTCAATCTTAC
AACGTGCAGGTGGCGACTACCGACTACAACCAATTCGCTATGGTGTTCTTCCGCAAAACAAGCGAGAACAAG
CAGTATTTTAAAATCACTCTGTACGGTAGAACTAAGGAGCTGAGCCCTGAACTTAAGGAGCGGTTCACCAGA
TTCGCTAAGTCCCTGGGACTGAAGGATGATAATATAATCTTTTCCGTCCCCACCGATCAGTGTATCGATAAT
TCAGCTTGGTCACATCCCCAGTTCGAGAAAGGAGGCGGTGGATCCATGCACCAGAAGAGAACCGCCATGTTC
CAGGAcCCaCAAGAGCGGCCCCGGAAACTGCCCCAACTGTGCACTGAATTGCAGACCACCATCCACGACATC
ATTTTGGAATGTGTCTACTGTAAGCAGCAGCTCCTCAGGCGAGAGGTGTATGACTTCGCCTTCCGGGATTTG
TGTATTGTCTACAGGGATGGTAATCCCTATGCCGTTTGTGATAAGTGCCTGAAATTTTATAGCAAGATCAGC
GAGTACCGACATTACTGTTACAGCGTTTATGGAACAACATTGGAGCAGCAGTACAACAAACCTCTTTGCGAC
CTCCTGATTCGCTGCATCAACTGCCAGAAGCCCTGTGCCCCGAAGAGAAACAAAGGCATTTGGATAAGAAG
CAGAGGTTCCACAACATCCGCGGTCGCTGGACGGGGCGCTGCATGAGTTGCTGCAGGAGTTCCCGCACTCGG
CGCGAGACCCAACTCTGACGGACCGCCTCTCCCTCCC
```

IgK-H6-murineScn-StrepII-GGGGS (SEQ ID NO: 105)-E6.18
gi|30172005|gb|AAP20594.1|E6 protein [HPV18]

SEQ ID NO: 58

```
CTCGAGACCATGGAGACCGACACGCTCTTGTTGTGGGTTCTCTTGTTGTGGGTGCCTGGGTCTACAGGCGAC
CACCACCATCATCACCACCTCGTTCCTAGAGGCAGCCAGGATAGTACCCAGAATCTTATCCCAGCACCATCT
TTGCTCACAGTACCATTGCAACCCGACTTTCGGTCTGATCAATTTCGGGGACGCTGGTACGTGGTTGGACTG
GCCGGCAATGCTGTACAGAAAAAAACAGAGGGCAGTTTCACCATGTACTCAACAATCTATGAGCTCCAAGAG
AATAATAGTTACAACGTTACCTCCATCTTGGTGAGGGACCAGGATCAGGGATGTCGCTACTGGATTCGGACA
TTCGTACCAAGTTCTCGGGCCGGTCAGTTTACTCTGGGCAACATGCACAGGTATCCCCAAGTTCAATCTTAC
AACGTGCAGGTGGCGACTACCGACTACAACCAATTCGCTATGGTGTTCTTCCGCAAAACAAGCGAGAACAAG
CAGTATTTTAAAATCACTCTGTACGGTAGAACTAAGGAGCTGAGCCCTGAACTTAAGGAGCGGTTCACCAGA
TTCGCTAAGTCCCTGGGACTGAAGGATGATAATATAATCTTTTCCGTCCCCACCGATCAGTGTATCGATAAT
TCAGCTTGGTCACATCCCCAGTTCGAGAAAGGAGGCGGTGGATCCATGGCCAGATTTGAAGACCCCACAAGG
CGCCCCTATAAACTGCCGGATCTTTGCACCGAACTGAATACTAGCCTGCAAGATATTGAGATTACCTGCGTG
TACTGTAAAACGGTGCTCGAATTGACCGAGGTTTTTGAGTTCGCATTCAAGGACCTGTTGTTGTATATCGC
GATTCCATCCCGCACGCAGCTTGCCATAAATGCATTGACTTTTACTCCCGGATACGCGAGCTGCGACACTAT
AGTGATAGCGTGTACGGCGATACACTTGAGAAGCTTACCAACACCGGTCTGTACAATCTTCTGATTCGGTGT
TTGAGGTGCCAGAAGCCGCTCAACCCAGCTGAGAAACTGCGGCATCTGAACGAAAAAGAAGATTCCACAAC
ATTGCTGGCCACTACAGGGCCAGTGCCATTCTTGTTGTAATAGAGCAAGGCAGGAGCGGCTGCAACGGCGG
CGCGAGACCCAGGTATGACGGACCGCCTCTCCCTCCC
```

-continued

IgK-H6-murineScn-StrepII-GGGGS (SEQ ID NO: 105)-E7.18
gi|285804409|gb|ADC35717.1|E7 [HPV18]

SEQ ID NO: 59

CTCGAGACCATGGAGACCGACACGCTCTTGTTGTGGGTTCTCTTGTTGTGGGTGCCTGGGTCTACAGGCGAC

CACCACCATCATCACCACCTCGTTCCTAGAGGCAGCCAGGATAGTACCCAGAATCTTATCCCAGCACCATCT

TTGCTCACAGTACCATTGCAACCCGACTTTCGGTCTGATCAATTTCGGGGACGCTGGTACGTGGTTGGACTG

GCCGGCAATGCTGTACAGAAAAAAACAGAGGGCAGTTTCACCATGTACTCAACAATCTATGAGCTCCAAGAG

AATAATAGTTACAACGTTACCTCCATCTTGGTGAGGGACCAGGATCAGGGATGTCGCTACTGGATTCGGACA

TTCGTACCAAGTTCTCGGGCCGGTCAGTTTACTCTGGGCAACATGCACAGGTATCCCCAAGTTCAATCTTAC

AACGTGCAGGTGGCGACTACCGACTACAACCAATTCGCTATGGTGTTCTTCCGCAAAACAAGCGAGAACAAG

CAGTATTTTAAAATCACTCTGTACGGTAGAACTAAGGAGCTGAGCCCTGAACTTAAGGAGCGGTTCACCAGA

TTCGCTAAGTCCCTGGGACTGAAGGATGATAATATAATCTTTTCCGTCCCCACCGATCAGTGTATCGATAAT

TCAGCTTGGTCACATCCCCAGTTCGAGAAAGGAGGCGGTGGATCCATGCACGGACCTAAAGCAACACTCCAG

GACATCGTCCTGCATTTGGAACCACAAAACGAAATACCCGTGGACCTTTTGTGTCACGAACAGCTTTCAGAT

TCTGAGGAAGAGAATGATGAAATCGACGGTGTCAACCACCAGCATCTCCCCGCTAGGCGGGCAGAACCCCAG

CGCCACACAATGCTGTGCATGTGTTGCAAATGCGAAGCTCGAATTGAACTCGTGGTTGAGTCCTCCGCGGAC

GACTTGAGGGCATTCCAGCAACTGTTCCTCAACACACTGAGCTTTGTCTGTCCTTGGTGCGCTAGTCAGCAG

TGACGGACCGCCTCTCCCTCCC

IgK-H6-murineScn-StrepII-GGGGS (SEQ ID NO: 105)-E6.33
gi|218931423|gb|ACL12326.1|E6 [HPV33]

SEQ ID NO: 60

CTCGAGACCATGGAGACCGACACGCTCTTGTTGTGGGTTCTCTTGTTGTGGGTGCCTGGGTCTACAGGCGAC

CACCACCATCATCACCACCTCGTTCCTAGAGGCAGCCAGGATAGTACCCAGAATCTTATCCCAGCACCATCT

TTGCTCACAGTACCATTGCAACCCGACTTTCGGTCTGATCAATTTCGGGGACGCTGGTACGTGGTTGGACTG

GCCGGCAATGCTGTACAGAAAAAAACAGAGGGCAGTTTCACCATGTACTCAACAATCTATGAGCTCCAAGAG

AATAATAGTTACAACGTTACCTCCATCTTGGTGAGGGACCAGGATCAGGGATGTCGCTACTGGATTCGGACA

TTCGTACCAAGTTCTCGGGCCGGTCAGTTTACTCTGGGCAACATGCACAGGTATCCCCAAGTTCAATCTTAC

AACGTGCAGGTGGCGACTACCGACTACAACCAATTCGCTATGGTGTTCTTCCGCAAAACAAGCGAGAACAAG

CAGTATTTTAAAATCACTCTGTACGGTAGAACTAAGGAGCTGAGCCCTGAACTTAAGGAGCGGTTCACCAGA

TTCGCTAAGTCCCTGGGACTGAAGGATGATAATATAATCTTTTCCGTCCCCACCGATCAGTGTATCGATAAT

TCAGCTTGGTCACATCCCCAGTTCGAGAAAGGAGGCGGTGGATCCATGTTCCAAGACACTGAGGAGAAGCCA

CGCACGCTGCACGATCTGTGCCAGGCCCTTGAGACTACCATCCATAACATCGAGCTCCAGTGTGTCGAATGC

AGGAATCCTCTTCAGCGGAGCGAGGTGTACGATTTTGCCTTCGCGGACCTGACGGTGGTCTACCGGGAAGGT

AACCCATTCGGGATTTGCAAGCTGTGTCTCAGATTTCTTAGTAAGATAAGTGAATACCGGCACTACAACTAT

TCAGTTTACGGTCACACTCTGGAACAGACCGTGAACAAACCCCTGAACGAGATCCTCATTCGATGTATCATC

TGTCAGAGACCTCTCTGTCCGCGCGAAAAGAAGAGGCACGTCGACCTGAATAAGCGATTTCATAATATCTCT

GGACGGTGGGCGGGGCGCTGTGCAGCCTGTTGGAGATCCCGGAGACGGGAAACAGCTCTTTGACGGACCGCC

TCTCCCTCCC

IgK-H6-murineScn-StrepII-GGGGS (SEQ ID NO: 105)-E7.33
gi|218931424|gb|ACL12327.1|E7 [HPV33]

SEQ ID NO: 61

CTCGAGACCATGGAGACCGACACGCTCTTGTTGTGGGTTCTCTTGTTGTGGGTGCCTGGGTCTACAGGCGAC

CACCACCATCATCACCACCTCGTTCCTAGAGGCAGCCAGGATAGTACCCAGAATCTTATCCCAGCACCATCT

TTGCTCACAGTACCATTGCAACCCGACTTTCGGTCTGATCAATTTCGGGGACGCTGGTACGTGGTTGGACTG

GCCGGCAATGCTGTACAGAAAAAAACAGAGGGCAGTTTCACCATGTACTCAACAATCTATGAGCTCCAAGAG

-continued

AATAATAGTTACAACGTTACCTCCATCTTGGTGAGGGACCAGGATCAGGGATGTCGCTACTGGATTCGGACA

TTCGTACCAAGTTCTCGGGCCGGTCAGTTTACTCTGGGCAACATGCACAGGTATCCCCAAGTTCAATCTTAC

AACGTGCAGGTGGCGACTACCGACTACAACCAATTCGCTATGGTGTTCTTCCGCAAAACAAGCGAGAACAAG

CAGTATTTTAAAATCACTCTGTACGGTAGAACTAAGGAGCTGAGCCCTGAACTTAAGGAGCGGTTCACCAGA

TTCGCTAAGTCCCTGGGACTGAAGGATGATAATATAATCTTTTCCGTCCCCACCGATCAGTGTATCGATAAT

TCAGCTTGGTCACATCCCCAGTTCGAGAAAGGAGGCGGTGGATCCATGCGGGACATGAACCTACTCTGAAG

GAGTACGTCCTGGACCTTTACCCGGAGCCGACAGATCTTTACTGTTACGAGCAATTGTCTGACTCCAGCGAC

GAGGATGAGGGCCTTGACAGACCTGATGGCCAGGCTCAGCCAGCTACTGCCGATTATTATATCGTTACGTGT

TGTCACACCTGCAACACAACCGTAAGGTTGTGTGTGAACTCCACCGCCAGTGACTTGAGAACGATACAACAA

CTCCTCATGGGCACTGTCAATATCGTCTGTCCTACATGTGCTCAGCTGCTGACGGACCGCCTCTCCCTCCC

IgK-H6-murineScn-StrepII-GGGGS (SEQ ID NO: 105)-E6.45
gi|145968371|gb|ABP99896.1|E6 [HPV45]

SEQ ID NO: 62

CTCGAGACCATGGAGACCGACACGCTCTTGTTGTGGGTTCTCTTGTTGTGGGTGCCTGGGTCTACAGGCGAC

CACCACCATCATCACCACCTCGTTCCTAGAGGCAGCCAGGATAGTACCCAGAATCTTATCCCAGCACCATCT

TTGCTCACAGTACCATTGCAACCCGACTTTCGGTCTGATCAATTTCGGGACGCTGGTACGTGGTTGGACTG

GCCGGCAATGCTGTACAGAAAAAAACAGAGGGCAGTTTCACCATGTACTCAACAATCTATGAGCTCCAAGAG

AATAATAGTTACAACGTTACCTCCATCTTGGTGAGGGACCAGGATCAGGGATGTCGCTACTGGATTCGGACA

TTCGTACCAAGTTCTCGGGCCGGTCAGTTTACTCTGGGCAACATGCACAGGTATCCCCAAGTTCAATCTTAC

AACGTGCAGGTGGCGACTACCGACTACAACCAATTCGCTATGGTGTTCTTCCGCAAAACAAGCGAGAACAAG

CAGTATTTTAAAATCACTCTGTACGGTAGAACTAAGGAGCTGAGCCCTGAACTTAAGGAGCGGTTCACCAGA

TTCGCTAAGTCCCTGGGACTGAAGGATGATAATATAATCTTTTCCGTCCCCACCGATCAGTGTATCGATAAT

TCAGCTTGGTCACATCCCCAGTTCGAGAAAGGAGGCGGTGGATCCATGGCCAGGTTCGATGATCCCACCCAG

CGACCCTATAAGTTGCCCGATCTCTGCACAGAACTTAACACTAGCTTGCAGGACGTAAGCATTGCATGTGTT

TACTGTAAAGCTACGCTGGAGCGAACCGAGGTGTACCAATTCGCCTTCAAAGACTTGTTCATCGTGTATAGA

GACTGTATCGCTTATGCCGCCTGCCACAAATGCATAGACTTTTACAGCAGGATCAGGGAATTGAGGTACTAT

TCCAACTCAGTCTATGGAGAAACGCTGGAGAAGATAACTAACACTGAGCTTTATAACCTCCTGATTCGCTGC

CTCCGGTGTCAGAAGCCACTGAATCCTGCCGAAAAGAGACGCCATCTGAAGGACAAGCGGCGCTTTCATAGC

ATTGCAGGACAGTACAGAGGCCAATGTAATACTTGCTGTGACCAAGCACGCCAAGAAAGGCTCAGGAGAAGG

AGAGAGACACAGGTGTGACGGACCGCCTCTCCCTCCC

IgK-H6-murineScn-StrepII-GGGGS (SEQ ID NO: 105)-E7.45
gi|145968372|gb|ABP99897.1|E7 [HPV45]

SEQ ID NO: 63

CTCGAGACCATGGAGACCGACACGCTCTTGTTGTGGGTTCTCTTGTTGTGGGTGCCTGGGTCTACAGGCGAC

CACCACCATCATCACCACCTCGTTCCTAGAGGCAGCCAGGATAGTACCCAGAATCTTATCCCAGCACCATCT

TTGCTCACAGTACCATTGCAACCCGACTTTCGGTCTGATCAATTTCGGGACGCTGGTACGTGGTTGGACTG

GCCGGCAATGCTGTACAGAAAAAAACAGAGGGCAGTTTCACCATGTACTCAACAATCTATGAGCTCCAAGAG

AATAATAGTTACAACGTTACCTCCATCTTGGTGAGGGACCAGGATCAGGGATGTCGCTACTGGATTCGGACA

TTCGTACCAAGTTCTCGGGCCGGTCAGTTTACTCTGGGCAACATGCACAGGTATCCCCAAGTTCAATCTTAC

AACGTGCAGGTGGCGACTACCGACTACAACCAATTCGCTATGGTGTTCTTCCGCAAAACAAGCGAGAACAAG

CAGTATTTTAAAATCACTCTGTACGGTAGAACTAAGGAGCTGAGCCCTGAACTTAAGGAGCGGTTCACCAGA

TTCGCTAAGTCCCTGGGACTGAAGGATGATAATATAATCTTTTCCGTCCCCACCGATCAGTGTATCGATAAT

TCAGCTTGGTCACATCCCCAGTTCGAGAAAGGAGGCGGTGGATCCATGCACGGCCCACAGGCAACCCTGCAA

GAGATCGTGCTGCATCTCGAACCACAGAATGAATTGGACCCTGTGGATCTGCTGTGTTACGAGCAGCTCTCT

GAAAGCGAAGAGGAGAATGACGAGGCCGACGGCGTGTCTCATGCACAGCTGCCTGCTCGCCGGGCCGAACCT
CAGCGACACAAAATTCTGTGCGTGTGCTGCAAATGCGACGGCCGCATAGAGCTGACGGTAGAATCATCAGCC
GACGATCTGCGAACTCTTCAACAACTCTTCCTGAGCACGCTCAGCTTCGTGTGTCCTTGGTGTGCTACAAAT
CAGTGACGGACCGCCTCTCCCTCCC

IgK-H6-murineScn-StrepII-GGGGS (SEQ ID NO: 105)-E6.31
gi|148727550|gb|ABR08438.1|E6 protein [HPV31]

SEQ ID NO: 64

CTCGAGACCATGGAGACCGACACGCTCTTGTTGTGGGTTCTCTTGTTGTGGGTGCCTGGGTCTACAGGCGAC
CACCACCATCATCACCACCTCGTTCCTAGAGGCAGCCAGGATAGTACCCAGAATCTTATCCCAGCACCATCT
TTGCTCACAGTACCATTGCAACCCGACTTTCGGTCTGATCAATTTCGGGGACGCTGGTACGTGGTTGGACTG
GCCGGCAATGCTGTACAGAAAAAAACAGAGGGCAGTTTCACCATGTACTCAACAATCTATGAGCTCCAAGAG
AATAATAGTTACAACGTTACCTCCATCTTGGTGAGGGACCAGGATCAGGGATGTCGCTACTGGATTCGGACA
TTCGTACCAAGTTCTCGGGCCGGTCAGTTTACTCTGGGCAACATGCACAGGTATCCCCAAGTTCAATCTTAC
AACGTGCAGGTGGCGACTACCGACTACAACCAATTCGCTATGGTGTTCTTCCGCAAAACAAGCGAGAACAAG
CAGTATTTTAAAATCACTCTGTACGGTAGAACTAAGGAGCTGAGCCCTGAACTTAAGGAGCGGTTCACCAGA
TTCGCTAAGTCCCTGGGACTGAAGGATGATAATATAATCTTTTCCGTCCCCACCGATCAGTGTATCGATAAT
TCAGCTTGGTCACATCCCCAGTTCGAGAAAGGAGGCGGTGGATCCATGTTCAAAAACCCGGCTGAGAGACCG
CGGAAGTTGCACGAGCTCTCATCCGCGCTGGAAATACCTTATGATGAGCTTCGCTTGAATTGTGTGTACTGC
AAAGGCCAGCTCACTGAGACCGAAGTACTTGATTTTGCCTTTACTGACCTGACAATCGTCTATAGAGACGAC
ACTCCACACGGGGTCTGTACAAAATGTCTGCGGTTTTATAGTAAAGTGAGCGAATTCCGGTGGTATCGCTAT
TCAGTGTATGGAACCACATTGGAGAAACTCACTAACAAAGGTATCTGTGACCTGCTGATCAGGTGCATAACT
TGTCAGAGGCCGCTCTGCCCCGAGGAGAAGCAGCGCCACCTGGATAAGAAGAAGAGATTCCACAACATTGGA
GGCAGATGGACAGGCCGGTGCATTGCTTGTTGGCGCAGGCCAAGAACCGAGACCCAAGTTTGACGGACCGCC
TCTCCCTCCC

IgK-H6-murineScn-StrepII-GGGGS (SEQ ID NO: 105)-E7.31
gi|338969947|gb|AEJ33624.1|E7, partial [HPV31]

SEQ ID NO: 65

CTCGAGACCATGGAGACCGACACGCTCTTGTTGTGGGTTCTCTTGTTGTGGGTGCCTGGGTCTACAGGCGAC
CACCACCATCATCACCACCTCGTTCCTAGAGGCAGCCAGGATAGTACCCAGAATCTTATCCCAGCACCATCT
TTGCTCACAGTACCATTGCAACCCGACTTTCGGTCTGATCAATTTCGGGGACGCTGGTACGTGGTTGGACTG
GCCGGCAATGCTGTACAGAAAAAAACAGAGGGCAGTTTCACCATGTACTCAACAATCTATGAGCTCCAAGAG
AATAATAGTTACAACGTTACCTCCATCTTGGTGAGGGACCAGGATCAGGGATGTCGCTACTGGATTCGGACA
TTCGTACCAAGTTCTCGGGCCGGTCAGTTTACTCTGGGCAACATGCACAGGTATCCCCAAGTTCAATCTTAC
AACGTGCAGGTGGCGACTACCGACTACAACCAATTCGCTATGGTGTTCTTCCGCAAAACAAGCGAGAACAAG
CAGTATTTTAAAATCACTCTGTACGGTAGAACTAAGGAGCTGAGCCCTGAACTTAAGGAGCGGTTCACCAGA
TTCGCTAAGTCCCTGGGACTGAAGGATGATAATATAATCTTTTCCGTCCCCACCGATCAGTGTATCGATAAT
TCAGCTTGGTCACATCCCCAGTTCGAGAAAGGAGGCGGTGGATCCATGCGGGGTGAGACACCAACTCTTCAG
GATTATGTTCTGGATCTGCAGCCAGAGGCCACAGATCTGCACTGTTACGAGCAATTGCCTGATTCCAGCGAC
GAGGAGGATGTCATCGATAGCCCTGCTGGGCAGGCCAAGCCAGACACTTCAAATTACAACATTGTAACGTTT
TGTTGTCAGTGCGAATCCACCCTCAGGCTTTGCGTCCAGAGCACTCAGGTTGACATTCGAATACTCCAGGAG
CTGTTGATGGGGAGCTTTGGAATCGTGTGCCCAAATTGTAGTACACGACTGTGACGGACCGCCTCTCCCTCC
C

IgK-H6-murineScn-StrepII-GGGGS (SEQ ID NO: 105)-E6.58
gi|425892429|gb|AFY09749.1|E6 [HPV58]
SEQ ID NO: 66
CTCGAGACCATGGAGACCGACACGCTCTTGTTGTGGGTTCTCTTGTTGTGGGTGCCTGGGTCTACAGGCGAC
CACCACCATCATCACCACCTCGTTCCTAGAGGCAGCCAGGATAGTACCCAGAATCTTATCCCAGCACCATCT
TTGCTCACAGTACCATTGCAACCCGACTTTCGGTCTGATCAATTTCGGGGACGCTGGTACGTGGTTGGACTG
GCCGGCAATGCTGTACAGAAAAAAACAGAGGGCAGTTTCACCATGTACTCAACAATCTATGAGCTCCAAGAG
AATAATAGTTACAACGTTACCTCCATCTTGGTGAGGGACCAGGATCAGGGATGTCGCTACTGGATTCGGACA
TTCGTACCAAGTTCTCGGGCCGGTCAGTTTACTCTGGGCAACATGCACAGGTATCCCCAAGTTCAATCTTAC
AACGTGCAGGTGGCGACTACCGACTACAACCAATTCGCTATGGTGTTCTTCCGCAAAACAAGCGAGAACAAG
CAGTATTTTAAAATCACTCTGTACGGTAGAACTAAGGAGCTGAGCCCTGAACTTAAGGAGCGGTTCACCAGA
TTCGCTAAGTCCCTGGGACTGAAGGATGATAATATAATCTTTTCCGTCCCCACCGATCAGTGTATCGATAAT
TCAGCTTGGTCACATCCCCAGTTCGAGAAAGGAGGCGGTGGATCCATGTTTCAGGACGCTGAGGAGAAGCCC
AGAACTCTGCACGATCTGTGTCAGGCCTTGGAGACGTCTGTGCATAAAATTGAGCTTAAATGTGTCGAATGT
AAGAAGACACTCCAGCGCAGCGAAGTTTATGACTTCGTGTTCGCGGATCTGAGAATCGTGTATCGGGACGGC
AACCCTTTTGCTGTTTGCAAGGTTTGCCTTAGGCTCCTGTCCAAAATTAGCGAGTACCGCCACTATAACTAC
TCTCTCTACGGTGATACTCTCGAGCAAACACTGAAGAAGTGCTTGAACGAGATCCTGATTAGATGCATCATT
TGTCAAAGGCCACTTTGTCCACAGGAGAAGAAGAGGCACGTGGACCTGAATAAGCGCTTTCATAACATCTCT
GGCAGATGGACAGGCCGATGCGCTGTATGTTGGCGCCCACGGAGAAGGCAAACCCAGGTGTGACGGACCGCC
TCTCCCTCCC IgK-H6-murineScn-StrepII-GGGGS (SEQ ID NO: 105)-E7.58
gi|414090989|gb|AFW98384.1|E7 [HPV58]
SEQ ID NO: 67
CTCGAGACCATGGAGACCGACACGCTCTTGTTGTGGGTTCTCTTGTTGTGGGTGCCTGGGTCTACAGGCGAC
CACCACCATCATCACCACCTCGTTCCTAGAGGCAGCCAGGATAGTACCCAGAATCTTATCCCAGCACCATCT
TTGCTCACAGTACCATTGCAACCCGACTTTCGGTCTGATCAATTTCGGGGACGCTGGTACGTGGTTGGACTG
GCCGGCAATGCTGTACAGAAAAAAACAGAGGGCAGTTTCACCATGTACTCAACAATCTATGAGCTCCAAGAG
AATAATAGTTACAACGTTACCTCCATCTTGGTGAGGGACCAGGATCAGGGATGTCGCTACTGGATTCGGACA
TTCGTACCAAGTTCTCGGGCCGGTCAGTTTACTCTGGGCAACATGCACAGGTATCCCCAAGTTCAATCTTAC
AACGTGCAGGTGGCGACTACCGACTACAACCAATTCGCTATGGTGTTCTTCCGCAAAACAAGCGAGAACAAG
CAGTATTTTAAAATCACTCTGTACGGTAGAACTAAGGAGCTGAGCCCTGAACTTAAGGAGCGGTTCACCAGA
TTCGCTAAGTCCCTGGGACTGAAGGATGATAATATAATCTTTTCCGTCCCCACCGATCAGTGTATCGATAAT
TCAGCTTGGTCACATCCCCAGTTCGAGAAAGGAGGCGGTGGATCCATGCGGGGAATAACCCCACCCTGCGC
GAGTACATTCTTGACCTGCACCCAGAGCCTACGGATCTGTTTTGTTACGAACAACTGTGCGACTCCTCCGAC
GAGGATGAGATCGGGCTGGATGCCCAGACGGGCAGGCACAGCCTGCTACAGCTAACTACTATATTGTGACA
TGTTGCTACACATGCGGAACGACGGTCAGACTGTGCATTAATAGCACTGCCACAGACGTGCGGACCCTGCAG
CAACTGCTCATGGGGACCTGCACTATTGTGTGTCCTTCATGTGCGCAGCAATGACGGACCGCCTCTCCCTCC
C Human Scn construct for downstream viral fusions:
IgK-sFLAG-H6-GGS-humanScn-GGS-ENLYFQ (SEQ ID NO: 95)-GG-Adv2E3/19K
SEQ ID NO: 68
METDTLLLWVLLLWVPGSTGDYKDEHHHHHHGGSQDSTSDLIPAPPLSKVPLQQNFQDNQFQGKWYVVGLAG
NAILREDKDPQKMYATIYELKEDKSYNVTSVLFRKKKCDYWIRTFVPGSQPGEFTLGNIKSYPGLTSYLVRV
VSTNYNQHAMVFFKKVSQNREYFKITLYGRTKELTSELKENFIRFSKSLGLPENHIVFPVPIDQCIDGGGSE

NLYFQGGAKKVEFKEPACNVTFKSEANECTTLIKCTTEHEKLIIRHKDKIGKYAVYAIWQPGDTNDYNVTVF
QGENRKTFMYKFPFYEMCDITMYMSKQYKLW

IgK-sFLAG-H6-GGS-humanScn-GGS-ENLYFQ (SEQ ID NO: 95)-GG-SF162gp120
SEQ ID NO: 69

METDTLLLWVLLLWVPGSTGDYKDEHHHHHHGGSQDSTSDLIPAPPLSKVPLQQNFQDNQFQGKWYVVGLAG
NAILREDKDPQKMYATIYELKEDKSYNVTSVLFRKKKCDYWIRTFVPGSQPGEFTLGNIKSYPGLTSYLVRV
VSTNYNQHAMVFFKKVSQNREYFKITLYGRTKELTSELKENFIRFSKSLGLPENHIVFPVPIDQCIDGGGSE
NLYFQGGWVTVYYGVPVWKEATTTLFCASDAKAYDTEVHNVWATHACVPTDPNPQEIVLENVTENFNMWKNN
MVEQMHEDIISLWDQSLKPCVKLTPLCVTLHCTNLKNATNTKSSNWKEMDRGEIKNCSFKVTTSIRNKMQKE
YALFYKLDVVPIDNDNTSYKLINCNTSVITQACPKVSFEPIPIHYCAPAGFAILKCNDKKFNGSGPCTNVST
VQCTHGIRPVVSTQLLLNGSLAEEGVVIRSENFTDNAKTIIVQLKESVEINCTRPNNNTRKSITIGPGRAFY
ATGDIIGDIRQAHCNISGEKWNNTLKQIVTKLQAQFGNKTIVFKQSSGGDPEIVMHSFNCGGEFFYCNSTQL
FNSTWNNTIGPNNTNGTITLPCRIKQIINRWQEVGKAMYAPPIRGQIRCSSNITGLLLTRDGGKEISNTTEI
FRPGGGDMRDNWRSELYKYKVVKIEPLGVAPTKAKRRVVQQGLNDIFEAQKIEWHE

IgK-sFLAG-H6-GGS-humanScn-GGS-ENLYFQ (SEQ ID NO: 95)-GG-QH0692120
SEQ ID NO: 70

METDTLLLWVLLLWVPGSTGDYKDEHHHHHHGGSQDSTSDLIPAPPLSKVPLQQNFQDNQFQGKWYVVGLAG
NAILREDKDPQKMYATIYELKEDKSYNVTSVLFRKKKCDYWIRTFVPGSQPGEFTLGNIKSYPGLTSYLVRV
VSTNYNQHAMVFFKKVSQNREYFKITLYGRTKELTSELKENFIRFSKSLGLPENHIVFPVPIDQCIDGGGSE
NLYFQGGWVTVYYGVPVWKEATTTLFCASDAKAYETEKHNVWATHACVPTDPNPQEVVLGNVTENFNMWKNN
MVEQMHEDIISLWDESLKPCVKLTPLCVTLNCTDEVKTSYANKTSNETYKTSNETFGEIKNCSFSVPTGIKD
KVQNVYALFYKLDVIPIDDNNNSSKNNNGSYSSYRLINCNTSVITQACPKVSFEPIPIHYCAPAGFAILKCN
NKTFNGTGPCTNVSTVQCTHGIRPVVSTQLLLNGSLAEEEVVIRSENFTNNAKTIIVHLKKSVEINCTRPGN
NTRKSIHIGPGRAFYATGDIIGDIRQAHCNLSSVQWNDTLKQIVIKLGEQFGTNKTIAFNQSSGGDPEIVMH
SFNCGGEFFYCNTTQLFNSTWEFHGNWTRSNFTESNSTTITLPCRIKQIVNMWQEVGKAMYAPPIRGQIRCS
SNITGLLLTRDGGVNGTRETFRPGGGDMRDNWRSELYKYKVVKIEPLGVAPTKAKRRVVQGLNDIFEAQKIE
WHE

Human Scn Construct for Downstream Peptide Fusions:

IgK-sFLAG-H6-GGS-humanScn-GGS-
ENLYFQ (SEQ ID NO: 95)-GG-ITPR-1
SEQ ID NO: 71

METDTLLLWVLLLWVPGSTGDYKDEHHHHHHGGSQDSTSDLIPAPPLSK
VPLQQNFQDNQFQGKWYVVGLAGNAILREDKDPQKMYATIYELKEDKSY
NVTSVLFRKKKCDYWIRTFVPGSQPGEFTLGNIKSYPGLTSYLVRVVST
NYNQHAMVFFKKVSQNREYFKITLYGRTKELTSELKENFIRFSKSLGLP
ENHIVFPVPIDQCIDGGGSENLYFQGGSKCRVFNTTERDEQGSKVNDFF
QQTEDLYNEMKWQK

IgK-sFLAG-H6-GGS-humanScn-GGS-
ENLYFQ (SEQ ID NO: 95)-GG-ITPR-2
SEQ ID NO: 72

METDTLLLWVLLLWVPGSTGDYKDEHHHHHHGGSQDSTSDLIPAPPLSK
VPLQQNFQDNQFQGKWYVVGLAGNAILREDKDPQKMYATIYELKEDKSY
NVTSVLFRKKKCDYWIRTFVPGSQPGEFTLGNIKSYPGLTSYLVRVVST
NYNQHAMVFFKKVSQNREYFKITLYGRTKELTSELKENFIRFSKSLGLP
ENHIVFPVPIDQCIDGGGSENLYFQGGPPHELTEEEKQQILHSEEFLSF
FDHSTRIVERALSE

IgK-sFLAG-H6-GGS-humanScn-GGS-
ENLYFQ (SEQ ID NO: 95)-GG-ITPR-3
SEQ ID NO: 73

METDTLLLWVLLLWVPGSTGDYKDEHHHHHHGGSQDSTSDLIPAPPLSK
VPLQQNFQDNQFQGKWYVVGLAGNAILREDKDPQKMYATIYELKEDKSY
NVTSVLFRKKKCDYWIRTFVPGSQPGEFTLGNIKSYPGLTSYLVRVVST
NYNQHAMVFFKKVSQNREYFKITLYGRTKELTSELKENFIRFSKSLGLP
ENHIVFPVPIDQCIDGGGSENLYFQGGPPPRCISTNKCTAPEVENAIRV
PGNRSFFSLTEIVR

IgK-sFLAG-H6-GGS-humanScn-GGS-
ENLYFQ (SEQ ID NO: 95)-GG-ITPR-4
SEQ ID NO: 74

METDTLLLWVLLLWVPGSTGDYKDEHHHHHHGGSQDSTSDLIPAPPLSK
VPLQQNFQDNQFQGKWYVVGLAGNAILREDKDPQKMYATIYELKEDKSY

-continued
NVTSVLFRKKKCDYWIRTFVPGSQPGEFTLGNIKSYPGLTSYLVRVVST
NYNQHAMVFFKKVSQNREYFKITLYGRTKELTSELKENFIRFSKSLGLP
ENHIVFPVPIDQCIDGGGSENLYFQGGTERDEQGSKINDFFLRSEDLFN
EMNWQKKLRAQPVL IgK-sFLAG-H6-GGS-humanScn-GGS-
ENLYFQ (SEQ ID NO: 95)-GG-ITPR-5
SEQ ID NO: 75
METDTLLLWVLLLWVPGSTGDYKDEHHHHHGGSQDSTSDLIPAPPLSK
VPLQQNFQDNQFQGKWYVVGLAGNAILREDKDPQKMYATIYELKEDKSY
NVTSVLFRKKKCDYWIRTFVPGSQPGEFTLGNIKSYPGLTSYLVRVVST
NYNQHAMVFFKKVSQNREYFKITLYGRTKELTSELKENFIRFSKSLGLP
ENHIVFPVPIDQCIDGGGSENLYFQGGLTEETKHRLFTTTEQDEQGSKV
SDFFDQSSFLHNEM IgK-sFLAG-H6-GGS-humanScn-GGS-
ENLYFQ (SEQ ID NO: 95)-GG-ITPR-8
SEQ ID NO: 76
METDTLLLWVLLLWVPGSTGDYKDEHHHHHGGSQDSTSDLIPAPPLSK
VPLQQNFQDNQFQGKWYVVGLAGNAILREDKDPQKMYATIYELKEDKSY
NVTSVLFRKKKCDYWIRTFVPGSQPGEFTLGNIKSYPGLTSYLVRVVST
NYNQHAMVFFKKVSQNREYFKITLYGRTKELTSELKENFIRFSKSLGLP
ENHIVFPVPIDQCIDGGGSENLYFQGGGAQPPFDAQSPLDSQPQPSGQP
WNFHASTSWYWRQS Human Scn Construct for Downstream HMOX1 Fusions:

IgK-sFLAG-H6-GGS-humanScn-GGS-
ENLYFQ (SEQ ID NO: 95)-GG-human HMOX1
SEQ ID NO: 77
METDTLLLWVLLLWVPGSTGDYKDEHHHHHGGSQDSTSDLIPAPPLSK
VPLQQNFQDNQFQGKWYVVGLAGNAILREDKDPQKMYATIYELKEDKSY
NVTSVLFRKKKCDYWIRTFVPGSQPGEFTLGNIKSYPGLTSYLVRVVST
NYNQHAMVFFKKVSQNREYFKITLYGRTKELTSELKENFIRFSKSLGLP
ENHIVFPVPIDQCIDGGGSENLYFQGGMERPQPDSMPQDLSEALKEATK
EVHTQAENAEFMRNFQKGQVTRDGFKLVMASLYHIYVALEEEIERNKES
PVFAPVYFPEELHRKAALEQDLAFWYGPRWQEVIPYTPAMQRYVKRLHE
VGRTEPELLVAHAYTRYLGDLSGGQVLKKIAQKALDLPSSGEGLAFFTF
PNIASATKFKQLYRSRMNSLEMTPAVRQRVIEEAKTAFLLNIQLFEELQ
ELLTHDTKDQSPSRAPGLRQRASNKVQDSAPVETPRGKPPLNTRSQA IgK-sFLAG-H6GGS-humanScn-GGS-
ENLYFQ (SEQ ID NO: 95)-GG-murineHMOX1
SEQ ID NO: 78
METDTLLLWVLLLWVPGSTGDYKDEHHHHHGGSQDSTSDLIPAPPLSK
VPLQQNFQDNQFQGKWYVVGLAGNAILREDKDPQKMYATIYELKEDKSY
NVTSVLFRKKKCDYWIRTFVPGSQPGEFTLGNIKSYPGLTSYLVRVVST
NYNQHAMVFFKKVSQNREYFKITLYGRTKELTSELKENFIRFSKSLGLP
ENHIVFPVPIDQCIDGGGSENLYFQGGMERPQPDSMPQDLSEALKEATK
EVHIQAENAEFMKNFQKGQVSREGFKLVMASLYHIYTALEEEIERNKQN
PVYAPLYFPEELHRRAALEQDMAFWYGPHWQEIIPCTPATQHYVKRLHE -continued
VGRTHPELLVAHAYTRYLGDLSGGQVLKKIAQKAMALPSSGEGLAFFTF
PNIDSPTKFKQLYRARMNTLEMTPEVKHRVTEEAKTAFLLNIELFEELQ
VMLTEEHKDQSPSQMASLRQRPASLVQDTAPAETPRGKPQISTSSSQ* humanScn-humanHMOX1 (Second Generation)
SEQ ID NO: 79
MPLGLLWLGLALLGALHAQAQDSTSDLIPAPPLSKVPLQQNFQDNQFQG
KWYVVGLAGNAILREDKDPQKMYATIYELKEDKSYNVTSVLFRKKKCDY
WIRTFVPGSQPGEFTLGNIKSYPGLTSYLVRVVSTNYNQHAMVFFKKVS
QNREYFKITLYGRTKELTSELKENFIRFSKSLGLPENHIVFPVPIDQCI
DGGGSENLYFQGGGMERPQPDSMPQDLSEALKEATKEVHTQAENAEFMR
NFQKGQVTRDGFKLVMASLYHIYVALEEEIERNKESPVFAPVYFPEELH
RKAALEQDLAFWYGPRWQEVIPYTPAMQRYVKRLHEVGRTEPELLVAHA
YTRYLGDLSGGQVLKKIAQKALDLPSSGEGLAFFTFPNIASATKFKQLY
RSRMNSLEMTPAVRQRVIEEAKTAFLLNIQLFEELQELLTHDTKDQSPS
RAPGLRQRASNKVQDSAPVETPRGKPPLNTRSQAGGLVPRGSHHHHHH humanScn-cTHAP4
SEQ ID NO: 80
MPLGLLWLGLALLGALHAQAQDSTSDLIPAPPLSKVPLQQNFQDNQFQG
KWYVVGLAGNAILREDKDPQKMYATIYELKEDKSYNVTSVLFRKKKCDY
WIRTFVPGSQPGEFTLGNIKSYPGLTSYLVRVVSTNYNQHAMVFFKKVS
QNREYFKITLYGRTKELTSELKENFIRFSKSLGLPENHIVFPVPIDQCI
DGGGSENLYFQGGGPPKMNPVVEPLSWMLGTWLSDPPGAGTYPTLQPFQ
YLEEVHISHVGQPMLNFSFNSFHPDTRKPMHRECGFIRLKPDTNKVAFV
SAQNTGVVEVEEGEVNGQELCIASHSIARISFAKEPHVEQITRKFRLNS
EGKLEQTVSMATTTQPMTQHLHVTYKKVTPGGLVPRGSHHHHHH Human Scn Construct for Downstream Multimer Fusions:

IgK-sFLAG-H6-GGS-humanScn-GGS-
ENLYFQ (SEQ ID NO: 95)-GG-heptamer
SEQ ID NO: 81
METDTLLLWVLLLWVPGSTGDYKDEHHHHHGGSQDSTSDLIPAPPLSK
VPLQQNFQDNQFQGKWYVVGLAGNAILREDKDPQKMYATIYELKEDKSY
NVTSVLFRKKKCDYWIRTFVPGSQPGEFTLGNIKSYPGLTSYLVRVVST
NYNQHAMVFFKKVSQNREYFKITLYGRTKELTSELKENFIRFSKSLGLP
ENHIVFPVPIDQCIDGGGSENLYFQGGGRSAGAHAGWETPEGCEQVLTG
KRLMQCLPNPEDVKMALEVYKLSLEIEQLELQRDSARQSTLDKELVPRG
S IgK-sFLAG-H6-GGS-humanScn-GGS-
ENLYFQ (SEQ ID NO: 95)-GG-CD80heptamer
SEQ ID NO: 82
METDTLLLWVLLLWVPGSTGDYKDEHHHHHGGSQDSTSDLIPAPPLSK
VPLQQNFQDNQFQGKWYVVGLAGNAILREDKDPQKMYATIYELKEDKSY
NVTSVLFRKKKCDYWIRTFVPGSQPGEFTLGNIKSYPGLTSYLVRVVST
NYNQHAMVFFKKVSQNREYFKITLYGRTKELTSELKENFIRFSKSLGLP
ENHIVFPVPIDQCIDGGGSENLYFQGGGIIQVNKTVKEVAVLSCDYNIS

```
TTELMKVRIYWQKDDEVVLAVTSGQTKVWSKYENRTFADFTNNLSIVIM

ALRLSDNGKYTCIVQKTEKRSYKVKHMTSVMLLVRADFPVPSITDLGNP

SHDIKRIMCSTSGGFPKPHLSWWENEEELNAANTTVSQDPDTELYTISS

ELDFNITSNHSFVCLVKYGDLTVSQIFNWQKSVEPHPPNNSAWSHPQFE

KGGSLVPRGSGSAGAHAGWETPEGCEQVLTGKRLMQCLPNPEDVKMALX

VYKLSLEIEQLELQRDSARQSTLDKELVPRGS
```

IgK-sFLAG-H6-GGS-humanScn-GGS-
ENLYFQ (SEQ ID NO: 95)-GG-trimer
SEQ ID NO: 83

```
METDTLLLWVLLLWVPGSTGDYKDEHHHHHHGGSQDSTSDLIPAPPLSK

VPLQQNFQDNQFQGKWYVVGLAGNAILREDKDPQKMYATIYELKEDKSY

NVTSVLFRKKKCDYWIRTFVPGSQPGEFTLGNIKSYPGLTSYLVRVVST

NYNQHAMVFFKKVSQNREYFKITLYGRTKELTSELKENFIRFSKSLGLP

ENHIVFPVPIDQCIDGGGSENLYFQGGGRNLVTAFSNMDDMLQKAHLVI

EGTFIYLRDSTEFFIRVRDGWKKLQLGELIPIPA
```

IgK-sFLAG-H6-GGS-humanScn-GGS-
ENLYFQ (SEQ ID NO: 95)-GG-CD80trimer
SEQ ID NO: 84

```
METDTLLLWVLLLWVPGSTGDYKDEHHHHHHGGSQDSTSDLIPAPPLSK

VPLQQNFQDNQFQGKWYVVGLAGNAILREDKDPQKMYATIYELKEDKSY

NVTSVLFRKKKCDYWIRTFVPGSQPGEFTLGNIKSYPGLTSYLVRVVST

NYNQHAMVFFKKVSQNREYFKITLYGRTKELTSELKENFIRFSKSLGLP

ENHIVFPVPIDQCIDGGGSENLYFQGGGIIQVNKTVKEVAVLSCDYNIS

TTELMKVRIYWQKDDEVVLAVTSGQTKVWSKYENRTFADFTNNLSIVIM

ALRLSDNGKYTCIVQKTEKRSYKVKHMTSVMLLVRADFPVPSITDLGNP

SHDIKRIMCSTSGGFPKPHLSWWENEEELNAANTTVSQDPDTELYTISS

ELDFNITSNHSFVCLVKYGDLTVSQIFNWQKSVEPHPPNNSAWSHPQFE

KGGSLVPRGSGNLVTAFSNMDDMLQKAHLVIEGTFIYLRDSTEFFIRVR

DGWKKLQLGELIPIPA
```

IgK-sFLAG-H6-GGS-humanScn-GGS-
ENLYFQ (SEQ ID NO: 95)-GG-pentamer
SEQ ID NO: 85

```
METDTLLLWVLLLWVPGSTGDYKDEHHHHHHGGSQDSTSDLIPAPPLSK

VPLQQNFQDNQFQGKWYVVGLAGNAILREDKDPQKMYATIYELKEDKSY

NVTSVLFRKKKCDYWIRTFVPGSQPGEFTLGNIKSYPGLTSYLVRVVST

NYNQHAMVFFKKVSQNREYFKITLYGRTKELTSELKENFIRFSKSLGLP

ENHIVFPVPIDQCIDGGGSENLYFQGGGRSSNAKWDQWSSDWQTWNAKW

DQWSNDWNAWRSDWQAWKDDWARWNQRWDNWAT
```

Human Scn Construct for Downstream Subdomain Fusions:

IgK-sFLAG-H6-GGS-humanScn-GGS-
ENLYFQ (SEQ ID NO: 95)-GG-ROR1Kringle
SEQ ID NO: 86

```
METDTLLLWVLLLWVPGSTGDYKDEHHHHHHGGSQDSTSDLIPAPPLSK

VPLQQNFQDNQFQGKWYVVGLAGNAILREDKDPQKMYATIYELKEDKSY

NVTSVLFRKKKCDYWIRTFVPGSQPGEFTLGNIKSYPGLTSYLVRVVST

NYNQHAMVFFKKVSQNREYFKITLYGRTKELTSELKENFIRFSKSLGLP

ENHIVFPVPIDQCIDGGGSENLYFQGGCYNSTGVDYRGTVSVTKSGRQC

QPWNSQYPHTHTFTALRFPELNGGHSYCRNPGNQKEAPWCFTLDENFKS

DLCDIPAC
```

IgK-sFLAG-H6-GGS-humanScn-GGS-
ENLYFQ (SEQ ID NO: 95)-GG-CTLA4
SEQ ID NO: 87

```
METDTLLLWVLLLWVPGSTGDYKDEHHHHHHGGSQDSTSDLIPAPPLSK

VPLQQNFQDNQFQGKWYVVGLAGNAILREDICDPQKMYATIYELKEDKS

YNVTSVLFRKKKCDYWIRTFVPGSQPGEFTLGNIKSYPGLTSYLVRVVS

TNYNQHAMVFFKKVSQNREYFKITLYGRTKELTSELKENFIRFSKSLGL

PENHIVFPVPIDQCIDGGGSENLYFQGGMHVAQPAVVLASSRGVASFVC

EYGSSGNAAEVRVTVLRQAGSQMTEVCAATYTVEDELAFLDDSTCTGTS

SGNKVNLTIQGLRAMDTGLYICKVELMYPPPYYVGMGNGTQIYVIDPEP

C
```

Human Scn Construct for Downstream Knottin Fusions:

IgK-sFLAG-H6-GGS-humanScn-GGS-
ENLYFQ (SEQ ID NO: 95)-GG-Imperatoxin
SEQ ID NO: 88

CTCGAGACCATGGAGACAGACACACTCCTGCTATGGGTACTGCTGCTCT

GGGTTCCAGGTTCCACTGGTGACTACAAGGACGAGCATCACCATCATCA

CCATGGTGGAAGCCAGGACTCCACCTCAGACCTGATCCCAGCCCCACCT

CTGAGCAAGGTCCCTCTGCAGCAGAACTTCCAGGACAACCAATTCCAGG

GGAAGTGGTATGTGGTAGGCCTGGCAGGGAATGCAATTCTCAGAGAAGA

CAAAGACCCGCAAAAGATGTATGCCACCATCTATGAGCTGAAAGAAGAC

AAGAGCTACAATGTCACCTCCGTCCTGTTTAGGAAAAAGAAGTGTGACT

ACTGGATCAGGACTTTTGTTCCAGGTTGCCAGCCCGGCGAGTTCACGCT

GGGCAACATTAAGAGTTACCCTGGATTAACGAGTTACCTCGTCCGAGTG

GTGAGCACCAACTACAACCAGCATGCTATGGTGTTCTTCAAGAAAGTTT

CTCAAAACAGGGAGTACTTCAAGATCACCCTCTACGGGAGAACCAAGGA

GCTGACTTCGGAACTAAAGGAGAACTTCATCCGCTTCTCCAAATCTCTG

GGCCTCCCTGAAAACCACATCGTCTTCCCTGTCCCAATCGACCAGTGTA

TCGACGGCGGAGGTAGCGAAAACCTGTATTTTCAGGGAGGCGACTGCCT

GCCCCACCTGAGGAGGTGCAGGGCCGACAACGACTGCTGCGGCAGGAGG

TGCAGGAGGAGGGGCACCAACGCCGAGAGGAGGTGCAGGTAAGCTAAGG

ATCC

IgK SP: Murine IgK light chain signal peptide:

SEQ ID NO: 89

METDTLLLWVLLLWVPGSTG

SEQ ID NO: 90

ATGGAGACAGACACACTCCTGCTATGGGTACTGCTGCTCTGGGTTCCAG

GTTCCACTGGT sFLAG: Shortened FLAG epitope:
SEQ ID NO: 91
DYKDE

SEQ ID NO: 92
GACTACAAGGACGAG

HIS: 6xhistidine tag
SEQ ID NO: 93
HHHHHH

SEQ ID NO: 94
CATCATCATCATCATCAT

TEV: Tobacco Etch Virus Protease recognition site:
SEQ ID NO: 95
ENLYFQ

SEQ ID NO: 96
GAGAATTTATATTTTCAG

Furin-furin cleavage site with BamHI site (GGATCC):
SEQ ID NO: 99
RARYKRGS

SEQ ID NO: 100
CGGGCCCGGTATAAACGGGGATCC

SEQ ID NO: 106
METDTLLLWVLLLWVPGSTGDYKDEHHHHHHGGSQDSTSDLIPAPPLSKVPLQQNFQDNQ
FQGKWYVVGLAGNAILREDKDPQKMYATIYELKEDKSYNVTSVLFRKKKCDYWIRTFVPG
CQPGEFTLGNIKSYPGLTSYLVRVVSTNYNQHAMVFFKKVSQNREYFKITLYGRTKELTS
ELKENFIRFSKSLGLPENHIVFPVPIDQCIDGGGSENLYFQGGDTCGSGYNVDQRRTNSG
CKAGNGDRHFCGCDRTGVVECKGGKWTEVQDCGSSSCKGTSNGGATC

SEQ ID NO: 107
METDTLLLWVLLLWVPGSTGDYKDEHHHHHHGGSQDSTSDLIPAPPLSKVPLQQNFQDNQ
FQGKWYVVGLAGNAILREDKDPQKMYATIYELKEDKSYNVTSVLFRKKKCDYWIRTFVPG
CQPGEFTLGNIKSYPGLTSYLVRVVSTNYNQHAMVFFKKVSQNREYFKITLYGRTKELTS
ELKENFIRFSKSLGLPENHIVFPVPIDQCIDGGGSENLYFQGGDQNCDIGNITSQCQMQH
KNCEDANGCDTIIEECKTSMVERCQNQEFESAAGSTTLGPQ

SEQ ID NO: 108
METDTLLLWVLLLWVPGSTGDYKDEHHHHHHGGSQDSTSDLIPAPPLSKVPLQQNFQDNQ
FQGKWYVVGLAGNAILREDKDPQKMYATIYELKEDKSYNVTSVLFRKKKCDYWIRTFVPG
CQPGEFTLGNIKSYPGLTSYLVRVVSTNYNQHAMVFFKKVSQNREYFKITLYGRTKELTS
ELKENFIRFSKSLGLPENHIVFPVPIDQCIDGGGSENLYFQGGGHACYRNCWREGNDEET
CKERC

SEQ ID NO: 109
METDTLLLWVLLLWVPGSTGDYKDEHHHHHHGGSQDSTSDLIPAPPLSKVPLQQNFQDNQ
FQGKWYVVGLAGNAILREDKDPQKMYATIYELKEDKSYNVTSVLFRKKKCDYWIRTFVPG
CQPGEFTLGNIKSYPGLTSYLVRVVSTNYNQHAMVFFKKVSQNREYFKITLYGRTKELTS
ELKENFIRFSKSLGLPENHIVFPVPIDQCIDGGGSENLYFQGGECRYLFGGCKTTSDCCK
HLGCKFRDKYCAWDFTFS

SEQ ID NO: 110
METDTLLLWVLLLWVPGSTGDYKDEHHHHHHGGSQDSTSDLIPAPPLSKVPLQQNFQDNQ
FQGKWYVVGLAGNAILREDKDPQKMYATIYELKEDKSYNVTSVLFRKKKCDYWIRTFVPG
CQPGEFTLGNIKSYPGLTSYLVRVVSTNYNQHAMVFFKKVSQNREYFKITLYGRTKELTS
ELKENFIRFSKSLGLPENHIVFPVPIDQCIDGGGSENLYFQGGEISCEPGKTFKDKCNTC
RCGADGKSAACTLKACPNQ

SEQ ID NO: 111
METDTLLLWVLLLWVPGSTGDYKDEHHHHHHGGSQDSTSDLIPAPPLSKVPLQQNFQDNQ
FQGKWYVVGLAGNAILREDKDPQKMYATIYELKEDKSYNVTSVLFRKKKCDYWIRTFVPG
CQPGEFTLGNIKSYPGLTSYLVRVVSTNYNQHAMVFFKKVSQNREYFKITLYGRTKELTS

-continued

ELKENFIRFSKSLGLPENHIVFPVPIDQCIDGGGSENLYFQGGVCRDWFKETACRHAKSL
GNCRTSQKYRANCAKTCELC

SEQ ID NO: 112
METDTLLLWVLLLWVPGSTGDYKDEHHHHHGGSQDSTSDLIPAPPLSKVPLQQNFQDNQ
FQGKWYVVGLAGNAILREDKDPQKMYATIYELKEDKSYNVTSVLFRKKKCDYWIRTFVPG
CQPGEFTLGNIKSYPGLTSYLVRVVSTNYNQHAMVFFKKVSQNREYFKITLYGRTKELTS
ELKENFIRFSKSLGLPENHIVFPVPIDQCIDGGGSENLYFQGGVSITKCSSDMNGYCLHG
QCIYLVDMSQNYCRCEVGYTGVRCEHFFL

SEQ ID NO: 113
METDTLLLWVLLLWVPGSTGDYKDEHHHHHGGSQDSTSDLIPAPPLSKVPLQQNFQDNQ
FQGKWYVVGLAGNAILREDKDPQKMYATIYELKEDKSYNVTSVLFRKKKCDYWIRTFVPG
CQPGEFTLGNIKSYPGLTSYLVRVVSTNYNQHAMVFFKKVSQNREYFKITLYGRTKELTS
ELKENFIRFSKSLGLPENHIVFPVPIDQCIDGGGSENLYFQGGIPCGESCVWIPCISAA
LGCSCKNKVCYRN

SEQ ID NO: 114
METDTLLLWVLLLWVPGSTGDYKDEHHHHHGGSQDSTSDLIPAPPLSKVPLQQNFQDNQ
FQGKWYVVGLAGNAILREDKDPQKMYATIYELKEDKSYNVTSVLFRKKKCDYWIRTFVPG
CQPGEFTLGNIKSYPGLTSYLVRVVSTNYNQHAMVFFKKVSQNREYFKITLYGRTKELTS
ELKENFIRFSKSLGLPENHIVFPVPIDQCIDGGGSENLYFQGGQDKCKKVYENYPVSKCQ
LANQCNYDCKLDKHARSGECFYDEKRNLQCICDYCEY

SEQ ID NO: 115
METDTLLLWVLLLWVPGSTGDYKDEHHHHHGGSQDSTSDLIPAPPLSKVPLQQNFQDNQ
FQGKWYVVGLAGNAILREDKDPQKMYATIYELKEDKSYNVTSVLFRKKKCDYWIRTFVPG
CQPGEFTLGNIKSYPGLTSYLVRVVSTNYNQHAMVFFKKVSQNREYFKITLYGRTKELTS
ELKENFIRFSKSLGLPENHIVFPVPIDQCIDGGGSENLYFQGGMCMPCFTTDHQMARKCD
DCCGGKGRGKCYGPQCLCR

SEQ ID NO: 117
METDTLLLWVLLLWVPGSTGDYKDEHHHHHGGSQDSTSDLIPAPPLSKVPLQQNFQDNQ
FQGKWYVVGLAGNAILREDKDPQKMYATIYELKEDKSYNVTSVLFRKKKCDYWIRTFVPG
CQPGEFTLGNIKSYPGLTSYLVRVVSTNYNQHAMVFFKKVSQNREYFKITLYGRTKELTS
ELKENFIRFSKSLGLPENHIVFPVPIDQCIDGGGSENLYFQSDCKYKFENWGACDGGTGT
KVRQGTLKKARYNAQCQETIRVTKPC

SEQ ID NO: 118
METDTLLLWVLLLWVPGSTGDYKDEHHHHHGGSQDSTSDLIPAPPLSKVPLQQNFQDNQ
FQGKWYVVGLAGNAILREDKDPQKMYATIYELKEDKSYNVTSVLFRKKKCDYWIRTFVPG
CQPGEFTLGNIKSYPGLTSYLVRVVSTNYNQHAMVFFKKVSQNREYFKITLYGRTKELTS
ELKENFIRFSKSLGLPENHIVFPVPIDQCIDGGGSENLYFQGGSAISCGETCFKFKCYTP
RCSCSYPVCK

SEQ ID NO: 119
METDTLLLWVLLLWVPGSTGDYKDEHHHHHGGSQDSTSDLIPAPPLSKVPLQQNFQDNQ
FQGKWYVVGLAGNAILREDKDPQKMYATIYELKEDKSYNVTSVLFRKKKCDYWIRTFVPG
CQPGEFTLGNIKSYPGLTSYLVRVVSTNYNQHAMVFFKKVSQNREYFKITLYGRTKELTS
ELKENFIRFSKSLGLPENHIVFPVPIDQCIDGGGSENLYFQGGVCCGYKLCHPC

```
                                                   SEQ ID NO: 120
METDTLLLWVLLLWVPGSTGDYKDEHHHHHGGSQDSTSDLIPAPPLSKVPLQQNFQDNQ

FQGKWYVVGLAGNAILREDKDPQKMYATIYELKEDKSYNVTSVLFRKKKCDYWIRTFVPG

CQPGEFTLGNIKSYPGLTSYLVRVVSTNYNQHAMVFFKKVSQNREYFKITLYGRTKELTS

ELKENFIRFSKSLGLPENHIVFPVPIDQCIDGGGSENLYFQGGNGVCCGYKLCHPC

SEQ ID NO: 121
METDTLLLWVLLLWVPGSTGDYKDEHHHHHGGSQDSTSDLIPAPPLSKVPLQQNFQDNQ

FQGKWYVVGLAGNAILREDKDPQKMYATIYELKEDKSYNVTSVLFRKKKCDYWIRTFVPG

CQPGEFTLGNIKSYPGLTSYLVRVVSTNYNQHAMVFFKKVSQNREYFKITLYGRTKELTS

ELKENFIRFSKSLGLPENHIVFPVPIDQCIDGGGSENLYFQGGQQHADPICNKPCKTHDD

CSGAWFCQACWNSARTCGPYVG
```

---

What is claimed is:

1. A method for producing a fusion protein, the method comprising:
   expressing, in a cell, a fusion protein, the fusion protein comprising:
   a knotted-peptide selected from PMP-D2, potato carboxypeptidase inhibitor, huwentoxin, imperatoxin, epiregulin, midkine, bubble protein and conotoxin CIVC; and
   a siderocalin protein selected from human siderocalin, murine siderocalin, chicken Ex-FABP, and quail Q83, thereby producing the fusion protein.

2. The method of claim 1, further comprising separating the knotted-peptide from the siderocalin protein.

3. The method of claim 2, wherein the fusion protein further comprises a cleavage site.

4. The method of claim 3, wherein the cleavage site is a furin cleavage site, a trypsin cleavage site, or a TEV cleavage site.

5. The method of claim 3, wherein the separating of the knotted-peptide from the siderocalin protein results from cleavage at the cleavage site in the fusion protein.

6. The method of claim 2, wherein the separating of the knotted-peptide from the siderocalin protein occurs following secretion of the fusion protein from the cell.

7. The method of claim 6, wherein the cell is a mammalian cell.

8. The method of claim 1, wherein the fusion protein comprises the following construct: IgK starter sequence-signal sequence-sFLAG-HIS6 (SEQ ID NO: 93)-siderocalin protein-TEV cleavage site-knotted peptide.

9. A composition comprising a fusion protein, the fusion protein comprising:
   a knotted-peptide selected from PMP-D2, potato carboxypeptidase inhibitor, huwentoxin, imperatoxin, epiregulin, midkine, bubble protein and conotoxin CIVC; and
   a siderocalin protein selected from human siderocalin, murine siderocalin, chicken Ex-FABP, and quail Q83.

10. The composition of claim 9, wherein the fusion protein further comprises at least one of an IgK starter sequence, a sFLAG, a HIS6(SEQ ID NO: 93), or a TEV cleavage site.

11. The composition of claim 9, wherein the fusion protein is generated by direct fusion of the knotted-peptide to the siderocalin protein.

12. The composition of claim 9, further comprising a linker sequence between the knotted-peptide peptide and the siderocalin protein.

13. The method of claim 1, further comprising loading the siderocalin protein with a ligand.

14. The method of claim 13, wherein the ligand comprises a chemotherapeutic or radioactive agent.

15. The composition of claim 1, further comprising a cleavage site between the knotted-peptide and the siderocalin protein.

16. The composition of claim 15, wherein the cleavage site is a furin cleavage site, a trypsin cleavage site, or a TEV cleavage site.

17. The composition of claim 9, wherein the siderocalin protein is loaded with a ligand.

18. The composition of claim 17, wherein the ligand comprises a chemotherapeutic or radioactive agent.

19. The method of claim 1, wherein the siderocalin protein is human siderocalin having a C87S mutation.

20. The method of claim 1, wherein the siderocalin protein is human siderocalin having a C87S mutation, an 18C mutation and a N39C mutation.

21. The composition of claim 9, wherein the siderocalin protein is human siderocalin having a C87S mutation.

22. The composition of claim 9, wherein the siderocalin protein is human siderocalin having a C87S mutation, an 18C mutation and a N39C mutation.

* * * * *